(12) United States Patent
Bressi et al.

(10) Patent No.: US 8,178,534 B2
(45) Date of Patent: May 15, 2012

(54) CMET INHIBITORS

(75) Inventors: Jerome C. Bressi, San Diego, CA (US);
Shaosong Chu, San Diego, CA (US);
Philip Erickson, San Diego, CA (US);
Mallareddy Komandla, San Diego, CA (US); Lily Kwok, San Diego, CA (US);
John D Lawson, Carlsbad, CA (US);
Jeffrey A Stafford, San Diego, CA (US); Michael B. Wallace, San Diego, CA (US); Zhiyuan Zhang, Carlsbad, CA (US); Sanjib Das, Bangalore (IN)

(73) Assignee: Takeda Pharmaceutical Company Limited, Osaka (JP)

( * ) Notice: Subject to any disclaimer, the term of this patent is extended or adjusted under 35 U.S.C. 154(b) by 252 days.

(21) Appl. No.: 12/541,724

(22) Filed: Aug. 14, 2009

(65) Prior Publication Data

US 2010/0063054 A1    Mar. 11, 2010

Related U.S. Application Data

(60) Provisional application No. 61/088,959, filed on Aug. 14, 2008, provisional application No. 61/117,910, filed on Nov. 25, 2008, provisional application No. 61/161,007, filed on Mar. 17, 2009.

(51) Int. Cl.
*A61K 31/50* (2006.01)
*A61K 31/495* (2006.01)
*C07D 487/04* (2006.01)

(52) U.S. Cl. .................................. 514/248; 544/236

(58) Field of Classification Search .............. 544/236; 514/248
See application file for complete search history.

(56) References Cited

U.S. PATENT DOCUMENTS

| 5,380,759 A | 1/1995 | Hodgson |
| 2007/0078136 A1 | 4/2007 | Vaccaro et al. |
| 2008/0045536 A1 | 2/2008 | Vaccaro et al. |
| 2010/0298315 A1 | 11/2010 | Albert et al. |

FOREIGN PATENT DOCUMENTS

| WO | WO 2007/038314 | | 4/2007 |
| WO | WO 2007/064797 | | 6/2007 |
| WO | WO 2007/075567 | | 7/2007 |
| WO | WO 2008/016192 | * | 2/2008 |
| WO | WO 2008/021781 | | 2/2008 |
| WO | WO 2008/025822 | | 3/2008 |
| WO | WO 2008/030579 | | 3/2008 |
| WO | WO 2008/051808 | | 5/2008 |
| WO | WO 2008/064157 | | 5/2008 |
| WO | WO 2008/016192 | | 7/2008 |
| WO | WO 2009/106577 | | 3/2009 |
| WO | WO 2009/056692 | | 5/2009 |
| WO | WO 2009/106577 | | 9/2009 |

* cited by examiner

*Primary Examiner* — Rebecca Anderson
(74) *Attorney, Agent, or Firm* — Mitchell R. Brustein; David M. Stemerick

(57) ABSTRACT

Compounds of the following formula are provided for use with cMET:

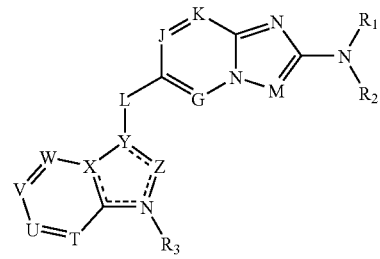

wherein the variables are as defined herein. Also provided are pharmaceutical compositions, kits and articles of manufacture comprising such compounds; methods and intermediates useful for making the compounds; and methods of using the compounds.

53 Claims, No Drawings

CMET INHIBITORS

RELATED APPLICATION

This application claims the benefit of U.S. Provisional Application No. 61/088,959, filed Aug. 14, 2008, U.S. Provisional Application No. 61/117,910 filed Nov. 25, 2008 and U.S. Provisional Application No. 61/161,007, filed on Mar. 17, 2009, which are incorporated herein by reference.

FIELD OF THE INVENTION

The present invention relates to compounds that may be used to inhibit cMET, as well as compositions of matter, kits and articles of manufacture comprising these compounds. The invention also relates to methods for inhibiting cMET and treatment methods using compounds according to the present invention. In addition, the invention relates to methods of making the compounds of the present invention, as well as intermediates useful in such methods.

BACKGROUND OF THE INVENTION cMET kinase is a receptor tyrosine kinase. HGF (hepatocyte growth factor, also known as scatter factor), the ligand for cMET, is secreted by cells of mesodermal origin whereas cMET is predominantly expressed on cells of epithelial/endothelial origin resulting in paracrine epithelial-mesenchymal cell signaling (Stoker, M. et al., Nature 327: 239-242 (1987)). Binding of HGF to the extracellular region of cMET activates the intracellular cMET tyrosine kinase activity. cMET is believed to be involved in protein phosphorylation events that regulate cell proliferation, apoptosis, motility, and dissociation of cell-cell interactions, morphogenesis, angiogenesis, and epithelial-mesenchymal transition. Misregulation of cMET can lead to unregulated cell proliferation and survival. cMET is thought to be a key regulator of invasive growth, cancer tumorgenesis, and progression to metastasis (Trusolino, T. and Comoglio, P. Nature Reviews Cancer: 2: 289-300 (2002)). cMET gene amplification, alteration, mutation, and protein over expression or activation of cMET through autocrine or paracrine mechanisms have been detected in a wide variety of carcinomas. For example, in human gastric cancer tissue, cMET has been found to be over expressed and amplified (Smolen, G. A., et al. PNAS 103: 2316-2321, (2006)). In human glioblastomas and carcinomas of lung, thyroid and breast, cMET has been found to be activated as a result of increased HGF levels and autocrine signaling (Birchmeier, C. et al. Rev. Mol. Cell Biol. 4: 915-925, (2003)). In human lung cancer tissue, cMET signaling has been found to be upregulated as a mechanism of drug resistance (Engelman, J. A., et al. Science 316: 1049-1043, (2007)). Activating mutations in cMET, although not as common, have been reported in sporadic and hereditary papillary renal carcinomas, head and neck squamous carcinomas as well as gastric and lung cancers. Furthermore, increased expression, the most common cMET alteration found in a wide variety of human tumors (including but not limited to renal, ovarian, hepatocellular, non-small cell lung, bone, liver metastasis of colon, oral squamous cell, esophageal, gastric, pancreatic, and prostatic cancers) correlates with poor prognosis (Benvenuti, S. and Comoglio, P. M., J. Cell. Physiol. 213: 316-325, (2007)).

There is a continued need to find new therapeutic agents to treat human diseases. Inhibition of cMET is an especially attractive target for the discovery of new therapeutics due to their important role in cancer and other diseases.

SUMMARY OF THE INVENTION

The present invention relates to compounds that have activity for inhibiting cMET. The present invention also provides compositions, articles of manufacture and kits comprising these compounds. In addition, the invention relates to methods of making the compounds of the present invention, as well as intermediates useful in such methods.

In one embodiment, a pharmaceutical composition is provided that comprises a cMET inhibitor according to the present invention as an active ingredient. Pharmaceutical compositions according to the invention may optionally comprise 0.001%-100% of one or more inhibitors of this invention. Pharmaceutical compositions according to the invention may optionally comprise one or more compounds selected from the group consisting of excipients, diluents, lubricants, binders, adjuvants, carriers, wetting agents, emulsifying agents, solubilizing agents, and pH buffering agents. The pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with cMET.

In one embodiment, a kit is provided that comprises a composition comprising at least one cMET inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one cMET inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit cMET.

In another embodiment, the compounds, compositions, kits and articles of manufacture are used to treat a disease state for which cMET possess activity that contributes to the pathology and/or symptomology of the disease state.

In another embodiment, a compound according to the present invention is administered to a subject wherein cMET activity within the subject is altered, preferably reduced.

In another embodiment, a prodrug of a compound according to the present invention is administered to a subject that is converted to the compound in vivo where it inhibits cMET.

In another embodiment, a method of inhibiting cMET is provided that comprises contacting a cMET with a compound according to the present invention.

In another embodiment, a method of inhibiting cMET is provided that comprises causing a compound according to the present invention to be present in a subject in order to inhibit cMET in vivo.

In another embodiment, a method of inhibiting a cMET is provided that comprises administering a first compound to a subject that is converted in vivo to a second compound wherein the second compound inhibits cMET in vivo. It is noted that the compounds of the present invention may be the first or second compounds.

In another embodiment, a therapeutic method is provided that comprises administering a compound according to the present invention.

In another embodiment, a method is provided for treating a condition in a patient that is known to be mediated by cMET, or which is known to be treated by cMET inhibitors, the method comprising administering to the patient a therapeutically effective amount of a compound according to the present invention.

In another embodiment, a method is provided for treating a disease state for which cMET possess activity that contributes to the pathology and/or symptomology of the disease state, the method comprising: causing a compound according to the present invention to be present in a subject in a therapeutically effective amount for the disease state.

In another embodiment, a method is provided for treating a disease state for which cMET possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which cMET possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by cMET, or that is known to be treated by cMET inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting cMET and thus may themselves be prodrugs for another compound. Such prodrugs of another compound may or may not themselves independently have cMET inhibitory activity.

Definitions

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $4^{TH}$ ED." Vols. A (2000) and B (2001), Plenum Press, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR═CR'— or —CR═CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a ($C_{2-20}$)alkenyl, a ($C_{2-15}$)alkenyl, a ($C_{2-10}$)alkenyl, a ($C_{2-5}$) alkenyl or a ($C_{2-3}$)alkenyl. Alternatively, "alkenyl," either alone or represented along with another radical, can be a $(C_2)$alkenyl, a $(C_3)$alkenyl or a $(C_4)$alkenyl.

"Alkenylene" means a straight or branched, divalent carbon chain having one or more carbon-carbon double bonds (—CR═CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a $(C_{2-20})$ alkenylene, a $(C_{2-15})$ alkenylene, a $(C_{2-10})$ alkenylene, a $(C_{2-5})$ alkenylene or a $(C_{2-3})$ alkenylene. Alternatively, "alkenylene," either alone or represented along with another radical, can be a $(C_2)$ alkenylene, a $(C_3)$ alkenylene or a $(C_4)$ alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). $(C_X)$alkyl and $(C_{X-Y})$alkyl are typically used where X and Y indicate the number of carbon atoms in the chain. For example, $(C_{1-6})$alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., $(C_{6-10})$aryl$(C_{1-3})$ alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a $(C_{1-20})$alkyl, a $(C_{1-15})$alkyl, a $(C_{1-10})$alkyl, a $(C_{1-5})$alkyl or a $(C_{1-3})$alkyl. Alternatively, "alkyl," either alone or represented along with another radical, can be a $(C_1)$alkyl, a $(C_2)$alkyl or a $(C_3)$alkyl.

"Alkylene", unless indicated otherwise, means a straight or branched, saturated or unsaturated, aliphatic, divalent radical. $(C_X)$alkylene and $(C_{X-Y})$alkylene are typically used where X and Y indicate the number of carbon atoms in the chain. For example, $(C_{1-6})$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH═CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like. In particular embodiments, "alkylene," either alone or represented along with another radical, can be a $(C_{1-20})$alkylene, a $(C_{1-15})$alkylene, a $(C_{1-10})$alkylene, a $(C_{1-5})$alkylene or a $(C_{1-3})$alkylene. Alternatively, "alkylene," either alone or represented along with another radical, can be a $(C_1)$alkylene, a $(C_2)$alkylene or a $(C_3)$alkylene.

"Alkylidene" means a straight or branched, saturated or unsaturated, aliphatic radical connected to the parent molecule by a double bond. $(C_X)$alkylidene and $(C_{X-Y})$alkylidene are typically used where X and Y indicate the number of carbon atoms in the chain. For example, $(C_{1-6})$alkylidene includes methylene (═CH$_2$), ethylidene (═CHCH$_3$), isopropylidene (═C(CH$_3$)$_2$), propylidene (═CHCH$_2$CH$_3$), allylidene (═CH—CH═CH$_2$), and the like. In particular embodiments, "alkylidene," either alone or represented along with another radical, can be a $(C_{1-20})$alkylidene, a $(C_{1-15})$ alkylidene, a $(C_{1-10})$alkylidene, a $(C_{1-5})$alkylidene or a $(C_{1-3})$alkylidene. Alternatively, "alkylidene," either alone or represented along with another radical, can be a $(C_1)$alkylidene, a $(C_2)$alkylidene or a $(C_3)$alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$ alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$ alkynylene, a $(C_{2-15})$ alkynylene, a $(C_{2-10})$ alkynylene, a $(C_{2-5})$ alkynylene or a $(C_{2-3})$ alkynylene. Alternatively, "alkynylene," either alone or represented along with another radical, can be a $(C_2)$ alkynylene, a $(C_3)$ alkynylene or a $(C_4)$ alkynylene.

"Amido" means the radical —C(═O)—NR—, —C(═O)—NRR', —NR—C(═O)— and/or —NR—C(═O)R', wherein each R and R' are independently hydrogen or a further substituent.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH((C$_{1-10}$)alkyl), —N((C$_{1-10}$)alkyl)$_2$, —NH(aryl), —NH (heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$ aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl., a $(C_9)$aryl or a $(C_{10})$aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a ($C_{1-10}$)azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a ($C_{4-15}$)bicycloalkyl, a ($C_{4-10}$)bicycloalkyl, a ($C_{6-10}$)bicycloalkyl or a ($C_{8-10}$)bicycloalkyl. Alternatively, "bicycloalkyl," either alone or represented along with another radical, can be a ($C_8$)bicycloalkyl, a ($C_9$)bicycloalkyl or a ($C_{10}$)bicycloalkyl.

"Bicycloaryl" means a fused, spiro or bridged bicyclic ring assembly wherein at least one of the rings comprising the assembly is aromatic. ($C_X$)bicycloaryl and ($C_{X-Y}$)bicycloaryl are typically used where X and Y indicate the number of carbon atoms in the bicyclic ring assembly and directly attached to the ring. In particular embodiments, "bicycloaryl," either alone or represented along with another radical, can be a (a ($C_{4-15}$)bicycloaryl, a ($C_{4-10}$)bicycloaryl, a ($C_{6-10}$)bicycloaryl or a ($C_{8-10}$)bicycloaryl. Alternatively, "bicycloalkyl," either alone or represented along with another radical, can be a ($C_8$)bicycloaryl, a ($C_9$)bicycloaryl or a ($C_{10}$) bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

As used herein, "cMet" is synonymous with "c-Met", "MET", "Met", "heptaocyte growth factor receptor" and other designations known to those skilled in the art.

"Cyano" means the radical —CN.

"Cycloalkyl" means a non-aromatic, saturated or partially unsaturated, monocyclic, bicyclic or polycyclic ring assembly. ($C_X$)cycloalkyl and ($C_{X-Y}$)cycloalkyl are typically used where X and Y indicate the number of carbon atoms in the ring assembly. For example, ($C_{3-10}$)cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a ($C_{3-14}$)cycloalkyl, a ($C_{3-10}$)cycloalkyl, a ($C_{3-7}$)cycloalkyl, a ($C_{8-10}$)cycloalkyl or a ($C_{5-7}$)cycloalkyl. Alternatively, "cycloalkyl," either alone or represented along with another radical, can be a ($C_5$)cycloalkyl, a ($C_6$)cycloalkyl, a ($C_7$)cycloalkyl, a ($C_8$)cycloalkyl., a ($C_9$)cycloalkyl or a ($C_{10}$)cycloalkyl.

"Cycloalkylene" means a divalent, saturated or partially unsaturated, monocyclic, bicyclic or polycyclic ring assembly. ($C_X$)cycloalkylene and ($C_{X-Y}$)cycloalkylene are typically used where X and Y indicate the number of carbon atoms in the ring assembly. In particular embodiments, "cycloalkylene," either alone or represented along with another radical, can be a ($C_{3-14}$)cycloalkylene, a ($C_{3-10}$)cycloalkylene, a ($C_{3-7}$)cycloalkylene, a ($C_{8-10}$)cycloalkylene or a ($C_{5-7}$)cycloalkylene. Alternatively, "cycloalkylene," either alone or represented along with another radical, can be a ($C_5$)cycloalkylene, a ($C_6$)cycloalkylene, a ($C_7$)cycloalkylene, a ($C_8$) cycloalkylene., a ($C_9$)cycloalkylene or a ($C_{10}$)cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero($C_{1-20}$)alkyl, a hetero($C_{1-15}$)alkyl, a hetero($C_{1-10}$) alkyl, a hetero($C_{1-5}$)alkyl, a hetero($C_{1-3}$)alkyl or a hetero($C_{1-2}$)alkyl. Alternatively, "heteroalkyl," either alone or represented along with another radical, can be a hetero($C_1$) alkyl, a hetero($C_2$)alkyl or a hetero($C_3$)alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]

pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl., a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O$^-$)═, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-4}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$)bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$)bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-3}$)cycloalkylene, a hetero($C_{1-9}$)cycloalkylene, a hetero($C_{1-6}$)cycloalkylene, a hetero($C_{5-9}$)cycloalkylene or a hetero($C_{2-6}$)cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$)cycloalkylene, hetero($C_7$)cycloalkylene, hetero($C_8$)cycloalkylene or a hetero($C_9$)cycloalkylene.

"Hydroxy" means the radical —OH.

"IC$_{50}$" means the molar concentration of an inhibitor that produces 50% inhibition of the target enzyme.

"Imino" means the radical —CR(═NR') and/or —C(═NR')—, wherein R and R' are each independently hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R— and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Moiety providing X atom separation" and "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-(L)$_x$—R' where each L is independently selected from the group consisting of CR"R''', NR'''', O, S, CO, CS, C═NR''''', SO, SO$_2$, and the like, where any two or more of R", R'", R"" and R""' can be taken together to form a substituted or unsubstituted ring.

"Nitro" means the radical —NO$_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa(C$_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid, or acid halide. For example, an oxo(C$_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

The term "pharmaceutically acceptable excipient" refers to those typically used in preparing pharmaceutical compositions and should be pharmaceutically pure and non-toxic in the amounts used. They generally are a solid, semi-solid, or liquid material which can serve as a vehicle or medium for the active ingredient or an aid to the storage, administration, or manufacture of the composition. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" include humans, non-human mammals (e.g., dogs, cats, rabbits, cattle, horses, sheep, goats, swine, deer, and the like) and non-mammals (e.g., birds, and the like).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [(CH$_3$)$_3$C—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; CH$_3$CH(NH$_2$)CO—), Arg (arginine), Asn (asparagine), Asp (aspartic acid), Cys (cysteine), Glu (glutamic acid), His (histidine), Ile (isoleucine), Leu (leucine; (CH$_3$)$_2$CHCH$_2$CH(NH$_2$)CO—), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [(CH$_3$)$_3$C—OCO—], and the like. Suitable peptide residues include peptide residues comprising two to five, and optionally two to three, of the aforesaid amino acid residues. Examples of such peptide residues include, but are not limited to, residues of such peptides as Ala-Ala [CH$_3$CH(NH$_2$)CO—NHCH(CH$_3$)CO—], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [(CH$_3$)$_3$C—OCO—], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and halogenoethoxycarbonyl groups (such as β,β,β-trichloroethoxycarbonyl and β-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —CH$_3$. In general, a non-hydrogen substituent may be any substituent that may be bound to an atom of the given moiety that is specified to be substituted. Examples of substituents include, but are not limited to, aldehyde, alicyclic, aliphatic, (C$_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, (C$_{9-12}$)bicycloalkyl, hetero(C$_{3-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sul-finyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a C$_1$ alkyl indicates that there is one carbon atom but does not indicate what the substituents on the carbon atom are. Hence, a (C$_1$)alkyl comprises methyl (i.e., —CH$_3$) as well as —CRR'R" where R, R', and R" may each independently be hydrogen or a further substituent where the atom attached to the carbon is a heteroatom or cyano. Hence, $CF_3$, $CH_2OH$ and $CH_2CN$, for example, are all ($C_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

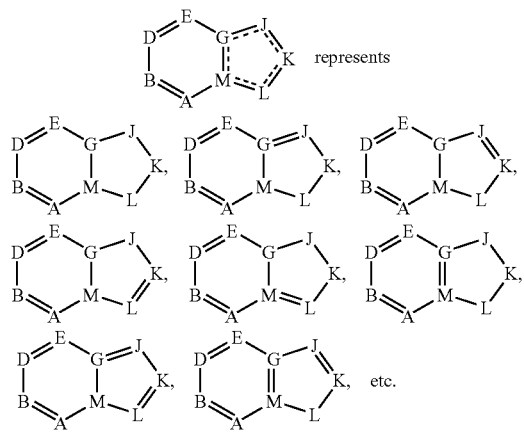

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

DETAILED DESCRIPTION OF THE INVENTION

The present invention relates to compounds that may be used to inhibit cMET. The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other members of the same protein family and thus may be used to address disease states associated with these other family members.

cMET belongs to the phosphoryl transferase family of enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) numbers starting with 2.7.-.- (See, Bairoch A., The ENZYME database in Nucleic Acids Res. 28:204-305 (2000)). Kinases are a class of enzymes that function in the catalysis of phosphoryl transfer. The protein kinases constitute one of the largest subfamilies of structurally related phosphoryl transferases and are responsible for the control of a wide variety of cellular signal transduction processes. (See, Hardie, G. and Hanks, S. (1995) The Protein Kinase Facts Book, I and II, Academic Press, San Diego, Calif.).

Disregulation of cMET is implicated in such diseases as cancers (including carcinomas (e.g., bladder, breast, cervical, cholangiocarcinoma, colorectal, esophageal, gastric, head and neck, kidney, liver, lung, nasopharygeal, ovarian, pancreatic, prostate and thyroid); musculoskeletal sarcomas (e.g., osteosarcoma, synovial sarcoma, and rhabdomyosarcoma); soft tissue sarcomas (e.g., MFH/fibrosrcoma, leiomyosarcoma, and Kaposi's sarcoma); hematopoietic malignancies (e.g., multiple myeloma, lymphomas, adult T cell leukemia, acute myelogenous leukemia, and chronic myeloid leukemia); and other neoplasms (e.g., glioblastomas, astrocytomas, melanoma, mesothelioma, and Wilm's tumor)); and proliferative diseases (e.g., myeloproliferative disorders, atherosclerosis, and fibrosis of the lung).

It is noted that the compounds of the present invention may also possess inhibitory activity for other receptor tyrosine kinase family members and thus may be used to address disease states associated with these other family members. In particular, the compounds of the present invention may be used to modulate the activity of other proteins in the Met subfamily (e.g., Ron and Sea).

cMET Inhibitors

In one of its aspects, the present invention relates to compounds that are useful as cMET inhibitors. In one embodiment, cMET inhibitors of the present invention comprise:

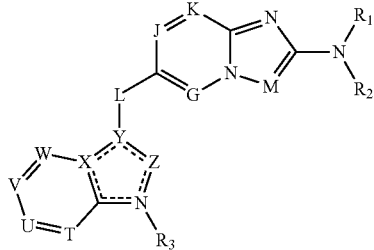

or a polymorph, solvate, ester, tautomer, enantiomer, pharmaceutically acceptable salt or prodrug thereof, wherein G is selected from the group consisting of $CR_4$ and N;
J is selected from the group consisting of $CR_5$ and N;
K is selected from the group consisting of $CR_6$ and N;
M is selected from the group consisting of $CR_7$ and N;
L is absent or a linker providing 1, 2, 3, 4, 5 or 6 atom separation between the rings to which L is attached, wherein the atoms of the linker providing the separation are selected from the group consisting of carbon, oxygen, nitrogen, and sulfur;
T is selected from the group consisting of $CR_8$ and N;
U is selected from the group consisting of $CR_9$ and N;
V is selected from the group consisting of $CR_{10}$ and N;
W is selected from the group consisting of $CR_{11}$ and N;
X is selected from the group consisting of $CR_{12}$ and N;
Y is selected from the group consisting of $CR_{13}$ and N;
Z is selected from the group consisting of $CR_{14}R_{15}$ and $NR_{16}$;
$R_1$ is selected from the group consisting of hydrogen, carbonyloxy, ($C_{1-10}$)alkoxy, ($C_{4-12}$)aryloxy, hetero($C_{1-10}$) aryloxy, carbonyl, oxycarbonyl, aminocarbonyl, ($C_{1-10}$) alkylcarbonyl, ($C_{3-12}$)cycloalkyl($C_{1-5}$)carbonyl, hetero ($C_{3-12}$)cycloalkyl($C_{1-10}$)carbonyl, aryl($C_{1-10}$)carbonyl, hetero($C_{1-10}$)aryl($C_{1-5}$)carbonyl, ($C_{9-12}$)bicycloaryl ($C_{1-5}$)carbonyl, hetero($C_{8-12}$)bicycloaryl($C_{1-5}$)carbonyl, amino, ($C_{1-10}$)alkylamino, sulfonamido, imino, sulfonyl, sulfinyl, ($C_{1-10}$)alkyl, halo($C_{1-10}$)alkyl, hydroxy ($C_{1-10}$)alkyl, carbonyl($C_{1-10}$)alkyl, thiocarbonyl($C_{1-10}$) alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted, or $R_1$ has the formula

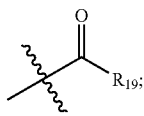

$R_2$ is hydrogen or a substituent convertible in vivo to hydrogen;

$R_3$ is selected from the group consisting of hydrogen, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted, or $R_3$ is absent when the nitrogen to which it is bound forms part of a double bond;

$R_4$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_6$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_7$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_9$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, amido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, amino($C_{1-10}$)alkyl, amido($C_{1-10}$)alkylamino($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)

alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, carbonyl$(C_{4-12})$aryl, hetero$(C_{4-10})$aryl, $(C_{9-12})$bicycloaryl and hetero$(C_{4-12})$bicycloaryl, each substituted or unsubstituted;

$R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, amido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, amino$(C_{1-10})$alkyl, amido$(C_{1-10})$alkylamino$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, carbonyl$(C_{4-12})$aryl, hetero$(C_{4-10})$aryl, $(C_{9-12})$bicycloaryl and hetero$(C_{4-12})$bicycloaryl, each substituted or unsubstituted;

$R_{11}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted, or $R_{12}$ is absent when the carbon to which it is bound forms part of a double bond;

$R_{13}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted, or $R_{13}$ is absent when the carbon to which it is bound forms part of a double bond;

$R_{14}$ and $R_{15}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted, or $R_{15}$ is absent when the carbon to which it is bound forms part of a double bond;

$R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted, or $R_{16}$ is absent when the nitrogen to which it is bound forms part of a double bond; and $R_{19}$ selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another embodiment, cMET inhibitors of the present invention comprise:

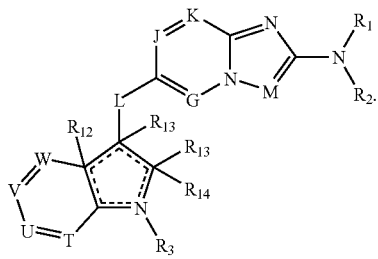

In another embodiment, cMET inhibitors of the present invention comprise:

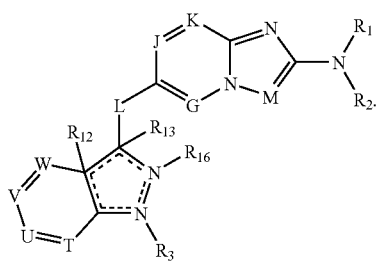

In another embodiment, cMET inhibitors of the present invention comprise:

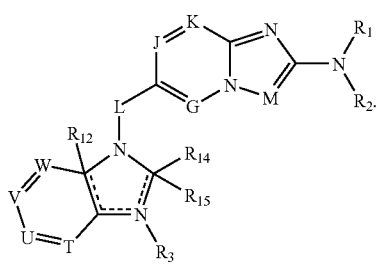

In another embodiment, cMET inhibitors of the present invention comprise:

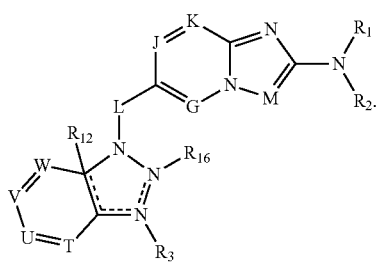

In another embodiment, cMET inhibitors of the present invention comprise:

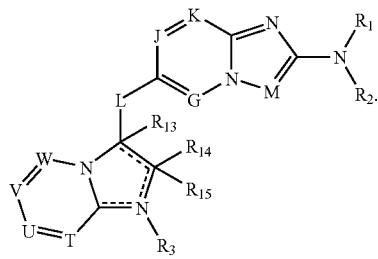

In another embodiment, cMET inhibitors of the present invention comprise:

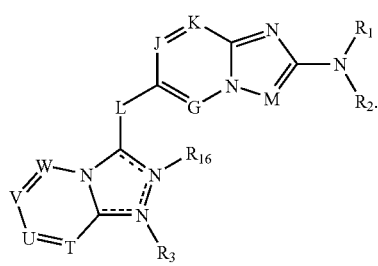

In another embodiment, cMET inhibitors of the present invention comprise:

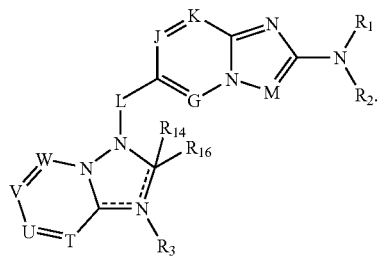

In another embodiment, cMET inhibitors of the present invention comprise:

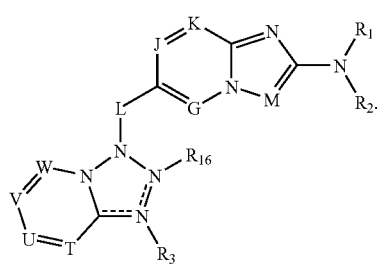

In a further embodiment, cMET inhibitors of the present invention comprise:

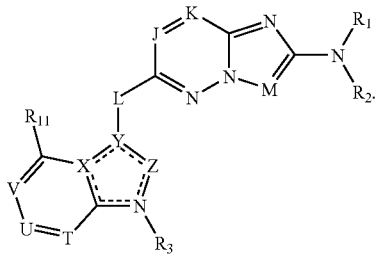

In still a further embodiment, cMET inhibitors of the present invention comprise:

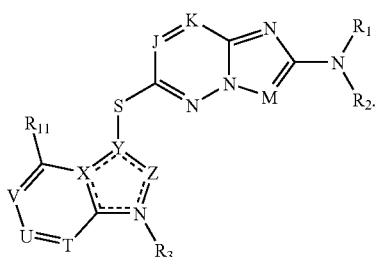

In yet a further embodiment, cMET inhibitors of the present invention comprise:

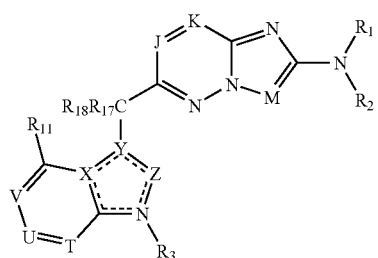

wherein $R_{17}$ and $R_{18}$ are each independently elected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl $(C_{1-5})$alkyl, hetero$(C_{8-12})$bicycloaryl$(C_{1-5})$alkyl, hetero $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another embodiment, cMET inhibitors of the present invention comprise:

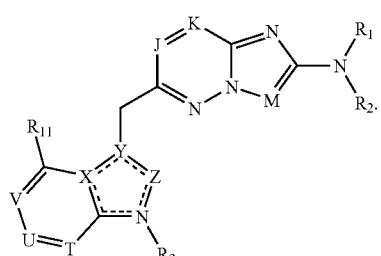

In still another embodiment, cMET inhibitors of the present invention comprise:

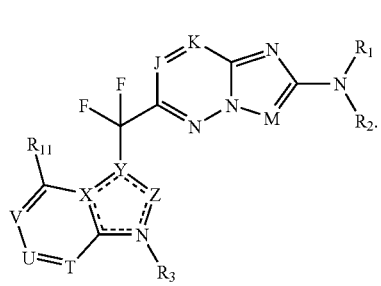

In yet another embodiment, cMET inhibitors of the present invention comprise:

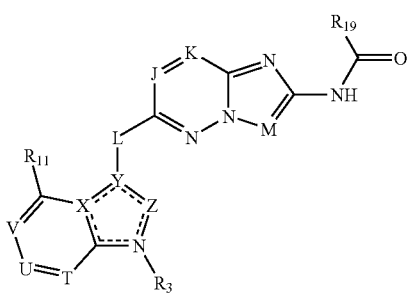

wherein $R_{19}$ selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$ alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{4-10})$aryl, $(C_{9-12})$bicycloaryl and hetero$(C_{4-12})$bicycloaryl, each substituted or unsubstituted.

In a further embodiment, cMET inhibitors of the present invention comprise:

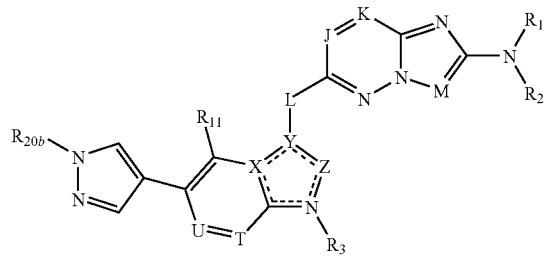

wherein R$_{20b}$ selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$) alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$) alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$) bicycloaryl, each substituted or unsubstituted.

In still a further embodiment, cMET inhibitors of the present invention comprise:

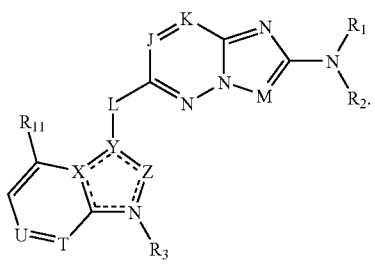

In yet a further embodiment, cMET inhibitors of the present invention comprise:

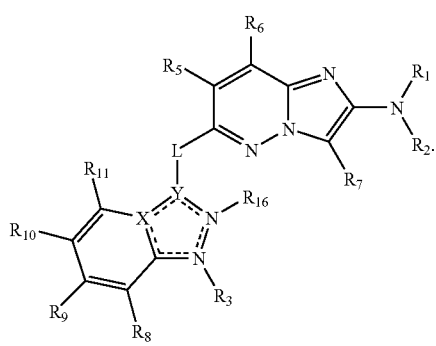

In another embodiment, cMET inhibitors of the present invention comprise:

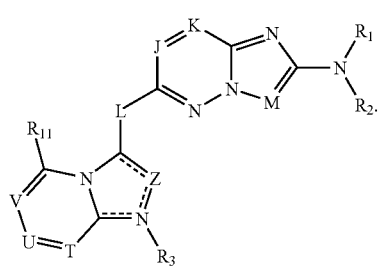

In still another embodiment, cMET inhibitors of the present invention comprise:

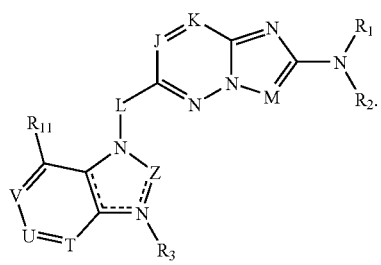

In a further embodiment, cMET inhibitors of the present invention comprise:

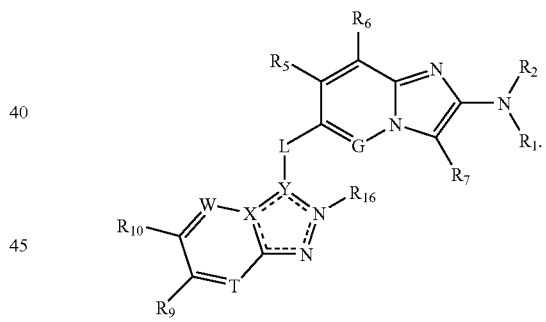

In another embodiment, cMET inhibitors of the present invention comprise:

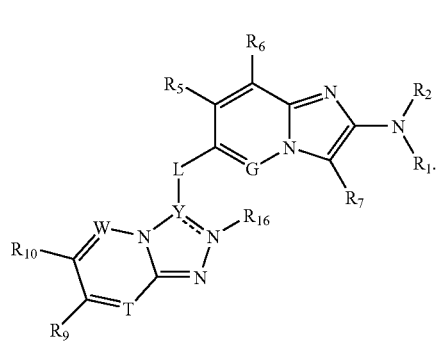

In still another embodiment, cMET inhibitors of the present invention comprise:

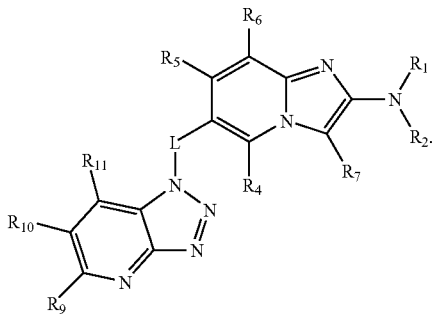

In yet another embodiment, cMET inhibitors of the present invention comprise:

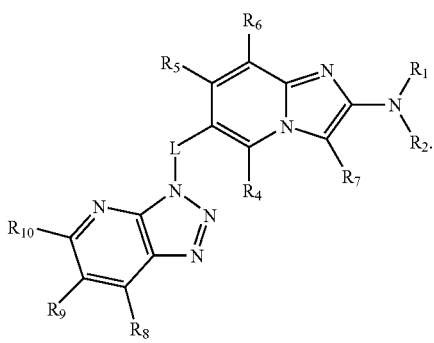

In a further embodiment, cMET inhibitors of the present invention comprise:

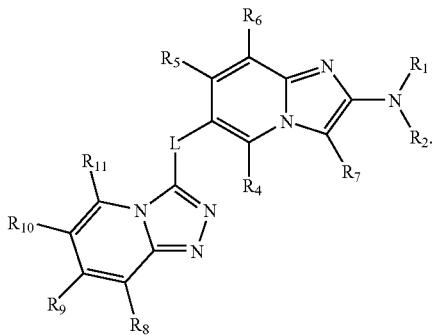

In still a further embodiment, cMET inhibitors of the present invention comprise:

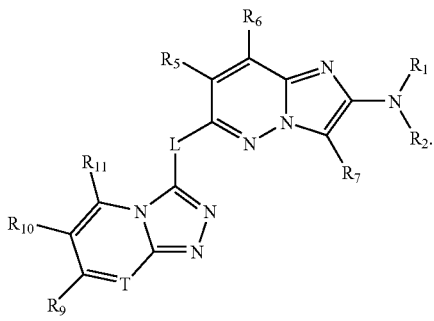

In yet a further embodiment, cMET inhibitors of the present invention comprise:

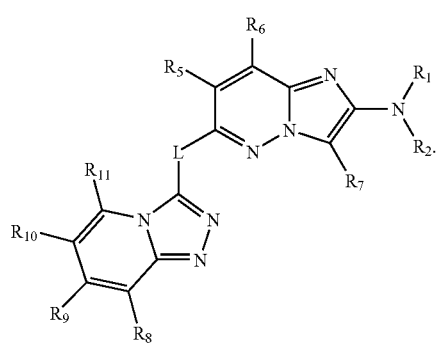

In still another embodiment, cMET inhibitors of the present invention comprise:

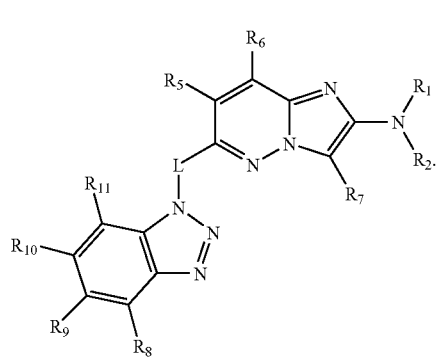

In another embodiment, cMET inhibitors of the present invention comprise:

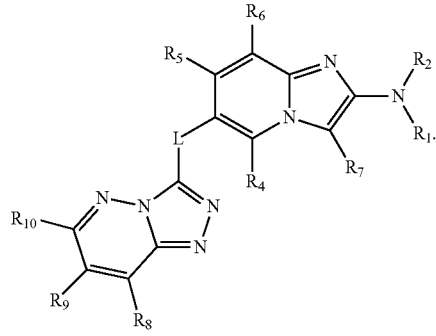

In still another embodiment, cMET inhibitors of the present invention comprise:

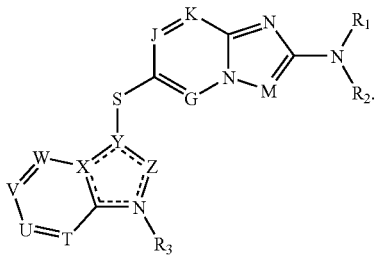

In yet another embodiment, cMET inhibitors of the present invention comprise:

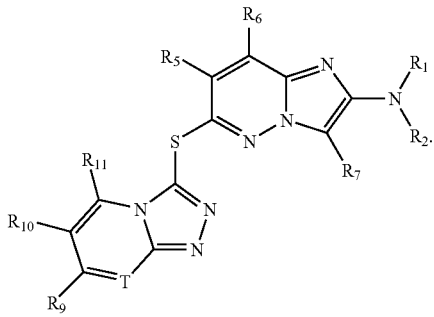

In a further embodiment, cMET inhibitors of the present invention comprise:

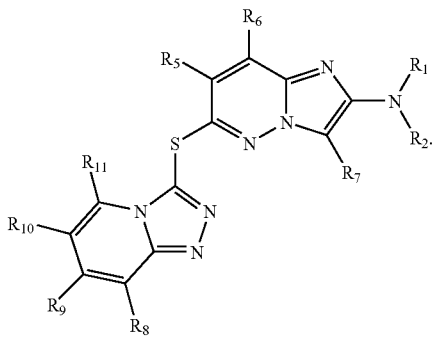

In still a further embodiment, cMET inhibitors of the present invention comprise:

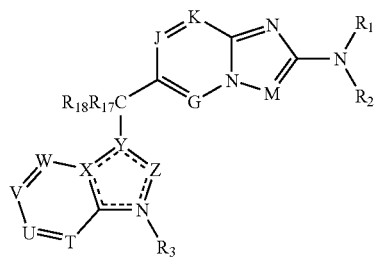

wherein $R_{17}$ and $R_{18}$ are each independently elected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{4-10})$aryl, $(C_{9-12})$bicycloaryl and hetero$(C_{4-12})$bicycloaryl, each substituted or unsubstituted.

In yet a further embodiment, cMET inhibitors of the present invention comprise:

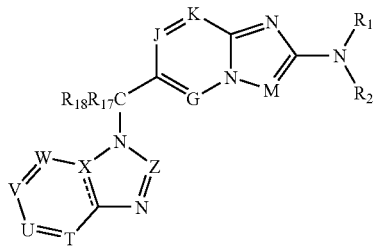

wherein $R_{17}$ and $R_{18}$ are each independently elected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{4-10})$aryl, $(C_{9-12})$bicycloaryl and hetero$(C_{4-12})$bicycloaryl, each substituted or unsubstituted.

In another embodiment, cMET inhibitors of the present invention comprise:

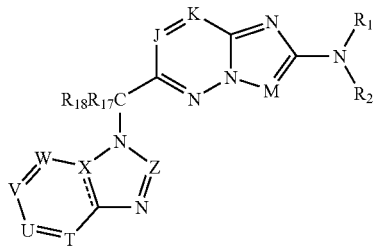

wherein $R_{17}$ and $R_{18}$ are each independently elected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{4-10})$aryl, $(C_{9-12})$bicycloaryl and hetero$(C_{4-12})$bicycloaryl, each substituted or unsubstituted.

In still another embodiment, cMET inhibitors of the present invention comprise:

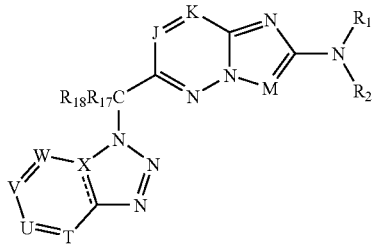

wherein $R_{17}$ and $R_{18}$ are each independently elected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further embodiment, cMET inhibitors of the present invention comprise:

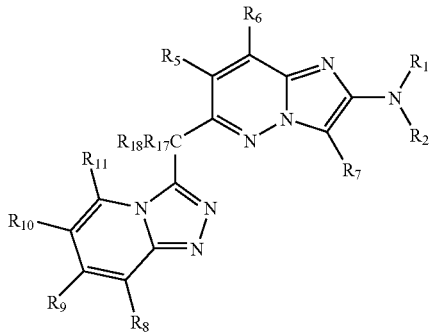

wherein $R_{17}$ and $R_{18}$ are each independently elected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another embodiment, cMET inhibitors of the present invention comprise:

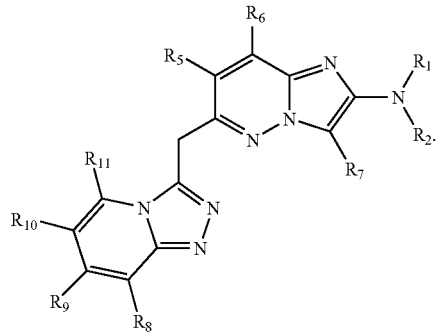

In still another embodiment, cMET inhibitors of the present invention comprise:

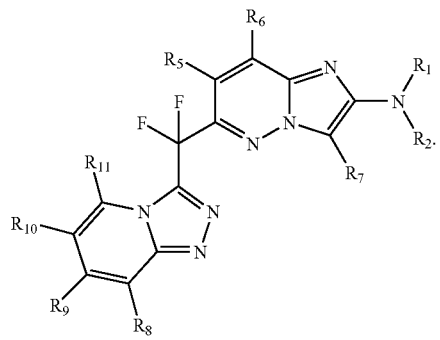

In still a further embodiment, cMET inhibitors of the present invention comprise:

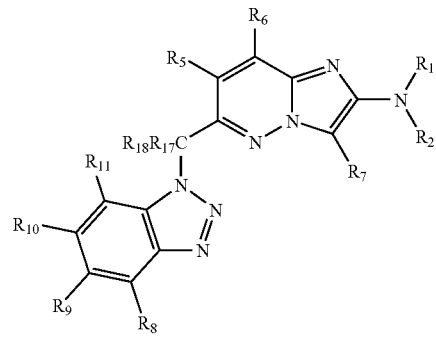

wherein $R_{17}$ and $R_{18}$ are each independently elected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$ bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In another embodiment, cMET inhibitors of the present invention comprise:

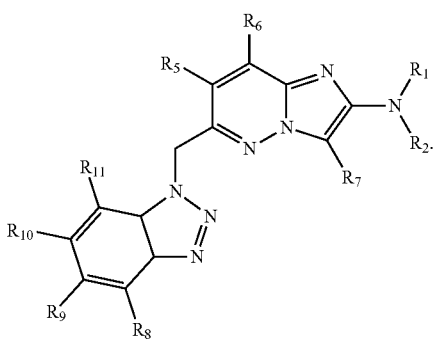

In another of its aspects, the present invention relates to methods of making compounds that are useful as cMET inhibitors.

In still another of its aspects, the present invention relates to intermediates that are useful in making cMET inhibitors.

In one variation of each of the above embodiments and variations, G is $CR_4$. In another variation of each of the above embodiments and variations, G is N.

In still another variation of each of the above embodiments and variations, J is $CR_5$. In yet another variation of each of the above embodiments and variations, J is N.

In a further variation of each of the above embodiments and variations, K is $CR_6$. In still a further variation of each of the above embodiments and variations, K is N.

In yet a further variation of each of the above embodiments and variations, M is $CR_7$. In another variation of each of the above embodiments and variations, M is N.

In another variation of each of the above embodiments and variations,

L is a linker selected from the group consisting of —($CR_{27}R_{28}$)$_r$—, —CO—, —CS—, —C(=N$R_{29}$)—, —N$R_{30}$—, —O—, —S—, —SO—, —SO$_2$— and combinations thereof;

r is selected from the group consisting of 1, 2 and 3;

$R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_{28}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_{29}$ is selected from the group consisting of hydrogen, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted; and $R_{30}$ is selected from the group consisting of hydrogen, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In still another variation of each of the above embodiments and variations, L is a substituted or unsubstituted ($C_{1-5}$)alkyl. In yet another variation of each of the above embodiments and variations, L is —CH$_2$—. In a further variation of each of the above embodiments and variations, L is —CH(CH$_3$)—. In still a further variation of each of the above embodiments and variations, L is —C(CH$_3$)$_2$—. In yet a further variation of each of the above embodiments and variations, L is —CF$_2$—. In a further variation of each of the above embodiments and variations, L is —S—. In another variation of each of the above embodiments and variations, L is —SO—. In still another variation of each of the above embodiments and variations, L is —SO$_2$—. In yet another variation of each of the above embodiments and variations, L is —CO—. In another variation of each of the above embodiments and variations, L is —O—. In still another variation of each of the above embodiments and variations, L is —NH—. In yet another variation of each of the above embodiments and variations, L is —CH$_2$—. In a further variation of each of the above embodiments and variations, L is —CO—NH—. In still a further variation of each of the above embodiments and variations, L is —NH—CO—. In yet a further variation of each of the above embodiments and variations, L is —SO$_2$—NH—. In another variation of each of the above embodiments and variations, L is —NH—SO$_2$—. In still another variation of each of the above embodiments and variations, L is —NH—NH—. In yet another variation of each of the above embodiments and variations, L is —CO—O—. In a further variation of each of the above embodiments and variations, L is —O—CO—.

In still a further variation of each of the above embodiments and variations, T is $CR_8$. In yet a further variation of each of the above embodiments and variations, T is N.

In another variation of each of the above embodiments and variations, U is $CR_9$. In still another variation of each of the above embodiments and variations, U is N.

In yet another variation of each of the above embodiments and variations, V is $CR_{10}$. In a further variation of each of the above embodiments and variations, V is N.

In still a further variation of each of the above embodiments and variations, W is $CR_{11}$. In yet a further variation of each of the above embodiments and variations, W is N.

In another variation of each of the above embodiments and variations, X is $CR_{12}$. In still another variation of each of the above embodiments and variations, X is N.

In yet another variation of each of the above embodiments and variations, Y is $CR_{13}$. In a further variation of each of the above embodiments and variations, Y is N.

In still a further variation of each of the above embodiments and variations, Z is $CR_{14}R_{15}$. In yet a further variation of each of the above embodiments and variations, Z is $NR_{16}$.

In another variation of each of the above embodiments and variations, T, Y and Z are each N. In still another variation of each of the above embodiments and variations, G is $CR_4$, J is $CR_5$, K is $CR_6$, M is $CR_7$, T is $CR_8$, U is $CR_9$, V is $CR_{10}$, W is $CR_{11}$, X is $CR_{12}$ and Y is $CR_{13}$. In yet another variation of each of the above embodiments and variations, G is $CR_4$, J is $CR_5$, K is $CR_6$, M is $CR_7$, T is $CR_8$, U is $CR_9$, V is $CR_{10}$, W is $CR_{11}$, and Y is $CR_{13}$. In a further variation of each of the above embodiments and variations, G, J, K, M, U, V, W, and X are each CH. In still a further variation of each of the above embodiments and variations, W, Y and Z are each N. In yet a further variation of each of the above embodiments and variations, G, J, K, M, T, U, V, and X are each CH. In another variation of each of the above embodiments and variations, G, X and Z are each N. In still another variation of each of the above embodiments and variations, J, K, M, T, U, V, W and Y are each CH. In yet another variation of each of the above embodiments and variations, X and Z are each N. In a further variation of each of the above embodiments and variations, G, J, K, M, T, U, V, W and Y are each CH. In still a further variation of each of the above embodiments and variations, T is $CR_8$, U is $CR_9$, V is $CR_{10}$, W is $CR_{11}$, X is $CR_{12}$, Y is N and Z is $CR_{14}R_{15}$. In yet a further variation of each of the above embodiments and variations, T is $CR_8$, U is $CR_9$, V is $CR_{10}$, W is $CR_{11}$, X is N, Y is $CR_{13}$ and Z is $NR_{16}$. In another variation of each of the above embodiments and variations, G is N, J is $CR_5$, K is $CR_6$ and M is $CR_7$. In a further variation of each of the above embodiments and variations, J is $CR_5$, K is $CR_6$, T is $CR_8$, U is $CR_9$, V is $CR_{10}$ and Z is $NR_{16}$. In still a further variation of each of the above embodiments and variations, one and only one of G and W is N. In another variation of each of the above embodiments and variations, G is N and W is $CR_{11}$. In still another variation of each of the above embodiments and variations, G is $CR_4$ and W is N. In yet a further variation of each of the above embodiments and variations, one and only one of W and Z is N. In another variation of each of the above embodiments and variations, one and only one of W and X is N. In still another variation of each of the above embodiments and variations, one and only one of W, X and Z is N. In a further variation of each of the above embodiments and variations, G is N; and J, K, M, T, U, V and W are each CH. In still a further variation of each of the above embodiments and variations, G is N, J; K, M, T, U and W are each CH; and V is $CR_{10}$. In still a further variation of each of the above embodiments and variations, G is N, J; K, M, T, U and W are each CH; and V is $CR_{10}$, wherein $R_{10}$ is a substituted or unsubstituted hetero($C_{1-10}$)aryl.

In a further variation of each of the above embodiments and variations, $CR_5$, $CR_6$, $CR_7$, $CR_8$ and $CR_9$ are each hydrogen.

In a further variation of each of the above embodiments and variations, $R_1$ is selected from the group consisting of hydrogen, carbonyl, oxycarbonyl, aminocarbonyl, ($C_{1-10}$)alkylcarbonyl, ($C_{3-12}$)cycloalkyl($C_{1-5}$)carbonyl, hetero($C_{3-12}$)cycloalkyl($C_{1-10}$)carbonyl, aryl($C_{1-10}$)carbonyl, hetero($C_{1-10}$)aryl($C_{1-5}$)carbonyl, ($C_{9-12}$)bicycloaryl($C_{1-5}$)carbonyl, hetero($C_{8-12}$)bicycloaryl($C_{1-5}$)carbonyl, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

In yet another variation of each of the above embodiments and variations, $R_1$ is hydrogen. In a further variation of each of the above embodiments and variations, $R_1$ has the formula

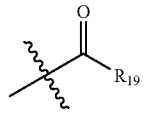

wherein $R_{19}$ selected from the group consisting of hydrogen, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In still a further variation of each of the above embodiments and variations, $R_2$ is hydrogen. In another variation of each of the above embodiments and variations, $R_2$ is halo. In another variation of each of the above embodiments and variations, $R_2$ is a substituted or unsubstituted ($C_{1-3}$)alkyl. In still another variation of each of the above embodiments and variations, $R_2$ is methyl.

In yet a further variation of each of the above embodiments and variations, $R_3$ is absent. In still a further variation of each of the above embodiments and variations, $R_3$ is hydrogen. In another variation of each of the above embodiments and variations, $R_3$ is a substituted or unsubstituted ($C_{1-3}$)alkyl. In still another variation of each of the above embodiments and variations, $R_3$ is methyl.

In still a further variation of each of the above embodiments and variations, $R_4$ is hydrogen. In another variation of each of the above embodiments and variations, $R_4$ is halo. In another variation of each of the above embodiments and variations, $R_4$ is a substituted or unsubstituted $(C_{1-3})$alkyl. In still another variation of each of the above embodiments and variations, $R_4$ is methyl.

In still a further variation of each of the above embodiments and variations, $R_5$ is hydrogen. In another variation of each of the above embodiments and variations, $R_5$ is halo. In another variation of each of the above embodiments and variations, $R_5$ is a substituted or unsubstituted $(C_{1-3})$alkyl. In still another variation of each of the above embodiments and variations, $R_5$ is methyl.

In still a further variation of each of the above embodiments and variations, $R_6$ is hydrogen. In another variation of each of the above embodiments and variations, $R_6$ is halo. In another variation of each of the above embodiments and variations, $R_6$ is a substituted or unsubstituted $(C_{1-3})$alkyl. In still another variation of each of the above embodiments and variations, $R_6$ is methyl.

In still a further variation of each of the above embodiments and variations, $R_7$ is hydrogen. In another variation of each of the above embodiments and variations, $R_7$ is halo. In another variation of each of the above embodiments and variations, $R_7$ is a substituted or unsubstituted $(C_{1-3})$alkyl. In still another variation of each of the above embodiments and variations, $R_7$ is methyl.

In still a further variation of each of the above embodiments and variations, $R_8$ is hydrogen. In another variation of each of the above embodiments and variations, $R_8$ is halo. In another variation of each of the above embodiments and variations, $R_8$ is a substituted or unsubstituted $(C_{1-3})$alkyl. In still another variation of each of the above embodiments and variations, $R_8$ is methyl.

In yet a further variation of each of the above embodiments and variations, $R_9$ has the formula —C(=O)—NHR$_{20a}$ wherein R$_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another variation of each of the above embodiments and variations, $R_9$ has the formula —(($C_{1-3}$)alkyl)-NHR$_{20a}$ wherein R$_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still another variation of each of the above embodiments and variations, $R_9$ has the formula —CH$_2$—NHR$_{20a}$ wherein R$_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet another variation of each of the above embodiments and variations, $R_9$ has the formula —NHR$_{20a}$ wherein R$_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, wherein $R_9$ has the formula —NH—C(=O)R$_{20a}$ wherein R$_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further variation of each of the above embodiments and variations, $R_9$ is a substituted or unsubstituted $(C_{1-3})$alkoxy. In another variation of each of the above embodiments and variations, $R_9$ is hydrogen. In another variation of each of the above embodiments and variations, $R_9$ is halo. In a further variation of each of the above embodiments and variations, $R_9$ is a substituted or unsubstituted $(C_{1-3})$alkyl. In still another variation of each of the above embodiments and variations, $R_9$ is methyl. In another variation of each of the above embodiments and variations, $R_9$ is —CF$_3$.

In still another variation of each of the above embodiments and variations, $R_9$ has the formula

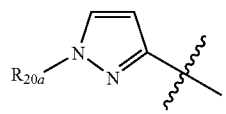

wherein $R_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet another variation of each of the above embodiments and variations, $R_9$ has the formula

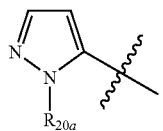

wherein $R_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $R_9$ has the formula

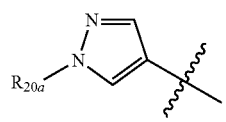

wherein $R_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further variation of each of the above embodiments and variations, $R_9$ has the formula

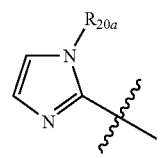

wherein $R_{20a}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet a further variation of each of the above embodiments and variations, $R_9$ has the formula

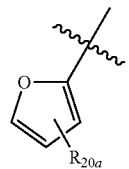

wherein $R_{20a}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another variation of each of the above embodiments and variations, $R_9$ has the formula

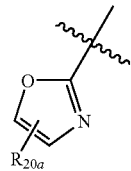

wherein $R_{20a}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still another variation of each of the above embodiments and variations, $R_9$ has the formula

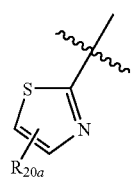

wherein $R_{20a}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet another variation of each of the above embodiments and variations, $R_9$ has the formula

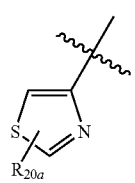

wherein $R_{20a}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $R_9$ has the formula

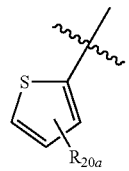

wherein $R_{20a}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further variation of each of the above embodiments and variations, $R_9$ has the formula

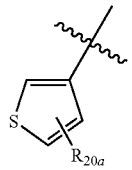

wherein $R_{20a}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In yet a further variation of each of the above embodiments and variations, $R_9$ has the formula

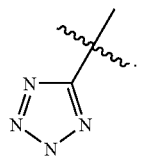

In another variation of each of the above embodiments and variations, $R_9$ has the formula

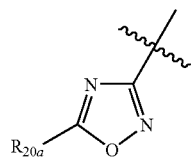

wherein $R_{20a}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In still another variation of each of the above embodiments and variations, $R_9$ has the formula

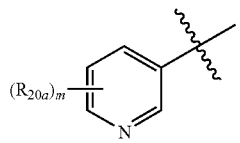

wherein m is selected from the group consisting of 0, 1, 2, 3 and 4; and $R_{20a}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$) alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In yet another variation of each of the above embodiments and variations, $R_9$ has the formula

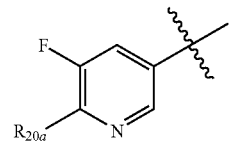

wherein $R_{20a}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$) oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{4-10}$)aryl, ($C_{9-12}$) bicycloaryl and hetero($C_{4-12}$)bicycloaryl, each substituted or unsubstituted.

In a further variation of each of the above embodiments and variations, $R_9$ has the formula

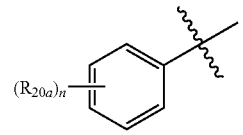

wherein n is selected from the group consisting of 0, 1, 2, 3, 4 and 5; and $R_{20a}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$) alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In still a further variation of each of the above embodiments and variations, $R_9$ has a formula selected from the group consisting of

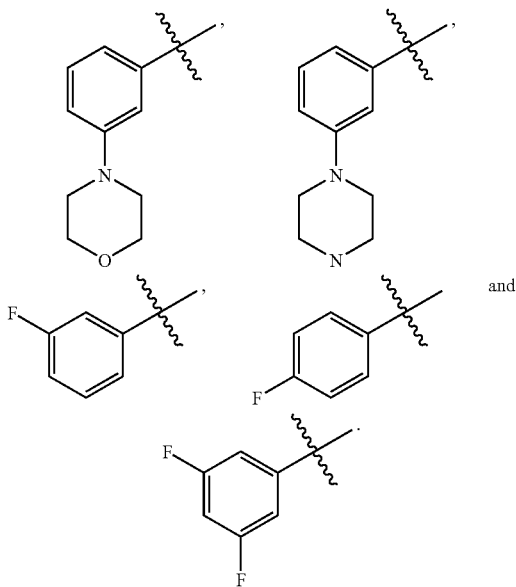

In yet a further variation of each of the above embodiments and variations, $R_9$ has a formula selected from the group consisting of

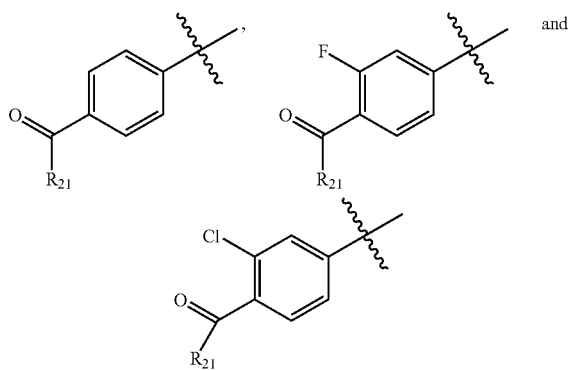

wherein $R_{21}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In still another variation of each of the above embodiments and variations, $R_{10}$ has the formula $—C(=O)—NHR_{20b}$ wherein $R_{20b}$ selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$ alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In yet another variation of each of the above embodiments and variations, $R_{10}$ has the formula $—((C_{1-3})$alkyl$)-NHR_{20b}$ wherein $R_{20b}$ selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$ alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In a further variation of each of the above embodiments and variations, $R_{10}$ has the formula $—CH_2—NHR_{20b}$ wherein $R_{20b}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, aza $(C_{1-10})$alkyl, $(C_{1-10})$oxaalkyl, $(C_{1-10})$oxoalkyl, imino$(C_{1-10})$ alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further variation of each of the above embodiments and variations, $R_{10}$ has the formula $—NHR_{20b}$ wherein $R_{20b}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, aza $(C_{1-10})$alkyl, $(C_{1-10})$oxaalkyl, $(C_{1-10})$oxoalkyl, imino$(C_{1-10})$ alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In yet a further variation of each of the above embodiments and variations, R$_{10}$ has the formula —NH—C(=O)R$_{20b}$ wherein R$_{20b}$ selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In a further variation of each of the above embodiments and variations, R$_{10}$ is hydrogen. In still another variation of each of the above embodiments and variations, R$_{10}$ is halo. In a further variation of each of the above embodiments and variations, R$_{10}$ is selected from the group consisting of Cl, Br and I. In still a further variation of each of the above embodiments and variations, R$_{10}$ is a substituted or unsubstituted (C$_{1-3}$)alkyl. In a further variation of each of the above embodiments and variations, R$_{10}$ is methyl. In still a further variation of each of the above embodiments and variations, R$_{10}$ is —CF$_3$. In another variation of each of the above embodiments and variations, R$_{10}$ is a substituted or unsubstituted (C$_{1-3}$)alkoxy. In a further variation of each of the above embodiments and variations, R$_{10}$ is cyano.

In yet a further variation of each of the above embodiments and variations, R$_{10}$ has the formula

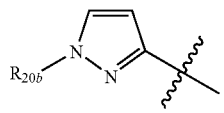

wherein R$_{20b}$ selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In another variation of each of the above embodiments and variations, R$_{10}$ has the formula

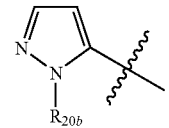

wherein R$_{20b}$ selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In still another variation of each of the above embodiments and variations, R$_{10}$ has the formula

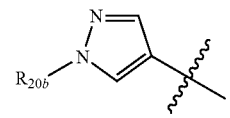

wherein R$_{20b}$ selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In yet another variation of each of the above embodiments and variations, R$_{10}$ has the formula

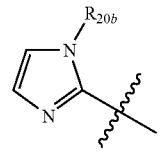

wherein R$_{20b}$ selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet another variation of each of the above embodiments and variations, $R_{10}$ has the formula

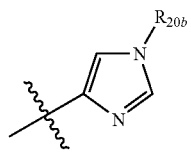

wherein $R_{20b}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet another variation of each of the above embodiments and variations, $R_{10}$ has the formula

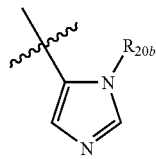

wherein $R_{20b}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another variation of each of the above embodiments and variations, $R_{10}$ is a substituted or unsubstituted hetero$(C_{1-10})$aryl. In still another variation of each of the above embodiments and variations, $R_{10}$ is a substituted or unsubstituted hetero$(C_{1-5})$aryl. In yet another variation of each of the above embodiments and variations, $R_{10}$ is a substituted or unsubstituted hetero$(C_{3-12})$cycloalkyl. In a further variation of each of the above embodiments and variations, $R_{10}$ is a substituted or unsubstituted hetero$(C_{3-6})$cycloalkyl.

In a further variation of each of the above embodiments and variations, $R_{10}$ is a substituted 5-membered heteroaryl group having 1-3 heteroatoms, wherein the heteroaryl ring has at least one oxo group in the ring or at least one hydroxy substituent. In one particular variation, the heteroaryl group has 1-3 nitrogen atoms.

In a further variation of each of the above embodiments and variations, $R_{10}$ is a substituted 5-membered heterocycloalkyl group having 1-3 heteroatoms, wherein the heterocycloalkyl ring has at least one oxo group in the ring or at least one hydroxy substituent. In one particular variation, the heterocycloalkyl group has 1-3 nitrogen atoms.

In a further variation of each of the above embodiments and variations, $R_{10}$ is a substituted 6-membered heteroaryl group having 1-3 heteroatoms, wherein the heteroaryl ring has at least one oxo group in the ring or at least one hydroxy substituent. In one particular variation, the heteroaryl group has 1-3 nitrogen atoms.

In a further variation of each of the above embodiments and variations, $R_{10}$ is a substituted 6-membered heterocycloalkyl group having 1-3 heteroatoms, wherein the heterocycloalkyl ring has at least one oxo group in the ring or at least one hydroxy substituent. In one particular variation, the heterocycloalkyl group has 1-3 nitrogen atoms.

In yet another variation of each of the above embodiments and variations, $R_{10}$ has the formula

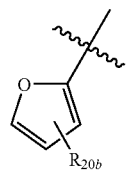

wherein $R_{20b}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, R$_{10}$ has the formula

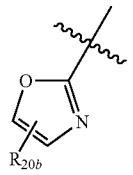

wherein R$_{20b}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$) oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{4-10}$)aryl, (C$_{9-12}$) bicycloaryl and hetero(C$_{4-12}$)bicycloaryl, each substituted or unsubstituted.

In still a further variation of each of the above embodiments and variations, R$_{10}$ has the formula

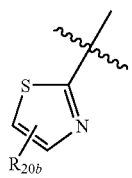

wherein R$_{20b}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$) oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{4-10}$)aryl, (C$_{9-12}$) bicycloaryl and hetero(C$_{4-12}$)bicycloaryl, each substituted or unsubstituted.

In yet a further variation of each of the above embodiments and variations, R$_{10}$ has the formula

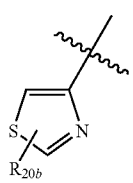

wherein R$_{20b}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$) oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{4-10}$)aryl, (C$_{9-12}$) bicycloaryl and hetero(C$_{4-12}$)bicycloaryl, each substituted or unsubstituted.

In another variation of each of the above embodiments and variations, R$_{10}$ has the formula

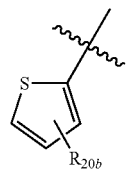

wherein R$_{20b}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$) oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{4-10}$)aryl, (C$_{9-12}$) bicycloaryl and hetero(C$_{4-12}$)bicycloaryl, each substituted or unsubstituted.

In still another variation of each of the above embodiments and variations, R$_{10}$ has the formula

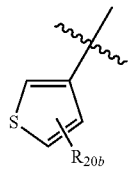

wherein R$_{20b}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, aza(C$_{1-10}$)alkyl, (C$_{1-10}$)oxaalkyl, (C$_{1-10}$) oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero ($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In yet another variation of each of the above embodiments and variations, $R_{10}$ has the formula

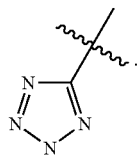

In a further variation of each of the above embodiments and variations, $R_{10}$ has the formula

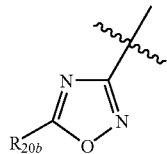

wherein $R_{20b}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In still a further variation of each of the above embodiments and variations, $R_{10}$ has the formula

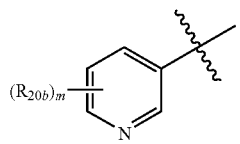

wherein
m is selected from the group consisting of 0, 1, 2, 3 and 4; and
$R_{20b}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$) alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In yet a further variation of each of the above embodiments and variations, $R_{10}$ has the formula

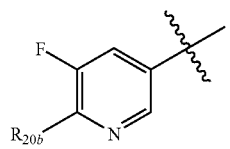

wherein $R_{20b}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In another variation of each of the above embodiments and variations, $R_{10}$ has the formula

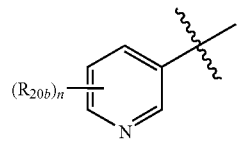

wherein n is selected from the group consisting of 0, 1, 2, 3, 4 and 5; and $R_{20b}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$) alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In still another variation of each of the above embodiments and variations, $R_{10}$ has a formula selected from the group consisting of

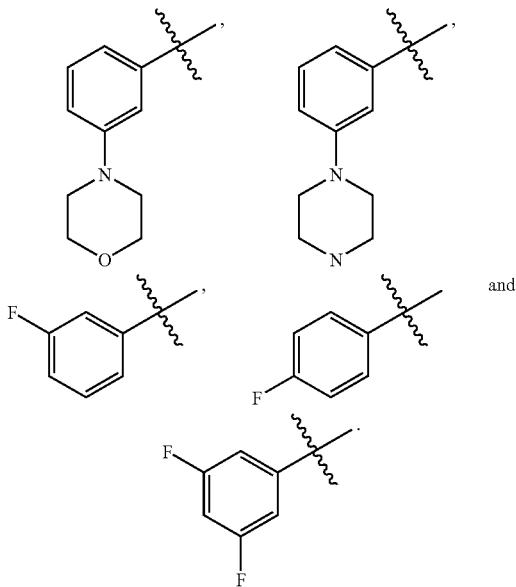

In yet another variation of each of the above embodiments and variations, $R_{10}$ has a formula selected from the group consisting of

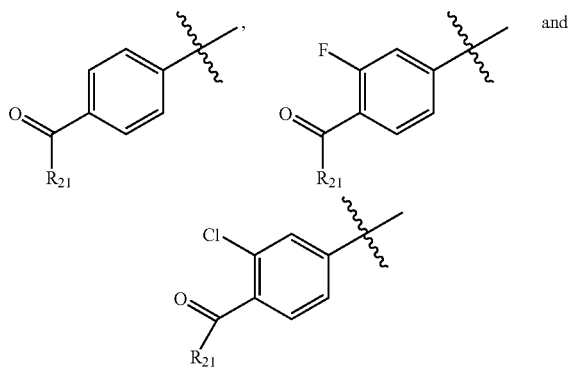

wherein $R_{21}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $R_{11}$ is hydrogen. In still a further variation of each of the above embodiments and variations, $R_{11}$ is halo. In yet a further variation of each of the above embodiments and variations, $R_{11}$ is a substituted or unsubstituted $(C_{1-3})$alkyl. In another variation of each of the above embodiments and variations, $R_{11}$ is methyl.

In yet a further variation of each of the above embodiments and variations, $R_{12}$ is absent. In a further variation of each of the above embodiments and variations, $R_{12}$ is hydrogen. In still a further variation of each of the above embodiments and variations, $R_{12}$ is halo. In yet a further variation of each of the above embodiments and variations, $R_{12}$ is a substituted or unsubstituted $(C_{1-3})$alkyl. In another variation of each of the above embodiments and variations, $R_{12}$ is methyl.

In still another variation of each of the above embodiments and variations, $R_{13}$ is absent. In a further variation of each of the above embodiments and variations, $R_{13}$ is hydrogen. In still a further variation of each of the above embodiments and variations, $R_{13}$ is halo. In yet a further variation of each of the above embodiments and variations, $R_{13}$ is a substituted or unsubstituted $(C_{1-3})$alkyl. In another variation of each of the above embodiments and variations, $R_{13}$ is methyl.

In a further variation of each of the above embodiments and variations, $R_{14}$ is hydrogen. In still a further variation of each of the above embodiments and variations, $R_{14}$ is halo. In yet a further variation of each of the above embodiments and variations, $R_{14}$ is a substituted or unsubstituted $(C_{1-3})$alkyl. In another variation of each of the above embodiments and variations, $R_{14}$ is methyl.

In still a further variation of each of the above embodiments and variations, $R_{15}$ is absent. In a further variation of each of the above embodiments and variations, $R_{15}$ is hydrogen. In still a further variation of each of the above embodiments and variations, $R_{15}$ is halo. In yet a further variation of each of the above embodiments and variations, $R_{15}$ is a substituted or unsubstituted $(C_{1-3})$alkyl. In another variation of each of the above embodiments and variations, $R_{15}$ is methyl.

In yet a further variation of each of the above embodiments and variations, $R_{16}$ is absent. In a further variation of each of the above embodiments and variations, $R_{16}$ is hydrogen. In still a further variation of each of the above embodiments and variations, $R_{16}$ is halo. In yet a further variation of each of the above embodiments and variations, $R_{16}$ is a substituted or unsubstituted $(C_{1-3})$alkyl. In another variation of each of the above embodiments and variations, $R_{16}$ is methyl.

In a further variation of each of the above embodiments and variations, $R_{17}$ is hydrogen. In still a further variation of each of the above embodiments and variations, $R_{17}$ is halo. In another variation of each of the above embodiments and variations, $R_{17}$ is fluoro. In yet a further variation of each of the above embodiments and variations, $R_{17}$ is a substituted or unsubstituted $(C_{1-3})$alkyl. In another variation of each of the above embodiments and variations, $R_{17}$ is methyl. In one variation of each of the above embodiments and variations containing $R_{17}$, $R_{17}$ is unsubstituted.

In a further variation of each of the above embodiments and variations, $R_{18}$ is hydrogen. In still a further variation of each of the above embodiments and variations, $R_{18}$ is halo. In another variation of each of the above embodiments and variations, $R_{18}$ is fluoro. In yet a further variation of each of the above embodiments and variations, $R_{18}$ is a substituted or unsubstituted $(C_{1-3})$alkyl. In another variation of each of the above embodiments and variations, $R_{18}$ is methyl. In one variation of each of the above embodiments and variations containing $R_{18}$, $R_{18}$ is unsubstituted.

In another variation of each of the above embodiments and variations, $R_{19}$ is selected from the group consisting of hydrogen, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In another variation of each of the above embodiments and variations, $R_{19}$ is a substituted or unsubstituted $(C_{1-5})$alkyl. In still another variation of each of the above embodiments and variations, $R_{19}$ is methyl. In yet another variation of each of the above embodiments and variations, $R_{19}$ is trifluoromethyl. In a further variation of each of the above embodiments and variations, $R_{19}$ is isopropyl. In still a further variation of each of the above embodiments and variations, $R_{19}$ is butyl. In yet a further variation of each of the above embodiments and variations, $R_{19}$ is a substituted or unsubstituted $(C_{3-6})$cycloalkyl. In another variation of each of the above embodiments and variations, $R_{19}$ is cyclopropyl. In still another variation of each of the above embodiments and variations, $R_{19}$ is cyclopentyl. In another variation of each of the above embodiments and variations, $R_{19}$ is a substituted or unsubstituted hetero$(C_{3-12})$cycloalkyl. In another variation of each of the above embodiments and variations, $R_{19}$ is a substituted or unsubstituted $(C_{4-12})$aryl. In another variation of each of the above embodiments and variations, $R_{19}$ is a substituted or unsubstituted hetero$(C_{4-10})$aryl.

In yet another variation of each of the above embodiments and variations, $R_{19}$ has the formula

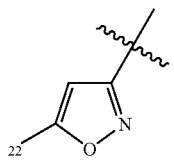

wherein $R_{22}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In a further variation of each of the above embodiments and variations, $R_{19}$ has the formula

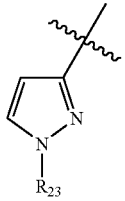

wherein $R_{23}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In still a further variation of each of the above embodiments and variations, $R_{19}$ has the formula

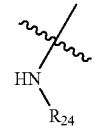

wherein $R_{24}$ selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In one variation of each of the above embodiments and variations containing $R_{19}$, $R_{19}$ is unsubstituted.

In a further variation of each of the above embodiments and variations, $R_{20a}$ is selected from the group consisting of hydrogen, carbonyl, oxycarbonyl, aminocarbonyl, $(C_{1-10})$ alkylcarbonyl, $(C_{3-12})$cycloalkyl$(C_{1-5})$carbonyl, hetero $(C_{3-12})$cycloalkyl$(C_{1-10})$carbonyl, aryl$(C_{1-10})$carbonyl, hetero$(C_{1-10})$aryl$(C_{1-5})$carbonyl, $(C_{9-12})$bicycloaryl$(C_{1-5})$carbonyl, hetero$(C_{8-12})$bicycloaryl$(C_{1-5})$carbonyl, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$) oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{4-10}$)aryl, ($C_{9-12}$) bicycloaryl and hetero($C_{4-12}$)bicycloaryl, each substituted or unsubstituted;

In yet a further variation of each of the above embodiments and variations, $R_{20a}$ is hydrogen. In another variation of each of the above embodiments and variations, $R_{20a}$ is a substituted or unsubstituted ($C_{1-5}$)alkyl. In still another variation of each of the above embodiments and variations, $R_{20a}$ is methyl. In yet another variation of each of the above embodiments and variations, $R_{20a}$ is ethyl. In a further variation of each of the above embodiments and variations, $R_{20a}$ is propyl. In still a further variation of each of the above embodiments and variations, $R_{20a}$ is a substituted or unsubstituted aryl. In yet a further variation of each of the above embodiments and variations, $R_{20a}$ is a substituted or unsubstituted phenyl. In another variation of each of the above embodiments and variations, $R_{20a}$ is a substituted or unsubstituted ($C_{3-12}$)cycloalkyl. In still another variation of each of the above embodiments and variations, $R_{20a}$ is a substituted or unsubstituted cyclohexyl. In yet another variation of each of the above embodiments and variations, $R_{20a}$ is a substituted or unsubstituted hetero($C_{4-10}$)aryl. In a further variation of each of the above embodiments and variations, $R_{20a}$ is a substituted or unsubstituted hydroxy($C_{1-6}$)alkyl. In still a further variation of each of the above embodiments and variations, $R_{20a}$ is hydroxyethyl. In yet a further variation of each of the above embodiments and variations, $R_{20a}$ is halo. In another variation of each of the above embodiments and variations, $R_{20a}$ is fluoro. In still another variation of each of the above embodiments and variations, $R_{20a}$ is a substituted or unsubstituted hetero($C_{3-6}$)cycloalkyl($C_{1-4}$)alkyl.

In yet another variation of each of the above embodiments and variations, $R_{20a}$ has the formula

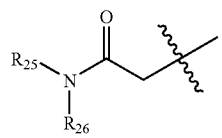

wherein $R_{25}$ and $R_{26}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl ($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl($C_{1-10}$) alkyl, hetero($C_{1-10}$)aryl($C_{1-5}$)alkyl, ($C_{9-12}$)bicycloaryl($C_{1-5}$) alkyl, hetero($C_{8-12}$)bicycloaryl($C_{1-5}$)alkyl, hetero($C_{1-10}$) alkyl, ($C_{3-12}$)cycloalkyl, hetero($C_{3-12}$)cycloalkyl, ($C_{9-12}$) bicycloalkyl, hetero($C_{3-12}$)bicycloalkyl, ($C_{4-12}$)aryl, hetero ($C_{4-10}$)aryl, ($C_{9-12}$)bicycloaryl and hetero($C_{4-12}$)bicycloaryl, each substituted or unsubstituted.

In one variation of each of the above embodiments and variations containing $R_{20a}$, $R_{20a}$ is unsubstituted.

In a further variation of each of the above embodiments and variations, $R_{20b}$ is selected from the group consisting of hydrogen, carbonyl, oxycarbonyl, aminocarbonyl, ($C_{1-10}$) alkylcarbonyl, ($C_{3-12}$)cycloalkyl($C_{1-5}$)carbonyl, hetero ($C_{3-12}$)cycloalkyl($C_{1-10}$)carbonyl, aryl($C_{1-10}$)carbonyl, hetero($C_{1-10}$)aryl($C_{1-5}$)carbonyl, ($C_{9-12}$)bicycloaryl($C_{1-5}$)carbonyl, hetero($C_{8-12}$)bicycloaryl($C_{1-5}$)carbonyl, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$) oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{4-10}$)aryl, ($C_{9-12}$) bicycloaryl and hetero($C_{4-12}$)bicycloaryl, each substituted or unsubstituted;

In yet a further variation of each of the above embodiments and variations, $R_{20b}$ is hydrogen. In another variation of each of the above embodiments and variations, $R_{20b}$ is a substituted or unsubstituted ($C_{1-5}$)alkyl. In still another variation of each of the above embodiments and variations, $R_{20b}$ is methyl. In yet another variation of each of the above embodiments and variations, $R_{20b}$ is ethyl. In a further variation of each of the above embodiments and variations, $R_{20b}$ is propyl. In still a further variation of each of the above embodiments and variations, $R_{20b}$ is a substituted or unsubstituted aryl. In yet a further variation of each of the above embodiments and variations, $R_{20b}$ is a substituted or unsubstituted phenyl. In another variation of each of the above embodiments and variations, $R_{20b}$ is a substituted or unsubstituted ($C_{3-12}$)cycloalkyl. In still another variation of each of the above embodiments and variations, $R_{20b}$ is a substituted or unsubstituted cyclohexyl. In yet another variation of each of the above embodiments and variations, $R_{20b}$ is a substituted or unsubstituted hetero($C_{4-10}$)aryl. In a further variation of each of the above embodiments and variations, $R_{20b}$ is a substituted or unsubstituted hydroxy($C_{1-6}$)alkyl. In still a further variation of each of the above embodiments and variations, $R_{20b}$ is hydroxyethyl. In yet a further variation of each of the above embodiments and variations, $R_{20b}$ is halo. In another variation of each of the above embodiments and variations, $R_{20b}$ is fluoro. In still another variation of each of the above embodiments and variations, $R_{20b}$ is a substituted or unsubstituted hetero($C_{3-6}$)cycloalkyl($C_{1-4}$)alkyl.

In yet another variation of each of the above embodiments and variations, $R_{20b}$ has the formula

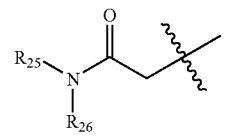

wherein $R_{25}$ and $R_{26}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl ($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In one variation of each of the above embodiments and variations containing $R_{20b}$, $R_{20b}$ is unsubstituted.

In a further variation of each of the above embodiments and variations, $R_{21}$ is a substituted or unsubstituted ($C_{1-5}$)alkylamino. In still a further variation of each of the above embodiments and variations, $R_{21}$ is $CH_3NH—$. In one variation of each of the above embodiments and variations containing $R_{21}$, $R_{21}$ is unsubstituted.

In yet a further variation of each of the above embodiments and variations, $R_{22}$ is a substituted or unsubstituted ($C_{1-3}$) alkyl. In another variation of each of the above embodiments and variations, $R_{22}$ is methyl. In one variation of each of the above embodiments and variations containing $R_{22}$, $R_{22}$ is unsubstituted.

In still another variation of each of the above embodiments and variations, $R_{23}$ is a substituted or unsubstituted ($C_{1-3}$) alkyl. In yet another variation of each of the above embodiments and variations, $R_{23}$ is methyl. In one variation of each of the above embodiments and variations containing $R_{23}$, $R_{23}$ is unsubstituted.

In a further variation of each of the above embodiments and variations, $R_{24}$ is a substituted or unsubstituted ($C_{1-5}$)alkyl. In still a further variation of each of the above embodiments and variations, $R_{24}$ is isopropyl. In yet a further variation of each of the above embodiments and variations, $R_{24}$ is tert-butyl. In another variation of each of the above embodiments and variations, $R_{24}$ is a substituted or unsubstituted ($C_{3-6}$)cycloalkyl. In still another variation of each of the above embodiments and variations, $R_{24}$ is cyclopropyl. In yet another variation of each of the above embodiments and variations, $R_{24}$ is cyclopentyl. In another variation of each of the above embodiments and variations, $R_{24}$ is a substituted or unsubstituted aryl. In a further variation of each of the above embodiments and variations, $R_{24}$ is a substituted or unsubstituted phenyl. In still a further variation of each of the above embodiments and variations, $R_{24}$ is a substituted or unsubstituted hetero($C_{3-12}$)cycloalkyl. In yet a further variation of each of the above embodiments and variations, $R_{24}$ is a substituted or unsubstituted pyrrolidinyl. In another variation of each of the above embodiments and variations, $R_{24}$ is a substituted or unsubstituted piperidinyl. In one variation of each of the above embodiments and variations containing $R_{24}$, $R_{24}$ is unsubstituted.

In still another variation of each of the above embodiments and variations, $R_{25}$ is hydrogen. In still a further variation of each of the above embodiments and variations, $R_{25}$ is halo. In yet a further variation of each of the above embodiments and variations, $R_{25}$ is a substituted or unsubstituted ($C_{1-3}$)alkyl. In another variation of each of the above embodiments and variations, $R_{25}$ is methyl. In one variation of each of the above embodiments and variations containing $R_{25}$, $R_{25}$ is unsubstituted.

In yet another variation of each of the above embodiments and variations, $R_{26}$ is hydrogen. In still a further variation of each of the above embodiments and variations, $R_{26}$ is halo. In yet a further variation of each of the above embodiments and variations, $R_{26}$ is a substituted or unsubstituted ($C_{1-3}$)alkyl. In another variation of each of the above embodiments and variations, $R_{26}$ is methyl. In one variation of each of the above embodiments and variations containing $R_{26}$, $R_{26}$ is unsubstituted.

In yet another variation of each of the above embodiments and variations, $R_{27}$ is hydrogen. In a further variation of each of the above embodiments and variations, $R_{27}$ is halo. In still a further variation of each of the above embodiments and variations, $R_{27}$ is a substituted or unsubstituted ($C_{1-3}$) alkyl.

In yet another variation of each of the above embodiments and variations, $R_{28}$ is hydrogen. In a further variation of each of the above embodiments and variations, $R_{28}$ is halo. In still a further variation of each of the above embodiments and variations, $R_{28}$ is a substituted or unsubstituted ($C_{1-3}$) alkyl.

In yet a further variation of each of the above embodiments and variations, $R_{29}$ is hydrogen. In still another variation of each of the above embodiments and variations, $R_{29}$ is a substituted or unsubstituted ($C_{1-3}$)alkyl.

In another variation of each of the above embodiments and variations, $R_{30}$ is selected from the group consisting of hydrogen, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted. In yet a further variation of each of the above embodiments and variations, $R_{30}$ is hydrogen. In still another variation of each of the above embodiments and variations, $R_{30}$ is a substituted or unsubstituted ($C_{1-3}$)alkyl.

In a further variation of each of the above embodiments and variations, n is 1. In still a further variation of each of the above embodiments and variations, n is 2. In still another variation of each of the above embodiments and variations, r is 1. In yet another variation of each of the above embodiments and variations, r is 2.

In yet a further variation of each of the above embodiments and variations, m is 1. In another variation of each of the above embodiments and variations, m is 2.

It is noted that the compounds of the present invention may be in the form of a pharmaceutically acceptable salt, ester, solvate, hydrate or prodrug thereof. For example, the compound optionally comprises a substituent that is convertible in vivo to a different substituent such as hydrogen. Examples of substituents that are convertible in vivo to a biologically active compound include, but are not limited to, biohydrolyzable moieties such as biohydrolyzable esters, biohydrolyzable amides and biohydrolyzable carbamates.

It is further noted that the compound may be present as a mixture of stereoisomers, or the compound may be present as a single stereoisomer.

In another of its aspects, there is provided a pharmaceutical composition comprising as a compound according to any one of the above embodiments and variations; and one or more pharmaceutically acceptable excipients. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

The present invention also provides a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting cMET comprising contacting cMET with a compound of any one of the above embodiments and variations.

In yet another of its aspects, there is provided a method of inhibiting cMET comprising causing a compound of any one of the above embodiments and variations to be present in a subject in order to inhibit cMET in vivo.

In a further of its aspects, there is provided a method of inhibiting cMET comprising administering a first compound to a subject that is converted in vivo to a second compound wherein the second compound inhibits cMET in vivo, the second compound being a compound according to any one of the above embodiments and variations.

In another of its aspects, there is provided a method of treating a disease state for which cMET possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which cMET possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which cMET possesses activity that contributes to the pathology and/or symptomology of the disease state, the method comprising administering a first compound to a subject that is converted in vivo to a second compound wherein the second compound inhibits cMET in vivo, the second compound being a compound according to any one of the above embodiments and variations.

In one variation of each of the above methods, the disease state is cancer. In particular variations, the cancer is selected from the group consisting of carcinomas (e.g., bladder, breast, cervical, cholangiocarcinoma, colorectal, esophageal, gastric, head and neck, kidney, liver, lung, nasopharygeal, ovarian, pancreatic, prostate and thyroid); musculoskeletal sarcomas (e.g., osteosarcoma, synovial sarcoma, and rhabdomyosarcoma); soft tissue sarcomas (e.g., MFH/fibrosrcoma, leiomyosarcoma, and Kaposi's sarcoma); hematopoietic malignancies (e.g., multiple myeloma, lymphomas, adult T cell leukemia, acute myelogenous leukemia, and chronic myeloid leukemia); and other neoplasms (e.g., glioblastomas, astrocytomas, melanoma, mesothelioma, and Wilm's tumor). In other particular variations, the cancer is selected from the group consisting of gastric cancer, lung cancer, colon cancer, breast cancer and other solid tumors.

In another variation of each of the above methods, the disease state is a proliferative disease. In particular variations, the proliferative disease is selected from the group consisting of myeloproliferative disorders, atherosclerosis, and fibrosis of the lung.

Salts, Hydrates, and Prodrugs of cMET Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine(benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine(tromethamine). It should be recognized that the free acid forms will typically differ from their respective salt forms somewhat in physical properties such as solubility in polar solvents, but otherwise the salts are equivalent to their respective free acid forms for the purposes of the present invention.

The present invention also relates to N-oxides of compounds according to the present invention. N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material. It is understood that N-oxides can be prepared by metabolic processes in vitro and in vivo.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), Bioorganic and Medicinal Chemistry Letters, Vol. 4, p. 1985.

Protected derivatives of compounds of the present invention can also be made. Examples of techniques applicable to the creation of protecting groups and their removal can be found in T. W. Greene, Protecting Groups in Organic Synthesis, 3$^{rd}$ edition, John Wiley & Sons, Inc. 1999.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Compositions Comprising cMET Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The cMET inhibitors and compositions comprising them may be administered or coadministered in any conventional dosage form. Co-administration in the context of this invention is intended to mean the administration of more than one therapeutic agent, one of which includes a cMET inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an inhibitor of the present invention to reduce cMET activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more cMET inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the cMET inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The cMET inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a cMET inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The cMET inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the cMET inhibitor alone or in combination with other pharmaceutically acceptable excipients can also be administered.

Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Kits Comprising cMET Inhibitors

The invention is also directed to kits and other articles of manufacture for treating diseases associated with cMET. It is noted that diseases are intended to cover all conditions for which the cMET possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as cMet inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Combination Therapies

A wide variety of therapeutic agents may have a therapeutic additive or synergistic effect with the inhibitors of the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. For example, such therapeutic agents may additively or synergistically combine with the inhibitors of the present invention to inhibit undesirable cell growth, such as inappropriate cell growth resulting in undesirable benign conditions or tumor growth.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with the inhibitors of the present invention include, but are not limited to, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including an inhibitor of the present invention and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including an inhibitor of the present invention and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including an inhibitor of the present invention and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including an inhibitor of the present invention and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), and taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including an inhibitor of the present invention and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including an inhibitor of the present invention and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with inhibitors of the present invention include, but are not limited to, interleukin 2 (IL-2), and interleukin 4 (IL-4), interleukin 12 (IL-12).

Interferons include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with the inhibitors of the present invention include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with an inhibitor of the present invention to reduce chemotherapy-induced myelopoietic toxicity.

Other immuno-modulating agents other than cytokines may also be used in conjunction with the inhibitors of the present invention to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including an inhibitor of the present invention and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20$^+$ pre-B and mature B cells. RITUXAN® is used as single agent for the treatment of patients with relapsed or refractory low-grade or follicular, CD20+, B cell non-Hodgkin's lymphoma. Combination therapy including an inhibitor of the present invention and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1, and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including an inhibitor of the present invention and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

EXAMPLES

Preparation of cMET Inhibitors

Various methods can be used for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), Bioorganic and Medicinal Chemistry Letters, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, Protecting Groups in Organic Synthesis, 3$^{rd}$ edition, John Wiley & Sons, Inc. 1999.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification.

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Scheme A

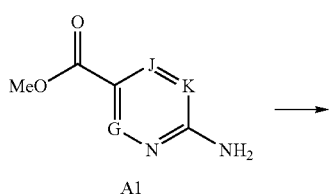

A1

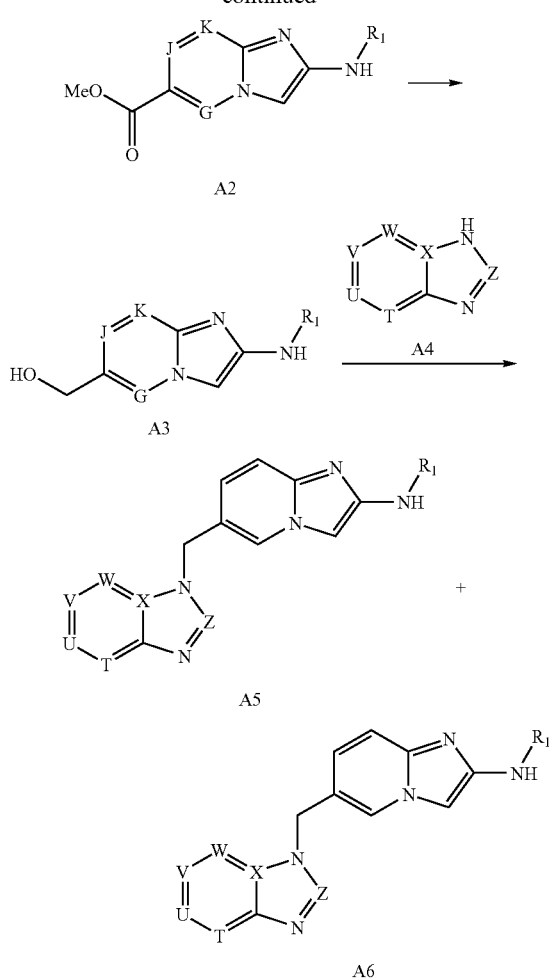

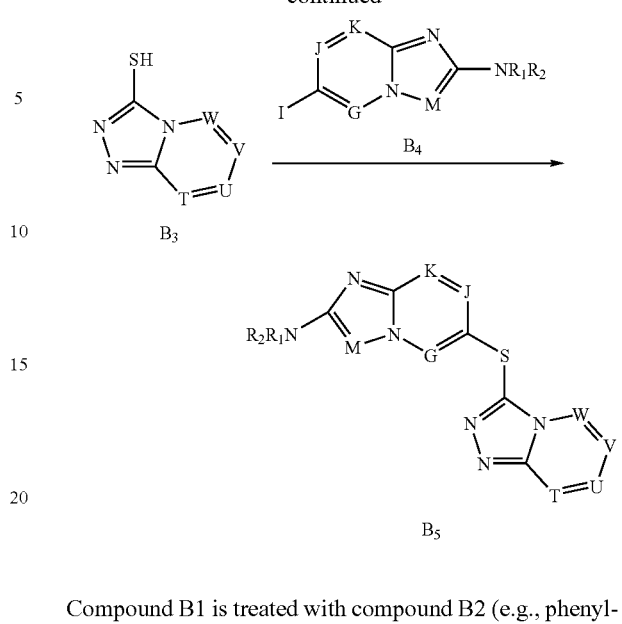

Compound B1 is treated with compound B2 (e.g., phenylisothiocyanate or p-nitrophenylisothiocyanate) in DME at 100-120° C. in a microwave for 1-8 hrs to provide thiol (B3). A palladium mediated coupling of compound B3 and B4 in DME with $Pd_2(dba)_3$ and 4,5-bis(phenylphosphino)-9,9-dimethylxanthene at 100-120° C. in a microwave for 1-8 hrs can be used to provide compound B5.

Compound A2 can be prepared starting from compound A1 in three steps following an analogous method to that described in U.S. Pat. No. 6,358,971, which is incorporated by reference herein in its entirety. Reduction of the ester can be accomplished in the presence of a reducing agent such as $LAH$ or $NaBH_4$ in THF or dioxane at 0-80° C. for 1-8 hrs to provide alcohol (A3). Standard Mitsunobu coupling of A3 and A4 in the presence of triphenylphosphine and an azodicarboxalate, such as DEAD or DIAD, at 0-80° C. for 1-24 hrs can be used to provide compounds A5 and A6. Compounds A5 and A6 can be separated using any of a variety of techniques known in the art including, for example, preparative LCMS.

Scheme B

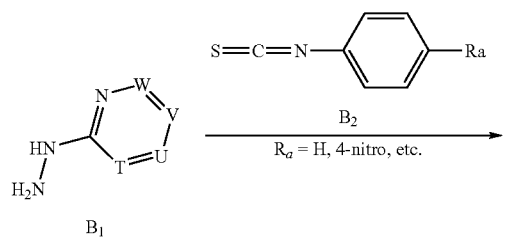

Scheme C

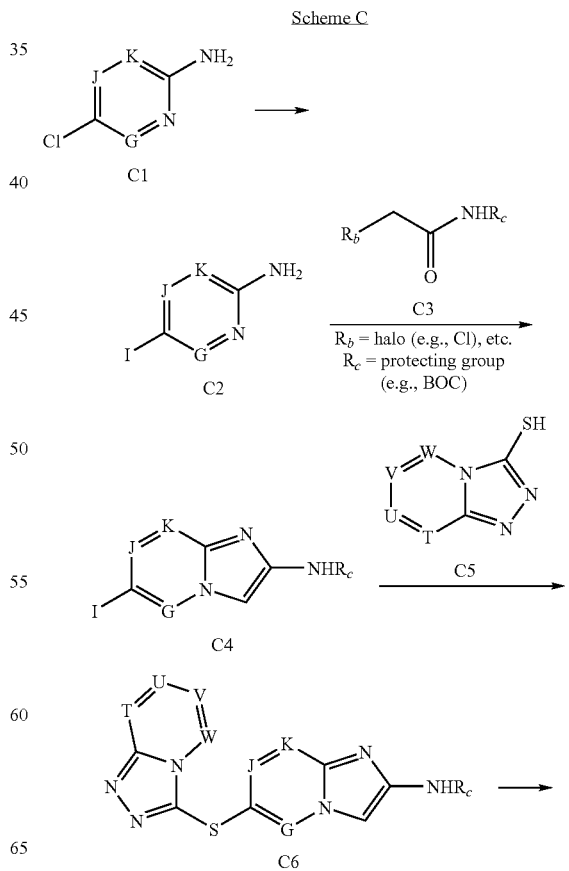

-continued

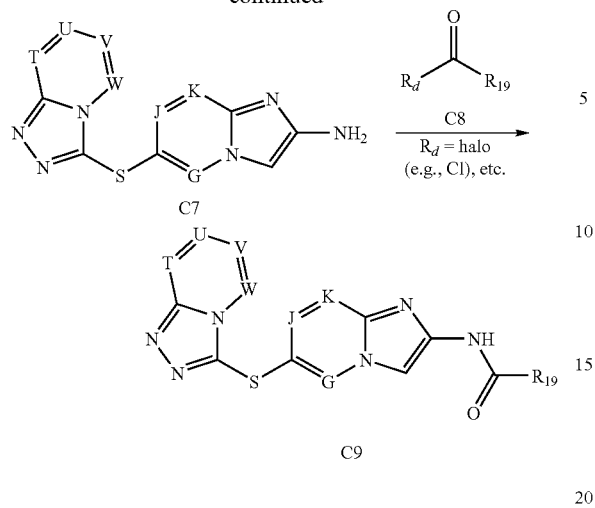

-continued

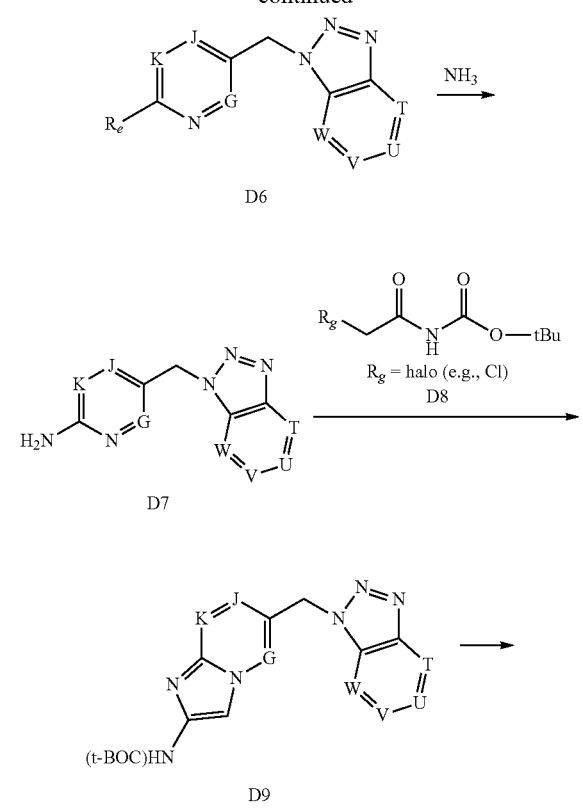

Aniline (C1) is heated in HI at 100° C. for 18 hrs to provide compound C2. Aniline (C2) is treated with acetamide (C3) and a base such as sodium hydrogen phosphate in a polar solvent (eg. DMA, DMF, or DMSO) and heated at 100-120° C. in a microwave for 1-8 hrs to afford cyclized product C4. Palladium mediated coupling of C4 and C5 can be accomplished in DME with $Pd_2(dba)_3$ and 4,5-bis(phenylphosphino)-9,9-dimethylxanthene at 100-120° C. in a microwave for 1-8 hrs to provide compound C6. Removal of the $R_c$ group from C6 can be accomplished in a solvent such as THF or dioxane or an alcohol such as MeOH, EtOH, or iPrOH in the presence of an acid such as HCl or TFA at 0-100° C. for 1-24 hrs to provide compound C7. Compound C7 is treated with the appropriate acylchloride in a solvent (e.g., DCM, THF, or $CHCl_3$) in the presence of a base (e.g., TEA, DIEA, or pyridine) at 0-80° C. for 1-24 hrs to provide compound C9.

Scheme D

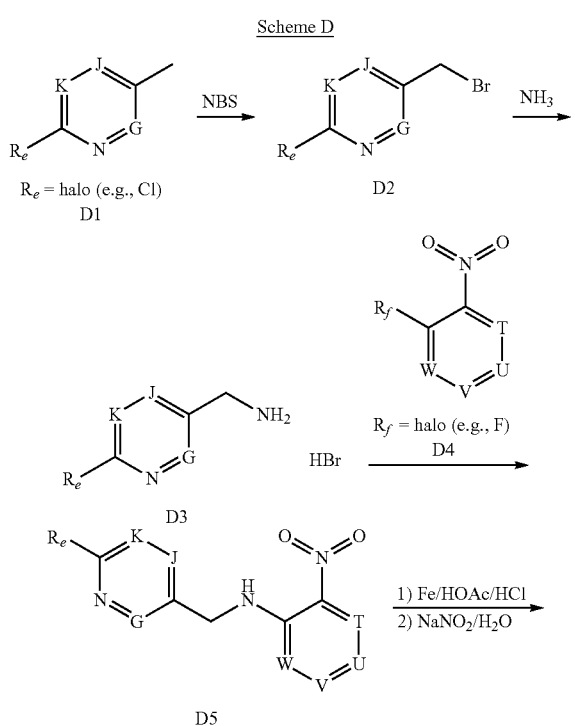

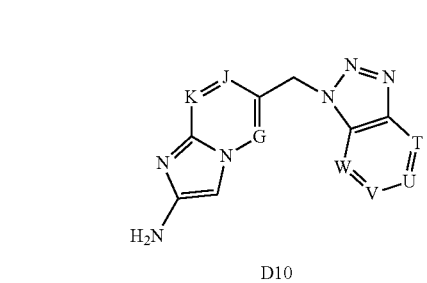

Compound D1 is brominated under standard conditions such as NBS in the presence of a peroxide, AIBN, or 200-400 w light in $CCl_4$ at reflux (e.g., for 1-8 hrs). Displacement of bromide (D2) with ammonia in an alcoholic solvent (e.g., MeOH, EtOH, or i-PrOH) at 0-80° C. for 1-24 hrs provides compound D3. The substitution reaction with compounds D3 and D4 is accomplished in a solvent (e.g., DMF, DMA, or EtOH) in the presence of a base (e.g., TEA, DIEA, or pyridine) at 0-80° C. for 1-24 hrs to provide the arylnitro D5. Reduction of the arylnitro (D5) is accomplished under standard conditions using a palladium catalyst such as 10% Pd/C or metal (e.g., Fe or Zn) in acidic medium. Subsequent ring closure of the resulting aniline to the triazole is accomplished in the presence of aqueous $NaNO_2$ to provide compound D6. Treatment of compound D6 in ammonia saturated solvent (e.g., EtOH or i-PrOH in a sealed vessel) at 100-150° C. for 1-4 days provides aniline D7. Aniline (D7) is treated with acetamide (D8) and a base such as sodium hydrogen phosphate in a polar solvent (e.g., DMA, DMF, or DMSO) and heated at 100-120° C. in a microwave for 1-8 hrs to afford cyclized product D9. Treatment of compound D9 with acid (e.g., HCl or TFA) provides compound D10.

Scheme E
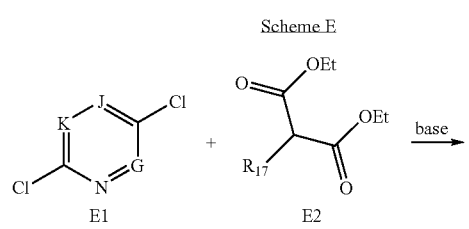
E1 + E2 →(base)
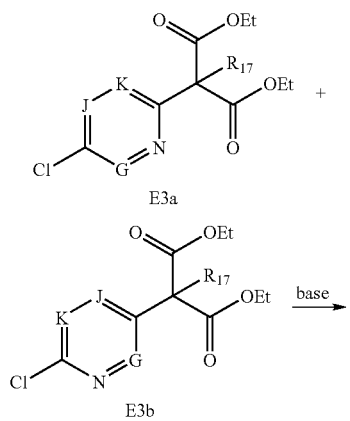
E3a
E3b →(base)
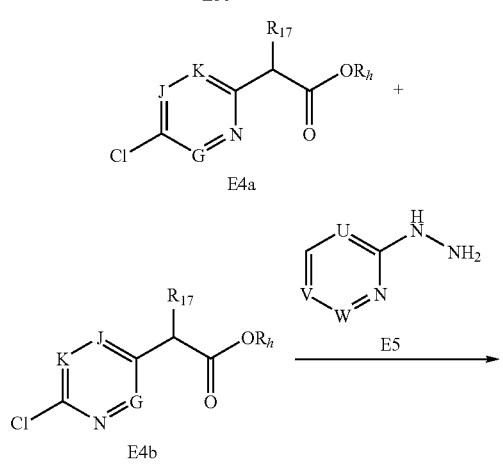
E4a
E4b +
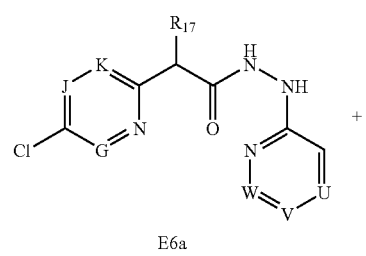
E5 →
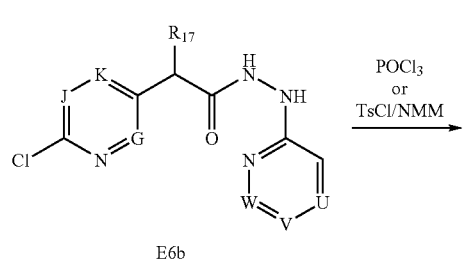
E6a
E6b →(POCl₃ or TsCl/NMM)
-continued
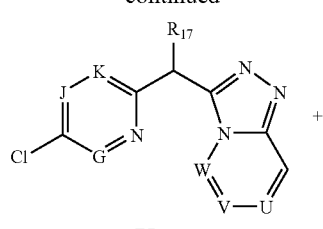
E7a +
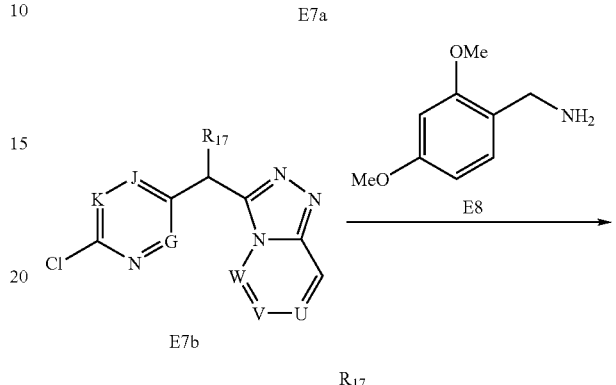
E7b + E8 →
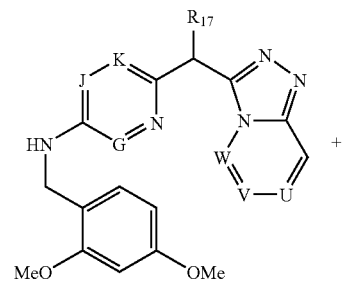
E9a +
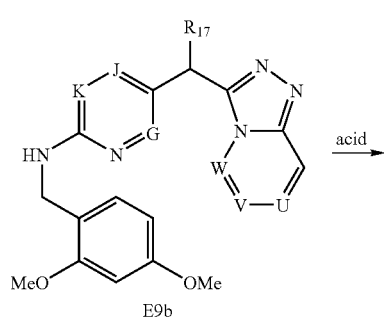
E9b →(acid)
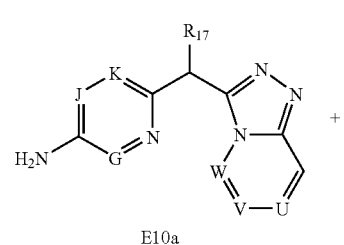
E10a +
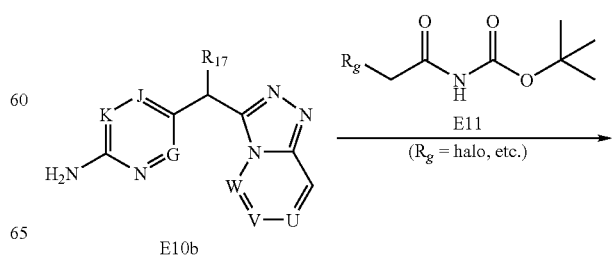
E10b + E11 ($R_g$ = halo, etc.) →

-continued

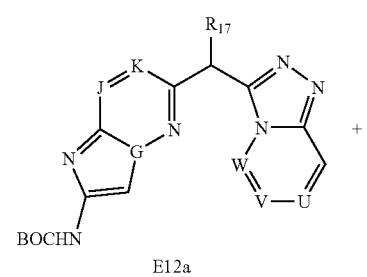

E12a

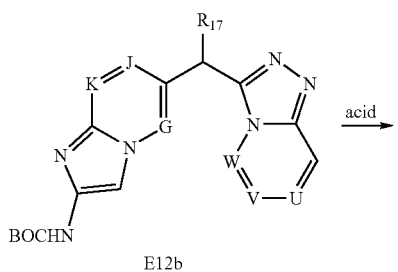

E12b acid →

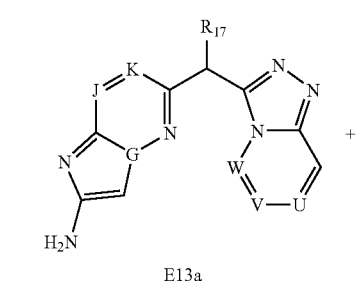

E13a

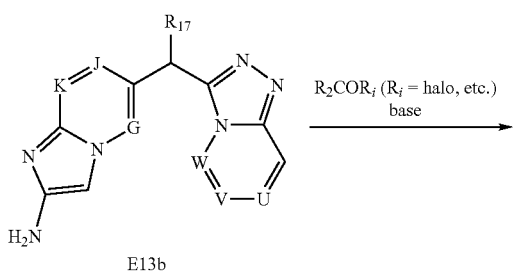

E13b

R₂COR_i (R_i = halo, etc.)
base →

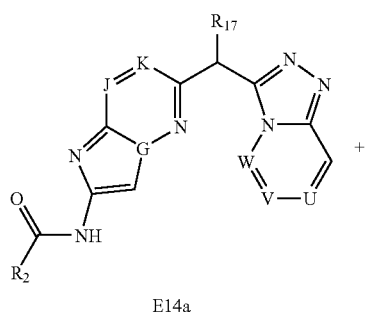

E14a

-continued

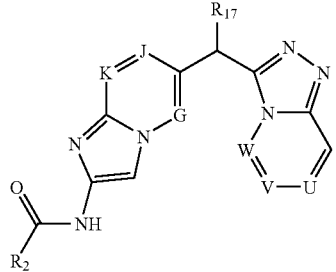

E14b

R_h = Li, Na, etc.

Compounds E3a and E3b can be prepared starting from compounds E1 and E2 by treating compound E2 with a base such as NaH in a solvent such as THF or dioxane at −78-0° C. and subsequent treatment with compound E1. Compound E3a and E3b are optionally separated prior to further use. Treatment of compound E3a and/or E3b with a base such as LiOH or NaOH at −20-75° C. for 1-8 hrs provides compounds E4a and/or E4b as the lithium or sodium salt, respectively. Treatment of compounds E4a and/or E4b with compound E5 in the presence of EDC or DCC for 1-24 hrs provides compounds E6a and/or E6b. Treatment of compounds E6a and/or E6b with POCl₃ at 80-160° C. provides compounds E7a and/or E7b. Alternatively, compounds E7a and/or E7b can be prepared by treating compounds E6a and/or E6b with TsCl/N-methylmorpholine at ambient temperature to 100° C. for 30 min to 8 hrs. Coupling of compound E8 and compounds E7a and/or E7b is achieved in a solvent such as THF, Dioxane, or DMF at 25-100° C. for 2-24 hrs in the presence of a co-base such as DIEA or Et₃N. Removal of the dimethoxy benzyl group from compounds E9a and/or E9b is achieved by treating compounds E9a and/or E9b with an acid such as TFA at 25-75° C. for 2-24 hrs to provide compounds E10a and/or E10b. Treatment of compounds E10a and/or E10b with compound E11 in the presence of a base such as Na₂HPO₄ in a solvent such as DMA at 120° C. provides compounds E12a and/or E12b. Treatment of compounds E12a and/or E12b with an acid such as TFA or HCl provides compounds E13a and/or E13b. Treatment of compounds E13a and/or E13b with an acid halide in the presence of a co-base such as DIEA or Et₃N at 25-75° C. in a solvent such as DCM, THF, dioxane or DMF provides compounds E14a and/or E14b.

Scheme F

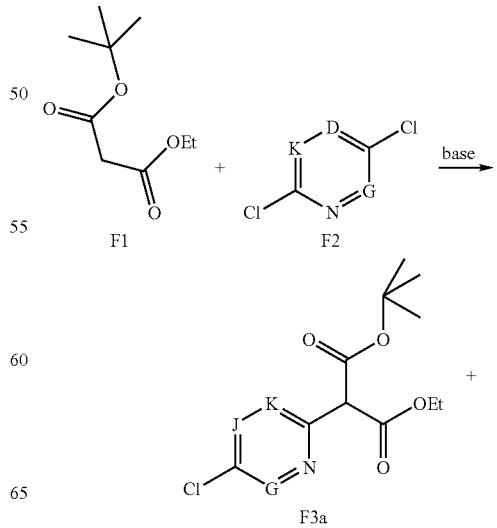

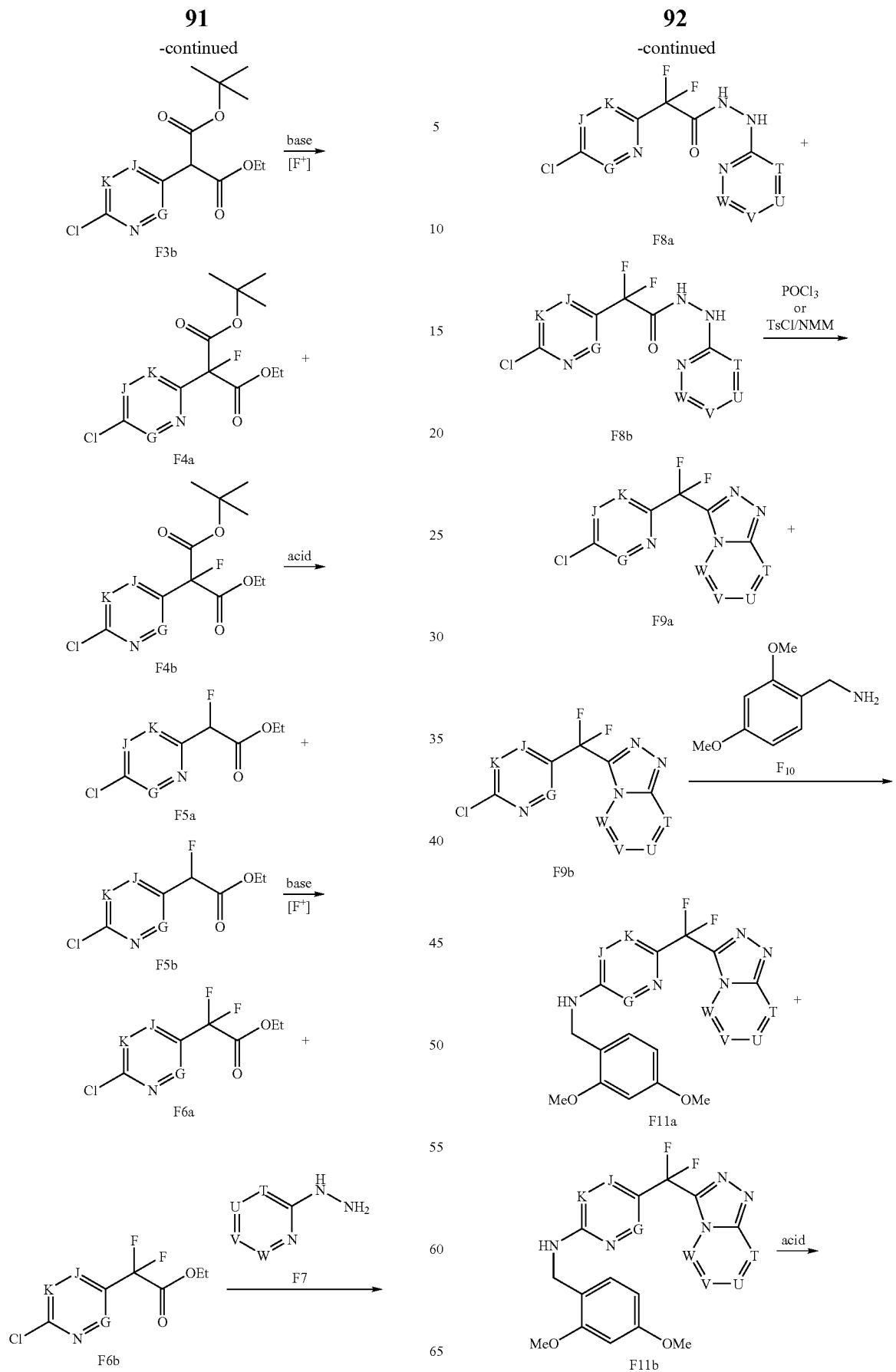

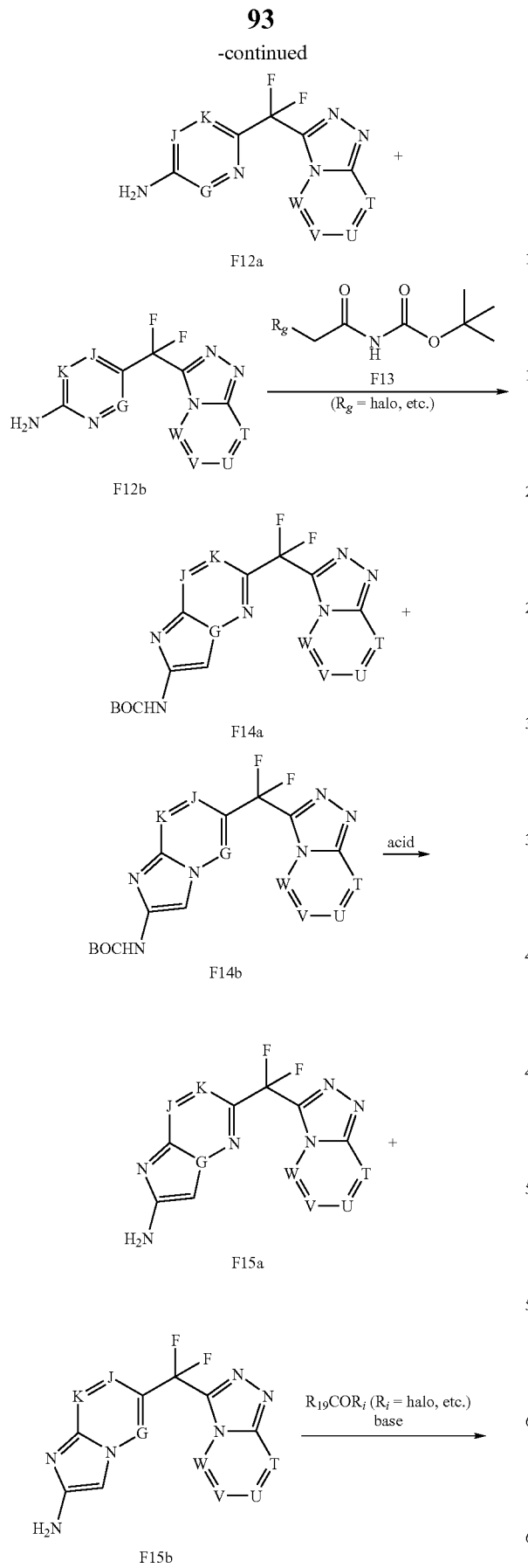

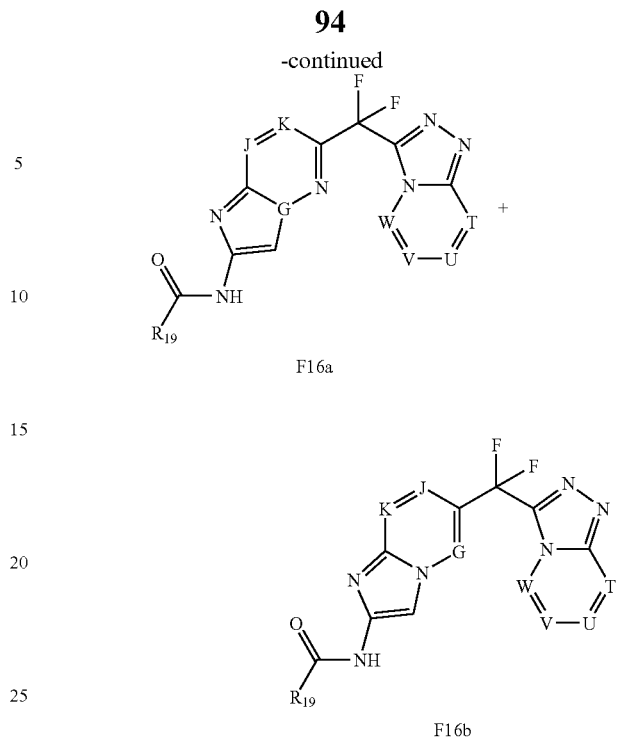

Compounds F3a and F3b can be prepared starting from compounds F1 and F2 by treating compound F1 with a base such as NaH in a solvent such as THF or dioxane at −78-0° C. and subsequent treatment with compound F2. Compound F3a and F3b are optionally separated prior to further use. Treatment of compounds F3a and/or F3b with a base such as NaH and a fluoride ion source provides compounds F4a and/or F4b. Subsequent treatment of compounds F4a and/or F4b with an acid such as TFA or HCl in a solvent such as THF, DCM, or dioxane at 0-75° C. for 1-8 hrs provides compounds F5a and/or F5b. Treatment of compounds F5a and/or F5b with a base such as NaH and a fluoride ion source provides compounds F6a and/or F6b. Treatment of compounds F6a and/or F6b with compound F7 in the presence of base such as TEA or DIEA in solvents such as MeOH or EtOH for 1-24 hrs provides compounds F8a and/or F8b. Treatment of compounds F8a and/or F8b with $POCl_3$ at 80-160° C. provides compounds F9a and/or F9b. Alternatively, compounds F9a and/or F9b can be prepared by treating compounds F8a and/or F8b with TsCl/N-methylmorpholine at ambient temperature to 100° C. for 30 min to 8 hrs. Coupling of compounds F9a and/or F9b with compound F10 is achieved in a solvent such as THF, Dioxane, or DMF at 25-100° C. for 2-24 hrs in the presence of a co-base such as DIEA or $Et_3N$. Removal of the dimethoxy benzyl group from compounds F11a and/or F11b is achieved by treating compounds F11a and/or F11b with an acid such as TFA at 25-75° C. for 2-24 hrs to provide compounds F12a and/or F12b. Treatment of compounds F12a and/or F12b with compound F13 in the presence of a base such as $Na_2HPO_4$ in a solvent such as DMA at 120° C. provides compounds F14a and/or F14b. Treatment of compounds F14a and/or F14b with an acid such as TFA or HCl provides compounds F15a and/or F15b. Treatment of compounds F15a and/or F15b with an acid halide in the presence of a co-base such as DIEA or $Et_3N$ at 25-75° C. in a solvent such as DCM, THF, dioxane or DMF provides compounds F16a and/or F16b.

Scheme G

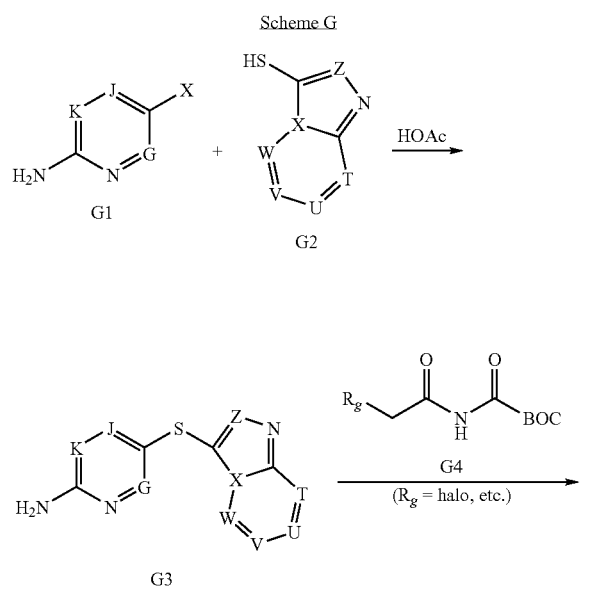

Heating compound G1 and G2 in HOAc at 50-100° C. for 2-24 hrs provides compound G3. Treatment of compound G3 with compound G4 in the presence of a base such as Na₂HPO₄ in a solvent such as DMA at 120° C. provides compound G5.

Scheme H

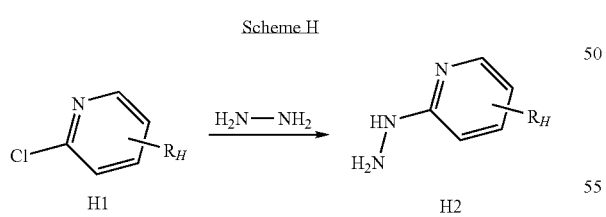

A solution of H1 (5 mmol; wherein $R_H$ is $R_8$, $R_9$, $R_{10}$ or $R_{11}$) and hydrazine (30 mmol) in isopropanol or EtOH (5 mL) is heated under microwave conditions at 60-160° C. for 2-5 h dependent on substrates. The solid product is filtered, washed with water and dried under high vacuum. Excess hydrazine can optionally be removed by concentrating the mixture and co-evaporating it with MeOH and Et₃N. The product can be suspended in ether, filtered and dried under high vacuum (e.g., overnight).

Scheme I

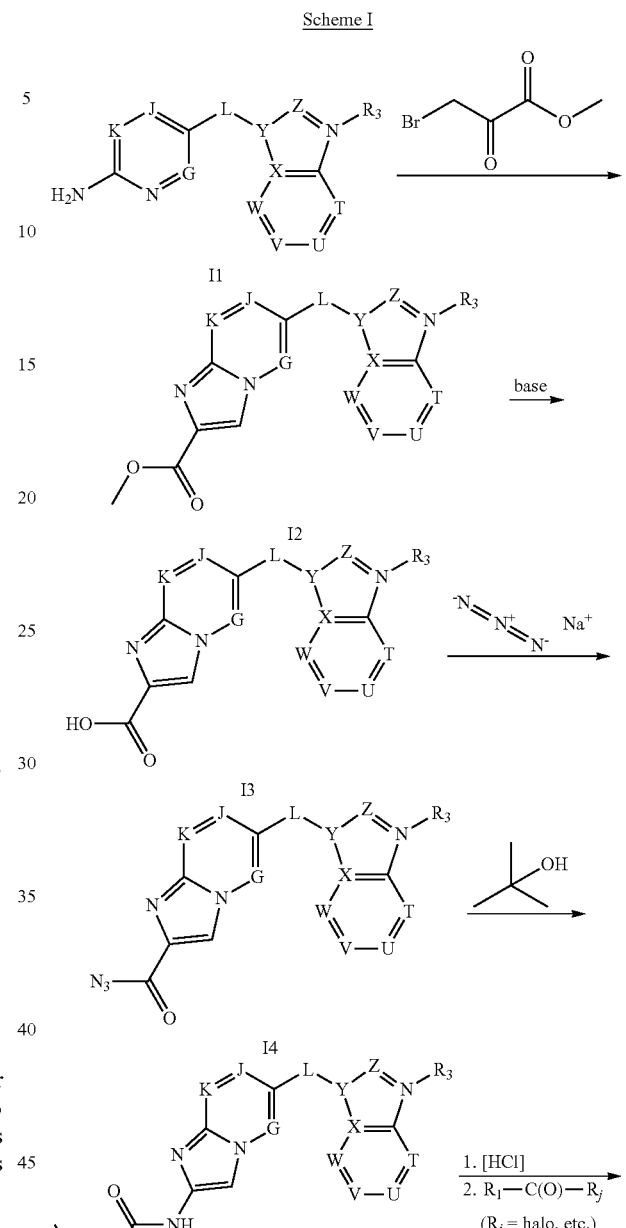

Compound I1 is treated with methyl 3-bromo-2-oxopropanoate in the presence of a base such as NaHCO₃, Na₂CO₃, sodium phosphate (mono, di, or tri-basic), or K₂CO₃ in a solvent such as dioxane or THF and heated at 50-100° C. for 1-18 hrs to provide compound of structure I2. Compound I2 is saponified with a base such as NaOH, KOH, or LiOH in a solvent such as MeOH, EtOH, or alcohol water mixtures with stirring for 1-18 hrs at 25-100° C. to provide compound of structure I3. Compound I3 can be treated with sodium azide and PyBOB in the presence of a base such as TEA, DIEA, or pyridine in an anhydrous solvent such as DMA or DMF and stirred for 1-18 hrs at ambient temperature to provide compound I4. Compound I4 is stirred in t-butanol for 1-18 hrs at 25-120° C. to provide compound I5. Compound I5 is treated with an acid such as TFA or HCl in a solvent such as DCM or dioxane and stirred for 1-18 hrs at 25-100° C. This deprotected product is then treated with an acylchloride in the presence of a base such as TEA, DIEA, or pyridine (which gives rise to a bis acylated product) or without a base (which gives rise to a mono acylated product) in a solvent such as DCM, THF, dioxane, or DMF and stirred for 1-18 hrs at 25-100° C. to yield compounds of structure I6.

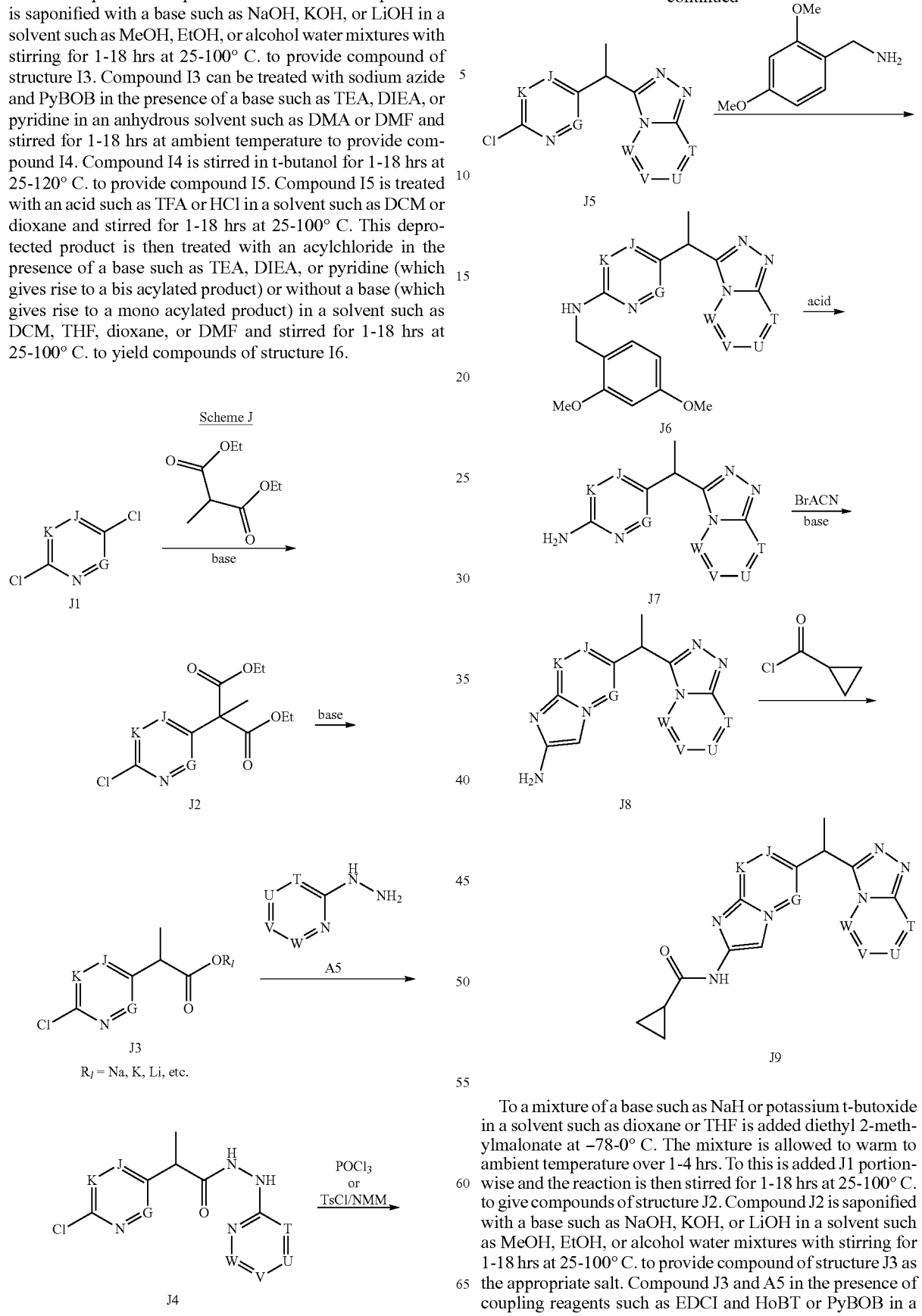

To a mixture of a base such as NaH or potassium t-butoxide in a solvent such as dioxane or THF is added diethyl 2-methylmalonate at −78-0° C. The mixture is allowed to warm to ambient temperature over 1-4 hrs. To this is added J1 portionwise and the reaction is then stirred for 1-18 hrs at 25-100° C. to give compounds of structure J2. Compound J2 is saponified with a base such as NaOH, KOH, or LiOH in a solvent such as MeOH, EtOH, or alcohol water mixtures with stirring for 1-18 hrs at 25-100° C. to provide compound of structure J3 as the appropriate salt. Compound J3 and A5 in the presence of coupling reagents such as EDCI and HoBT or PyBOB in a solvent such as DMF or DMA are stirred for 1-8 hrs at 25-100° C. to provide compounds of structure J4. Compound J4 is heated in phosphorous oxychloride for 1-18 hrs at 80-160° C. to give compounds of structure J5. Alternatively, compound J5 can be prepared by treating compound J4 with TsCl/N-methylmorpholine at ambient temperature to 100° C. for 30 min to 8 hrs. Compound J5 is treated with 2,4-dimethoxybenzylamine in the presence of a base such as NaHCO$_3$, Na$_2$CO$_3$, sodium phosphate (mono, di, or tri-basic), or K$_2$CO$_3$ and in a solvent such as IPA and is heated in a microwave for 1-24 hrs at 75-150° C. to give compounds of structure J6. Compound J6 is treated with an acid such as TFA or HCl in a solvent such as DCM or dioxane for 1-18 hrs at 25-100° C. to give compounds of structure J7. Compound J7 is treated with bromoacetonitrile in the presence of a base such as NaHCO$_3$, Na$_2$CO$_3$, sodium phosphate (mono, di, or tri-basic), or K$_2$CO$_3$ and in a solvent such as IPA for 1-18 hrs at 100° C. in a sealed tube to provide compounds of structure J8. Compound J8 is treated with cyclopropanecarbonyl chloride in the presence of a base such as TEA, DIEA, or pyridine or in the absence of a base and in a solvent such as DCM, THF, or dioxane for 1-8 hrs at ambient temperature to provide compounds of structure J9.

Scheme K

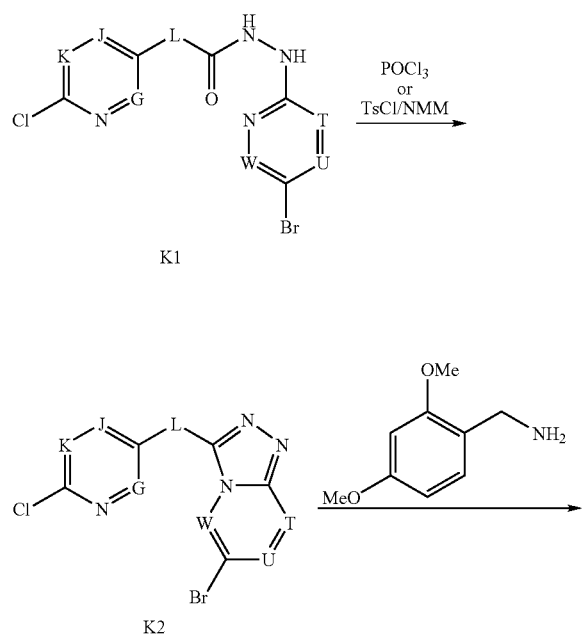

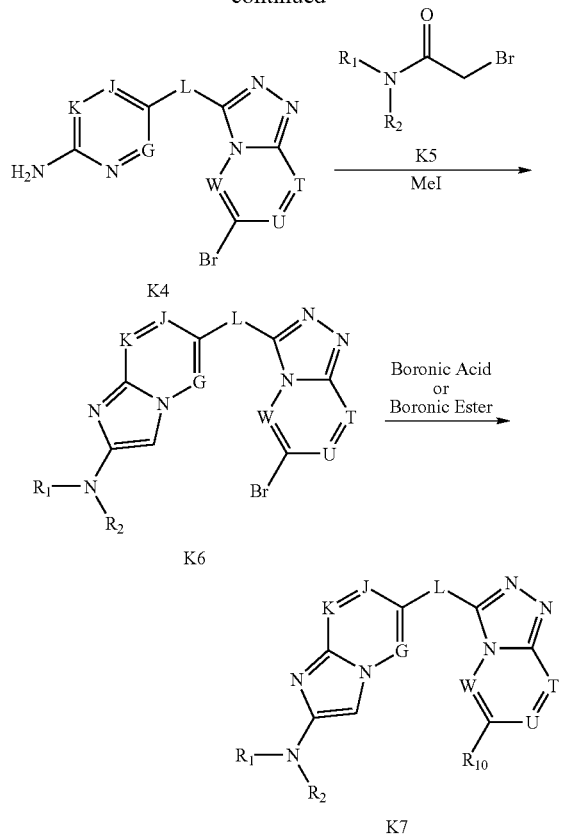

Compound K1 is heated in phosphorous oxychloride for 1-18 hrs at 80-160° C. to give compounds of structure K2. Alternatively, compound K2 can be prepared by treating compound K1 with TsCl/N-methylmorpholine at ambient temperature to 100° C. for 30 min to 8 hrs. Compound K2 is treated with 2,4-dimethoxybenzylamine in the presence of a base such as NaHCO$_3$, Na$_2$CO$_3$, sodium phosphate (mono, di, or tri-basic), or K$_2$CO$_3$ and in a solvent such as IPA and is heated in a microwave for 1-24 hrs at 75-150° C. to give compounds of structure K3. Compound K3 is treated with an acid such as TFA or HCl in a solvent such as DCM or dioxane for 1-18 hrs at 25-100° C. to give compounds of structure K4. Compounds of structure K4 is heated with compounds of structure K5 in the presence of KI and a base such as sodium hydrogenphosphate and in a solvent such as DMA or DME for 1-24 hrs at 50-120° C. to provide compounds of structure K6. Compound K6 is treated with the appropriate boronic acid or boronic ester in the presence of a catalyst such as tetrakis(triphenylphosphine)palladium(0) and a base such as Cs$_2$CO$_3$ (aq) or K$_2$CO$_3$ (aq) in a solvent such as dioxane, THF, or DME for 15 min –8 hrs at 50-120° C. to give compounds of structure K7.

Scheme L

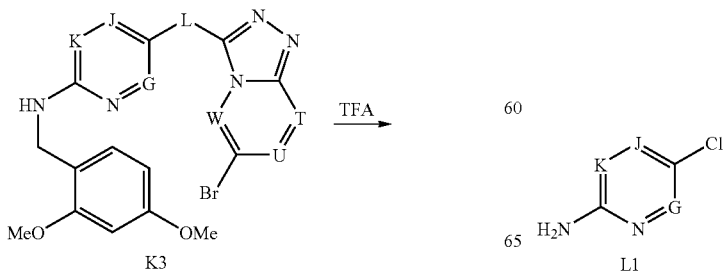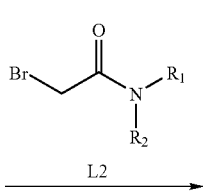

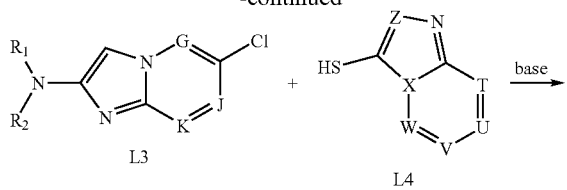

L3  L4

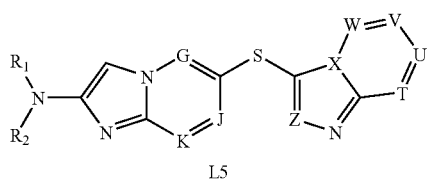

L5

Compound L1 is treated with compound L2 and a base (eg., K₂HPO₄) in a polar solvent (eg., DMA, DMF or DMSO) and heated at 65-85° C. to provide compound L3. Compound L3 was reacted with Compound L4 and a base (eg., K₂CO₃) in a polar solvent (eg., DMA, DMF or DMSO) at 130-160° C. and atmospheric pressure to 125 psi N₂ to provide compound L5.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Watrers ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

In each of the above reaction procedures or schemes, the various substituents may be selected from among the various substituents otherwise taught herein.

Descriptions of the syntheses of particular compounds according to the present invention based on the above reaction scheme are set forth herein.

Examples of cMET Inhibitors

The present invention is further exemplified, but not limited by, the following examples that describe the synthesis of particular compounds according to the invention.

Compounds 1 and 2: N-(6-((3H-[1,2,3]triazolo[4,5-b]pyridin-3-yl)methyl)imidazo[1,2-a]pyridin-2-yl)-2,2,2-trifluoroacetamide and N-(6-((1H-[1,2,3]triazolo[4,5-b]pyridin-1-yl)methyl)imidazo-[1,2-a]pyridin-2-yl)-2,2,2-trifluoroacetamide

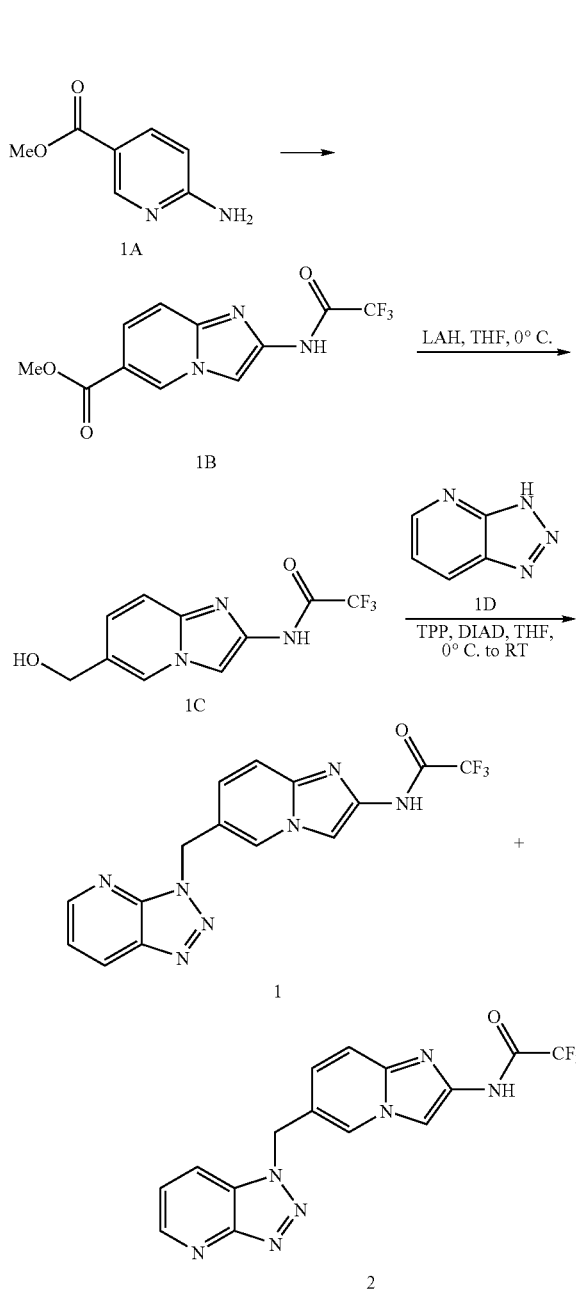

Methyl 2-(2,2,2-trifluoroacetamido)imidazo[1,2-a]pyridine-6-carboxylate (1B): Compound 1B was prepared starting from compound 1A in three steps following an analogous method to that described in U.S. Pat. No. 6,358,971, which is incorporated by reference herein in its entirety. Specifically, a mixture of methyl 6-aminonicotinate (1A, 3 g, 19.7 mmol) and tosylchloride (4.5 g, 23.6 mmol) in pyridine (40 mL) was heated at 80° C. for 16 hrs. The reaction was cooled to room temperature and pyridine was removed in vacuo. The resulting residue was diluted with water and allowed to stir for 10 min. The resulting solid was filtered and dried under vacuum to provide methyl 6-(4-methylphenylsulfonamido)nicotinate which was used without further purification. To a suspension of methyl 6-(4-methylphenylsulfonamido)nicotinate (5.3 g, 17.3 mmol) in anhydrous DMF was sequentially added DIEA (3.31 mL, 19.03 mmol) and then 2-bromoacetamide (2.63 g, 19.03 mmol). The reaction was stirred at ambient temperature for 24 hrs and then poured into water. The resulting solid was filtered and dried under vacuum to provide methyl 1-(2-amino-2-oxoethyl)-6-(4-methylphenylsulfonamido)-1,6-dihydropyridine-3-carboxylate which was used without further purification. To a suspension of methyl 1-(2-amino-2-oxoethyl)-6-(4-methylphenylsulfonamido)-1,6-dihydropyridine-3-carboxylate (1.0 g, 2.8 mmol) in DCM (20 mL) was added TFAA (8.0 mL, 57.5 mmol) dropwise at ambient temperature. The reaction was refluxed for 2 hrs, cooled to ambient temperature, and then concentrated in vacuo. The resulting residue was suspended in saturated sodium bicarbonate and stirred for 15 min. The resulting solid was filtered and dried under vacuum to provide methyl 2-(2,2,2-trifluoroacetamido)imidazo[1,2-a]pyridine-6-carboxylate (1B) which was used without further purification.

2,2,2-Trifluoro-N-(6-(hydroxymethyl)imidazo[1,2-a]pyridin-2-yl)acetamide (1C): To a stirred solution of compound 1B (470 mg, 1.64 mmol) in anhydrous THF (20 mL) were portion wise added lithium aluminum hydride (155 mg, 4.09 mmol) at 0° C. After being stirred for 1 h at 0° C., the reaction was quenched with 0.16 mL of water, followed by 0.16 mL of 15% NaOH and 0.48 mL of water. The heterogenous reaction mixture was stirred for 0.5 h at room temperature and then filtered through celite. Residue was washed with THF. Filtrate and washings were concentrated and the crude residue was purified by column chromatography to furnish compound 1C (220 mg, 52%). $^1$H NMR (400 MHz, DMSO-$d_6$) δ ppm 12.41 (s, 1H), 8.52 (s, 1H), 8.21 (s, 1H), 7.47 (d, J=9.2 Hz, 1H), 7.25 (d, J=9.6 Hz, 1H), 5.36 (t, J=5.6 Hz, 1H) 4.48 (d, J=5.6 Hz, 2 H) ESI-MS:m/z 260.2 (M+H)$^+$.

N-(6-((3H-[1,2,3]triazolo[4,5-b]pyridin-3-yl)methyl)imidazo[1,2-a]pyridin-2-yl)-2,2,2-trifluoroacetamide and N-(6-((1H-[1,2,3]triazolo[4,5-b]pyridin-1-yl)methyl)imidazo-[1,2-a]pyridin-2-yl)-2,2,2-trifluoroacetamide (1 and 2): To a stirred solution of compound 1C (30 mg, 0.12 mmol) in anhydrous THF (3.0 mL) were sequentially added compound 1D (28 mg, 0.23 mmol) and triphenyl phosphine (61 mg, 0.23 mmol). The reaction mixture was cooled to 0° C., and to it diisopropyl-azodicarboxylate (0.05 mL, 0.23 mmol) was added in drop wise manner. After the addition was over, stirring continued for another 0.5 h at 0° C. and then for 12 h at room temperature. Solvents were removed in vacuum and the residue was purified by preparative HPLC to provide compounds 1 and 2 as TFA salts. ESI-MS for both compounds:m/z 362.1 (M+H)$^+$.

Compound 3: N-(6-([1,2,4]triazolo[4,3-a]pyridin-3-ylthio)imidazo[1,2-b]pyridazin-2-yl)cyclo-propanecarboxamide Method A

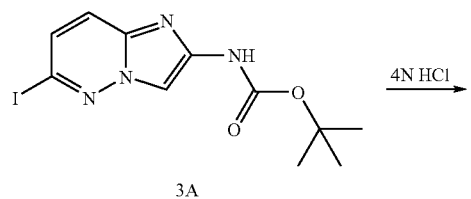

3A

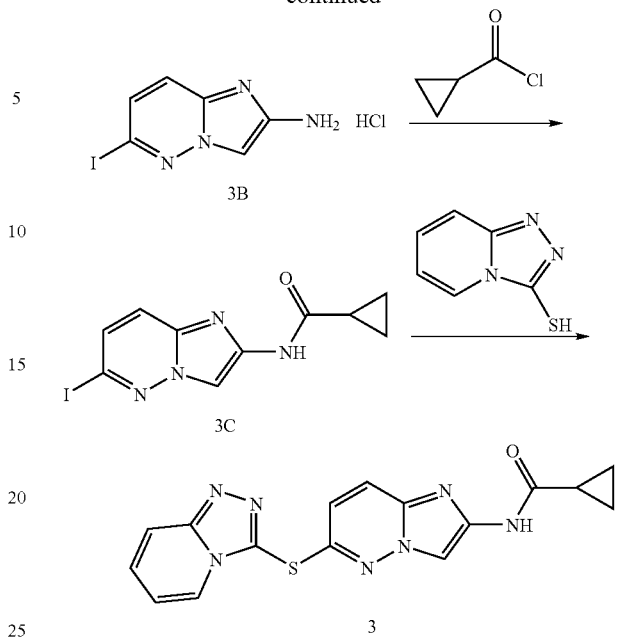

6-iodoimidazo[1,2-b]pyridazin-2-amine hydrochloride (3B): Compound 3B was synthesized according to a procedure analogous to that described in International Patent Publication No. WO 2008/06192 (Takeda Pharmaceutical Company Limited), which is incorporated by reference herein in its entirety. Specifically, tert-butyl 6-iodoimidazo[1,2-b]pyridazin-2-ylcarbamate (3A, 5.9 g, 16.38 mmol) was dissolved in 4N HCl in dioxane (60 mL) and stirred at ambient temperature for 4 hours. Ether (140 mL) was added to the reaction and a brown precipitate formed. The precipitate was filtered and washed with ether to give 6-iodoimidazo[1,2-b]pyridazin-2-amine hydrochloride in quantitative yield. This material was used without purification. ESI-MS:m/z 261.0 (M+H)$^+$.

N-(6-iodoimidazo[1,2-b]pyridazin-2-yl)cyclopropanecarboxamide (3C): Compound 3C was synthesized according to a procedure analogous to that described in International Patent Publication No. WO 2008/06192 (Takeda Pharmaceutical Company Limited), which is incorporated by reference herein in its entirety. 6-Iodoimidazo[1,2-b]pyridazin-2-amine hydrochloride (4.45 g, 17.11 mmol) and cyclopropanecarbonyl chloride (1.35 mL, 18.82 mmol) were dissolved in DMA (85 mL) and stirred for 3 hours at ambient temperature. The reaction mixture was then poured into water (400 mL) resulting in the formation of a brown precipitate. The solid was filtered and dried under vacuum to give N-(6-iodoimidazo[1,2-b]pyridazin-2-yl)cyclopropanecarboxamide (4.2 g, 77%). $^1$H NMR (400 MHz, DMSO-$d_6$) δ=11.21 (s, 1 H), 8.26-8.17 (m, 1 H), 7.74 (d, J=9.3 Hz, 1 H), 7.49 (d, J=9.1 Hz, 1 H), 2.07-1.87 (m, 1 H), 0.97-0.77 (m, 4 H) ESI-MS:m/z 329.1 (M+H)$^+$.

N-(6-([1,2,4]triazolo[4,3-a]pyridin-3-ylthio)imidazo[1,2-b]pyridazin-2-yl)cyclopropanecarboxamide (3): N-(6-iodoimidazo[1,2-b]pyridazin-2-yl)cyclopropanecarboxamide (0.5 g, 1.52 mmol), [1,2,4]triazolo[4,3-a]pyridine-3-thiol (0.23 g, 1.52 mmol), Tris(dibenzylideneacetone)dipalladium (0) (84 mg, 0.09 mmol), 9,9-Dimethyl-4,5-bis(diphenylphosphino)xanthene (106 mg g, 0.18 mmol), and DIEA (0.531 mL, 3.05 mmol) were dissolved in DME (15.2 mL) and heated in a microwave at 120° C. for 30 min. The reaction mixture was concentrated to dryness, reconstituted in DMSO, and purified by preparative LCMS to give N-(6-([1,2,4]triazolo[4,3-a]pyridin-3-ylthio)imidazo[1,2-b]pyridazin-2-yl)cyclopropanecarboxamide (1 g, 43%) as a TFA salt. $^1$H NMR (400 MHz, DMSO-$d_6$) δ=11.17 (s, 1 H), 8.57-8.44 (m, 1 H), 8.03-7.94 (m, 1 H), 7.96-7.88 (m, 2 H), 7.59 (ddd, J=1.0, 6.6, 9.3 Hz, 1 H), 7.22-7.11 (m, 1 H), 7.11-7.03 (m, 1 H), 1.97-1.84 (m, 1 H), 0.83-0.73 (m, 4 H) ESI-MS:m/z 352.3 (M+H)$^+$. MP 193-195° C.

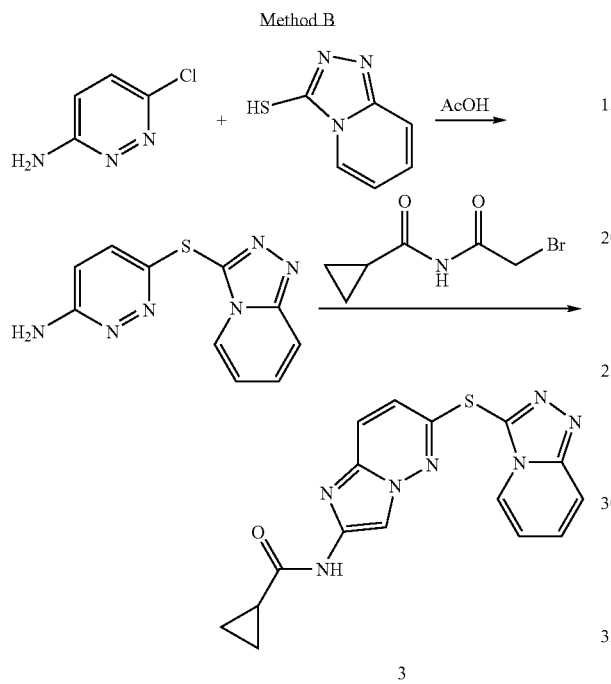

6-([1,2,4]Triazolo[4,3-a]pyridin-3-ylsulfanyl)-pyridazin-3-ylamine: A reaction mixture of [1,2,4]triazolo[4,3-a]pyridine-3-thiol (8.49 g, 55.0 mmol) and 6-chloropyridazin-3-amine (6.82 g, 50 mmol) in acetic acid (100 mL) was heated at 80° C. for 20 hrs. The reaction was stripped to dryness via rotary evaporation and the resulting material was suspended in H$_2$O (100 mL). To this suspension, solid Na$_2$CO$_3$ was added in portions until pH 10 was achieved and then the mixture was sonicated. The resulting solid was collected by filtration and rinsed thoroughly with water followed by ethyl ether. The solid was dried in vacuum over P$_2$O$_5$ to provide the title compound, 6-([1,2,4]Triazolo[4,3-a]pyridin-3-ylsulfanyl)-pyridazin-3-ylamine, as a white power (11.0 g). $^1$H NMR (400 MHz, DMSO-$d_6$) δ ppm 7.15-7.25 (m, 1 H) 7.53-7.58 (m, 1 H) 7.61 (ddd, J=9.22, 6.69, 1.26 Hz, 1 H) 7.84-7.90 (m, 1 H) 7.99 (dt, J=9.09, 1.01 Hz, 1 H) 8.51 (dt, J=7.01, 1.04 Hz, 1 H) 8.79 (br. s., 2 H). ESI-MS:m/z 553.2 (M+H)$^+$.

N-(6-([1,2,4]Triazolo[4,3-a]pyridin-3-ylthio)imidazo[1,2-b]pyridazin-2-yl)cyclopropanecarboxamide: A mixture of 6-([1,2,4]triazolo[4,3-a]pyridin-3-ylthio)pyridazin-3-amine (2.443 g, 10 mmol), N-(2-bromoacetyl)cyclopropanecarboxamide (3.09 g, 15.00 mmol), potassium hydrogenphosphate (5.23 g, 30.0 mmol) and potassium iodide (0.830 g, 5.00 mmol) in DMA (100 mL) was stirred at 120° C. for 2 hrs. Additional amounts of N-(2-bromoacetyl)cyclopropanecarboxamide (2.06 g, 10 mmol) and potassium hydrogenphosphate (1.74 g, 10 mmol) were added to the mixture and the reaction was stirred at 120° C. for another 2 hrs. The reaction was then stirred at room temperature overnight. The reaction mixture was again stirred at 140° C. for 3 hrs and then cooled to room temperature. The resulting solid was filtered off and rinsed with DMA. The filtrate was concentrated to 100 mL and then poured into water (300 mL). The resulting precipitate was collected by filtration and rinsed thoroughly with water. The solid material was re-suspended in 10% MeOH/CH2Cl2 (100 mL), sonicated, refluxed for 30 min and cooled to room temperature. The MeOH/CH2Cl2 solution was filtered through a silica plug, rinsed with 10% MeOH/CH2Cl2 (200 mL). To above organic solution, activated charcoal (0.5 g) was added, the solution was refluxed for 30 min, and then stirred at room temperature overnight. The charcoal was filtered through Celite, and the filtrate was concentrated to dryness to provide an off white solid. This solid was refluxed in MeOH (10 mL) for 30 min. and cooled to room temperature. The resulting off white solid was collected by filtration, rinsed with MeOH (2 mL) and dried in vacuum to provide the title compound, N-(6-([1,2,4]Triazolo[4,3-a]pyridin-3-ylthio)imidazo[1,2-b]pyridazin-2-yl)cyclopropanecarboxamide (1.2 g). $^1$H NMR (400 MHz, DMSO-$d_6$) δ=11.17 (s, 1 H), 8.57-8.44 (m, 1 H), 8.03-7.94 (m, 1 H), 7.96-7.88 (m, 2 H), 7.59 (ddd, J=1.0, 6.6, 9.3 Hz, 1 H), 7.22-7.11 (m, 1 H), 7.11-7.03 (m, 1 H), 1.97-1.84 (m, 1 H), 0.83-0.73 (m, 4 H) ESI-MS:m/z 352.3 (M+H)$^+$. MP 193-195° C.

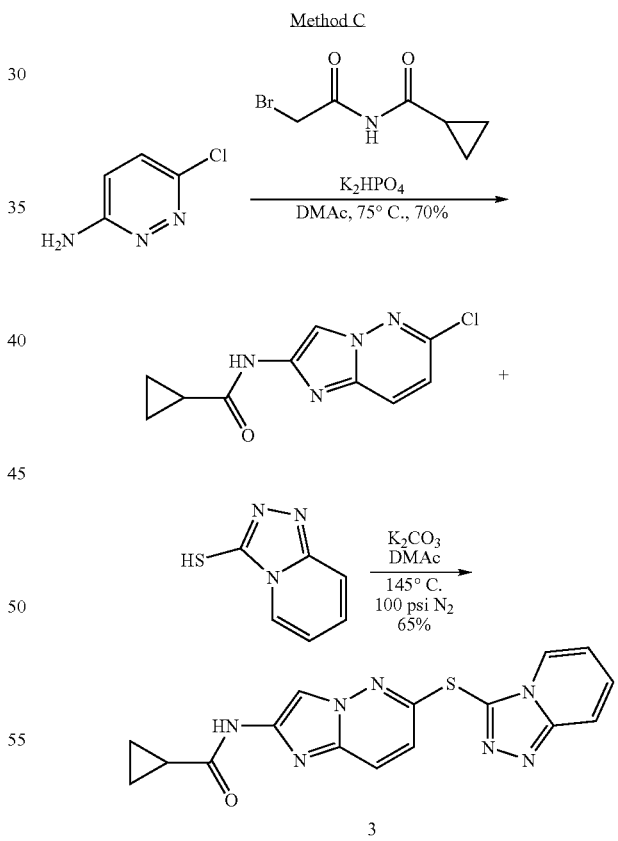

6-Chloropyridazin-3-amine, N-(2-bromoacetyl)cyclopropanecarboxamide, and potassium hydrogenphosphate were mixed in DMA at 75° C. to provide N-(6-chloroimidazo[1,2-b]pyridazin-2-yl)cyclopropanecarboxamide. N-(6-chloroimidazo[1,2-b]pyridazin-2-yl)cyclopropanecarboxamide was reacted with [1,2,4]triazolo[4,3-a]pyridine-3-thiol and K$_2$CO$_3$ in DMA at 145° C. and 100 psi N$_2$ to provide N-(6-

([1,2,4]triazolo[4,3-a]pyridin-3-ylthio)imidazo[1,2-b]pyridazin-2-yl)cyclo-propanecarboxamide.

Compound 4: N-(6-(6-bromo-[1,2,4]triazolo[4,3-a]pyridin-3-ylthio)imidazo[1,2-b]pyridazin-2-yl)cyclo-propanecarboxamide

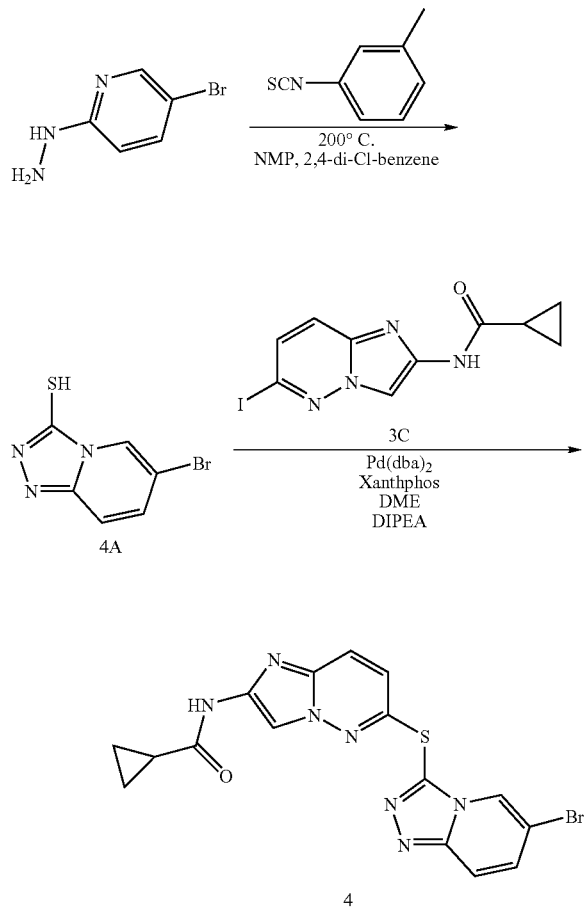

6-bromo-[1,2,4]triazolo[4,3-a]pyridine-3-thiol (4A): To the suspended solution of 5-Bromo-2-hydrazinylpyridine (1.85 g, 10 mmol) in a mixture of 1,4-dichlorobenzene and NMP (5:1, 10 ml) was added isothiocyanato-3-methylbenzene (1.5 g 10 mmol). The mixture was stirred at rt for 5 min, 70° C. for 15 min, and then heated under microwave condition at 200° C. for 1.5 h. The mixture was poured into Ether (20 mL). Solid was filtered and the washed with ether to give title product.

N-(6-(6-bromo-[1,2,4]triazolo[4,3-a]pyridin-3-ylthio)imidazo[1,2-b]pyridazin-2-yl)cyclopropanecarboxamide (4): To a sealed tube packed with N-(6-iodoimidazo[1,2-b]pyridazin-2-yl)cyclopropanecarboxamide (100 mg, 0.3 mmol), compound 4A, Pd(dba)$_2$ (3%/mol), xanthphos (5%/mol) and DIPEA (1.5 mmol) was added DME (2 mL). After degas under vacuum, the mixture was heated under microwave condition at 125° C. for 30 min. The mixture was purified by LCMS to give the title compound as a TFA salt. $^1$H NMR (400 MHz, CDCl$_3$—CD$_3$OD 10:1) δ ppm 8.5 (s, 1 H), 8.1 (s, 1 H), 7.8 (d, J=9.8 Hz, 1 H), 7.7 (d, J=9.2 Hz, 2H), 7.60 (d, J=9.6 Hz, 1 H), 7.1 (d, J=9.36 Hz, 1 H), 1.7 (m, 1 H), 1.05 (m, 2 H), 0.90 (m, 2H) ESI-MS:m/z 430.2 (M+H)$^+$.

Compound 5: N-(6-(6-(1-methyl-1H-pyrazol-4-yl)-[1,2,4]triazolo[4,3-a]pyridin-3-ylthio)-imidazo[1,2-b]pyridazin-2-yl)cyclopropanecarboxamide

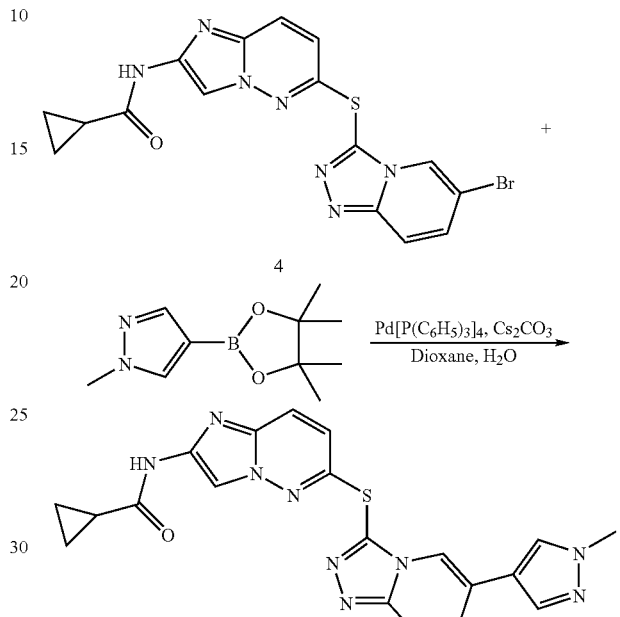

A of mixture Compound 4 (15 mg, 0.35 mmol), 1-methyl-4-(4,4,5,5-tetramethyl-1,3,2-dioxaborolan-2-yl)-1H-pyrazole (11 mg, 0.52 mmol), Cs$_2$CO$_3$ (350 mg), and tetrakis (triphenylphosphine)palladium(0) (i.e., Pd[P(C$_6$H$_5$)$_3$]$_4$) (1%/mol) in dioxane-H$_2$O (20:1, 1.5 mL) was heated under microwave condition at 140° C. for 30 min. The mixture was purified by LCMS to give title compound as a TFA salt. $^1$H NMR (400 MHz, CDCl$_3$—CD$_3$OD 10:1) δ ppm 8.33 (s, 1 H), 8.14(s, 1 H), 7.75 (s, 1H), 7.70 (s, 1H), 7.67 (d, J=9.5 Hz, 1 H), 7.56 (dd, J=9.4 and 1.6 Hz, 1 H), 7.06 (d, J=9.4 Hz, 1 H), 3.96 (s, 3 H), 1.67 (m, 1 H), 1.06 (m, 2 H), 0.90 (m, 2H) ESI-MS: m/z 432.2 (M+H)$^+$.

Compound 6: N-(6-(6-cyano-[1,2,4]triazolo[4,3-a]pyridin-3-ylthio)imidazo[1,2-b]pyridazin-2-yl)cyclo-propanecarboxamide

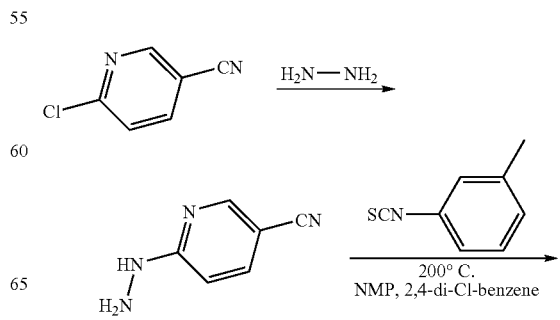

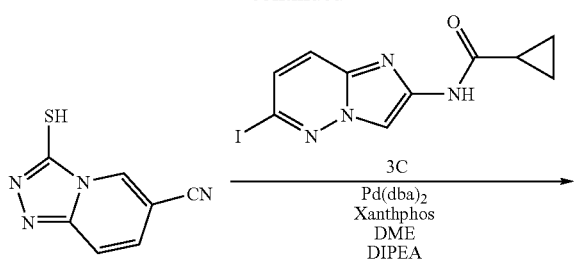

To a suspended mixture of 6-chloronicotinonitrile (7 g, 50.8 mmol) in EtOH (50 mL), was added NH$_2$NH$_2$ (10 g, 310.2 mmol). The mixture was stirred at room temperature for 10 min, and then 60° C. for 5 h. The mixture was cooled to room temperature. The solids were filtered out, washed with water and dried under high vacuum to give 6-hydrazinylnicotinonitrile (3.5 g). Compound 6 was prepared from 6-hydrazinylnicotinonitrile following the procedure of the synthesis of compound 4. $^1$H NMR (400 MHz, CDCl3-CD3OD 10:1) δ ppm 11.37 (s, 1H), 8.70 (t, J=1.2 Hz, 1 H), 8.14 (s, 1 H), 8.11(dd, J=1.04 and 9.52 Hz, 1 H), 7.96 (dd, J=1.12 and 9.52 Hz, 1 H), 7.61 (dd, J=1.52 and 9.48 Hz, 1 H), 7.38 (d, J=9.0 Hz, 1 H), 1.77 (m, 1 H), 1.06 (m, 2 H), 0.90 (m, 2H) ESI-MS:m/z 377.2 (M+H)$^+$.

Compound 7: tert-butyl 6-(6-chloro-[1,2,4]triazolo[4,3-a]pyridin-3-ylthio)imidazo[1,2-b]pyridazin-2-ylcarbamate 6-iodopyridazin-3-amine (7A): Compound 7A was synthesized according to a procedure analogous to that described in International Patent Publication No. WO 2007/30366 (Smithkline Beecham Corporation), which is incorporated by reference herein in its entirety. Specifically, 6-chloropyridazin-3-amine (10.0 g, 77.2 mmol) was mixed with hydroiodic acid (78 mL, aqueous 57%) and heated to 100° C. overnight. Ethyl acetate (50 mL) was added after the reaction was cooled to room temperature. The resulting mixture was sonicated and filtered. The filter cake was washed with copious amounts of ethyl acetate. The crude material was then dried under high vacuum to give 6-iodopyridazin-3-amine (7A; 24 g, 89%) as bright yellow solid, which was used without further purification. $^1$H NMR (400 MHz, DMSO-d$_6$) δ ppm 8.36-8.08 (m, 1 H), 7.95 (d, J=9.6 Hz, 1 H), 7.12-7.03 (m, 1 H). ESI-MS:m/z 221.9 (M+H)$^+$.

Tert-butyl 6-iodoimidazo[1,2-b]pyridazin-2-ylcarbamate (7B): A mixture containing compound 7A (2.5 g, 11.3 mmol), tert-butyl 2-chloroacetylcarbamate (2.4 g, 12.4 mmol), sodium hydrogen phosphate (3.2 g, 22.6 mmol) and DMA (23 mL) was heated at 120° C. for two hours. The mixture was cooled to room temperature, poured into a flask containing 400 mL of water and sonicated. The solids were filtered, rinsed with water then dried under vacuum. The solids were then taken up in 600 mL ethyl acetate and filtered over short plug of silica gel. The filtrate was concentrated down to give compound 7B (1.6 g, 39%), as a dark green solid, which was used without further purification. $^1$H NMR (400 MHz, DMSO-d$_6$) δ ppm 10.21 (br. s., 1 H), 8.06-8.00 (m, 1 H), 7.69 (d, J=9.9 Hz, 1 H), 7.46 (d, J=9.3 Hz, 1 H), 1.48 (s, 9 H) ESI-MS:m/z 361.1 (M+H)$^+$.

Tert-butyl 6-(6-chloro-[1,2,4]triazolo[4,3-a]pyridin-3-ylthio)imidazo[1,2-b]pyridazin-2-ylcarbamate (7): Combined compound 7B (50 mg, 0.14 mmol), 6-chloro-[1,2,4]triazolo[4,3-a]pyridine-3-thiol (28 mg, 0.15 mmol), Tris(dibenzylideneacetone)dipalladium(0) (11 mg, 0.01 mmol), 9,9-Dimethyl-4,5-bis(diphenylphosphino)xanthene (14 mg, 0.025 mmol), DIEA (48 uL, 0.28 mmol) and DME (1.4 mL) and heated in a microwave unit at high absorbance, 120° C. for 30 min. The resulting crude material was purified by silica gel using 5% MeOH in DCM. The cleanest fractions were concentrated to give compound 7 (0.06 g; quantitative yield). $^1$H NMR (400 MHz, DMSO-d$_6$) δ ppm 10.18 (br. s., 1 H), 8.86-8.82 (m, 1 H), 8.11-8.05 (m, 1 H), 7.89 (d, J=9.3 Hz, 1 H), 7.73 (s, 1 H), 7.66 (dd, J=1.9, 9.7 Hz, 1 H), 7.09 (d, J=9.6 Hz, 1 H), 1.48-1.41 (m, 9 H), ESI-MS:m/z 418.2.0 (M+H)$^+$.

Compound 8: 6-(6-chloro-[1,2,4]triazolo[4,3-a]pyridin-3-ylthio)imidazo[1,2-b]pyridazin-2-amine

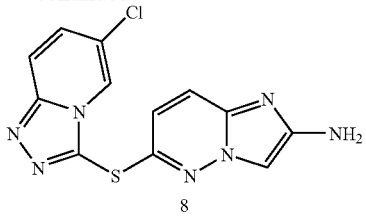

Compound 7 (0.15 g, 0.42 mmol) and 4N HCl in dioxane (2 mL) was combined and stirred at RT for 2 hours to yield compound 8. The crude reaction mixture was concentrated and used without purification. ESI-MS:m/z 318.2 (M+H)+.

Compound 9: N-(6-(6-chloro-[1,2,4]triazolo[4,3-a]pyridin-3-ylthio)imidazo[1,2-b]pyridazin-2-yl)cyclopropanecarboxamide

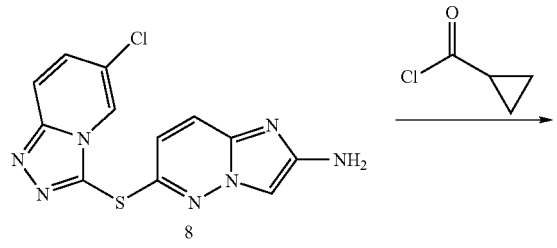

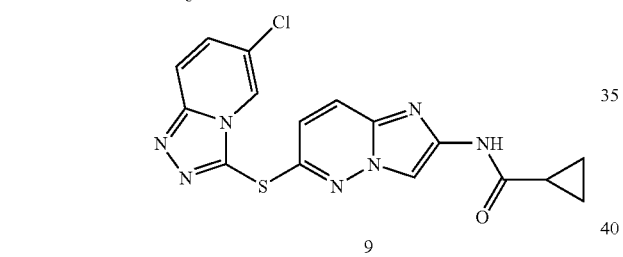

Compound 8 (0.13 g, 0.41 mmol), cyclopropanecarbonyl chloride (112 uL, 1.23 mmol), triethylamine (690 mL, 4.9 mmol) and DCE (2 mL) were combined and stirred for 2 hours to yield compound 9. The reaction mixture was concentrated and purified by preparative LC. ESI-MS:m/z 386.3 (M+H)+.

Compound 10: 6-(6-Bromo-benzotriazol-1-ylmethyl)-imidazo[1,2-b]pyridazin-2-ylamine hydrochloride

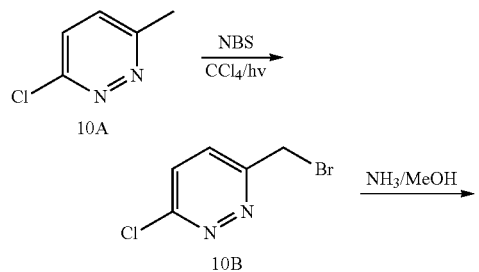

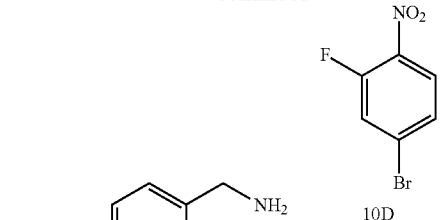

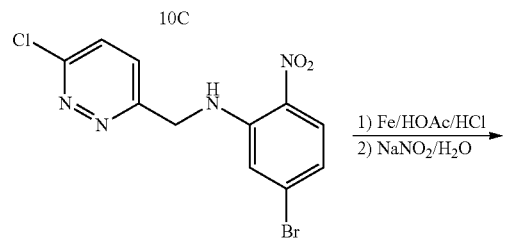

3-Bromomethyl-6-chloro-pyridazine (10B): A solution of 3-Chloro-6-methyl-pyridazine 10A (5.12 g, 40 mmol) and NBS (8.90 g, 50 mmol) in CCl₄ (300 mL) was refluxed under light (200 w) for 4 hours. The reaction mixture was cooled to room temperature and filtered. The solid residue was washed thoroughly with Cl₄C and filtered. The filtrates was combined, concentrated to small volume and loaded on to a silica gel column. The column was eluted with 50% hexane/ethyl acetate to give 2.2 g of desired product (10B) which was dried in vacuum and used immediately in next step. ESI-MS:m/z 206.9 (M+H)+.

C-(6-Chloro-pyridazin-3-yl)-methylamine Hydrobromide (10C): A solution of compound 10B (2.08 g, 10 mmol) in methanol (50 mL) was added into a pre-saturated ammonia/methanol solution (200 mL) at 0° C. The reaction solution was sealed and stirred at room temperature overnight. The methanol solution was concentrated and dried in vacuum to give 2.2 g of crude product (10C) as hydrobromide salt, which was used in next step without further purification. ESI-MS: m/z 144.1 (M+H)+.

(5-Bromo-2-nitro-phenyl)-(6-chloro-pyridazin-3-ylmethyl)-amine (10E): A solution of compound 10C (1.00 g, 4.46 mmol) and 4-bromo-2-fluoro-1-nitro-benzene (10D) (0.97 g, 4.40 mmol) in DMF (50 mL) with DIEA (1.30 g, 10 mmol) was stirred at 65° C. for two hours. The reaction was poured into ice/water and the solid precipitate was collected by filtration, washed with water and dried in vacuum over $P_2O_5$ overnight to give 1.5 g of desired product (10E). ESI-MS:m/z 342.9 (M+H)+.

6-Bromo-1-(6-chloro-pyridazin-3-ylmethyl)-1H-benzotriazole (10F): To a solution of compound 10E (1.40 g, 4.08 mmol) in HOAc/HCl (50/5 mL) was added iron power (2.2 g, 40 mmol). The reaction mixture was stirred at 50° C. for 30 minutes, then cooled to room temperature and filtered. A solution of $NaNO_2$ (0.35 g, 5 mmol) in water (2 mL) was then added drop wise into above acid solution at 0° C. The reaction solution was stirred for one hour and concentrated to dryness under reduced pressure. The resulting residue was sonicated in ethyl acetate/$NaHCO_3$ solution and the precipitate was filtered off and rinsed thoroughly with ethyl acetate. The organic solution was separated and dried with $MgSO_4$, filtered and concentrated to give 1.2 g of desired product (10F). ESI-MS:m/z 323.9 (M+H)+.

6-(6-Bromo-benzotriazol-1-ylmethyl)-pyridazin-3-ylamine (10G): To a suspension of compound 10F (1.2 g, 3.7 mmole) in isopropanol (15 mL) in a stainless pressure tube, an ammonia gas was bubbled through at −78° C. for 5 minutes. The pressure tube was sealed and heated in an oil bath at 140° C. for three days. The reaction solution was then re-cooled, transferred to a round bottle, concentrated and dried in vacuum to give 1.3 g of crude product (10G), which was used in next step without further purification. ESI-MS:m/z 305.1 (M+H)+.

[6-(6-Bromo-benzotriazol-1-ylmethyl)-imidazo[1,2-b]pyridazin-2-yl]-carbamic acid tert-butyl ester (10H): A mixture of compound 10G (1.0 g, 3.28 mmol), (2-chloro-acetyl)-carbamic acid tert-butyl ester (1.0 g, 5.0 mmol) and $Na_2HPO_4$ (1.4 g, 10 mmol) in DMA (50 mL) was stirred at 135° C. for four hours. Solvent was removed under reduced pressure. The residue was sonicated in ethyl acetate/water, and the precipitate was filtered off. Ethyl acetate solution was separated and concentrated and loaded on silica gel. The silica column was eluted with hexane/ethyl acetate (1/2) to give 0.45 g of desired product (10H). ESI-MS:m/z 444.1 (M+H)+.

6-(6-Bromo-benzotriazol-1-ylmethyl)-imidazo[1,2-b]pyridazin-2-ylamine Hydrochloride (10): A solution of compound 10H (0.44 g, 1.0 mmol) in 4N HCl/dioxane (10 mL) was stirred at room temperature for 60 minutes, concentrated and dried in vacuum to give 0.3 g of product (10) as a hydrochloride salt. ESI-MS:m/z 344.1 (M+H)+.

Compound 11: Cyclopropanecarboxylic acid [6-(6-bromo-benzotriazol-1-ylmethyl)-imidazo[1,2-b]pyridazin-2-yl]-amide

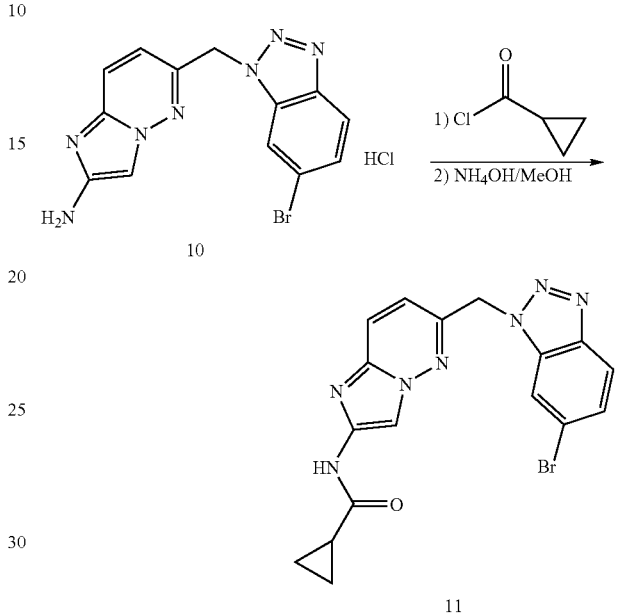

To a solution of compound 10 (0.34 g, 1 mmol) in $CH_2Cl_2$ (25 mL) was added DIEA (0.31 g, 3 mmol), followed by cyclopropanecarbonyl chloride (0.23 g, 2.2 mmol). The reaction solution was stirred at room temperature for 60 minutes and concentrated. The residue was re-dissolved in methanol (10 mL) and ammonium hydroxide (0.5 mL) was added. The reaction solution was stirred for 30 minutes and concentrated. The residue was dissolved in ethyl acetate and washed with 5% citric acid and then saturated $NaHCO_3$. The organic phase was dried with $MgSO_4$ and concentrated to give 0.25 g of desired product (11). ESI-MS:m/z 412.1 (M+H)+.

Compound 12: N-(6-((6-methyl-1H-benzo[d][1,2,3]triazol-1-yl)methyl)imidazo[1,2-b]pyridazin-2-yl)cyclopropanecarboxamide

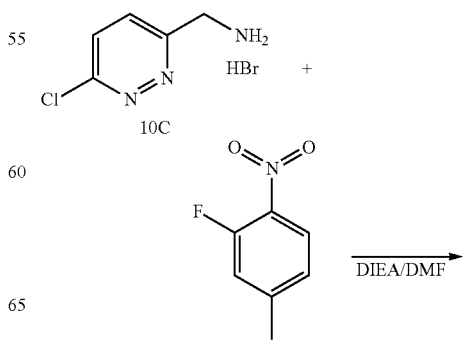

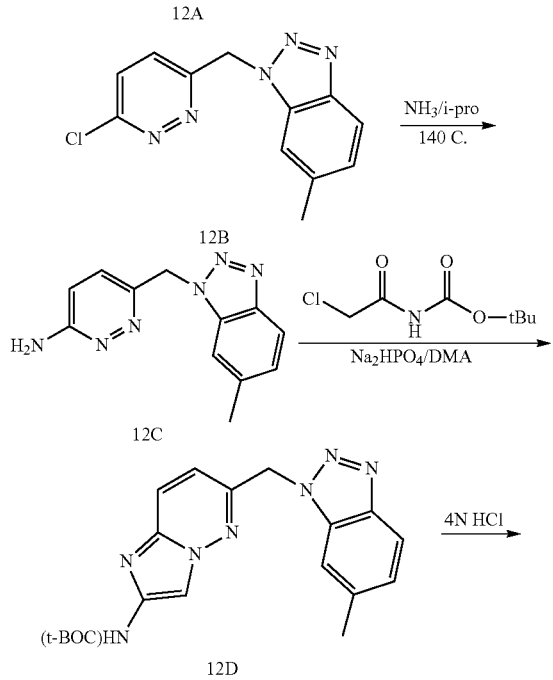

12A

12B

12C

12D

12E

12

Compound 12E was prepared using a similar procedure to that described in connection with compound 10, except that 2-fluoro-4-methyl-1-nitro-benzene was used in place of compound 10D. Compound 12 was then prepared from compound 12E using the method described in connection with compound 11. $^1$H NMR (DMSO-$d_6$): δ ppm 11.20 (s, 1H), 8.20 (s,1H), 7.96 (m, 2H), 7.68 (s, 1H), 7.28 (d, 1H), 7.10 (d, 1H), 6.14 (s, 2H), 2.46 (s, 3H), 1.94 (m, 1H), 0.80 (m, 4H).

Compound 13: Cyclopropanecarboxylic acid {6-[6-(1-methyl-1H-pyrazol-4-yl)-benzotriazol-1-ylmethyl]-imidazo[1,2-b]pyridazin-2-yl}-amide

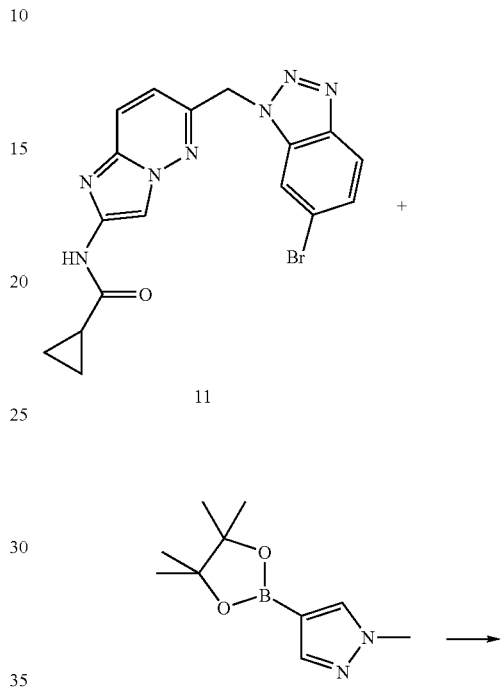

11

13

A mixture of compound 11 (20 mg, 0.05 mmol), 1-methylpyrazole-4-boronic acid pinacol ester (20 mg, 0.1 mmol) and catalytic amount of Pd(dppf)Cl$_2$ in a NaHCO$_3$ saturated dioxane/H2O (2/1) solution (0.5 mL) was heated using a microwave oven at 120° C. for 30 minutes. After preparative LCMS purification, 11 mg of the desired product was obtained as the TFA salt. $^1$H NMR (DMSO-$d_6$): δ ppm 11.40 (s, 1H), 8.32 (s, 1H), 8.16 (s, 1H), 8.08 (s, 1H), 8.04 (d, 1H), 7.96 (m, 2H), 7.64 (m, 1H), 7.14 (d, 1H), 6.16 (s, 2H), 3.90 (s, 3H), 1.94 (m, 1H), 0.80 (m, 4H) ESI-MS:m/z 414.2 (M+H)$^+$.

In a similar manner as compound 13, compounds 14-24 were synthesized and purified from compound 11 and the corresponding boronic acid or ester.

| Compound | Structure | LC/MS | NMR |
|---|---|---|---|
| 14 | N-(6-((6-(3-fluorophenyl)-1H-benzo[d][1,2,3]triazol-1-yl)methyl)imidazo[1,2-b]pyridazin-2-yl)cyclopropanecarboxamide | 427 | $^1$H NMR (400 MHz, DMSO-d$_6$) δ ppm 11.17 (s, 1H), 8.40-8.28 (m, 1H), 8.21-8.11 (m, 1H), 7.97 (d, J = 9.3 Hz, 1H), 7.86-7.78 (m, 1H), 7.69-7.45 (m, 4H), 7.31-7.21 (m, 1H), 7.16 (d, J = 9.3 Hz, 1H), 6.30-6.17 (m, 2H), 1.92 (quin, J = 6.1 Hz, 1H), 0.86-0.75 (m, 4H) |
| 15 | N-(6-((6-phenyl-1H-benzo[d][1,2,3]triazol-1-yl)methyl)imidazo[1,2-b]pyridazin-2-yl)cyclopropanecarboxamide | 409 | $^1$H NMR (400 MHz, DMSO-d$_6$) δ ppm 11.18 (s, 1H), 8.24 (s, 1H), 8.19-8.13 (m, 2H), 7.97 (d, J = 9.3 Hz, 1H), 7.81-7.73 (m, 3H), 7.52 (t, J = 7.6 Hz, 2H), 7.45-7.38 (m, 1H), 7.16 (d, J = 9.1 Hz, 1H), 6.28-6.19 (m, 2H), 1.92 (quin, J = 6.1 Hz, 1H), 0.85-0.78 (m, 4H) |
| 16 | N-(6-((6-pyridin-3-yl)-1H-benzo[d][1,2,3]triazol-1-yl)methyl)imidazo[1,2-b]pyridazin-2-yl)cyclopropanecarboxamide | 410 | — |
| 17 | N-(6-((6-(4-(methylsulfonyl)phenyl)-1H-benzo[d][1,2,3]triazol-1-yl)methyl)imidazo[1,2-b]pyridazin-2-yl)cyclopropanecarboxamide | 487 | $^1$H NMR (400 MHz, DMSO-d$_6$) δ ppm 11.18 (s, 1H), 8.39 (s, 1H), 8.25-8.20 (m, 1H), 8.14 (s, 1H), 8.09-8.03 (m, 4H), 7.98 (d, J = 9.9 Hz, 1H), 7.86-7.80 (m, 1H), 7.17 (d, J = 9.3 Hz, 1H), 6.27 (s, 2H), 3.28 (s, 3H), 1.98-1.85 (m, 1H), 0.85-0.77 (m, 4H) |

-continued

| Compound | Structure | LC/MS | NMR |
|---|---|---|---|
| 18 | N-(6-((6-(3-(ethylsulfonyl)phenyl)-1H-benzo[d][1,2,3]triazol-1-yl)methyl)imidazo[1,2-b]pyridazin-2-yl)cyclopropanecarboxamide | 501 | ¹H NMR (400 MHz, DMSO-d₆) δ ppm 11.17 (s, 1H), 8.39 (s, 1H), 8.28-8.20 (m, 2H), 8.13 (s, 2H), 7.95 (dd, J = 8.7, 14.8 Hz, 3H), 7.90-7.79 (m, 2H), 7.15 (d, J = 9.3 Hz, 1H), 6.28 (s, 2H), 1.92 (d, J = 5.3 Hz, 1H), 1.14 (t, J = 7.2 Hz, 4H), 0.88-0.76 (m, 4H) |
| 19 | N-(6-((6-(5-methoxypyridin-3-yl)-1H-benzo[d][1,2,3]triazol-1-yl)methyl)imidazo[1,2-b]pyridazin-2-yl)cyclopropanecarboxamide | 440 | ¹H NMR (400 MHz, DMSO-d₆) δ ppm 11.18 (s, 1H), 8.64 (d, J = 1.8 Hz, 1H), 8.47-8.36 (m, 2H), 8.21 (d, J = 8.8 Hz, 1H), 8.14 (s, 1H), 7.98 (d, J = 9.3 Hz, 1H), 7.91-7.79 (m, 2H), 7.17 (d, J = 9.3 Hz, 1H), 6.26 (s, 2H), 3.97-3.93 (m, 3H), 2.02-1.86 (m, 1H), 0.83-0.78 (m, 4H) |
| 20 | N-(6-((6-(3,5-dimethyl-1H-pyrazol-4-yl)-1H-benzo[d][1,2,3]triazol-1-yl)methyl)imidazo[1,2-b]pyridazin-2-yl)cyclopropanecarboxamide | 427 | ¹H NMR (400 MHz, DMSO-d₆) δ ppm 11.20 (s, 1H), 8.17 (s, 1H), 8.08 (d, J = 8.6 Hz, 1H), 7.99 (d, J = 9.3 Hz, 1H), 7.71 (s, 1H), 7.44-7.35 (m, 1H), 7.17 (d, J = 9.3 Hz, 1H), 6.20 (s, 2H), 2.26-2.16 (m, 6H), 2.02-1.88 (m, 1H), 0.90-0.77 (m, 4H) |
| 21 | N-(6-((6-(5-(methylsulfonyl)pyridin-3-yl)-1H-benzo[d][1,2,3]triazol-1-yl)methyl)imidazo[1,2-b]pyridazin-2-yl)cyclopropanecarboxamide | 488 | ¹H NMR (400 MHz, DMSO-d₆) δ ppm 11.17 (s, 1H), 9.35 (d, J = 2.0 Hz, 1H), 9.19-9.04 (m, 1H), 8.70-8.65 (m, 1H), 8.54 (s, 1H), 8.30-8.25 (m, 1H), 8.18-8.10 (m, 1H), 8.00-7.91 (m, 2H), 7.17 (d, J = 9.3 Hz, 1H), 6.29 (s, 2H), 3.42 (s, 3H), 1.96-1.86 (m, 1H), 0.85-0.77 (m, 4H) |

| Compound | Structure | LC/MS | NMR |
|---|---|---|---|
| 22 | (S)-N-(6-((6-(1-(2,3-dihydroxypropyl)-1H-pyrazol-4-yl)-1H-benzo[d][1,2,3]triazol-1-yl)methyl)imidazo[1,2-b]pyridazin-2-yl)cyclopropanecarboxamide | 474 | ¹H NMR (400 MHz, DMSO-d₆) δ ppm 11.18 (s, 1H), 8.30 (s, 1H), 8.25 (s, 1H), 8.14 (d, 2H), 8.00 (m, 3H), 7.70 (d, 1H), 7.20 (d, 1H), 6.16 (s, 2H), 4.26 (m, 1H), 4.10 (m, 1H), 3.34 (m, 1H), 1.94 (m, 1H), 0.83 (m, 4H) |
| 23 | (R)-N-(6-((6-(1-(2,3-dihydroxypropyl)-1H-pyrazol-4-yl)-1H-benzo[d][1,2,3]triazol-1-yl)methyl)imidazo[1,2-b]pyridazin-2-yl)cyclopropanecarboxamide | 474 | ¹H NMR (400 MHz, DMSO-d₆) δ ppm 11.18 (s, 1H), 8.30 (s, 1H), 8.25 (s, 1H), 8.14 (d, 2H), 8.00 (m, 3H), 7.70 (d, 1H), 7.20 (d, 1H), 6.16 (s, 2H), 4.26 (m, 1H), 4.10 (m, 1H), 3.34 (m, 1H), 1.94 (m, 1H), 0.83 (m, 4H) |
| 24[a] | N-(6-((6-(1-(2-hydroxyethyl)-1H-pyrazol-4-yl)-1H-benzo[d][1,2,3]triazol-1-yl)methyl)imidazo[1,2-b]pyridazin-2-yl)cyclopropanecarboxamide hydrochloride | 444 | ¹H NMR (DMSO-d₆): δ 11.21 (s, 1H), 8.30 (s, 1H), 8.20 (s, 1H), 8.12 (s, 1H), 8.02 (m, 3H), 7.70 (d, 1H), 7.14 (d, 1H), 6.16 (s, 2H), 4.17 (t, 2H), 3.77 (m, 2H), 1.94 (m, 1H), 0.83 (m, 4H) |

[a] Melting point: >200° C.

123

Compound 13: N-(6-((6-(1-methyl-1H-pyrazol-4-yl)-1H-benzo[d][1,2,3]triazol-1-yl)methyl)imidazo[1,2-b]pyridazin-2-yl)cyclopropanecarboxamide

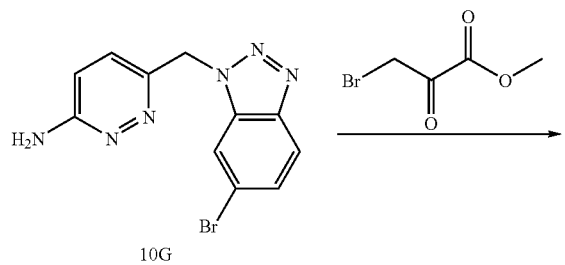
10G

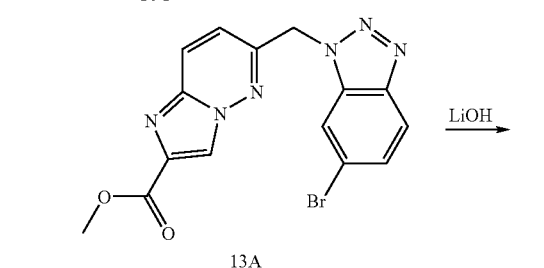
13A

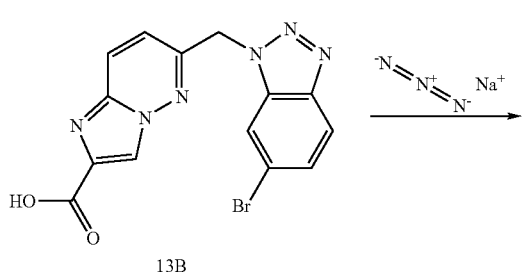
13B

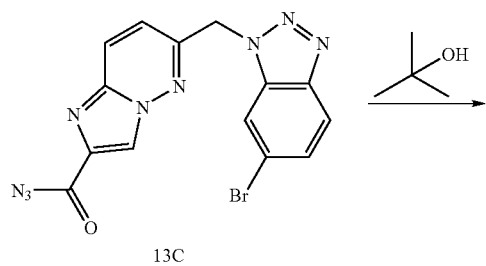
13C

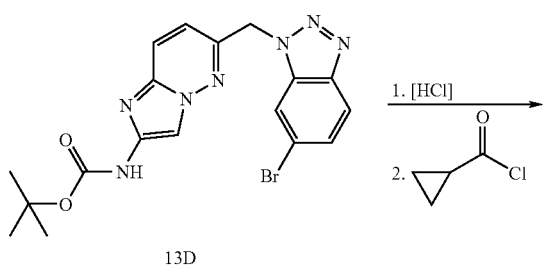
13D

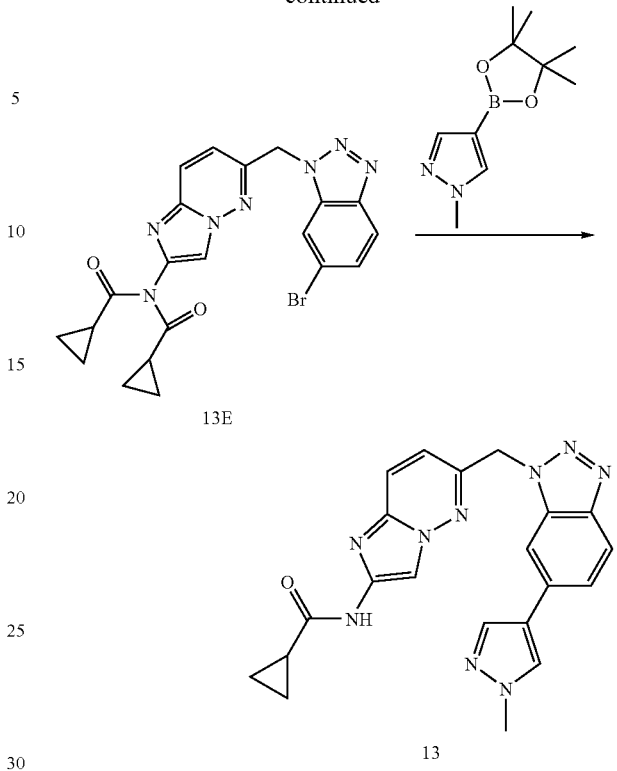
13E

13

Ethyl 6-((6-bromo-1H-benzo[d][1,2,3]triazol-1-yl)methyl)imidazo[1,2-b]pyridazine-2-carboxylate: A mixture of 6-((6-bromo-1H-benzo[d][1,2,3]triazol-1-yl)methyl)pyridazin-3-amine 10G (4.8 g, 15.73 mmol), ethyl 3-bromo-2-oxopropanoate (4.60 g, 23.60 mmol) and NaHCO$_3$ (4.0 g) in dioxane was heated at 60° C. for 1 hr. Additional ethyl 3-bromo-2-oxopropanoate (1.5 g, 7.87 mmol, 0.5 eq) was added and stirred at 60° C. for an additional hour. The reaction mixture was filtered and rinsed with dioxane. 4-Methylbenzenesulfonic acid (2.71 g, 15.73 mmol) was added to the filtrate, and the reaction was heated at 75° C. for 2 hrs. The reaction was evaporated to dryness via rotary evaporation and the resulting residue was dissolved in EtOAc. The organic phase was washed with saturated NaHCO$_3$ followed by 0.1 N NaOH (3×150 mL). The solution was dried with MgSO$_4$, filtered, concentrated to dryness and purified by MPLC (10% MeOH/CH$_2$Cl$_2$) to provide the title compound, ethyl 6-((6-bromo-1H-benzo[d][1,2,3]triazol-1-yl)methyl)imidazo[1,2-b]pyridazine-2-carboxylate 13A (4.7 g, 11.6 mmol, 50%). $^1$H NMR (400 MHz, DMSO-d$_6$) δ ppm 1.30 (t, J=7.07 Hz, 3 H) 4.30 (q, J=7.07 Hz, 2 H) 6.26 (s, 2 H) 7.33 (d, J=9.60 Hz, 1 H) 7.59 (dd, J=8.72, 1.64 Hz, 1H) 8.08 (d, J=8.84 Hz, 1 H) 8.23 (d, J=9.60 Hz, 1 H) 8.31 (d, J=1.26 Hz, 1 H) 8.77 (s, 1 H). MS:m/z 401.2 (M+H)$^+$.

6-((6-bromo-1H-benzo[d][1,2,3]triazol-1-yl)methyl)imidazo[1,2-b]pyridazine-2-carboxylic acid: To a solution of ethyl 6-((6-bromo-1H-benzo[d][1,2,3]triazol-1-yl)methyl)imidazo[1,2-b]pyridazine-2-carboxylate 13A (5 g, 12.46 mmol) in 10% H$_2$O/MeOH (200 mL), LiOH (0.597 g, 24.92 mmol) was added. The reaction was stirred at ambient temperature for 18 hrs and then concentrated to remove the MeOH. H$_2$O (100 mL) was added and the pH was adjusted to 4 with concentrated HCl. The resulting solid was collected by filtration, rinsed with water followed by EtOAc, and dried in vacuum over P$_2$O$_5$ to provide the title compound, 6-((6- bromo-1H-benzo[d][1,2,3]triazol-1-yl)methyl)imidazo[1,2-b]pyridazine-2-carboxylic acid 13B (3.6 g 9.65 mmol, 77%). The filtrate was extracted with EtOAc (3×150 mL) and the organics were combined, dried with MgSO$_4$, filtered and concentrated to dryness to give an additional 0.6 g of product. $^1$H NMR (400 MHz, DMSO-d$_6$) δ ppm 6.24 (s, 2 H) 7.24 (d, J=9.35 Hz, 1 H) 7.58 (dd, J=8.84, 1.77 Hz, 1 H) 8.04-8.14 (m, 2H) 8.32 (d, J=1.01 Hz, 1 H) 8.47 (s, 1 H). MS:m/z 373.2 (M+H)$^+$.

6-((6-bromo-1H-benzo[d][1,2,3]triazol-1-yl)methyl)imidazo[1,2-b]pyridazine-2-carbonyl azide: To a stirred solution of 6-((6-bromo-1H-benzo[d][1,2,3]triazol-1-yl)methyl)imidazo[1,2-b]pyridazine-2-carboxylic acid 13B (3.6 g, 9.65 mmol), N-ethyl-N-isopropylpropan-2-amine (7.48 g, 57.9 mmol) and sodium azide (6.27 g, 96 mmol) in anhydrous DMF (60 mL), PyBOP (6.02 g, 11.58 mmol) was added in portions at ambient temperature over 5 min. The reaction was stirred for another 30 min and then poured into a EtOAc/H$_2$O (100/300 mL) mixture and shaken well. The resulting precipitate was filtered, rinsed with H$_2$O followed by EtOAc, and dried in vacuum over P$_2$O$_5$ for 18 hrs to provide the title compound, 6-((6-bromo-1H-benzo[d][1,2,3]triazol-1-yl)methyl)imidazo[1,2-b]pyridazine-2-carbonyl azide 13C (2.1 g, 5.28 mmol, 55%). The EtOAc solution washed with 5% citric acid (2×100 mL), NaHCO$_3$, dried with MgSO$_4$, filtered and concentrated to dryness to give additional crude product (1.6 g of 80% pure material). $^1$H NMR (400 MHz, DMSO-d$_6$) δ ppm 6.28 (s, 2 H) 7.37 (d, J=9.60 Hz, 1 H) 7.59 (dd, J=8.84, 1.77 Hz, 1 H) 8.09 (d, J=8.84 Hz, 1 H) 8.26 (d, J=10.10 Hz, 1 H) 8.32 (d, J=1.26 Hz, 1 H) 8.92 (s, 1H). MS:m/z 398.2 (M+H)$^+$.

tert-Butyl 6-((6-bromo-1H-benzo[d][1,2,3]triazol-1-yl)methyl)imidazo[1,2-b]pyridazin-2-ylcarbamate: A suspension of 6-((6-bromo-1H-benzo[d][1,2,3]triazol-1-yl)methyl)imidazo[1,2-b]pyridazine-2-carbonyl azide 13C (1 g, 2.51 mmol) in 2-methylpropan-2-ol (50 mL, 753 mmol) was heated at 100° C. in a microwave for 3 hrs. The reaction was repeated once. The reactions were combined and the solvent was removed via rotary evaporation. The resulting residue was suspended in EtOAc/H$_2$O and sonicated. The resulting solid was collected by filtration, rinsed with H$_2$O followed by EtOAc, and dried in vacuum over P$_2$O$_5$ to provide the title compound, tert-Butyl 6-((6-bromo-1H-benzo[d][1,2,3]triazol-1-yl)methyl)imidazo[1,2-b]pyridazin-2-ylcarbamate 13D (1.7 g, 3.83 mmol, 77%). $^1$H NMR (400 MHz, DMSO-d$_6$) δ ppm 1.47 (s, 9 H) 6.18 (s, 2 H) 7.13 (d, J=9.35 Hz, 1 H) 7.58 (dd, J=8.72, 1.64 Hz, 1 H) 7.94 (d, J=9.85 Hz, 2 H) 8.07 (d, J=8.84 Hz, 1 H) 8.31 (d, J=1.77 Hz, 1 H) 10.24 (br, 1 H). MS:m/z 444.2 (M+H)$^+$.

N-(6-((6-bromo-1H-benzo[d][1,2,3]triazol-1-yl)methyl)imidazo[1,2-b]pyridazin-2-yl)-N-(cyclopropanecarbonyl)cyclopropanecarboxamide: A mixture of tert-butyl 6-((6-bromo-1H-benzo[d][1,2,3]triazol-1-yl)methyl)imidazo[1,2-b]pyridazin-2-ylcarbamate 13D (1.7 g, 3.83 mmol) in 4N HCl/dioxane (30 mL) was stirred at ambient temperature for 2 hrs. The solvent was removed via rotary evaporation, and the resulting residue was dried in vacuum for 18 hrs to yield the 6-((6-bromo-1H-benzo[d][1,2,3]triazol-1-yl)methyl)imidazo[1,2-b]pyridazin-2-amine as an HCl salt. This material was used without further purification. To a solution of 6-((6-bromo-1H-benzo[d][1,2,3]triazol-1-yl)methyl)imidazo[1,2-b]pyridazin-2-amine HCl (1.8 g, 5.23 mmol) in CH$_2$Cl$_2$ was added N-ethyl-N-isopropylpropan-2-amine (2.70 g, 20.92 mmol) followed by cyclopropanecarbonyl chloride (1.640 g, 15.69 mmol) at 0° C. The reaction was stirred at ambient temperature for 2 hrs. The reaction was then washed with 5% citric acid solution followed by saturated NaHCO$_3$, dried with MgSO$_4$, filtered and concentrated to dryness. The resulting residue was purified by MPLC (5% MeOH/CH$_2$Cl$_2$) to provide the title compound, N-(6-((6-bromo-1H-benzo[d][1,2,3]triazol-1-yl)methyl)imidazo[1,2-b]pyridazin-2-yl)-N-(cyclopropanecarbonyl)cyclopropanecarboxamide 13E (2.0 g, 4.1 mmol, 80%). $^1$H NMR (400 MHz, DMSO-d$_6$) δ ppm 0.75-0.86 (m, 8 H) 1.93 (m, 2 H) 6.19 (s, 2 H) 7.16 (d, J=9.35 Hz, 1 H) 7.51-7.64 (m, 1 H) 7.99 (d, J=9.35 Hz, 1 H) 8.01-8.10 (m, 1 H) 8.13 (s, 1 H) 8.31 (d, J=1.77 Hz, 1 H). MS:m/z 480.2 (M+H)$^+$.

N-(6-((6-(1-methyl-1H-pyrazol-4-yl)-1H-benzo[d][1,2,3]triazol-1-yl)methyl)imidazo[1,2-b]pyridazin-2-yl)cyclopropanecarboxamide: A mixture of N-(6-((6-bromo-1H-benzo[d][1,2,3]triazol-1-yl)methyl)imidazo[1,2-b]pyridazin-2-yl)-N-(cyclopropanecarbonyl)cyclopropanecarboxamide 13E (0.7 g, 1.457 mmol), 1-methyl-4-(4,4,5,5-tetramethyl-1,3,2-dioxaborolan-2-yl)-1H-pyrazole (0.303 g, 1.457 mmol) and PdCl$_2$(dppf)-CH$_2$Cl$_2$ (0.06 g, 0.075 mmol) in Na$_2$CO$_3$ (2N, 6 mL)/dioxane (12 mL) was heated in a microwave at 110° C. for 45 min. The reaction was filtered and rinsed with EtOAc. This reaction was repeated twice. The organic solutions were combined and washed with 5% citric acid followed by NaHCO$_3$, dried with MgSO$_4$, and filtered. MeOH was added to the EtOAc solution to give 5% MeOH (v/v), and the resulting solution was filtered through a short silica column and rinsed thoroughly with 5% MeOH/EtOAc. Activated charcoal (1 g) was added to the eluent and stirred at ambient temperature for 1 hr. The solution was filtered through Celite and concentrated to dryness via rotary evaporation. The resulting material was suspended in EtOAc (50 mL) and sonicated. The resulting solid was collected by filtration and rinsed with EtOAc to provide the title compound, N-(6-((6-(1-methyl-1H-pyrazol-4-yl)-1H-benzo[d][1,2,3]triazol-1-yl)methyl)imidazo[1,2-b]pyridazin-2-yl)cyclopropanecarboxamide 13 (820 mg, 1.98 mmol, 45%). The filtrate was concentrated and reconstituted in 10% MeOH/EtOAc, loaded on a short silica column and eluted with 10% MeOH/EA to give provide additional product (190 mg). $^1$H NMR (400 MHz, DMSO-d$_6$) δ ppm 0.76-0.86 (m, 4 H) 1.88-1.97 (m, 1 H) 3.88 (s, 3H) 6.15 (s, 2 H) 7.12 (d, J=9.35 Hz, 1 H) 7.66 (dd, J=8.72, 1.39 Hz, 1 H) 7.93-8.01 (m, 2 H) 8.04 (d, J=8.84 Hz, 1 H) 8.10 (s, 1 H) 8.17 (s, 1 H) 8.26 (s, 1 H) 11.18 (s, 1 H). MS:m/z 414.2 (M+H)$^+$. MP 250.2-251.6° C.

Compound 25: N-(6-(6-(prop-1-en-2-yl)-[1,2,4]triazolo[4,3-a]pyridin-3-ylthio)imidazo[1,2-b]pyridazin-2-yl)cyclopropanecarboxamide

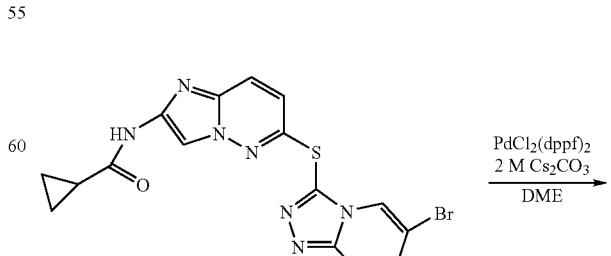

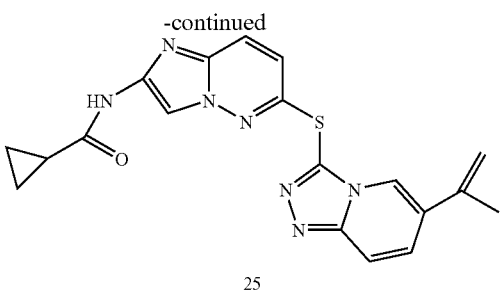

A of mixture Compound 4 (50 mg, 0.10 mmol), 4,4,5,5-tetramethyl-2-(prop-1-en-2-yl)-1,3,2-dioxaborolane (71 mg, 0.43 mmol), Cs$_2$CO$_3$ (3 M; 0.11 mL, 0.30 mmol), and PdCl$_2$(dppf)$_2$ (4.0 mg, 0.0005 mmol) in DME (1.0 mL) was heated in a microwave at 100° C. for 1 hr. The reaction mixture was then concentrated to dryness via rotary evaporation. The resulting crude material was reconstituted in DMSO (1.0 mL) and purified via preparative mass trigger LCMS using a gradient eluant of 25-50% ACN:0.05% TFA (aq). The collected fractions were combined and the ACN was removed via rotary evaporation. The resulting mixture was lyophilized to provide the TFA salt of the title compound. $^1$H NMR (400 MHz, DMSO-d6) δ ppm 11.17 (s, 1 H) 8.31 (s, 1 H) 8.14(s, 1 H) 7.95 (s, 1H) 7.91 (d, J=9.5 Hz, 1 H) 7.64 (dd, J=9.4 and 1.6 Hz, 1 H) 7.05 (d, J=9.4 Hz, 1 H) 5.67 (s, 1 H) 5.29 (s, 1 H) 2.08 (m, 3 H) 1.89 (m, 1 H) 1.06 (m, 2 H) 0.90 (m, 2H) ESI-MS: m/z 391.1 (M+H)$^+$.

Compound 26: N-(6-(6-isopropyl-[1,2,4]triazolo[4,3-a]pyridin-3-ylthio)imidazo[1,2-b]pyridazin-2-yl)cyclopropanecarboxamide

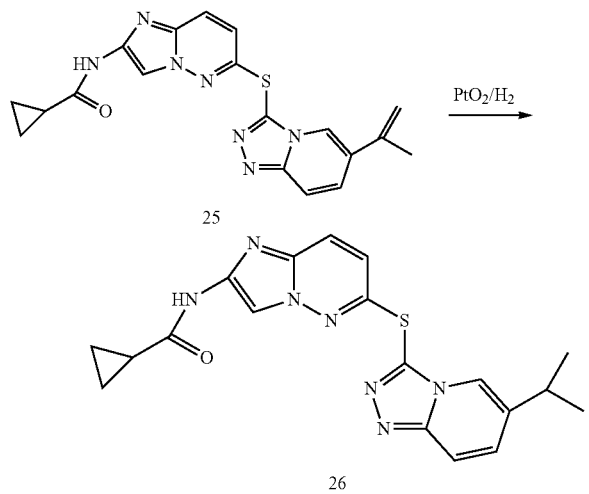

To a solution of N-(6-(6-(prop-1-en-2-yl)-[1,2,4]triazolo[4,3-a]pyridin-3-ylthio)imidazo[1,2-b]pyridazin-2-yl)cyclopropanecarboxamide (150 mg, 0.383 mmol) in ethanol (20 mL) was added platinum (IV) oxide (4.35 mg, 0.019 mmol). The reaction was stirred for 24 hr at 25° C. under 10 psi of H$_2$. The reaction mixture was then filtered through Celite and the filtrate was concentrated to dryness via rotary evaporation. The resulting crude material was reconstituted in DMSO (1.0 mL) and purified via preparative mass trigger LCMS using a gradient eluant of 25-50% ACN:0.05% TFA (aq). The collected fractions were combined and the ACN was removed via rotary evaporation. The resulting mixture was lyophilized to provide the TFA salt of the title compound (6.0 mg, 0.015 mmol, 3.98% yield) as a yellow solid. $^1$H NMR (400 MHz, DMSO-d$_6$) δ ppm 0.71-0.87 (m, 4 H) 1.19 (d, J=6.82 Hz, 6 H) 1.79-1.98 (m, 1 H) 3.02 (dt, J=13.71, 6.92 Hz, 1 H) 7.03 (d, J=9.35 Hz, 1 H) 7.62 (dd, J=9.47, 1.64 Hz, 1 H) 7.90-7.97 (m, 3 H) 8.26 (s, 1 H) 11.17 (s, 1 H). ESI-MS:m/z 394.3 (M+H)$^+$.

Compound 27: 1-(6-(6-(3-fluorophenyl)-[1,2,4]triazolo[4,3-a]pyridin-3-ylthio)imidazo[1,2-b]pyridazin-2-yl)-3-(2-hydroxyethyl)urea

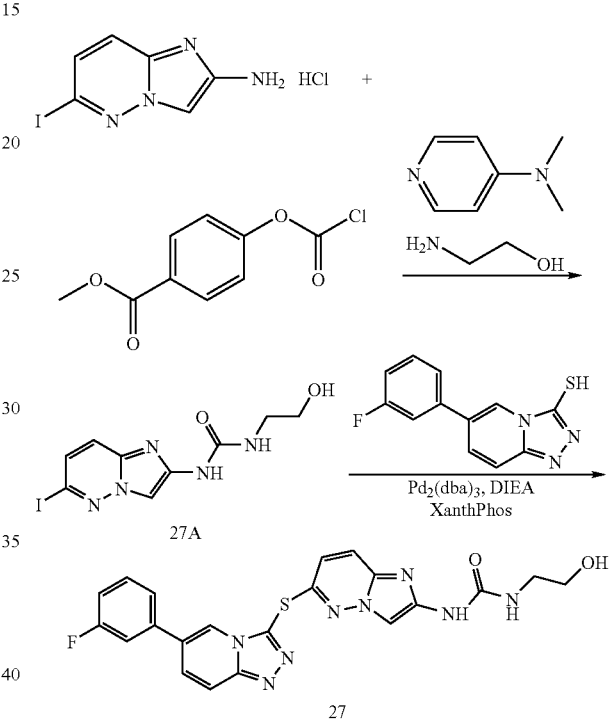

1-(2-Hydroxyethyl)-3-(6-iodoimidazo[1,2-b]pyridazin-2-yl)urea: To a solution of 6-iodoimidazo[1,2-b]pyridazin-2-amine hydrochloride (250 mg, 0.843 mmol) and DMAP (227 mg, 1.855 mmol) in DCM (Volume: 5.0 mL) was added methyl 4-(chlorocarbonyloxy)benzoate (199 mg, 0.927 mmol) at 25° C. The reaction was stirred at 25° C. for 1 hr to provide a dark green heterogeneous mixture which was filtered. The solid was resuspended in DCM (Volume: 5.0 mL), treated with ethanolamine (2M in MeOH, 0.843 mL, 1.686 mmol) at room temperature, and then stirred for an additional 1 hr. The reaction was then evaporated to dryness via rotary evaporation, and the resulting residue was suspended in EtOAc (Volume: 10.0 mL). The mixture was filtered, and the resulting black solid was dried under high vacuum and used without further purification.

1-(6-(6-(3-Fluorophenyl)-[1,2,4]triazolo[4,3-a]pyridin-3-ylthio)imidazo[1,2-b]pyridazin-2-yl)-3-(2-hydroxyethyl)urea: A mixture of 1-(2-hydroxyethyl)-3-(6-iodoimidazo[1,2-b]pyridazin-2-yl)urea (125 mg, 0.360 mmol), 6-(3-fluorophenyl)-[1,2,4]triazolo[4,3-a]pyridine-3-thiol (88 mg, 0.360 mmol), Pd$_2$(dba)$_3$ (19.79 mg, 0.22 mmol), XANT-PHOS (25.00 mg, 0.043 mmol), and DIEA (0.126 mL, 0.720 mmol) in DME (Volume: 2.0 mL) was heated in the microwave on high absorbance for 30 min at 120° C. The reaction mixture was then concentrated to dryness via rotary evaporation. The resulting crude material was reconstituted in DMSO (Volume: 1.0 mL) and purified via preparative mass trigger LCMS using a gradient eluant of 20-45% ACN:0.05% TFA (aq). The collected fractions were combined and the ACN was removed via rotary evaporation. The resulting mixture was lyophilized and reconstituted in water:ACN (1:10, 5.0 mL) Two drops of [HCl] were added and the resulting solution was lyophilized to provide the HCl salt of the title compound (20 mg, 0.043 mmol, 11.96% yield) as a brown solid. $^1$H NMR (400 MHz, DMSO-$d_6$) δ ppm 3.14 (q, J=5.47 Hz, 2 H), 341 (m, 2 H), 6.61 (br. s., 1 H) 6.97-7.07 (m, 2 H) 7.21-7.32 (m, 1 H) 7.53 (td, J=7.96, 6.06 Hz, 1 H) 7.62 (d, J=8.34 Hz, 1 H) 7.65-7.72 (m, 1 H) 7.83 (d, J=9.35 Hz, 1 H) 7.99 (dd, J=9.60, 1.77 Hz, 1 H) 8.11 (dd, J=9.60, 1.01 Hz, 1 H) 8.69-8.93 (m, 1 H) 9.17 (s, 1H). ESI-MS:m/z 465.3 (M+H)$^+$.

Compound 28: 2-chloro-4-(3-(2-(cyclopropanecarboxamido)imidazo[1,2-b]pyridazin-6-ylthio)-[1,2,4]triazolo[4,3-a]pyridin-6-yl)-N-methylbenzamide

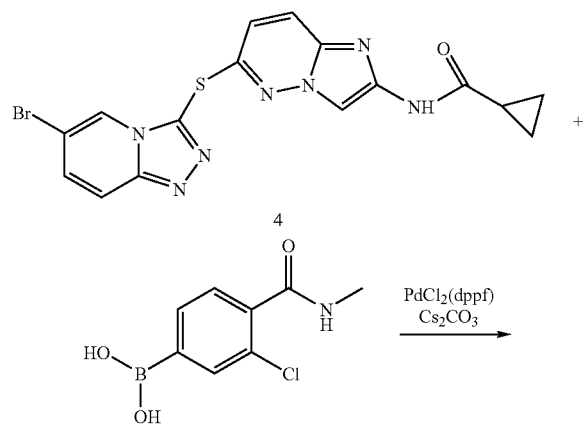

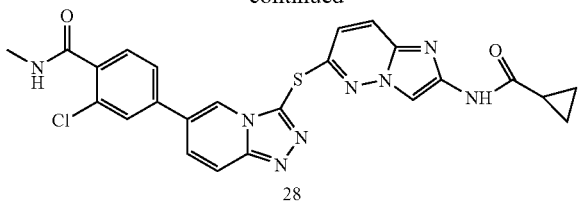

A mixture of N-(6-(6-bromo-[1,2,4]triazolo[4,3-a]pyridin-3-ylthio)imidazo[1,2-b]pyridazin-2-yl)cyclopropanecarboxamide (150 mg, 0.349 mmol), 3-chloro-4-(methylcarbamoyl)phenylboronic acid (112 mg, 0.523 mmol), PdCl$_2$(dppf) (12.75 mg, 0.017 mmol), and cesium carbonate (0.349 mL, 1.046 mmol) in DME (Volume: 1.0 mL) was heated in a microwave on high absorbance for 1 hr at 100° C. The reaction mixture was then concentrated to dryness via rotary evaporation. The resulting crude material was reconstituted in DMSO (Volume: 1.0 mL) and purified via preparative mass trigger LCMS using a gradient eluant of 20-45% ACN:0.05% TFA (aq). The collected fractions were combined and the ACN was removed via rotary evaporation. The resulting mixture was lyophilized to provide the TFA salt of the titled compound (6.0 mg, 0.012 mmol, 3.32% yield) as a pale yellow solid. $^1$H NMR (400 MHz, DMSO-$d_6$) δ ppm 0.69-0.85 (m, 4 H) 1.81-1.96 (m, 1 H) 2.75 (d, J=4.55 Hz, 3 H) 7.07 (d, J=9.60 Hz, 1 H) 7.51 (d, J=8.08 Hz, 1 H) 7.79 (dd, J=7.83, 1.77 Hz, 1 H) 7.87-7.97 (m, 3 H) 8.00 (dd, J=9.60, 1.77 Hz, 1 H) 8.11 (dd, J=9.60, 1.01 Hz, 1 H) 8.39 (d, J=4.80 Hz, 1 H) 8.86 (d, J=1.52 Hz, 1 H) 11.15 (s, 1 H). ESI-MS:m/z 419.2 (M+H)$^+$.

Compound 29: N-(6-(6-(1-((2-methoxyethoxy)methyl)-1H-pyrazol-4-yl)-[1,2,4]triazolo[4,3-a]pyridin-3-ylthio)imidazo[1,2-b]pyridazin-2-yl)cyclopropanecarboxamide

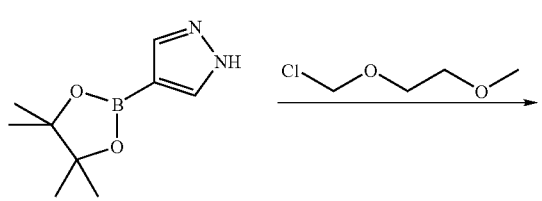

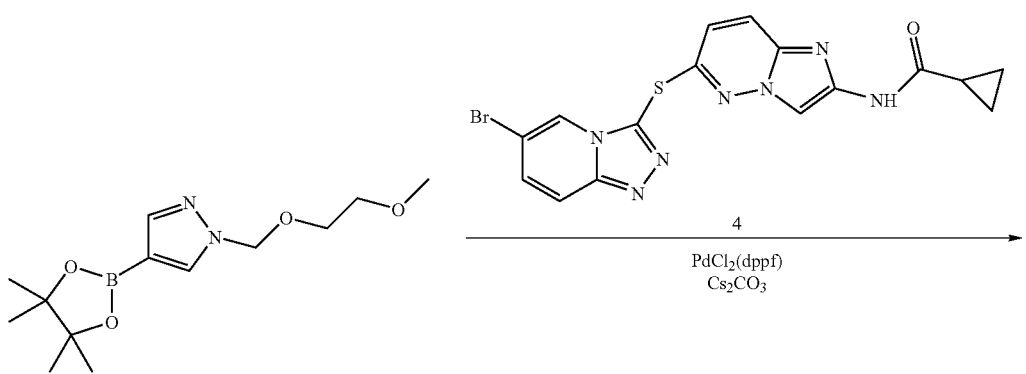

-continued

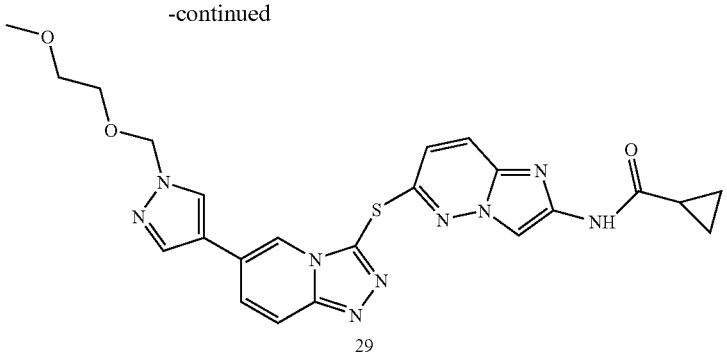

29

A solution of 4-(4,4,5,5-tetramethyl-1,3,2-dioxaborolan-2-yl)-1H-pyrazole (0.8 g, 4.1 mmol), cesium carbonate (2.0 g, 6.2 mmol), and 1-(chloromethoxy)-2-methoxyethane (0.59 mL, 5.2 mmol) in DMF (14 mL) was heated in a microwave at 90° C. for 1 hr. After the initial heating, additional 1-(chloromethoxy)-2-methoxyethane (0.59 mL) and cesium carbonate (2 g) was added. Heating was repeated for an additional 1 hr. The crude reaction mixtures were then diluted with water (250 mL) and extracted with ethyl acetate (3×50 mL). The title compound was purified by silica gel column using DCM/EtOAc/MeOH (8/1.5/0.5) as eluent to give 1-(2-methoxyethyl)-4-(4,4,5,5-tetramethyl-1,3,2-dioxaborolan-2-yl)-1H-pyrazole (1.6 g) as a light yellow oil. ESI-MS:m/z 283.2 (M+H)⁺.

A mixture of N-(6-(6-bromo-[1,2,4]triazolo[4,3-a]pyridin-3-ylthio)imidazo[1,2-b]pyridazin-2-yl)cyclopropanecarboxamide (100 mg, 0.232 mmol), 1-((2-methoxyethoxy)methyl)-4-(4,4,5,5-tetramethyl-1,3,2-dioxaborolan-2-yl)-1H-pyrazole (328 mg, 1.162 mmol), pdcl2(dppf) (8.50 mg, 0.012 mmol), and cesium carbonate (0.232 mL, 0.697 mmol) in Dioxane (Volume: 1.0 mL) was heated in a microwave on high absorbance for 1 hr at 100° C. The reaction mixture was then concentrated to dryness via rotary evaporation. The resulting crude material was reconstituted in DMSO (Volume: 1.0 mL) and purified via preparative mass trigger LCMS using a gradient eluant of 15-40% ACN:0.05% TFA (aq). The collected fractions were combined and the ACN was removed via rotary evaporation. The resulting mixture was lyophilized to provide the TFA salt of the title compound (8.0 mg, 0.016 mmol, 6.81% yield) as a pale yellow solid. ¹H NMR (400 MHz, DMSO-d₆) δ ppm 0.72-0.78 (m, 4 H) 1.90 (m, 1 H) 3.20 (m, 3 H) 3.38-3.42 (m, 2 H) 3.54-3.58 (m, 2 H) 7.00 (m, 1 H) 7.67 (m, 1 H) 7.91-7.96 (m, 3 H) 8.04 (m, 1 H) 8.59 (m, 1 H), 8.76 (m, 1 H) 11.16 (s, 1 H). ESI-MS:m/z 506.3 (M+H)⁺.

Compound 30: N-(6-(6-(1-(2-(dimethylamino)-2-oxoethyl)-1H-pyrazol-4-yl)-[1,2,4]triazolo[4,3-a]pyridin-3-ylthio)imidazo[1,2-b]pyridazin-2-yl)cyclopropanecarboxamide

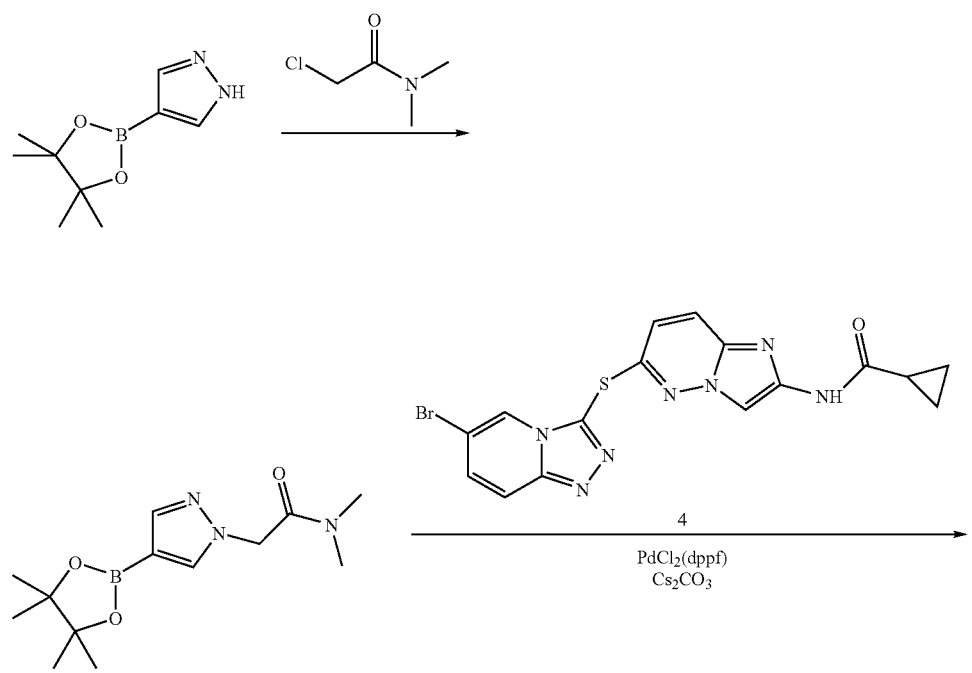

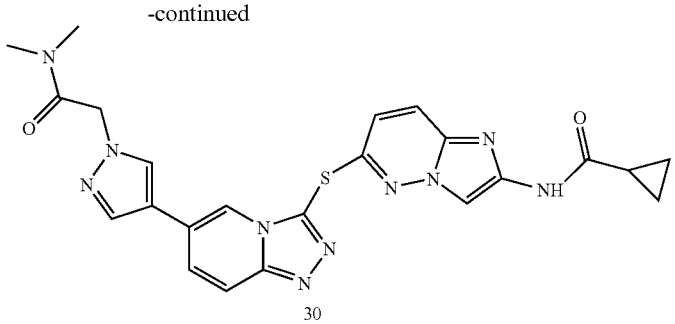

A solution of 4-(4,4,5,5-tetramethyl-1,3,2-dioxaborolan-2-yl)-1H-pyrazole (0.8 g, 4.1 mmol), cesium carbonate (2.0 g, 6.2 mmol), and 2-chloro-N,N-dimethylacetamide (0.47 mL, 4.5 mmol) in DMF (14 mL) was heated in a microwave at 90° C. for 1 hr. The crude reaction mixtures were then diluted with water (300 mL) and extracted with ethyl acetate (3×50 mL). Product was purified by silica gel column using DCM/EtOAc/MeOH (8/1.5/0.5) as eluent to provide N,N-dimethyl-2-(4-(4,4,5,5-tetramethyl-1,3,2-dioxaborolan-2-yl)-1H-pyrazol-1-yl)acetamide (1.3 g) as a light yellow oil. ESI-MS:m/z 280.3 (M+H)$^+$.

A mixture of N-(6-(6-bromo-[1,2,4]triazolo[4,3-a]pyridin-3-ylthio)imidazo[1,2-b]pyridazin-2-yl)cyclopropanecarboxamide (100 mg, 0.232 mmol), N,N-dimethyl-2-(4-(4,4,5,5-tetramethyl-1,3,2-dioxaborolan-2-yl)-1H-pyrazol-1-yl)acetamide (324 mg, 1.162 mmol), pdcl2(dppf) (8.50 mg, 0.012 mmol), and cesium carbonate (0.232 mL, 0.697 mmol) in Dioxane (Volume: 1.0 mL) was heated in a microwave on high absorbance for 1 hr at 100° C. The reaction mixture was then concentrated to dryness via rotary evaporation. The resulting crude material was reconstituted in DMSO (Volume: 1.0 mL) and purified via preparative mass trigger LCMS using a gradient eluant of 15-40% ACN:0.05% TFA (aq). The collected fractions were combined and the ACN was removed via rotary evaporation. The resulting mixture was lyophilized to provide the TFA salt of the title compound (4.8 mg, 9.55 µmol, 4.11% yield) as a yellow solid. $^1$H NMR (400 MHz, DMSO-d$_6$) δ ppm 0.79 (d, J=6.06 Hz, 4 H) 1.90 (d, J=6.57 Hz, 1 H) 2.84 (s, 3 H) 3.03 (s, 3 H) 5.12 (s, 2 H) 7.00 (d, J=9.35 Hz, 1 H) 7.87-7.97 (m, 3 H) 8.01-8.08 (m, 2 H) 8.31 (s, 1 H) 8.71 (s, 1 H) 11.16 (s, 1 H). ESI-MS:m/z 503.3 (M+H)$^+$.

Compound 31: N-(6-(6-(1-(2-methoxyethyl)-1H-pyrazol-4-yl)-[1,2,4]triazolo[4,3-a]pyridin-3-ylthio)imidazo[1,2-b]pyridazin-2-yl)cyclopropanecarboxamide

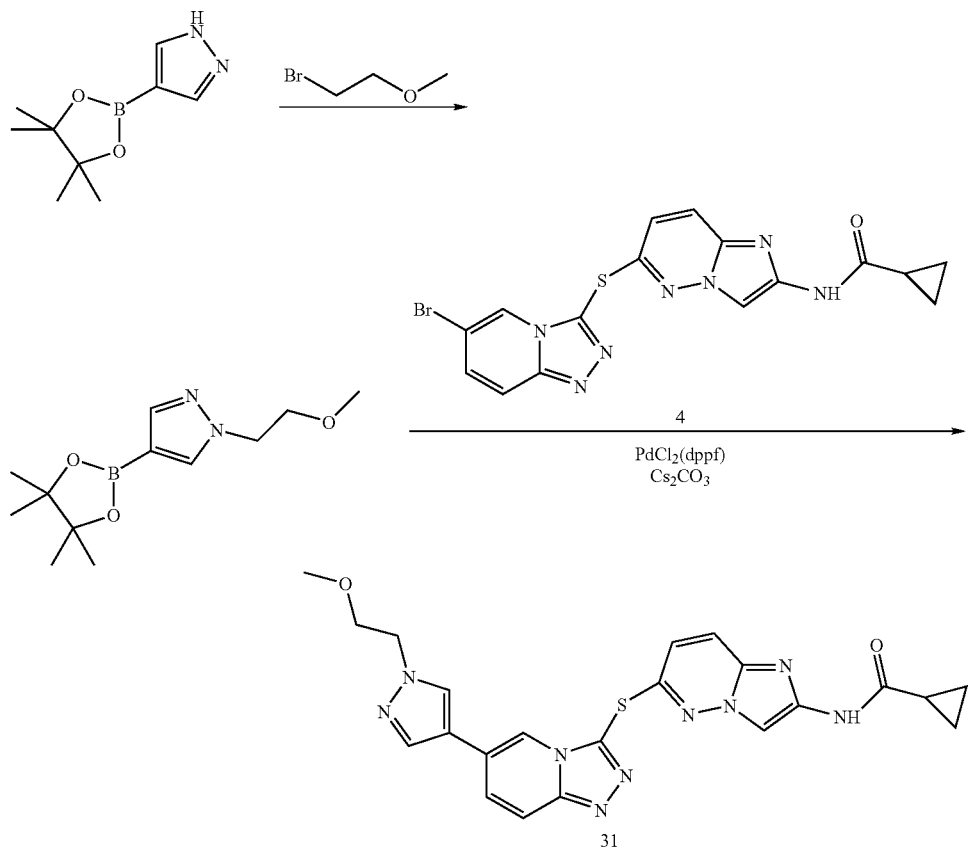

A solution of 4-(4,4,5,5-tetramethyl-1,3,2-dioxaborolan-2-yl)-1H-pyrazole (0.8 g, 4.1 mmol), cesium carbonate (2.0 g, 6.2 mmol), and 1-bromo-2-methoxyethane (0.41 mL, 4.3 mmol) in DMF (14 mL) was heated in a microwave at 90° C. for 1 hr. After the initial heating, additional 1-bromo-2-methoxyethane (0.41 mL) was added to the reaction. Heating was repeated for an additional 1 hr. The crude reaction mixtures were then diluted with water (250 mL) and extracted with ethyl acetate (3×50 mL). Product was purified by silica gel column using DCM/EtOAc/MeOH (8/1.5/0.5) as eluent to give 1-(2-methoxyethyl)-4-(4,4,5,5-tetramethyl-1,3,2-dioxaborolan-2-yl)-1H-pyrazole (1.2 g) as a light yellow oil. ESI-MS:m/z 253.2 (M+H)$^+$.

A mixture of N-(6-(6-bromo-[1,2,4]triazolo[4,3-a]pyridin-3-ylthio)imidazo[1,2-b]pyridazin-2-yl)cyclopropanecarboxamide (100 mg, 0.232 mmol), 1-(2-methoxyethyl)-4-(4,4,5,5-tetramethyl-1,3,2-dioxaborolan-2-yl)-1H-pyrazole (410 mg, 1.627 mmol), pdcl2(dppf) (8.50 mg, 0.012 mmol), and cesium carbonate (0.232 mL, 0.697 mmol) in Dioxane (Volume: 1.0 mL) was heated in a microwave on high absorbance for 1 hr at 100° C. The reaction mixture was then concentrated to dryness via rotary evaporation. The resulting crude material was reconstituted in DMSO (Volume: 1.0 mL) and purified via preparative mass trigger LCMS using a gradient eluant of 15-40% ACN:0.05% TFA (aq). The collected fractions were combined and the ACN was removed via rotary evaporation. The resulting mixture was lyophilized to provide the TFA salt of the title compound (6.0 mg, 0.013 mmol, 5.43% yield) as a yellow solid. $^1$H NMR (400 MHz, DMSO-d$_6$) δ ppm 0.69-0.86 (m, 4 H) 1.90 (m, 1 H) 3.20 (m, 3 H) 3.63-3.70 (m, 2 H) 4.22-4.27 (m, 2 H) 7.00 (m, 1 H) 7.57 (m, 1 H) 7.86-7.95 (m, 3 H) 8.04 (m, 1 H) 8.08 (m, 1 H) 8.37 (m, 1 H), 11.16 (s, 1 H). ESI-MS:m/z 476.3 (M+H)$^+$.

Compound 32: N-(6-(6-(1-(2-hydroxyoxyethyl)-1H-pyrazol-4-yl)-[1,2,4]triazolo[4,3-a]pyridin-3-ylthio)imidazo[1,2-b]pyridazin-2-yl)cyclopropanecarboxamide

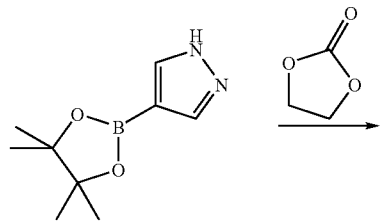

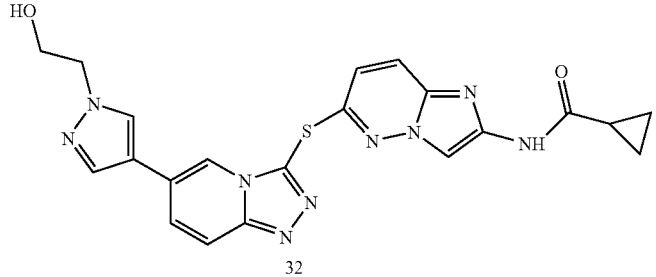

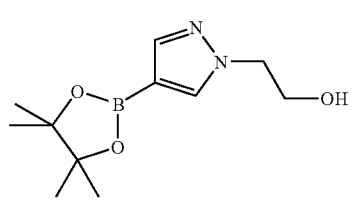

2-(4-(4,4,5,5-tetramethyl-1,3,2-dioxaborolan-2-yl)-1H-pyrazol-1-yl)ethanol was synthesized according to the procedure in PCT Publication No. WO 2008/44022, which is incorporated herein in its entirety. Specifically, 4-(4,4,5,5-tetramethyl-1,3,2-dioxaborolan-2-yl)-1H-pyrazole (5.0 g, 25.8 mmol), 1,3-dioxolan-2-one (2.5 g, 28.3 mmol), and sodium hydroxide (pellets, 1.0 g, 25.8 mmol) were dissolved in DMF (206 mL). The reaction mixture was heated to reflux for 2 hours. Activated charcoal was added after reaction was cooled to ambient temperature and the reaction was stirred for 1 hr and then filtered through Celite. The filter cake was then rinsed with DMF (120 mL), and the filtrate was concentrated to provide 2-(4-(4,4,5,5-tetramethyl-1,3,2-dioxaborolan-2-yl)-1H-pyrazol-1-yl)ethanol as a yellow oil (6 g). The resulting material was used without further purification. ESI-MS: m/z 239.3 (M+H)$^+$.

A mixture of N-(6-(6-bromo-[1,2,4]triazolo[4,3-a]pyridin-3-ylthio)imidazo[1,2-b]pyridazin-2-yl)cyclopropanecarboxamide (500 mg, 1.2 mmol), 2-(4-(4,4,5,5-tetram ethyl-1,3,2-dioxaborolan-2-yl)-1H-pyrazol-1-yl)ethanol (1.4 g, 5.8 mmol), cesium carbonate (1.14 mL, 3 M solution), and [1,1'-bis(diphenylphosphino)ferrocene]-dichloropalladium(II) (85 mg, 0.12 mmol) in DME (5 mL) was heated in a microwave for 30 min at 100° C. The reaction mixture was then concentrated to dryness via rotary evaporation. The resulting crude material was reconstituted in DMSO (Volume: 1.0 mL) and purified via preparative mass trigger LCMS using a gradient eluant of 10-35% ACN:0.05% TFA (aq). The collected fractions were combined and the ACN was removed via rotary evaporation. The resulting mixture was lyophilized and reconstituted in water:ACN (1:10, 5.0 mL) Two drops of concentrated HCl were added and the resulting solution was lyophilized to provide the HCl salt of the title compound $^1$H NMR (400 MHz, DMSO-$d_6$) δ ppm 11.16 (s, 1 H) 8.69 (s, 1 H) 8.38 (s, 1 H) 8.04-8.08 (m, 1 H) 8.02 (d, J=1.01 Hz, 1 H) 7.91-7.95 (m, 1 H) 7.88-7.91 (m, 2 H) 6.99-7.05 (m, 1 H) 4.10-4.16 (m, 2 H) 3.73 (t, J=5.56 Hz, 2 H) 1.90 (quin, J=6.19 Hz, 1 H) 0.74-0.84 (m, 4 H) ESI-MS:m/z 462.3 (M+H)$^+$. MP 182-184° C.

Compound 33: 3-(2-(cyclopropanecarboxamido)imidazo[1,2-b]pyridazin-6-ylthio)-[1,2,4]triazolo[4,3-a]pyridine-6-carboxylic acid

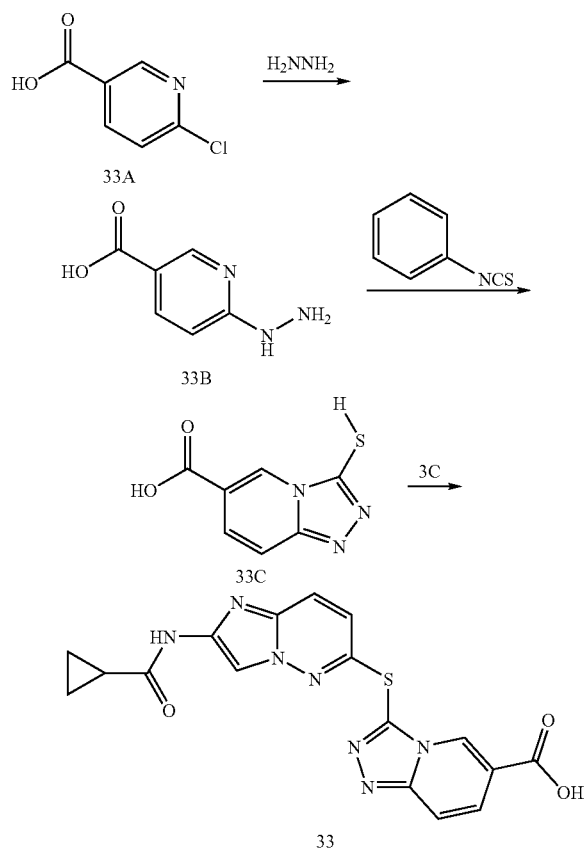

3-Mercapto-[1,2,4]triazolo[4,3-a]pyridine-6-carboxylic acid: 6-chloronicotinic acid (1.6 g ) in MeOH (10 mL) was treated with NH$_2$NH$_2$ (2 g) at 140° C. for 2 h. After cooling to −20° C., the solid was filtered to give 560 mg of compound 33B. Compound 33B was treated with isothiocyanatobenzene (141 mg) in 1,2-dichlorobenzene (5 mL) at 100° C. for 10 min, and then 180° C. for 1 h. The product was purified by LCMS to give 3-mercapto-[1,2,4]triazolo[4,3-a]pyridine-6-carboxylic acid (450 mg). ESI-MS:m/z 196.1 (M+H)$^+$.

3-(2-(Cyclopropanecarboxamido)imidazo[1,2-b]pyridazin-6-ylthio)-[1,2,4]triazolo[4,3-a]pyridine-6-carboxylic acid: Compound 33 was prepared from 3-mercapto-[1,2,4]triazolo[4,3-a]pyridine-6-carboxylic acid following the procedure described in the synthesis of compound 4. $^1$H NMR (400 MHz, CDCl$_3$—CD$_3$OD 10:1) δ ppm 9.03 (bs, 1 H), 8.01 (d, J=9.1 Hz, 1 H), 7.87 (d, J=9.6 Hz, 1 H), 7.68 (d, J=9.4 Hz, 1H), 7.36 (m, 1H), 7.09 (d, J=9.3 Hz, 1 H), 2.84 (m, 1 H), 1.72 (m, 1 H), 0.97 (m, 2 H), 0.84 (m, 2H) ESI-MS:m/z 396.1 (M+H)$^+$.

Compound 34: 3-(2-(cyclopropanecarboxamido)imidazo[1,2-b]pyridazin-6-ylthio)-N-cyclopropyl-[1,2,4]triazolo[4,3-a]pyridine-6-carboxamide

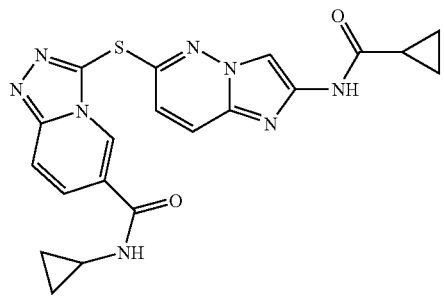

To a solution of compound 33 (10 mg), cyclopropanamine (30 mg) and DIEPA (100 uL) in DMF (1 mL) was added HATU (20 mg). The mixture was stirred at rt for 0.5 h and 60° C. for 5 h. The title compound was isolated by preparative LCMS. $^1$H NMR (400 MHz, CDCl$_3$—CD$_3$OD 10:1) δ ppm 8.95 (bs, 1 H), 8.06 (dd, J=9.4, 1.6 Hz, 1 H), 7.98 (dd, J=9.6, 1.0 Hz, 1 H), 7.93 (s, 1 H), 7.87 (d, J=9.4 Hz, 1 H), 7.29 (d, J=9.3 Hz, 1 H), 1.77 (m, 1 H), 1.04 (m, 1 H), 0.95 (m, 2H). 0.89 (m, 2H). 0.80 (m, 2H). 0.63 (m, 2H). ESI-MS:m/z 435.1 (M+H)$^+$.

Compound 35: 3-(2-(cyclopropanecarboxamido)imidazo[1,2-b]pyridazin-6-ylthio)-N-isobutyl-[1,2,4]triazolo[4,3-a]pyridine-6-carboxamide

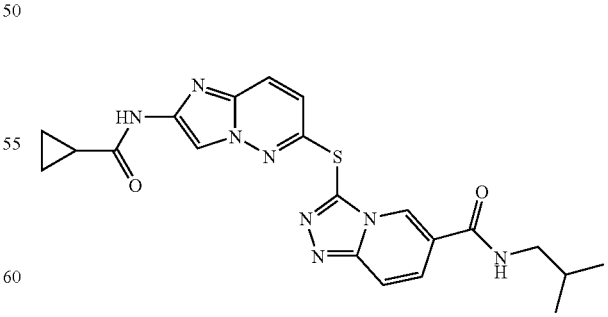

Compound 35 was prepared from 2-methylpropan-1-amine following the procedure described in the synthesis of compound 34. $^1$H NMR (400 MHz, CD$_3$OD) δ ppm 8.88 (bs, 1 H), 8.72 (bs, 1 H), 7.95-7.88 (m, 3H), 7.15 (bs, 1 H), 3.08 (t, J=6.0 Hz, 2H), 1.78 (m, 1H), 1.3-1.15 (m, 3H), 0.85 (m, 2H), 0.82 (d, J=6.8 Hz, 6H) ESI-MS:m/z 451.1 (M+H)⁺.

Compound 36: N-(6-(6-(4-(piperazin-1-yl)phenyl)-[1,2,4]triazolo[4,3-a]pyridin-3-ylthio)imidazo[1,2-b]pyridazin-2-yl)cyclopropanecarboxamide

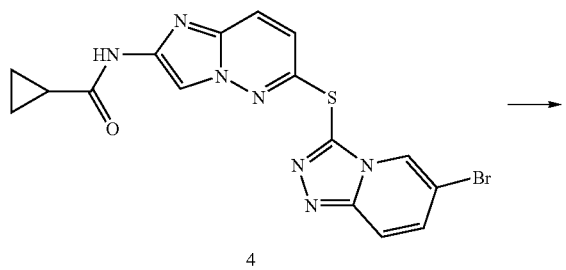

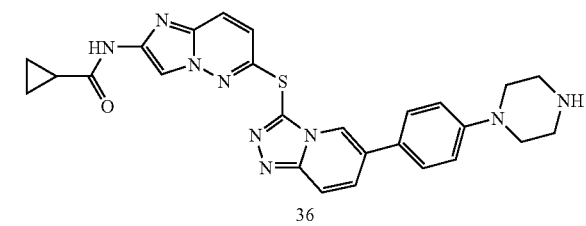

Compound 36 was prepared from N-(6-(6-bromo-[1,2,4]triazolo[4,3-a]pyridin-3-ylthio)imidazo[1,2-b]pyridazin-2-yl)cyclopropanecarboxamide and tert-butyl 4-(4-(4,4,5,5-tetramethyl-1,3,2-dioxaborolan-2-yl)phenyl)piperazine-1-carboxylate following an analogous procedure to that described in connection with the synthesis of compound 5. The crude product was treated with 4 M HCl-dioxane at 80° C. for 1 h. Purification of the mixture by LCMS gave the title compound as a TFA salt. ¹H NMR (400 MHz, CD₃OD) δ ppm 8.61 (bs, 1 H), 7.92-8.0 (m, 2H), 7.8 (bs, 1 H), 7.6 (m, 1H), 7.57, (d, J=8.9 Hz, 2H), 7.21 (bs, 1H), 7.08, (d, J=8.8 Hz, 2H), 3.47 (m, 4H), 3.36 (m, 4H), 1.82 (m, 1H), 1.3-1.15 (m, 2H), 0.85 (m, 2H). ESI-MS:m/z 512.2 (M+H)⁺.

Compound 37: N-(6-(6-(3-hydroxyprop-1-ynyl)-[1,2,4]triazolo[4,3-a]pyridin-3-ylthio)imidazo[1,2-b]pyridazin-2-yl)cyclopropanecarboxamide

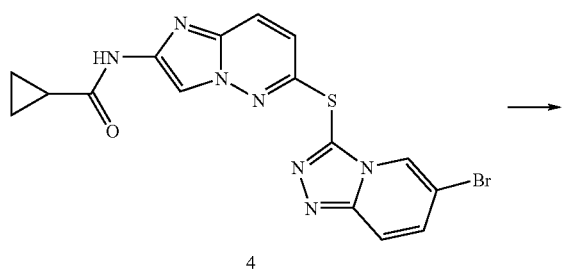

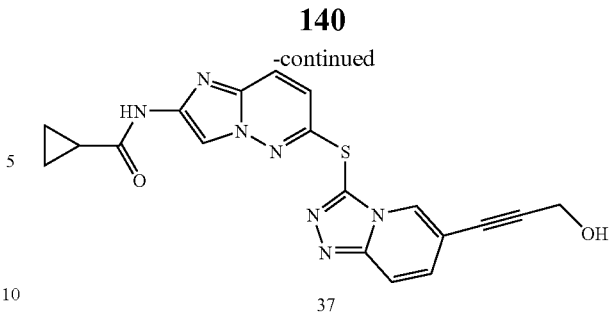

A mixture of N-(6-(6-bromo-[1,2,4]triazolo[4,3-a]pyridin-3-ylthio)imidazo[1,2-b]pyridazin-2-yl)cyclopropanecarboxamide (43 mg), prop-2-yn-1-ol (10 mg), Ph₃P (1.1 mg) and tetrakis(triphenylphosphine)palladium(0) (i.e., Pd[P(C₆H₅)₃]₄) (4 mg) in THF (1.5 mL), was stirred at rt for 10 min under N₂, and then CuI (1 mg) was added. The mixture was heated at 60° C. overnight. Purification of the mixture by LCMS gave the title compound as a TFA salt. ¹H NMR (400 MHz, DMSO) δ ppm 11.16 (s, 1H), 8.67 (t, J=1.0 Hz, 1H), 8.00 (dd, J=9.4 and 1.0 Hz, 1 H), 7.93 (dd, J=9.3 and 0.7 Hz, 1 H), 7.91 (s, 1H), 7.53 (dd, J=9.4 and 1.5 Hz, 1 H), 7.12 (d, J=9.4 Hz, 1 H), 1.91 (m, 1 H), 1.24 (m, 2 H), 0.80 (m, 2H). ESI-MS:m/z 406.2 (M+H)⁺.

Compound 38: N-(6-(6-(2H-tetrazol-5-yl)-[1,2,4]triazolo[4,3-a]pyridin-3-ylthio)imidazo[1,2-b]pyridazin-2-yl)cyclopropanecarboxamide

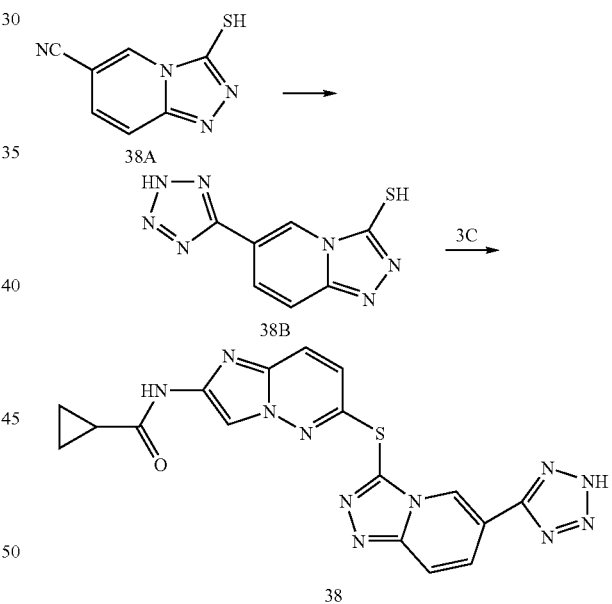

6-(2H-tetrazol-5-yl)-[1,2,4]triazolo[4,3-a]pyridine-3-thiol: A mixture of 3-mercapto-[1,2,4]triazolo[4,3-a]pyridine-6-carbonitrile (360 mg, 2 mmol), NaN₃ and NH₄Cl in DMF (10 mL) was heated at 140° C. for 10 h under microwave condition. The product was purified by LCMS to give compound 38B (320 mg). ESI-MS:m/z 220.1 (M+H)⁺.

3-(2-(cyclopropanecarboxamido)imidazo[1,2-b]pyridazin-6-ylthio)-N-isobutyl-[1,2,4]triazolo[4,3-a]pyridine-6-carboxamide: Compound 38 was prepared from compound 38B following the procedure described in the synthesis of compound 4. ¹H NMR (400 MHz, DMSO) δ ppm 11.16 (s, 1H), 9.14 (t, J=1.5 Hz, 1H), 8.22 (dd, J=9.6 and 1.0 Hz, 1 H), 8.14 (dd, J=9.6 and 0.7 Hz, 1 H), 7.95 (s, 1H), 7.94 (d, J=9.4 Hz, 1 H), 7.18 (d, J=9.6 Hz, 1 H), 1.90 (m, 1H), 0.78 (bd, J=5.8 Hz, 2H). ESI-MS:m/z 419.1 (M+H)⁺.

Compound 39: N-(6-(6-(5-(methoxymethyl)-1,2,4-oxadiazol-3-yl)-[1,2,4]triazolo[4,3-a]pyridin-3-ylthio)imidazo[1,2-b]pyridazin-2-yl)cyclopropanecarboxamide

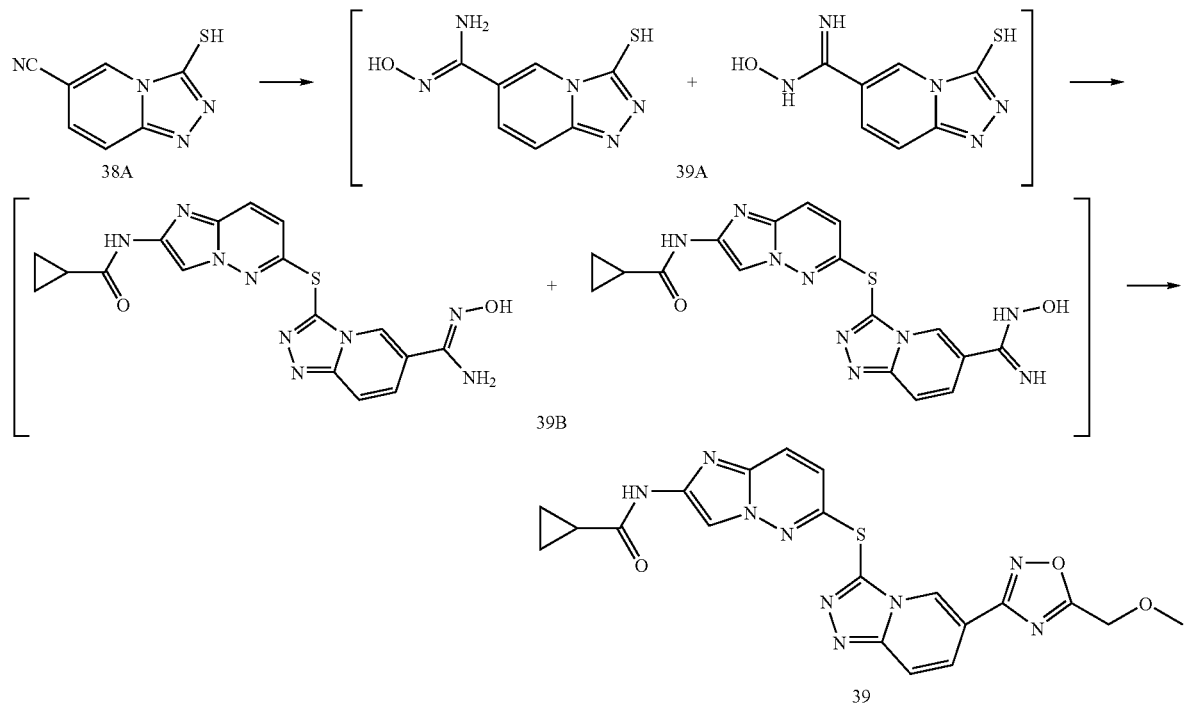

(Z)—N-hydroxy-3-mercapto-[1,2,4]triazolo[4,3-a]pyridine-6-carboximidamide: A mixture of 3-mercapto-[1,2,4]triazolo[4,3-a]pyridine-6-carbonitrile (390 mg, 2 mmol) and hydroxylamine (50% wt in water, 420 mg) in EtOH (4 mL) was heated at 120° C. for 10 h under microwave condition. The product was purified by LCMS to give compound 39A and its tautomer (128 mg). ESI-MS:m/z 210.0 (M+H)$^+$.

(Z)—N-(6-(6-(N'-hydroxycarbamimidoyl)-[1,2,4]triazolo[4,3-a]pyridin-3-ylthio)imidazo[1,2-b]pyridazin-2-yl)cyclopropanecarboxamide: Compound 39B and its tautomer were prepared from compound 39A and its tautomer following the procedure described in the synthesis of compound 4. ESI-MS:m/z 410.1 (M+H)$^+$.

N-(6-(6-(5-(methoxymethyl)-1,2,4-oxadiazol-3-yl)-[1,2,4]triazolo[4,3-a]pyridin-3-ylthio)imidazo[1,2-b]pyridazin-2-yl)cyclopropanecarboxamide: To a cooled (−10° C.) mixture of compound 39B (30 mg) and DIEPA (200 mL) in THF-DME (1-1, 1.5 mL) was added a solution of 2-methoxyacetyl chloride (11 mg) in THF (0.5 mL). The mixture was stirred at this temperature for 5 min, and then rt for 1 h. The mixture was heated at 140° C. under microwave condition for 30 min, and purified by LCMS to give the title compound as a TFA salt. $^1$H NMR (400 MHz, DMSO) δ ppm 11.49 (s, 1H), 9.09 (bs, 1H), 8.19 (dd, J=9.6 and 1.6 Hz, 1 H), 8.11-8.12 (m, 2H), 7.92 (d, J=9.3 Hz, 1 H), 7.37 (d, J=9.4 Hz, 1 H), 4.77 (s, 1 H), 3.56 (s, 3H), 1.77 (m, 1 H), 1.06 (m, 2H), 0.93 (m, 2H). ESI-MS:m/z 463.1 (M+H)$^+$.

Compound 40: N-(6-(6-(2-hydroxypropan-2-yl)-[1,2,4]triazolo[4,3-a]pyridin-3-ylthio)imidazo[1,2-b]pyridazin-2-yl)cyclopropanecarboxamide

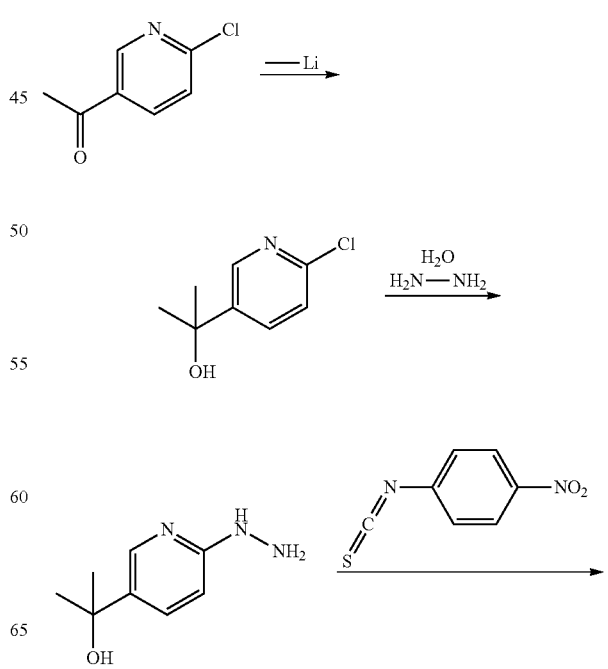

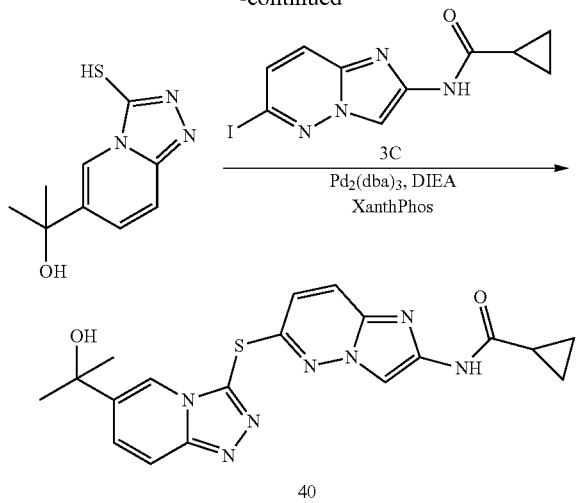

2-(6-Chloropyridin-3-yl)propan-2-ol: To a solution of 1-(6-chloropyridin-3-yl)ethanone (2.0 g, 12.85 mmol) in THF (Volume: 25 mL) was added methyllithium (16.07 mL, 25.7 mmol) at 0° C. The reaction was stirred for 1 hr and allowed to warm to room temperature. The resulting deep red solution was quenched with water (Volume: 50 mL), extracted with EtOAc (1×50 mL), and the organic layer was dried over MgSO$_4$. The organic phase was filtered and the filtrate was evaporated to dryness via rotary evaporation. The resulting material was purified via MPLC (DCM:MeOH, 95:5) to provide 2-(6-chloropyridin-3-yl)propan-2-ol (0.985 g, 5.74 mmol, 44.6% yield) as a dark red solid. $^1$H NMR (400 MHz, DMSO-d$_6$) δ ppm 1.44 (s, 5 H) 5.32 (s, 1 H) 7.44 (d, J=8.34 Hz, 1 H) 7.90 (dd, J=8.34, 2.53 Hz, 1 H) 8.49 (d, J=2.53 Hz, 1 H). ESI-MS:m/z 172.0 (M+H)$^+$.

2-(6-Hydrazinylpyridin-3-yl)propan-2-ol: A mixture of 2-(6-chloropyridin-3-yl)propan-2-ol (975 mg, 5.68 mmol), and hydrazine hydrate (5512 μl, 114 mmol) was heated in a microwave on high absorbance for 10 hr at 110° C. The mixture was cooled to room temperature and the hydrazine was removed via rotary evaporation. The resulting yellow residue was used without further work-up.

2-(3-Mercapto-[1,2,4]triazolo[4,3-a]pyridin-6-yl)propan-2-ol: A mixture of 2-(6-hydrazinylpyridin-3-yl)propan-2-ol (250 mg, 1.495 mmol) and 1-isothiocyanato-4-nitrobenzene (269 mg, 1.495 mmol) in ACN (Volume: 2.0 mL) was stirred at room temperature for 1 hr. The reaction was diluted with Et$_2$O (Volume: 5.0 mL), and the resulting solid was filtered. Minimal product was present in the solid. On standing for 1 hr, the filtrate had formed a precipitate. This was filtered to provide 2-(5-(2-hydroxypropan-2-yl)pyridin-2-yl)-N-(4-nitrophenyl)hydrazinecarbothioamide (175 mg, 0.504 mmol, 33.7% yield) as an orange solid. A solution of 2-(5-(2-hydroxypropan-2-yl)pyridin-2-yl)-N-(4-nitrophenyl)hydrazinecarbothioamide (275 mg, 0.792 mmol) in DME (Volume: 2.0 mL) was heated in a microwave on high absorbance for 3 hr at 110° C. The reaction was stripped to dryness onto silica gel via rotary evaporation and purified compound by MPLC with DCM:MeOH (98:2) to provide 2-(3-mercapto-[1,2,4]triazolo[4,3-a]pyridin-6-yl)propan-2-ol.

N-(6-(6-(2-hydroxypropan-2-yl)-[1,2,4]triazolo[4,3-a]pyridin-3-ylthio)imidazo[1,2-b]pyridazin-2-yl)cyclopropanecarboxamide: A mixture of N-(6-iodoimidazo[1,2-b]pyridazin-2-yl)cyclopropanecarboxamide (62.7 mg, 0.191 mmol), Pd$_2$(dba)$_3$ (10.50 mg, 0.011 mmol), XANTPHOS (13.27 mg, 0.023 mmol), DIEA (0.067 mL, 0.382 mmol), and 2-(3-mercapto-[1,2,4]triazolo[4,3-a]pyridin-6-yl)propan-2-ol (40 mg, 0.191 mmol) in DME (Volume: 1.5 mL) was heated in a microwave on high absorbance for 30 min at 120° C. The reaction mixture was then concentrated to dryness via rotary evaporation. The resulting crude material was reconstituted in DMSO (Volume: 1.0 mL) and purified via preparative mass trigger LCMS using a gradient eluant of 20-45% ACN:0.05% TFA (aq). The collected fractions were combined and the ACN was removed via rotary evaporation. The resulting mixture was lyophilized to provide the TFA salt of the title compound (3.3 mg, 8.06 μmol, 4.22% yield) as a brown solid. $^1$H NMR (400 MHz, DMSO-d$_6$) δ ppm 0.72-0.85 (m, 3H) 1.43 (s, 4 H) 1.91 (m, 1 H) 7.04 (d, J=9.35 Hz, 1 H) 7.70 (dd, J=9.60, 1.77 Hz, 1 H) 7.87-8.00 (m, 2 H) 8.32 (d, J=1.52 Hz, 1 H) 11.18 (s, 1 H). ESI-MS:m/z 410.3 (M+H)$^+$.

Compound 41: N-(6-(6-(trifluoromethyl)-[1,2,4]triazolo[4,3-a]pyridin-3-ylthio)imidazo[1,2-b]pyridazin-2-yl)cyclopropanecarboxamide

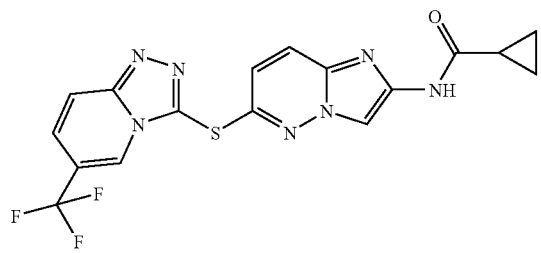

The title compound was prepared using an analogous procedure to that described in connection with compound 6. $^1$H NMR (400 MHz, DMSO-d$_6$) δ=11.16 (s, 1 H), 9.03 (d, J=1.3 Hz, 1 H), 8.25-8.17 (m, 1 H), 7.96-7.90 (m, 2 H), 7.83 (dd, J=1.5, 9.6 Hz, 1 H), 7.17 (d, J=9.6 Hz, 1 H), 1.91 (quin, J=6.3 Hz, 1 H), 0.84-0.76 (m, 4 H) ESI-MS:m/z 420.3 (M+H)$^+$.

Compound 42: N-(6-(6-methyl-[1,2,4]triazolo[4,3-a]pyridin-3-ylthio)imidazo[1,2-b]pyridazin-2-yl)cyclopropanecarboxamide

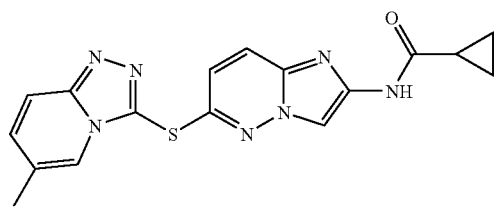

The title compound was prepared using an analogous procedure to that described in connection with compound 6. $^1$H NMR (400 MHz, DMSO-d$_6$) δ=11.17 (s, 1 H), 8.35 (d, J=1.3 Hz, 1 H), 7.96-7.87 (m, 3 H), 7.46 (dd, J=1.5, 9.3 Hz, 1 H), 7.00 (d, J=9.3 Hz, 1 H), 2.34-2.27 (m, 3 H), 1.95-1.86 (m, 1 H), 0.82-0.75 (m, 4 H) ESI-MS:m/z 366.3 (M+H)$^+$.

Compound 43: N-(6-(7-methyl-[1,2,4]triazolo[4,3-a]pyridin-3-ylthio)imidazo[1,2-b]pyridazin-2-yl)cyclopropanecarboxamide

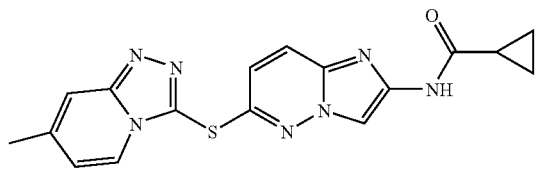

The title compound was prepared using an analogous procedure to that described in connection with compound 6. $^1$H NMR (400 MHz, DMSO-d$_6$) δ=11.17 (s, 1 H), 8.38 (d, J=7.1 Hz, 1 H), 7.96-7.88 (m, 2 H), 7.76 (d, J=1.3 Hz, 1 H), 7.06 (d, J=9.3 Hz, 1 H), 7.00 (dd, J=1.5, 7.1 Hz, 1 H), 2.44 (s, 3 H), 1.95-1.86 (m, 1 H), 0.83-0.73 (m, 4 H) ESI-MS:m/z 366.3 (M+H)$^+$.

Compound 44: N-(6-(6-(3-fluorophenyl)-[1,2,4]triazolo[4,3-a]pyridin-3-ylthio)imidazo[1,2-b]pyridazin-2-yl)cyclopropanecarboxamide

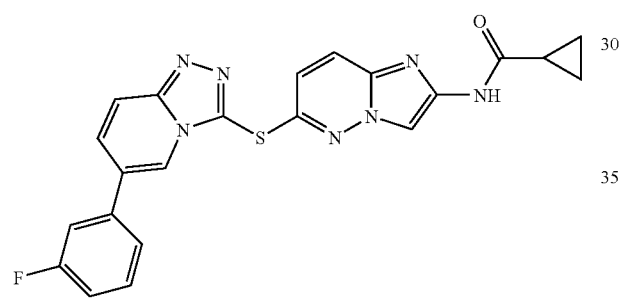

The title compound was prepared using an analogous procedure to that described in connection with compound 6. $^1$H NMR (400 MHz, DMSO-d$_6$) δ=11.15 (s, 1 H), 8.81 (d, J=1.5 Hz, 1 H), 8.11 (dd, J=1.0, 9.6 Hz, 1 H), 7.99 (dd, J=1.6, 9.5 Hz, 1 H), 7.95-7.89 (m, 1 H), 7.68 (dt, J=2.1, 10.4 Hz, 2 H), 7.62 (d, J=7.8 Hz, 1 H), 7.53 (td, J=6.2, 8.0 Hz, 1 H), 7.27 (td, J=2.1, 8.3 Hz, 1 H), 7.07 (d, J=9.6 Hz, 1 H), 1.89 (quin, J=6.3 Hz, 1 H), 0.86-0.74 (m, 4 H) ESI-MS:m/z 446.3 (M+H)$^+$.

Compound 45: N-(6-(difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide Method A

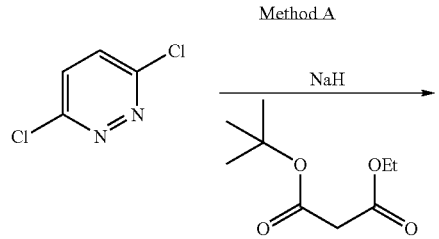

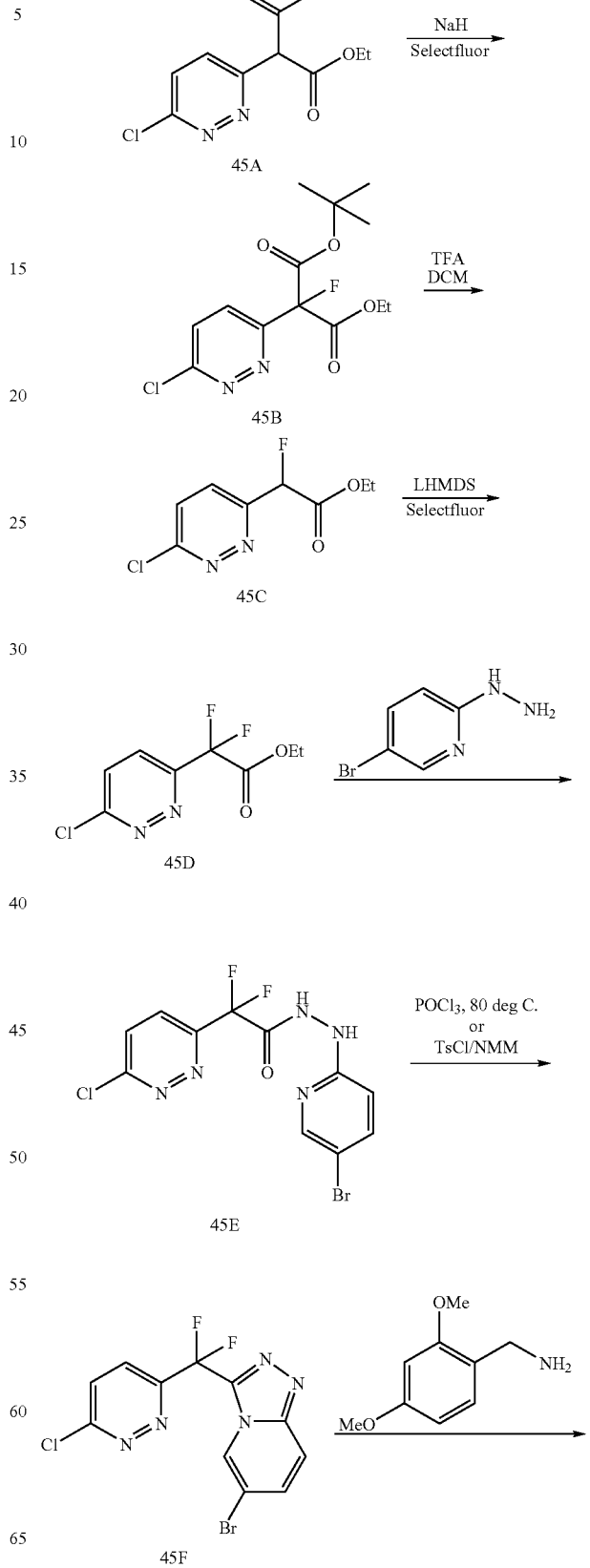

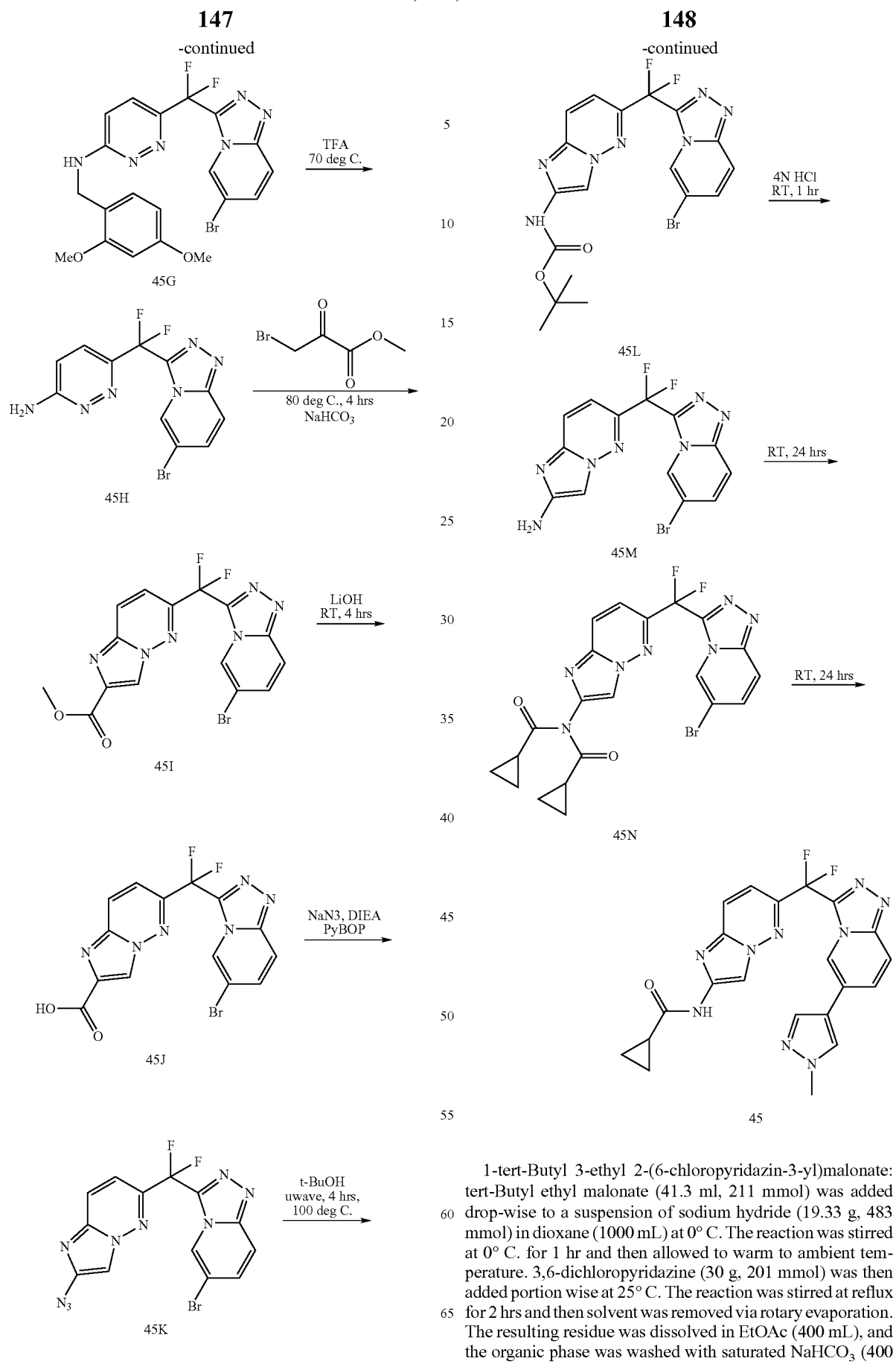

1-tert-Butyl 3-ethyl 2-(6-chloropyridazin-3-yl)malonate: tert-Butyl ethyl malonate (41.3 ml, 211 mmol) was added drop-wise to a suspension of sodium hydride (19.33 g, 483 mmol) in dioxane (1000 mL) at 0° C. The reaction was stirred at 0° C. for 1 hr and then allowed to warm to ambient temperature. 3,6-dichloropyridazine (30 g, 201 mmol) was then added portion wise at 25° C. The reaction was stirred at reflux for 2 hrs and then solvent was removed via rotary evaporation. The resulting residue was dissolved in EtOAc (400 mL), and the organic phase was washed with saturated NaHCO$_3$ (400 mL), dried over MgSO$_4$, filtered, and concentrated to dryness via rotary evaporation. This reaction was repeated. The combined crude residues from both batches was purified via MPLC (Hex:EtOAc, 8:2) to provide the title compound, 1-tert-butyl 3-ethyl 2-(6-chloropyridazin-3-yl)malonate (86.5 g, 288 mmol, 71.3%). $^1$H NMR (400 MHz, DMSO-d$_6$) δ ppm 1.12-1.23 (m, 3 H) 1.36-1.52 (m, 9 H) 4.20 (m, J=10.71, 7.22, 7.22, 3.85, 3.85 Hz, 2 H) 5.29 (s, 1 H) 7.85 (d, J=8.84 Hz, 1 H) 7.99 (d, J=8.84 Hz, 1 H). ESI-MS:m/z 301.2 (M+H)$^+$.

1-tert-Butyl 3-ethyl 2-(6-chloropyridazin-3-yl)-2-fluoromalonate: To a solution of 1-tert-butyl 3-ethyl 2-(6-chloropyridazin-3-yl)malonate 45A (86.5 g, 288 mmol) in THF (2400 mL) was added NaH (12.65 g, 316 mmol). The reaction was stirred at 0° C. for 15 min. A cloudy solution of Selectfluor (112 g, 316 mmol) in DMF (dry, 800 mL) was added drop-wise at 0° C. and then the reaction was allowed to warm to ambient temperature over a 2 hrs. The reaction was then quenched with saturated NH$_4$Cl (250 mL) and reduced in volume to about 1500 mL. To this mixture, Et$_2$O (300 mL) and water (50 mL) were added. Layers were separated, and the aqueous layer was extracted with Et$_2$O (3×300 mL). The combined organic layers were then washed with saturated NaHCO$_3$ solution (3×150 mL), dried with MgSO$_4$, filtered, and concentrated to dryness via rotary evaporation. The residue was purified via MPLC (Hex:EtOAc, 8:2) to provide 1-tert-butyl 3-ethyl 2-(6-chloropyridazin-3-yl)-2-fluoromalonate 45B (70.2 g, 220 mmol, 77%). $^1$H NMR (400 MHz, DMSO-d$_6$) δ ppm 1.24 (t, J=7.20 Hz, 3 H) 1.46 (s, 9 H) 4.28-4.43 (m, 2 H) 8.14 (s, 2 H). ESI-MS:m/z 319.2 (M+H)$^+$.

Ethyl 2-(6-chloropyridazin-3-yl)-2-fluoroacetate: A solution of 1-tert-butyl 3-ethyl 2-(6-chloropyridazin-3-yl)-2-fluoromalonate 45B (60.2 g, 189 mmol) in 300 mL TFA/DCM (1:1) was stirred at 25° C. for 2 hrs and then concentrated to dryness via rotary evaporation. The resulting residue was dissolved in EtOAc (300 mL), washed with saturated NaHCO$_3$ solution, dried over MgSO$_4$, and then concentrated to dryness to give the title compound, ethyl 2-(6-chloropyridazin-3-yl)-2-fluoroacetate 45C (36.6 g, 167 mmol, 89%). The material was used immediately without further purification. $^1$H NMR (400 MHz, DMSO-d$_6$) δ ppm 1.18 (t, J=7.20 Hz, 3 H) 4.23 (qd, J=7.12, 4.42 Hz, 2 H) 6.43-6.62 (m, 1 H) 8.00-8.12 (m, 2 H). ESI-MS:m/z 219.0 (M+H)$^+$.

Ethyl 2-(6-chloropyridazin-3-yl)-2,2-difluoroacetate: To a solution of ethyl 2-(6-chloropyridazin-3-yl)-2-fluoroacetate (36.6 g, 167 mmol) in anhydrous THF (500 mL) was added lithium hexamethyldisilazide (201 ml, 201 mmol) drop-wise at −78° C. After 15 minutes, a solution of Selectfluor (71.2 g, 201 mmol) in DMF (183 mL) was added drop-wise. Upon complete addition, the reaction was allowed to warm to ambient temperature over a 30 min period. Saturated NH$_4$Cl (70 mL) was then added, and THF was removed via rotary evaporation. The resulting residue was diluted with water (500 mL), extracted with Et$_2$O (3×100 mL), dried with MgSO$_4$, filtered, and concentrated to dryness. The resulting material was purified via MPLC (Hex:EtOAc, 8:2) to provide ethyl 2-(6-chloropyridazin-3-yl)-2,2-difluoroacetate 45D (20.8 g, 88 mmol, 52.5%). $^1$H NMR (400 MHz, DMSO-d$_6$) δ ppm 1.25 (t, J=7.07 Hz, 3 H) 4.38 (q, J=7.07 Hz, 2 H) 8.26 (d, J=9.09 Hz, 1 H) 8.33 (d, J=8.84 Hz, 1 H). ESI-MS:m/z 237.1 (M+H)$^+$.

N'-(5-Bromopyridin-2-yl)-2-(6-chloropyridazin-3-yl)-2,2-difluoroacetohydrazide: To a solution of ethyl 2-(6-chloropyridazin-3-yl)-2,2-difluoroacetate (10.8 g, 45.6 mmol) and 5-bromo-2-hydrazinylpyridine (8.58 g, 45.6 mmol) in anhydrous MeOH (100 mL) was added DIEA (5.90 g, 45.6 mmol). The reaction was stirred at ambient temperature for 18 hrs. The solvent was removed via rotary evaporation and the resulting material was reconstituted in EtOAc. The organic phase was washed with water and concentrated to dryness. The resulting residue was purified by MPLC (EtOAc) to provide the title compound, N'-(5-bromopyridin-2-yl)-2-(6-chloropyridazin-3-yl)-2,2-difluoroacetohydrazide 45E (13.3 g, 35.1 mmol, 77% yield). $^1$H NMR (400 MHz, CDCl$_3$) δ ppm 6.62 (d, J=8.84 Hz, 1 H) 7.11 (d, J=9.35 Hz, 1 H) 7.47-7.60 (m, 2 H) 8.06 (d, J=2.53 Hz, 1 H). ESI-MS:m/z 377.9 (M+H)$^+$.

6-Bromo-3-((6-chloropyridazin-3-yl)difluoromethyl)-[1,2,4]triazolo[4,3-a]pyridine: A mixture of N'-(5-bromopyridin-2-yl)-2-(6-chloropyridazin-3-yl)-2,2-difluoroacetohydrazide (1.0 g, 2.64 mmol) and PCl$_5$ (1.2 g, 8 mmol) in POCl$_3$ (40.5 g, 264 mmol) was heated at 140° C. in a sealed tube for 18 hrs. Solvent was removed via rotary evaporation, and the resulting residue was reconstituted in EtOAc. The organic solution was washed with saturated NaHCO$_3$, dried with MgSO$_4$, filtered, and concentrated to dryness. The resulting material was purified via MPLC (Hex:EtOAc, 50-100% gradient) to provide the title compound, 6-bromo-3-((6-chloropyridazin-3-yl)difluoromethyl)-[1,2,4]triazolo[4,3-a]pyridine 45F (0.8 g, 2.21 mmol, 84%). $^1$H NMR (400 MHz, DMSO-d$_6$) δ ppm 7.75 (dd, J=9.85, 1.77 Hz, 1 H) 8.01 (dd, J=9.85, 1.01 Hz, 1 H) 8.31 (d, J=9.09 Hz, 1 H) 8.42-8.51 (m, 1 H) 8.93 (s, 1 H). ESI-MS:m/z 359.9 (M+H)$^+$.

6-bromo-3-((6-chloropyridazin-3-yl)difluoromethyl)-[1,2,4]triazolo[4,3-a]pyridine 45F was also prepared by mixing N'-(5-bromopyridin-2-yl)-2-(6-chloropyridazin-3-yl)-2,2-difluoroacetohydrazide (1.514 g, 4 mmol) and 4-methylbenzene-1-sulfonyl chloride (0.839 g, 4.40 mmol) in ethyl acetate (Volume: 25 ml) and cooling the mixture to 10° C. under protection of nitrogen. 4-methylmorpholine (1.142 ml, 10.40 mmol) was added over 2 minutes. The reaction mixture was warmed up to room temperature and stirred for 6 hours. Additional 4-methylmorpholine (0.44 ml, 4 mmol) was added. The reaction mixture was heated at 60° C. for 24 hours to reduce the imidoyl chloride intermediate level to less than 1% by HPLC. The reaction mixture was cooled to room temperature. EtOAc (30 ml) and water (13 ml) was added, and the mixture was stirred for 30 minutes. The aqueous layer was separated. The organic layer was concentrated and the residue was purified by silica gel column to afford 1.28 g of product (89% yield).

6-((6-Bromo-[1,2,4]triazolo[4,3-a]pyridin-3-yl)difluoromethyl)-N-(2,4-dimethoxybenzyl)pyridazin-3-amine: A reaction mixture of 6-bromo-3-((6-chloropyridazin-3-yl)difluoromethyl)-[1,2,4]triazolo[4,3-a]pyridine (0.5 g, 1.387 mmol), (2,4-dimethoxyphenyl)methanamine (0.696 g, 4.16 mmol) and NaHCO$_3$ (0.58 g, 7.0 mmol) in IPA (10 mL) was heated at 140° C. in a microwave for 1 hr. The solvent was removed via rotary evaporation and the resulting residue was reconstituted in EtOAc. The organic solution was washed with water, separated and passed through a short silica plug to provide the title compound, 6-((6-bromo-[1,2,4]triazolo[4,3-a]pyridin-3-yl)difluoromethyl)-N-(2,4-dimethoxybenzyl)pyridazin-3-amine 45G (0.6 g, 1.22 mmol, 88%). $^1$H NMR (400 MHz, DMSO-d$_6$) δ ppm 3.71-3.76 (s, 3 H) 3.79 (s, 3 H) 3.85-3.89 (m, 2 H) 6.46 (dd, J=8.34, 2.53 Hz, 1 H) 6.57 (d, J=2.27 Hz, 1 H) 6.61-6.66 (m, 1 H) 7.08 (d, J=9.35 Hz, 1 H) 7.14 (d, J=8.34 Hz, 1 H) 7.81 (d, J=9.35 Hz, 1 H) 7.99 (dd, J=9.60, 1.01 Hz, 1 H) 8.70 (s, 1 H). ESI-MS:m/z 491.1 (M+H)$^+$.

6-Bromo-[1,2,4]triazolo[4,3-a]pyridin-3-yl)difluoromethyl)pyridazin-3-amine: A solution of 6-((6-bromo-[1,2,4]triazolo[4,3-a]pyridin-3-yl)difluoromethyl)-N-(2,4-dimethoxybenzyl)pyridazin-3-amine (16.5 g, 33.6 mmol) and anisole (5.45 g, 50.4 mmol) in TFA (150 mL) was stirred at 70° C. for 30 min. The reaction was concentrated to dryness via rotary evaporation and the resulting residue was sonicated in a solution of Et$_2$O/NaHCO$_3$ (pH=7). The resulting solid was collected by filtration, rinsed with water and then Et$_2$O, and dried in vacuum over P$_2$O$_5$ to provide the title compound, 6-((6-bromo-[1,2,4]triazolo[4,3-a]pyridin-3-yl)difluoromethyl)pyridazin-3-amine 45H (11.0 g, 32.2 mmol, 96%). $^1$H NMR (400 MHz, DMSO-d$_6$) δ ppm 7.14 (d, J=9.35 Hz, 1 H) 7.71 (dd, J=9.85, 1.77 Hz, 1 H) 7.92 (d, J=9.35 Hz, 1 H) 7.92 (d, J=10.20 Hz, 1 H) 8.02 (d, J=10.20, 1 H) 8.74 (s, 1 H). ESI-MS:m/z 340.9 (M+H)$^+$.

Methyl 6-((6-bromo-[1,2,4]triazolo[4,3-a]pyridin-3-yl)difluoromethyl)imidazo[1,2-b]pyridazine-2-carboxylate: A reaction mixture of 6-((6-bromo-[1,2,4]triazolo[4,3-a]pyridin-3-yl)difluoromethyl)pyridazin-3-amine (11.0 g, 32.2 mmol), methyl 3-bromo-2-oxopropanoate (11.67 g, 64.5 mmol), and NaHCO$_3$ (10.84 g) in dioxane (150 mL) was heated at 80° C. for 4 hrs to provide a red reaction mixture. Solids were filtered off, rinsed with dioxane, and the combined filtrates were concentrated via rotary evaporation. The resulting residue was dissolved in EtOAc and washed with 0.1 N NaOH until the red color no longer persisted. The organic phase was then separated and concentrated to dryness. The resulting material was purified via MPLC (5:95, MeOH/EtOAc) to provide the title compound, 45I (4.0 g, 9.45 mmol, 30%). $^1$H NMR (400 MHz, DMSO-d$_6$) δ ppm 3.88 (s, 3 H) 7.77 (dd, J=9.73, 1.64 Hz, 1 H) 7.85 (d, J=9.60 Hz, 1 H) 7.97-8.08 (m, 1 H) 8.53 (d, J=9.60 Hz, 1 H) 8.98 (d, J=1.01 Hz, 1 H) 9.02 (s, 1 H). ESI-MS:m/z 423.1 (M+H)$^+$.

6-((6-Bromo-[1,2,4]triazolo[4,3-a]pyridin-3-yl)difluoromethyl)imidazo[1,2-b]pyridazine-2-carboxylic acid: A solution of 3.methyl 6-((6-bromo-[1,2,4]triazolo[4,3-a]pyridin-3-yl)difluoromethyl)imidazo[1,2-b]pyridazine-2-carboxylate (4.0 g, 9.45 mmol) and LiOH (0.340 g, 14.18 mmol) in 10% H$_2$O/MeOH (150 mL) was stirred at ambient temperature for 4 hrs. Solvent was removed via rotary evaporation, and the resulting residue was diluted with H$_2$O (100 mL). The aqueous phase was adjusted to pH=5 with concentrated HCl. The resulting precipitate was collected, rinsed with water, rinsed with EtOAc, and dried under vacuum over P$_2$O$_5$ for 18 hrs to provide the title compound, 6-((6-bromo-[1,2,4]triazolo[4,3-a]pyridin-3-yl)difluoromethyl)imidazo[1,2-b]pyridazine-2-carboxylic acid 45J (3.5 g, 8.55 mmol, 90%). $^1$H NMR (400 MHz, DMSO-d$_6$) δ ppm 7.76 (dd, J=9.85, 1.77 Hz, 1 H) 7.82 (d, J=9.60 Hz, 1H) 8.02 (d, J=9.60 Hz, 1 H) 8.51 (d, J=9.85 Hz, 1 H) 8.90 (s, 1 H) 8.97 (s,1 H). ESI-MS:m/z 4.09 (M+H)$^+$.

6-((6-Bromo-[1,2,4]triazolo[4,3-a]pyridin-3-yl)difluoromethyl)imidazo[1,2-b]pyridazine-2-carbonyl azide: To a stirred solution of 6-((6-bromo-[1,2,4]triazolo[4,3-a]pyridin-3-yl)difluoromethyl)imidazo[1,2-b]pyridazine-2-carboxylic acid (3.5 g, 8.55 mmol), N-ethyl-N-isopropylpropan-2-amine (6.63 g, 51.3 mmol) and sodium azide (5.56 g, 86 mmol) in anhydrous DMF (60 mL), PyBOP (5.34 g, 10.27 mmol) was added in portions at ambient temperature over 5 min. The reaction was stirred for an additional 30 min and diluted with EtOAc (200 mL). The reaction was then poured into a 10% aqueous citric acid (200 mL), and the organic phase was separated and washed with citric acid solution (2×100 mL), saturated NaHCO$_3$ (3×100 mL), and saturated NaCl solution. The aqueous phases were back extracted with EtOAc (200 mL) and the organic phases were combined, dried with MgSO$_4$, filtered, and concentrated to dryness via rotary evaporation. The resulting residue was triturated in 1:1 Et$_2$O/hexane, and the solid was collected by filtration and dried in vacuum over P$_2$O$_5$ to provide the title compound, 6-((6-bromo-[1,2,4]triazolo[4,3-a]pyridin-3-yl)difluoromethyl)imidazo[1,2-b]pyridazine-2-carbonyl azide 45K (3.2 g, 7.37 mmol, 92%). $^1$H NMR (400 MHz, DMSO-d$_6$) δ ppm 7.77 (dd, J=9.85, 1.77 Hz, 1 H) 7.88 (d, J=9.60 Hz, 1 H) 8.00-8.05 (m, 1 H) 8.56 (d, J=9.60 Hz, 1 H) 8.98 (s, 1 H) 9.14 (s, 1 H). ESI-MS:m/z 434.0 (M+H)$^+$. ESI-MS:m/z 406.0 (M+H)$^+$.

tert-Butyl 6-((6-bromo-[1,2,4]triazolo[4,3-a]pyridin-3-yl)difluoromethyl)imidazo[1,2-b]pyridazin-2-ylcarbamate: 6-((6-bromo-[1,2,4]triazolo[4,3-a]pyridin-3-yl)difluoromethyl)imidazo[1,2-b]pyridazine-2-carbonyl azide (3.2 g, 7.37 mmol, divided into 4 portions) in t-butanol (10 mL) was heated in microwave oven at 100° C. for 1 hr. The solvent was removed via rotary evaporation, and the resulting residue was reconstituted in EtOAc, washed with 5% citric acid, and the washed with saturated NaHCO$_3$. The organic phase was passed through a silica plug, rinsed with EtOAc:MeOH (95: 5) and then concentrated to give the title compound, tert-Butyl 6-((6-bromo-[1,2,4]triazolo[4,3-a]pyridin-3-yl)difluoromethyl)imidazo[1,2-b]pyridazin-2-ylcarbamate 45L (2.8 g, 5.83 mmol, 79%), which was used in next step without further purification. $^1$H NMR (400 MHz, DMSO-d$_6$) δ ppm 1.47 (s, 9 H) 7.66 (d, J=9.35 Hz, 1 H) 7.72-7.78 (m, 1 H) 7.96-8.06 (m, 2 H) 8.22 (d, J=9.35 Hz, 1H) 8.93 (s, 1 H) 10.40 (br, 1H). ESI-MS:m/z 480.1 (M+H)$^+$.

6-((6-Bromo-[1,2,4]triazolo[4,3-a]pyridin-3-yl)difluoromethyl)imidazo[1,2-b]pyridazin-2-amine: A solution of tert-butyl 6-((6-bromo-[1,2,4]triazolo[4,3-a]pyridin-3-yl)difluoromethyl)imidazo[1,2-b]pyridazin-2-ylcarbamate (2.8 g, 5.83 mmol) in 4N HCl/dioxane (25 mL) was stirred at ambient temperature for 1 hr. The solvent was removed via rotary evaporation and the residue was dried under vacuum to provide the title compound, 6-((6-Bromo-[1,2,4]triazolo[4,3-a]pyridin-3-yl)difluoromethyl)imidazo[1,2-b]pyridazin-2-amine 45M (2.2 g, 5.84 mmol, 92%), as HCl salt. This material was used without further purification. ESI-MS:m/z 380.1 (M+H)$^+$.

N-(6-((6-Bromo-[1,2,4]triazolo[4,3-a]pyridin-3-yl)difluoromethyl)imidazo[1,2-b]pyridazin-2-yl)-N-(cyclopropanecarbonyl)cyclopropanecarboxamide: To a solution of 6-((6-bromo-[1,2,4]triazolo[4,3-a]pyridin-3-yl)difluoromethyl)imidazo[1,2-b]pyridazin-2-amine (2.2 g, 5.84 mmol) and DIEA (4.53 g, 35.0 mmol) in CH$_2$Cl$_2$ (250 mL), cyclopropanecarbonyl chloride (1.831 g, 17.52 mmol) was added dropwise at 0° C. The reaction was stirred at ambient temperature for 18 hrs. The reaction was then washed with 5% citric acid (2×100 mL) and then washed with NaHCO$_3$ (2×100 mL). The organic phase was then dried with MgSO$_4$, filtered, and concentrated to dryness via rotary evaporation. The resulting material was purified via MPLC (95:5, DCM:MeOH) to provide the title compound, N-(6-((6-Bromo-[1,2,4]triazolo[4,3-a]pyridin-3-yl)difluoromethyl)imidazo[1,2-b]pyridazin-2-yl)-N-(cyclopropanecarbonyl)cyclopropanecarboxamide 45N (2.2 g, 4.27 mmol, 73%). $^1$H NMR (400 MHz, DMSO-d$_6$) δ ppm 0.83-1.03 (m, 8 H) 2.05-2.12 (m, 2 H) 7.70-7.87 (m, 2 H) 7.97-8.06 (m, 1 H) 8.48 (d, J=9.60 Hz, 1 H) 8.65 (s, 1 H) 8.99 (s, 1 H). ESI-MS:m/z 516.1 (M+H)$^+$.

N-(6-(Difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide: A mixture of N-(6-((6-bromo-[1,2,4]triazolo[4,3-a]pyridin-3-yl)difluoromethyl)imidazo[1,2-b]pyridazin-2-yl)-N-(cyclopropanecarbonyl)cyclopropanecarboxamide (0.6 g, 1.16 mmol), 1-methyl-4-(4,4,5,5-tetramethyl-1,3,2-dioxaborolan-2-yl)-1H-pyrazole (0.242 g, 1.162 mmol), and PdCl$_2$(dppf):CH$_2$Cl$_2$ (0.048 g, 0.058 mmol) in dioxane (10 mL)/2N Na$_2$CO$_3$ (5 mL) was heated in a microwave at 110° C. for 30 min. This reaction was repeated 4 times and reaction mixtures were combined. The reaction was diluted with CH$_2$Cl$_2$ (500 mL) and washed with H$_2$O (3×200 mL). The organic phase was separated and concentrated to dryness via rotary evaporation. The resulting residue was suspended in EtOAc and sonicated. The resulting solid was collected by filtration and rinsed with EtOAc. The solid was the dissolved in MeOH/CH$_2$Cl$_2$ (5:95, 300 mL) and filtered through a silica plug and rinsed with MeOH/CH$_2$Cl$_2$ (5:95). Concentrated HCl (0.5 mL) was added to the collected eluent followed by active charcoal. The solution was stirred at ambient temperature for 1 hour and filtered through celite. The solvent was evaporated and the resulting residue was then triturated in EtOAc. The solid was collected by filtration, rinsed with EtOAc and dried in vacuum to provide the title compound, N-(6-(Difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide hydrochloride (0.92 g, 1.78 mmol, 38%). $^1$H NMR (400 MHz, DMSO-d$_6$) δ ppm 0.82 (d, J=6.32 Hz, 4 H) 1.91-2.01 (m, 1 H) 3.87 (s, 3 H) 7.70 (d, J=9.35 Hz, 1 H) 7.90 (dd, J=9.60, 1.52 Hz, 1 H) 7.98-8.11 (m, 2 H) 8.19-8.32 (m, 2 H) 8.40 (s, 1 H) 8.70 (s, 1 H) 11.35 (s, 1 H). ESI-MS:m/z 516.1 (M+H)$^+$. MP: 195° C. dec.

N-(6-(Difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide hydrochloride was also prepared by dissolving 0.5 g of crude N-(6-(difluoro(6-(1-methyl-1H-pyrazol-4-yl)-[1,2,4]triazolo[4,3-a]pyridin-3-yl)methyl)imidazo[1,2-b]pyridazin-2-yl) cyclopropanecarboxamide in AcOH (15 ml) at 80° C. to form a clear solution. The solution was cooled to room temperature, Sili-thiourea (commercially available from Silicycle; 0.25 g) was added and the mixture was stirred overnight. The mixture was filtered through celite and 6.5 ml of 1.7M HCl solution in MeOH was added to the AcOH solution. EtOAc (18 ml) was then added slowly to induce crystallization. The mixture was then stirred at rt for 1 hour until a heavy precipitate formed. Additional EtOAc (30 ml) was added and the mixture stirred for 60 min. The solid was then collected via filtration, wash with EtOAc (10 ml) and dried in vacuum at 60° C. over night.

Further, N-(6-(Difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide hydrochloride was prepared by suspending crude N-(6-(difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide (2.2 g; 4.9 mmol) in 333 ml of DCM. 50 ml of 0.2 M HCl in MeOH (10 mmol) was added. The mixture was stirred vigorously for 60 minutes and Sili-Thiourea (commercially available from Silicycle; 1.12 g) was added. The mixture was stirred at room temperature for 14 hours, filtered through Celite and washed with 10% MeOH in DCM (40 ml) to provide a total volume of filtrate of about 420 ml. 15 ml of a 2M HCl MeOH solution was added. The solution was concentrated by rotavap at 225 mbar, 22° C. bath temperature to remove about 325 ml of solvent. The solution was checked for clarity to ensure that solid formation was minimized. 10 ml of a 2M HCl MeOH solution was added. The solution was seeded with 25 mg of N-(6-(difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide hydrochloride salt. The solution was allowed to continue to concentrate at 130 mbar to remove 65 ml solvent in the presence of seed crystal. After the solution turned cloudy, the solution was maintained at room temperature for 40 minutes. The mixture was cooled to 0° C., stirred for 2 hours, and the solids collected by filtration. The solids were dried in vacuum at 60° C. overnight to afford 1.75 g of a pale-yellow solid.

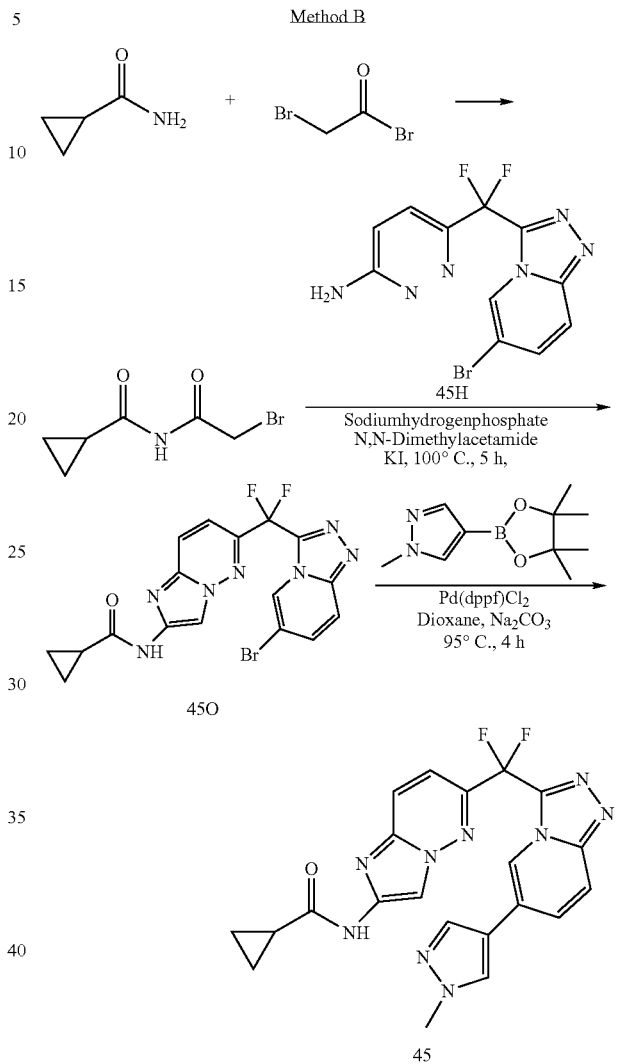

N-(6-((6-Bromo-[1,2,4]triazolo[4,3-a]pyridin-3-yl)difluoromethyl)imidazo[1,2-b]pyridazin-2-yl)cyclopropanecarboxamide (45O): Cyclopropanecarboxamide (58.7 g, 690 mmol) in 1,4-Dioxane (1600 ml) was added 2-bromoacetyl bromide (59.9 ml, 690 mmol) at room temperature and stirred for 4 h at 60° C. The reaction mixture was concentrated to dryness. The residue was dissolved in EtOAc and carefully washed with satd. NaHCO$_3$, water then with brine solution, dried over Na$_2$SO$_4$ and concentrated to get N-(2-bromoacetyl)cyclopropanecarboxamide (138 g, 670 mmol, 97% yield) as an off white solid. This material was used without purification. ESI-MS:m/z 208.0 (M+2H)$^+$.

To a mixture of 6-((6-bromo-[1,2,4]triazolo[4,3-a]pyridin-3-yl)difluoromethyl)pyridazin-3-amine (21.8 g, 63.9 mmol) and sodium hydrogenphosphate (27.2 g, 192 mmol) in N,N-Dimethylacetamide (250 ml) were added N-(2-bromoacetyl)cyclopropanecarboxamide (19.75 g, 96 mmol) and potassium iodide (10.61 g, 63.9 mmol) at room temperature. The reaction mixture was stirred for 5 h at 100° C. Reaction mixture cooled to room temperature, diluted with EtOAc (1000 ml) and washed with brine solution (5×), dried over Na$_2$SO$_4$, volatiles evaporated and the residue was purified by combiflash (2 to 30% MeOH in dichloromethane over 120 min). Product containing fractions were combined and concentrated to get N-(6-((6-bromo-[1,2,4]triazolo[4,3-a]pyridin-3-yl)difluoromethyl)imidazo[1,2-b]pyridazin-2-yl)cyclopropanecarboxamide (13.9 g, 31.0 mmol, 48.5% yield) as an off white solid. $^1$H NMR (400 MHz, DMSO-$d_6$) δ 11.31 (s, 1H), 8.92 (s, 1H), 8.18-8.35 (m, 2H), 7.92-8.06 (m, 1H), 7.61-7.80 (m, 2H), 1.91-2.02 (m, 1H), 0.78-0.89 (m, 4H). ESI-MS:m/z 450.0 (M+2H)$^+$.

N-(6-(Difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide (45): A mixture of N-(6-((6-bromo-[1,2,4]triazolo[4,3-a]pyridin-3-yl)difluoromethyl)imidazo[1,2-b]pyridazin-2-yl)cyclopropanecarboxamide (7.2 g, 16.06 mmol), 1-methyl-4-(4,4,5,5-tetramethyl-1,3,2-dioxaborolan-2-yl)-1H-pyrazole (5.01 g, 24.10 mmol) and PdCl$_2$(dppf):CH$_2$Cl$_2$ (0.655 g, 0.803 mmol) in 1,4-Dioxane:1M Na$_2$CO$_3$ (Ratio: 2.1, Volume: 100 ml) was heated at 95° C. for 4 h. The reaction mixture cooled and concentrated to dryness via rotary evaporation, diluted with EtOAc and water. The resulting solid was collected by filtration, rinsed with H$_2$O followed by EtOAc. The grey color solid dissolved in 20% MeOH in chloroform and treated with activated charcoal for overnight, filtered through a pad of celite and the celite pad rinsed with 20% MeOH in chloroform until no compound detected by HPLC. This solution passed through a silica gel column. The solvent evaporated and the resulting solid rinsed with EtOAc, MeOH, followed by EtOAc and then Et$_2$O, dried under vacuum to provide N-(6-(difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide (5.13 g, 11.41 mmol, 71.1% yield) as white solid. $^1$H NMR (400 MHz, DMSO-$d_6$) δ 11.35 (s, 1H), 8.71 (s, 1H), 8.41 (s, 1H), 8.19-8.34 (m, 2H), 8.00-8.12 (m, 2H), 7.91 (dd, J=1.64, 9.47 Hz, 1H), 7.71 (d, J=9.35 Hz, 1H), 3.88 (s, 3H), 1.88-2.02 (m, 1H), 0.83 (d, J=6.32 Hz, 4H). ESI-MS:m/z 450.1 (M+H)$^+$. MP: 274.9° C.

The bis HCl salt of Compound 45 was prepared as follows. N-(6-(Difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide bis hydrochloride: N-(6-(difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide (2.100 g, 4.67 mmol) in a mixture of MeOH and DCM (Ratio: 1:2, Volume: 100 ml) was added hydrogen chloride (12N, 0.973 ml, 11.68 mmol) at room temperature and stirred for 2 h. Volatiles evaporated to dryness and the solid was rinsed with EtOAc and ether then dried under vacuum to provide N-(6-(difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide, 2HCl (2.4 g, 4.59 mmol, 98% yield) as an off white solid. $^1$H NMR (400 MHz, DMSO-$d_6$) δ 12.21 (br. s., 2H), 11.32 (s, 1H), 8.66 (s, 1H), 8.36 (s, 1H), 8.14-8.27 (m, 2H), 7.94-8.08 (m, 2H), 7.87 (dd, J=1.52, 9.60 Hz, 1H), 7.65 (d, J=9.35 Hz, 1H), 3.82 (s, 3H), 1.84-1.99 (m, 1H), 0.77 (d, J=6.32 Hz, 4H). ESI-MS: m/z 450.1 (M+H)$^+$. 208° C.

Compound 46: N-(6-(difluoro(6-(isoxazol-4-yl)-[1,2,4]triazolo[4,3-a]pyridin-3-yl)methyl)imidazo[1,2-b]pyridazin-2-yl)cyclopropanecarboxamide

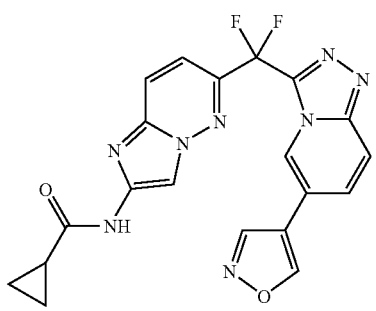

A mixture of N-(6-((6-bromo-[1,2,4]triazolo[4,3-a]pyridin-3-yl)difluoromethyl)imidazo[1,2-b]pyridazin-2-yl)-N(cyclopropanecarbonyl)cyclopropanecarboxamide (45N, 0.200 g, 0.38 mmol), 4-(4,4,5,5-tetramethyl-1,3,2-dioxaborolan-2-yl)isoxazole (0.1 g, 0.5 mmol) and PdCl$_2$(dppf): CH$_2$Cl$_2$ (5 mg, 0.006 mmol) in Na$_2$CO$_3$ (2N, 1 mL)/dioxane (2 mL) was heated at 110° C. in a microwave for 30 min. The reaction mixture was filtered and the solids washed with EtOAc. The filtrate was then washed with saturated NaCl, dried with MgSO$_4$, filtered, and concentrated to dryness via rotary evaporation. The resulting residue was purified by preparative LCMS. The collected fractions were combined and the resulting mixture was treated with two drops of concentrated HCl. The solution was lyophilized to provide the HCl salt of the title compound, N-(6-(difluoro(6-(isoxazol-4-yl)-[1,2,4]triazolo[4,3-a]pyridin-3-yl)methyl)imidazo[1,2-b]pyridazin-2-yl)cyclopropanecarboxamide (20 mg, 0.04 mmol, 12%). $^1$H NMR (400 MHz, DMSO-$d_6$) δ ppm 0.82 (d, J=6.32 Hz, 4 H) 1.91-2.01 (m, 1 H) 7.67 (dd, J=9.47, 5.43 Hz, 1 H) 7.75 (dd, J=9.73, 1.64 Hz, 1 H) 7.84 (dd, J=9.85, 1.77 Hz, 1 H) 7.98-8.07 (m, 1 H) 8.23-8.34 (m, 2 H) 8.46 (s, 1H) 9.02 (s, 1 H) 11.36 (d, J=2.27 Hz, 1 H). ESI-MS:m/z 437.2 (M+H)$^+$.

Compound 47: N-(6-(difluoro(6-(1-(2-hydroxyethyl)-1H-pyrazol-4-yl)-[1,2,4]triazolo[4,3-a]pyridin-3-yl)methyl)imidazo[1,2-b]pyridazin-2-yl)cyclopropanecarboxamide

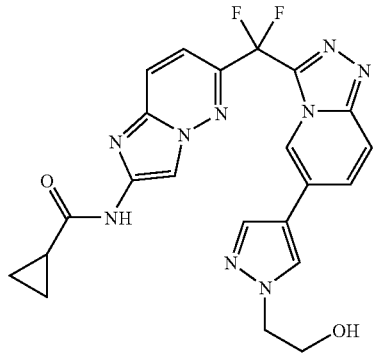

A mixture of N-(6-((6-bromo-[1,2,4]triazolo[4,3-a]pyridin-3-yl)difluoromethyl)imidazo[1,2-b]pyridazin-2-yl)-N(cyclopropanecarbonyl)cyclopropanecarboxamide (45N, 0.067 g, 0.13 mmol), 1-(2-(tetrahydro-2H-pyran-2-yloxy)ethyl)-4-(4,4,5,5-tetramethyl-1,3,2-dioxaborolan-2-yl)-1H-pyrazole (0.042 g, 0.130 mmol) and PdCl$_2$(dppf) (5 mg, 0.006 mmol) in Na$_2$CO$_3$ (2N, 1 mL)/dioxane (2 mL) was heated at 110° C. in a microwave for 30 min. Reaction mixture was filtered and washed with EtOAc. The organic phase was washed with saturated NaCl, dried with MgSO$_4$, filtered, and concentrated to dryness. The resulting residue was dissolved in 4 N HCl/dioxane and stirred at ambient temperature for 30 min and then concentrated to dryness. The resulting material was purified by preparative LCMS. The collected fractions were combined and the resulting mixture was treated with two drops of concentrated HCl. The solution was lyophilized to provide the HCl salt of the title compound, (18 mg, 0.037 mmol, 29%). $^1$H NMR (400 MHz, DMSO-$d_6$) δ ppm 0.83 (d, J=6.06 Hz, 4 H) 1.95 (d, J=5.81 Hz, 1 H) 3.77 (t, J=5.43 Hz, 2 H) 4.10-4.21 (m, 2 H) 7.71 (d, J=9.35 Hz, 1 H) 7.87-7.98 (m, 1 H) 8.00-8.07 (m, 1 H) 8.11 (s, 1 H) 8.20-8.33 (m, 2 H) 8.44 (s, 1 H) 8.73 (s, 1 H) 11.35 (s, 1 H). ESI-MS:m/z 480.2 (M+H)$^+$.

Compound 48: N-(6-(1-(6-bromo-[1,2,4]triazolo[4,3-a]pyridin-3-yl)ethyl)imidazo[1,2-b]pyridazin-2-yl)cyclopropanecarboxamide

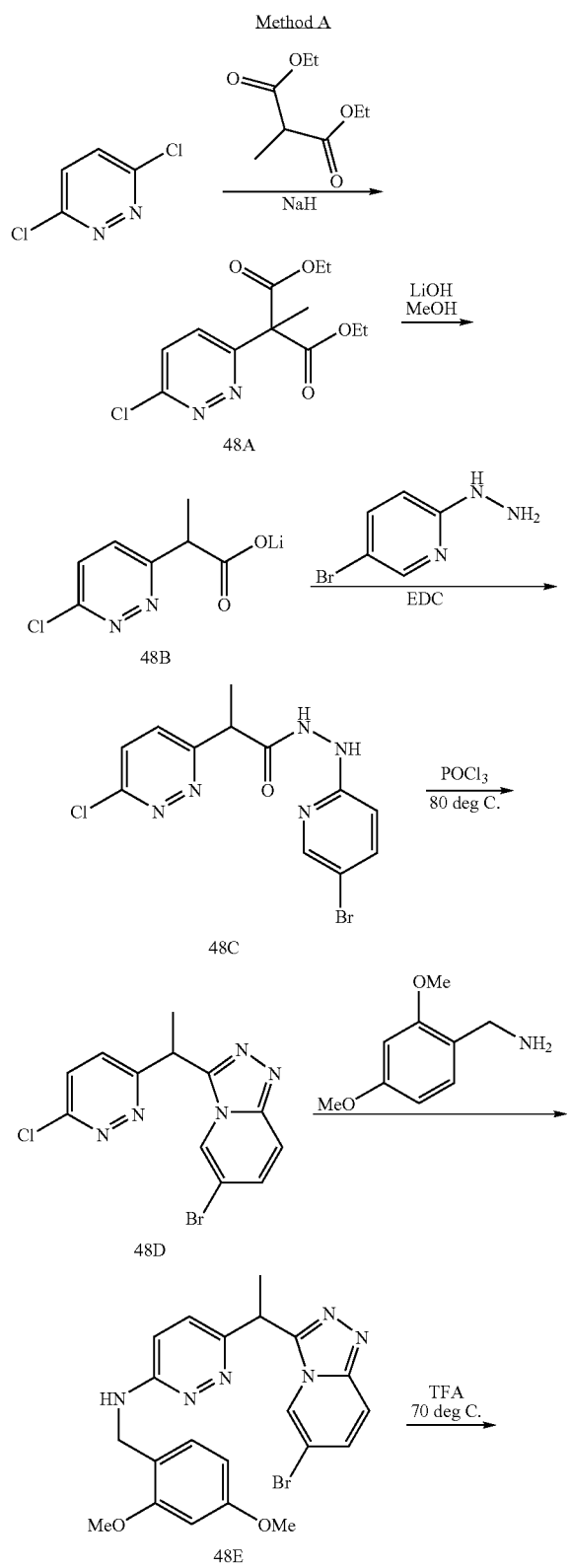

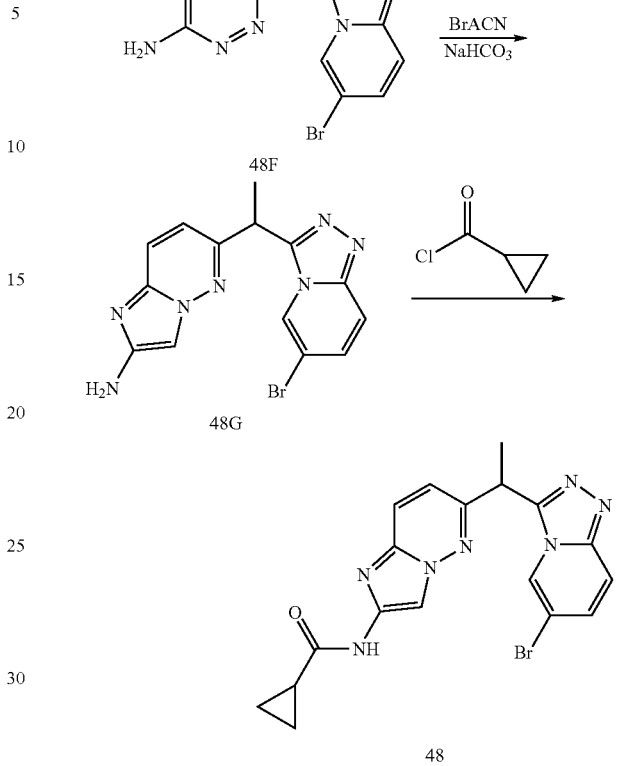

Diethyl 2-(6-chloropyridazin-3-yl)-2-methylmalonate: To a mixture of NaH (13.42 g, 336 mmol) in dioxane (800 mL) was added diethyl 2-methylmalonate (42.9 ml, 252 mmol) drop-wise at 0° C. The reaction was stirred at 0° C. for 1 hr and allowed to warm to ambient temperature. 3,6-dichloropyridazine (25 g, 168 mmol) was then added portion-wise at 25° C. The reaction was then stirred at reflux for 1 hr. Solvent was removed via rotary evaporation and the resulting residue was dissolved in EtOAc. The organic solution was washed with saturated NaHCO$_3$ (100 mL) followed by 5% citric acid. The organic layer was then dried with MgSO$_4$, filtered, and concentrated to dryness. The resulting residue was purified via MPLC (Hex:EtOAc, 3:1) to provide the title compound, diethyl 2-(6-chloropyridazin-3-yl)-2-methylmalonate 48A (12 g, 25% yield) as a yellow oil. $^1$H NMR (400 MHz, DMSO-d$_6$) δ ppm 1.18 (s, 6 H) 1.81 (s, 3H) 4.21 (dd, J=7.07, 2.27 Hz, 4 H) 8.00 (s, 2 H). ESI-MS:m/z 287.1 (M+H)$^+$.

Lithium 2-(6-chloropyridazin-3-yl)propanoate: A solution of diethyl 2-(6-chloropyridazin-3-yl)-2-methylmalonate (19.8 g, 69.1 mmol) and LiOH (3.31 g, 138 mmol) in MeOH:Water (3:1, 200 mL) was stirred at 25° C. for 3 hrs. MeOH was removed from the reaction via rotary evaporation, and the resulting residue was reconstituted in H$_2$O (300 mL). The aqueous mixture was washed with Et$_2$O (3×100 mL) and then lyophilized to dryness to provide lithium 2-(6-chloropyridazin-3-yl)propanoate 48B in quantitative yield. The material was used without further work-up. $^1$H NMR (400 MHz, DMSO-d$_6$) δ ppm 1.36 (3 H, d, J=7.33 Hz) 3.63 (1 H, q, J=7.24 Hz) 7.71 (2 H, s). ESI-MS:m/z 187.0 (M+H)$^+$.

N'-(5-Bromopyridin-2-yl)-2-(6-chloropyridazin-3-yl)propanehydrazide: A mixture of lithium 2-(6-chloropyridazin-3-yl)propanoate (7.2 g, 37.4 mmol), 5-bromo-2-hydrazinylpyridine (7.03 g, 37.4 mmol), 1H-benzo[d][1,2,3]triazol-1-ol (5.05 g, 37.4 mmol), and N1-((ethylimino)methylene)-N3,N3-dimethylpropane-1,3-diamine hydrochloride (7.89 g, 41.1 mmol) in DMF (Volume: 320 ml) was stirred for 4 hrs at 25° C. The reaction was poured into $H_2O$ (2 L) and extracted with EtOAc (3×500 mL). The organic phase was dried over $MgSO_4$, filtered, and evaporated to dryness. The resulting residue was purified by MPLC $CHCl_3$:MeOH (9:1) to provide the title compound, N'-(5-bromopyridin-2-yl)-2-(6-chloropyridazin-3-yl)propanehydrazide 48C (5.5 g, 15.42 mmol, 41.2% yield). $^1$H NMR (400 MHz, DMSO-d6) δ ppm 1.52 (d, J=7.33 Hz, 3 H) 4.17 (d, J=7.07 Hz, 1 H) 6.52 (d, J=8.84 Hz, 1 H) 7.67 (dd, J=8.84, 2.53 Hz, 1 H) 7.87 (d, J=9.09 Hz, 1 H) 7.94 (d, J=8.84 Hz, 1 H) 8.11 (d, J=1.77 Hz, 1 H) 8.66 (d, J=1.52 Hz, 1 H) 10.20 (d, J=1.52 Hz, 1 H). ESI-MS:m/z 356.1 $(M+H)^+$.

6-bromo-3-(1-(6-chloropyridazin-3-yl)ethyl)-[1,2,4]triazolo[4,3-a]pyridine: A solution of N'-(5-bromopyridin-2-yl)-2-(6-chloropyridazin-3-yl)propanehydrazide (5.0 g, 14.02 mmol) and phosphoryl trichloride (100 mL, 1073 mmol) was stirred at 90° C. for 5 hrs. The reaction was cooled, stripped to dryness, and the resulting material was reconstituted in a mixture of EtOAc and saturated $NaHCO_3$ (400 mL, 1:1)). The organic phase was isolated, washed with saturated $NaHCO_3$ (1×100 mL), and dried over $MgSO_4$. The organic phase was removed via rotary evaporation to provide the title compound, 6-bromo-3-(1-(6-chloropyridazin-3-yl)ethyl)-[1,2,4]triazolo[4,3-a]pyridine 48D (2.2 g, 6.50 mmol, 46.3% yield). This material was used without further purification. $^1$H NMR (400 MHz, DMSO-$d_6$) δ ppm 1.86 (d, J=7.07 Hz, 3 H) 5.27 (d, J=7.33 Hz, 1 H) 7.49 (dd, J=9.60, 1.77 Hz, 1 H) 7.78 (dd, J=9.85, 1.01 Hz, 1 H) 7.94 (s, 2 H) 8.79 (s, 1 H). ESI-MS:m/z 339.1 $(M+H)^+$.

N-(2,4-dimethoxybenzyl)-6-(1-(6-methyl-[1,2,4]triazolo[4,3-a]pyridin-3-yl)ethyl)pyridazin-3-amine: A mixture of 6-bromo-3-(1-(6-chloropyridazin-3-yl)ethyl)-[1,2,4]triazolo[4,3-a]pyridine (650 mg, 1.920 mmol), (2,4-dimethoxyphenyl)methanamine (0.577 mL, 3.84 mmol), and $NaHCO_3$ (645 mg, 7.68 mmol) in IPA (10.0 mL) was heated in a microwave on high absorbance for 18 hrs at 140° C. The reaction was cooled to ambient temperature, stripped to dryness via rotary evaporation, and reconstituted in EtOAc (25 mL). The insolubles were filtered off and the filtrate was reduced to dryness. The resulting residue was purified via MPLC (DCM:MeOH, 98:2) to provide the title compound, 6-(1-(6-bromo-[1,2,4]triazolo[4,3-a]pyridin-3-yl)ethyl)-N-(2,4-dimethoxybenzyl)pyridazin-3-amine 48E (750 mg, 1.598 mmol, 83% yield) as a yellow solid. $^1$H NMR (400 MHz, DMSO-d6) δ ppm 1.77 (d, J=7.07 Hz, 3 H) 3.72 (s, 3 H) 4.37 (d, J=5.81 Hz, 2 H) 4.95 (d, J=7.07 Hz, 1H) 6.44 (dd, J=8.34, 2.53 Hz, 1 H) 6.54 (d, J=2.27 Hz, 1 H) 6.85 (d, J=9.35 Hz, 1H) 7.03 (s, 1 H) 7.12 (d, J=8.34 Hz, 1 H) 7.29 (d, J=9.35 Hz, 1 H) 7.45 (dd, J=9.73, 1.64 Hz, 1 H) 7.69-7.79 (m, 1 H) 8.59 (s, 1 H). ESI-MS:m/z 469.2 $(M+H)^+$.

6-(1-(6-bromo-[1,2,4]triazolo[4,3-a]pyridin-3-yl)ethyl) pyridazin-3-amine: A mixture of 6-(1-(6-bromo-[1,2,4]triazolo[4,3-a]pyridin-3-yl)ethyl)-N-(2,4-dimethoxybenzyl)pyridazin-3-amine (750 mg, 1.598 mmol), anisole (0.349 mL, 3.20 mmol), and TFA (1.0 mL, 12.98 mmol) in DCM (5.0 mL) was heated in a microwave on high absorbance for 2 hrs at 75° C. The reaction was stripped to dryness via rotary evaporation, and the resulting oil was treated with $Et_2O$ to produce a solid. The solid was filtered and dried under vacuum to provide the title compound, 6-(1-(6-bromo-[1,2,4]triazolo[4,3-a]pyridin-3-yl)ethyl)pyridazin-3-amine 2,2,2-trifluoroacetate (400 mg, 0.923 mmol, 57.8% yield) as a yellow solid. $^1$H NMR 48F (400 MHz, DMSO-d6) δ ppm 1.77 (d, J=7.07 Hz, 3 H) 5.05 (d, J=7.07 Hz, 1 H) 7.44 (d, J=9.60 Hz, 1 H) 7.50 (dd, J=9.73, 1.64 Hz, 1 H) 7.73-7.84 (m, 1 H) 7.92 (d, J=9.60 Hz, 1 H) 8.56 (br. s., 2 H) 8.81 (s, 1 H). ESI-MS:m/z 319.1 $(M+H)^+$.

6-(1-(6-bromo-[1,2,4]triazolo[4,3-a]pyridin-3-yl)ethyl) imidazo[1,2-b]pyridazin-2-amine: A mixture of 6-(1-(6-bromo-[1,2,4]triazolo[4,3-a]pyridin-3-yl)ethyl)pyridazin-3-amine (1.0 g, 3.13 mmol), 2-bromoacetonitrile (0.251 ml, 3.76 mmol) and $NaHCO_3$ (0.053 g) in IPA (10 mL) was heated at 100° C. in a sealed tube for 2 hrs. The solid was filtered off, rinsed with IPA, and stripped to dryness via rotary evaporation. The resulting residue was purified by LCMS and lyophilized as a TFA salt to provide the title compound, 6-(1-(6-bromo-[1,2,4]triazolo[4,3-a]pyridin-3-yl)ethyl)imidazo[1,2-b]pyridazin-2-amine 48G (0.62 mg, 1.73 mmol, 55%). $^1$H NMR (400 MHz, DMSO-$d_6$) δ ppm 1.85 (d, J=7.07 Hz, 3 H) 5.17 (d, J=7.07 Hz, 1 H) 7.38-7.57 (m, 3 H) 7.80 (d, J=9.60 Hz, 1 H) 7.99 (d, J=9.09 Hz, 1 H) 8.78 (s, 1 H). ESI-MS:m/z 358.1 $(M+H)^+$.

N-(6-(1-(6-bromo-[1,2,4]triazolo[4,3-a]pyridin-3-yl) ethyl)imidazo[1,2-b]pyridazin-2-yl)cyclopropanecarboxamide: To a solution of 6-(1-(6-bromo-[1,2,4]triazolo[4,3-a]pyridin-3-yl)ethyl)imidazo[1,2-b]pyridazin-2-amine TFA salt (250 mg, 0.52 mmol) in $CH_2Cl_2$ was added DIEA (0.65 g, 5.0 mmol) followed by cyclopropanecarbonyl chloride (0.16 g, 1.5 mmol). The reaction was stirred at ambient temperature for 30 min. Solvent was removed via rotary evaporation and the resulting residue was reconstituted in MeOH (10 mL). $NH_4OH$ (0.5 mL) was added and the reaction was stirred at ambient temperature for 1 hr. The reaction was then concentrated to dryness and the resulting material was dissolved in EtOAc, washed with saturated $NaHCO_3$, dried with $MgSO_4$, filtered and concentrated to dryness. The crude material was purified via MPLC (5% MeOH/0.1% $NH_4OH$/EA) to provide the title compound, N-(6-(1-(6-bromo-[1,2,4]triazolo[4,3-a]pyridin-3-yl)ethyl)imidazo[1,2-b]pyridazin-2-yl)cyclopropanecarboxamide 48 (0.22 g, 0.52 mmol, 100%). $^1$H NMR (400 MHz, DMSO-$d_6$) δ ppm 0.73-0.87 (m, 4 H) 1.83-1.99 (m, 4 H) 5.17 (d, J=7.07 Hz, 1 H) 7.38-7.57 (m, 3 H) 7.80 (d, J=9.60 Hz, 1 H) 7.99 (d, J=9.09 Hz, 1 H) 8.78 (s, 1 H) 11.14 (s, 1 H). ESI-MS:m/z 426.2 $(M+H)^+$.

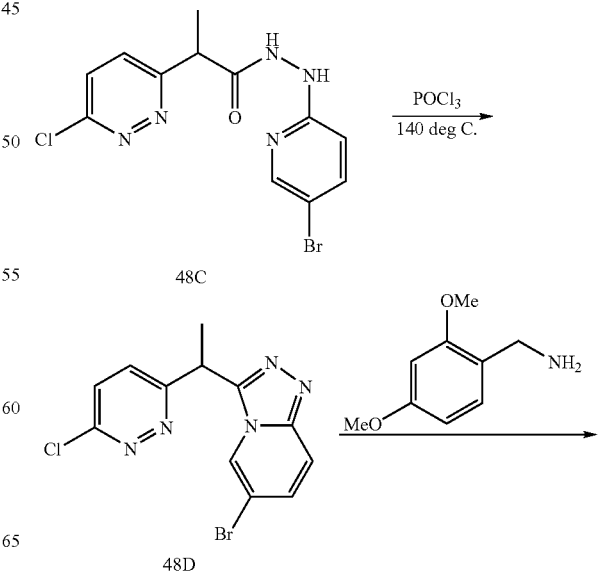

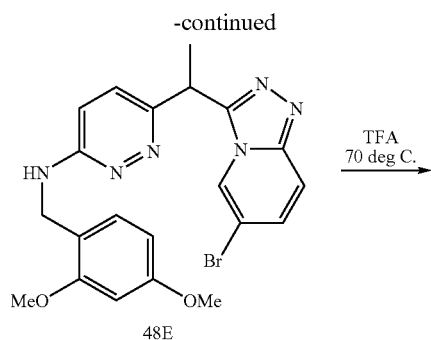

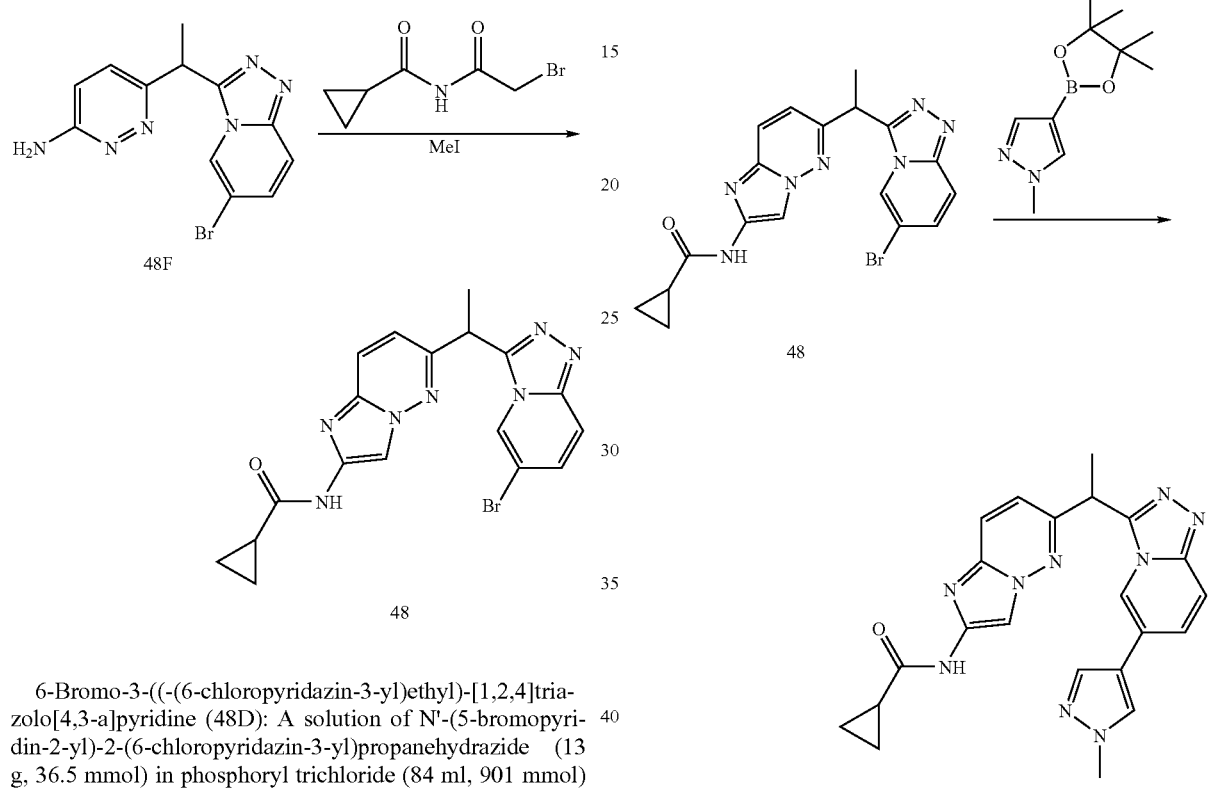

6-Bromo-3-((-(6-chloropyridazin-3-yl)ethyl)-[1,2,4]triazolo[4,3-a]pyridine (48D): A solution of N'-(5-bromopyridin-2-yl)-2-(6-chloropyridazin-3-yl)propanehydrazide (13 g, 36.5 mmol) in phosphoryl trichloride (84 ml, 901 mmol) was heated in the microwave at 140° C. for 15 min. The reaction was concentrated via rotary evaporation and the resulting mixture was added drop-wise to a mixture of EtOAc:Saturated Bicarbonate (aq) (4:6, 1 L). The organic phase was separated and the aqueous phase was extracted with EtOAc (3×75 mL). The EtOAc solutions were combined and evaporated to dryness. The resulting residue was purified by MPLC (DCM:MeOH, 97:3) to provide the title compound, 6-Bromo-3-(1-(6-chloropyridazin-3-yl)ethyl)-[1,2,4]triazolo[4,3-a]pyridine (48D, 3.3 g, 26.7%). $^1$H NMR (400 MHz, DMSO-d$_6$) δ ppm 1.86 (d, J=7.07 Hz, 3 H) 5.27 (d, J=7.33 Hz, 1 H) 7.49 (dd, J=9.60, 1.77 Hz, 1H) 7.78 (dd, J=9.85, 1.01 Hz, 1 H) 7.94 (s, 2 H) 8.79 (s, 1 H). ESI-MS:m/z 339.1 (M+H)$^+$.

6-(1-(6-Bromo-[1,2,4]triazolo[4,3-a]pyridin-3-yl)ethyl)-N-(2,4-dimethoxybenzyl)pyridazin-3-amine (48E): The title compound was synthesized using an analogous procedure to that described in the preparation of Compound 48E from Method A.

6-(1-(6-Bromo-[1,2,4]triazolo[4,3-a]pyridin-3-yl)ethyl)pyridazin-3-amine (48F): The title compound was synthesized using an analogous procedure to that described in the preparation of Compound 48E from Method A.

N-(6-(1-(6-Bromo-[1,2,4]triazolo[4,3-a]pyridin-3-yl)ethyl)imidazo[1,2-b]pyridazin-2-yl)cyclopropanecarboxamide (48): The title compound was synthesized using an analogous procedure to that described in the preparation of Compound 45O.

Compound 49: N-(6-(1-(6-(1-methyl-1H-pyrazol-4-yl)-[1,2,4]triazolo[4,3-a]pyridin-3-yl)ethyl)imidazo[1,2-b]pyridazin-2-yl)cyclopropanecarboxamide A mixture of N-(6-(1-(6-bromo-[1,2,4]triazolo[4,3-a]-pyridin-3-yl)imidazol[1,2-b]pyridazin-2-yl)cyclopropanecarboxamide (0.23 g, 0.54 mmol), 1-methyl-4-(4,4,5,5-tetramethyl-1,3,2-dioxaborolan-2-yl)-1H-pyrazole (0.16 g, 0.8 mmol) and PdCl$_2$(dppf)-CH$_2$Cl$_2$ (0.02 g, 0.02 mmol) in Na$_2$CO$_3$ (2N, 1 mL)/dioxane (2 mL) was heated in microwave at 110° C. for 45 min. The reaction mixture was filtered, rinsed with EtOAc and concentrated to dryness via rotary evaporation. The resulting material was purified by preparative LCMS. The collected fractions were combined and the resulting mixture was treated with two drops of concentrated HCl. The solution was lyophilized to provide the HCl salt of the title compound, N-(6-(1-(6-(1-methyl-1H-pyrazol-4-yl)-[1,2,4]triazolo[4,3-a]pyridin-3-yl)ethyl)imidazo[1,2-b]pyridazin-2-yl)cyclopropanecarboxamide 49 (0.11 g, 0.25 mmol, 47%). $^1$H NMR (400 MHz, DMSO-d$_6$) δ ppm 0.80 (d, J=6.32 Hz, 4 H) 1.84-1.99 (m, 4 H) 3.87 (s, 3 H) 5.35 (d, J=7.07 Hz, 1 H) 7.43 (d, J=9.35 Hz, 1 H) 8.02 (d, J=9.35 Hz, 1 H) 8.05-8.13 (m, 3 H) 8.19 (dd, J=9.60, 1.52 Hz, 1 H) 8.38 (s, 1 H) 9.01 (s, 1 H) 11.18 (s, 1 H). MS:m/z 428.2 (M+H)+.

Compound 50: (S)—N-(6-(1-(6-(1-methyl-1H-pyrazol-4-yl)-[1,2,4]triazolo[4,3-a]pyridin-3-yl)ethyl)imidazo[1,2-b]pyridazin-2-yl)cyclopropanecarboxamide

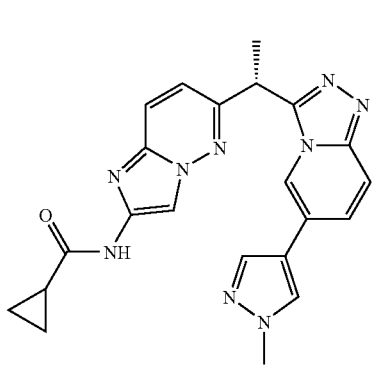

Compound 50 was obtained from chiral separation of Compound 49 under the following conditions: An SFC/UV system was used with mobile phases of 25% EtOH (plus 10 mM NH₄OAc) in CO₂ on ChiralCel AS-H column (21×250 mm) at a flow rate of 50 mL/min with UV detection at 220 nm. ¹H NMR (400 MHz, DMSO-d₆) δ ppm 0.73-0.88 (m, 3 H) 1.81-1.99 (m, 4 H) 3.87 (s, 3 H) 5.08-5.21 (m, 1 H) 7.27 (d, J=9.35 Hz, 1 H) 7.63 (dd, J=9.60, 1.52 Hz, 1 H) 7.80 (dd, J=9.60, 1.01 Hz, 1 H) 7.91-8.00 (m, 2 H) 8.12 (s, 1 H) 8.23 (s, 1 H) 8.62 (s, 1 H) 11.13 (s, 1 H). MS:m/z 428.2 (M+H)+.

Compound 51: (R)—N-(6-(1-(6-(1-methyl-1H-pyrazol-4-yl)-[1,2,4]triazolo[4,3-a]pyridin-3-yl)ethyl)imidazo[1,2-b]pyridazin-2-yl)cyclopropanecarboxamide

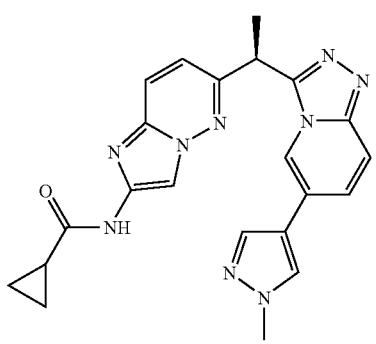

Compound 51 was obtained from chiral separation of Compound 49 under the following conditions: An SFC/UV system was used with mobile phases of 25% EtOH (plus 10 mM NH₄OAc) in CO₂ on ChiralCel AS-H column (21×250 mm) at a flow rate of 50 mL/min with UV detection at 220 nm. ¹H NMR (400 MHz, DMSO-d₆) δ ppm 0.73-0.88 (m, 3 H) 1.81-1.99 (m, 4 H) 3.87 (s, 3 H) 5.08-5.21 (m, 1 H) 7.27 (d, J=9.35 Hz, 1 H) 7.63 (dd, J=9.60, 1.52 Hz, 1 H) 7.80 (dd, J=9.60, 1.01 Hz, 1 H) 7.91-8.00 (m, 2 H) 8.12 (s, 1 H) 8.23 (s, 1 H) 8.62 (s, 1 H) 11.13 (s, 1 H). MS:m/z 428.2 (M+H)+.

Compound 52: N-(6-(1-([1,2,4]triazolo[4,3-a]pyridin-3-yl)ethyl)imidazo[1,2-b]pyridazin-2-yl)cyclopropanecarboxamide

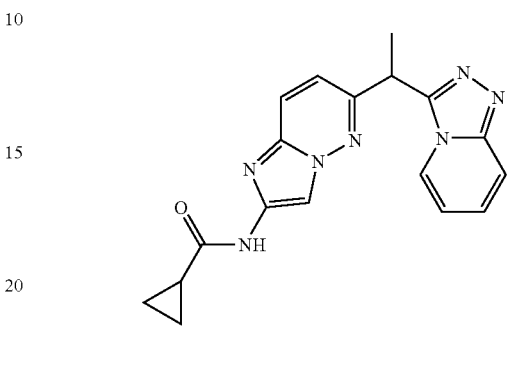

The title compound was synthesized using an analogous procedure to that described in the preparation of Compound 48 (Method A) using 2-hydrazinylpyridine. ¹H NMR (400 MHz, DMSO-d₆) δ ppm 0.73-0.87 (m, 4 H) 1.83-1.99 (m, 4 H) 5.04-5.15 (m, 1 H) 6.94-7.04 (m, 1 H) 7.19 (d, J=9.35 Hz, 1 H) 7.38-7.47 (m, 1 H) 7.80 (d, J=9.35 Hz, 1 H) 7.94 (d, J=9.85 Hz, 1 H) 8.10 (s, 1 H) 8.35 (d, J=7.07 Hz, 1 H) 11.14 (s, 1 H). MS:m/z 348.2 (M+H)+.

Compound 53: N-(6-(1-(6-methyl-[1,2,4]triazolo[4,3-a]pyridin-3-yl)ethyl)imidazo[1,2-b]pyridazin-2-yl)cyclopropanecarboxamide

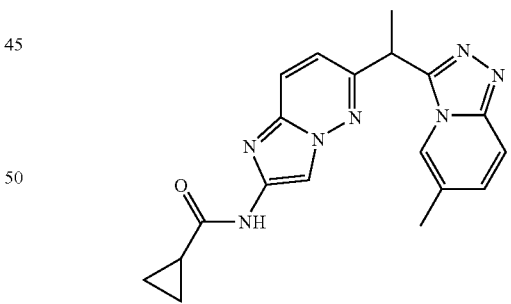

The title compound was synthesized using an analogous procedure to that described in the preparation of Compound 48 (Method A) using 2-hydrazinyl-5-methylpyridine. ¹H NMR (400 MHz, DMSO-d₆) δ ppm 0.76-0.86 (m, 4 H) 1.85 (d, J=7.07 Hz, 3 H) 1.92 (m, 1 H) 3.56 (s, 3 H) 5.02 (d, J=7.07 Hz, 1 H) 7.18 (d, J=9.35 Hz, 1 H) 7.23-7.31 (m, 1 H) 7.70 (d, J=8.84 Hz, 1H) 7.93 (d, J=9.85 Hz, 1 H) 8.10 (s, 1 H) 8.20 (s, 1 H) 11.13 (s, 1 H). MS:m/z 362.2 (M+H)+.

Compound 54: (6-(2-([1,2,4]Triazolo[4,3-a]pyridin-3-yl)propan-2-yl)imidazo[1,2-b]pyridazin-2-yl)(cyclopropyl)methanone

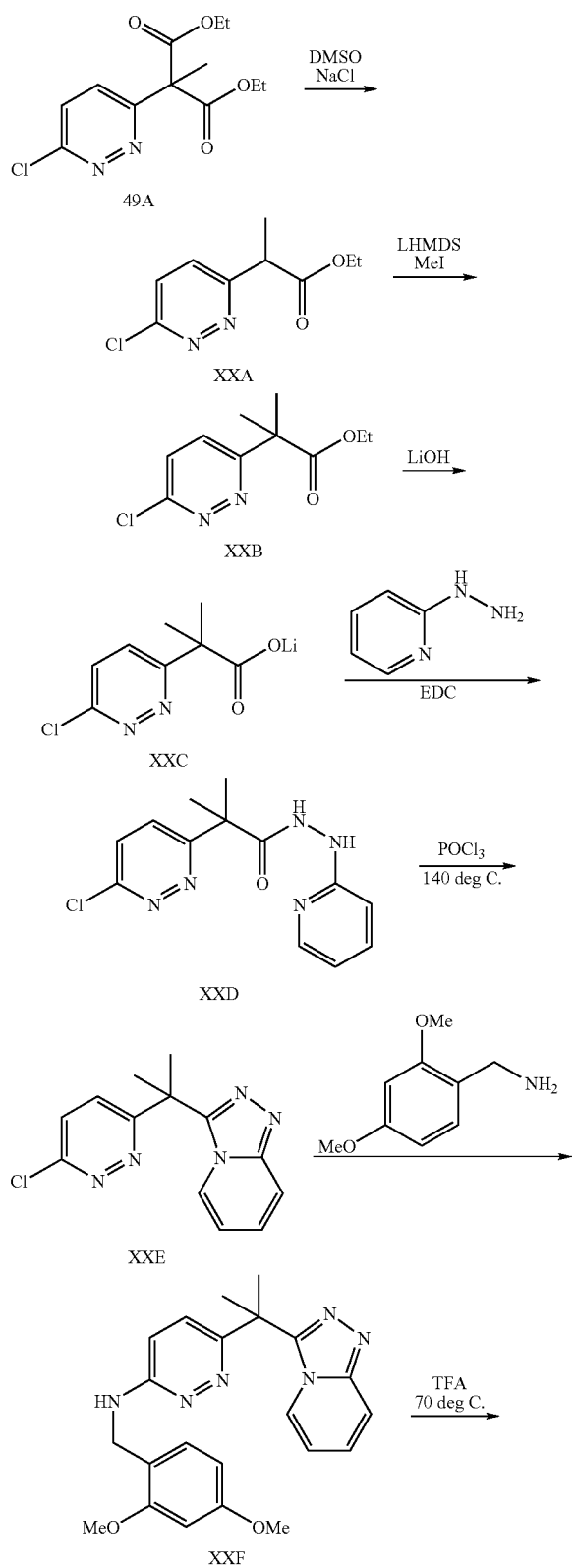

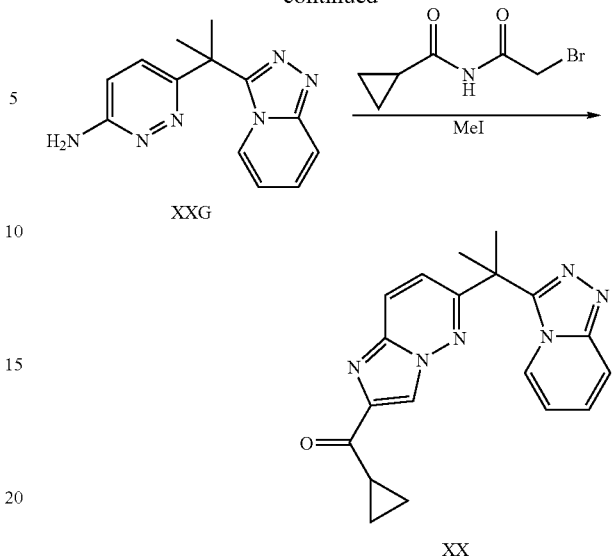

Ethyl 2-(6-chloropyridazin-3-yl)propanoate (54A): A solution of diethyl 2-(6-chloropyridazin-3-yl)-2-methylmalonate (11 g, 38.4 mmol) and NaCl (2.69 g, 46.0 mmol) in DMSO (91 mL) and H$_2$O (1.382 ml) was divided into eight separate microwave vials and each reaction was heated in a microwave at 175° C. for 90 mins on high absorbance. The reactions were combined and then poured into H$_2$O (300 mL). The aqueous phase was extracted with EtOAc (2×100 mL) and then the organic phase was washed with brine (2×100 mL). The organic phase was dried over MgSO$_4$, filtered and concentrated to dryness via rotary evaporation. The resulting oil was purified via MPLC (3:1, Hex:EtOAc) to provide the title compound, ethyl 2-(6-chloropyridazin-3-yl)propanoate (54A, 2.9 g, 35%). $_1$H NMR (400 MHz, DMSO-d$_6$) δ ppm 1.13 (s, 3 H) 1.49 (d, J=7.33 Hz, 3 H) 4.09 (dd, J=7.07, 2.02 Hz, 2 H) 4.23 (d, J=7.33 Hz, 1 H) 7.83 (d, J=8.84 Hz, 1 H) 7.93 (d, J=8.84 Hz, 1 H). ESI-MS:m/z 215.0 (M+H)$^+$.

Ethyl 2-(6-chloropyridazin-3-yl)-2-methylpropanoate (54B): To a solution of ethyl 2-(6-chloropyridazin-3-yl)propanoate (2.8 g, 13.04 mmol) in THF (28 mL) was added lithium hexamethyldisilazide (1.0 molar in THF, 15.65 mL, 15.65 mmol) at −70° C. in dropwise fashion. The reaction was stirred at −70 for 30 min and then iodomethane (0.816 mL, 13.04 mmol) was added. The reaction was stirred for 2 hrs as allowed to warm to room temperature. The reaction was concentrated to dryness via rotary evaporation and the resulting material was purified by MPLC (98:2, DCM:MeOH) to provide the title compound, ethyl 2-(6-chloropyridazin-3-yl)-2-methylpropanoate (54B, 2.82 g, 95%). $^1$H NMR (400 MHz, DMSO-d6) δ ppm 1.11 (t, J=7.07 Hz, 3 H) 1.58 (s, 6 H) 4.08 (q, J=7.07 Hz, 2 H) 7.83-7.97 (m, 2 H).

Lithium 2-(6-chloropyridazin-3-yl)-2-methylpropanoate (54C): The title compound was synthesized using an analogous procedure to that described in the preparation of Compound 48B.

2-(6-Chloropyridazin-3-yl)-2-methyl-N'-(pyridin-2-yl)propanehydrazide (54D): The title compound was synthesized using an analogous procedure to that described in the preparation of Compound 48C using 2-hydrazinylpyridine.

3-(2-(6-chloropyridazin-3-yl)propan-2-yl)-[1,2,4]triazolo[4,3-a]pyridine (54E): A mixture of 2-(6-chloropyridazin-3-yl)-N'-(pyridin-2-yl)propanehydrazide (1.2 g, 4.32 mmol) and phosphoryl trichloride (10.0 mL, 107 mmol) was heated in a microwave on high absorbance for 15 min at 140° C. The resulting reaction was stripped to dryness via rotary evaporation. The resulting residue was reconstituted in EtOAc (50 mL) and washed with saturated bicarbonate (3×50 mL). The organic layer was separated and dried over MgSO$_4$ and the EtOAc was removed via rotary evaporation to provide the title compound, 3-(2-(6-chloropyridazin-3-yl)propan-2-yl)-[1,2,4]triazolo[4,3-a]pyridine (54E, 0.750 g, 2.74 mmol, 63.4% yield). $_1$H NMR (400 MHz, DMSO-d$_6$) δ ppm 1.94 (6 H, s) 6.75-6.82 (1 H, m) 7.33 (1 H, ddd, J=9.35, 6.57, 1.01 Hz) 7.72-7.82 (2 H, m) 7.87-7.99 (2 H, m). ESI-MS:m/z 274.1 (M+H)$^+$.

6-(2-([1,2,4]Triazolo[4,3-a]pyridin-3-yl)propan-2-yl)-N-(2,4-dimethoxybenzyl)pyridazin-3-amine (54F): The title compound was synthesized using an analogous procedure to that described in the preparation of Compound 48E.

6-(2-([1,2,4]Triazolo[4,3-a]pyridin-3-yl)propan-2-yl)pyridazin-3-amine (54G): The title compound was synthesized using an analogous procedure to that described in the preparation of Compound 48F.

(6-(2-([1,2,4]Triazolo[4,3-a]pyridin-3-yl)propan-2-yl)imidazo[1,2-b]pyridazin-2-yl)(cyclopropyl)methanone (54): A mixture of 6-(2-([1,2,4]triazolo[4,3-a]pyridin-3-yl)propan-2-yl)pyridazin-3-amine 2,2,2-trifluoroacetate (50 mg, 0.136 mmol), N-(2-bromoacetyl)cyclopropanecarboxamide (28.0 mg, 0.136 mmol), sodium hydrogenphosphate (57.8 mg, 0.407 mmol), and potassium iodide (22.54 mg, 0.136 mmol) in DMA (Volume: 1160 µl) was heated in a microwave on high absorbance for 1 hr at 100° C. The reaction was purified by preparative LCMS to provide the title compound, (6-(2-([1,2,4]triazolo[4,3-a]pyridin-3-yl)propan-2-yl)imidazo[1,2-b]pyridazin-2-yl)(cyclopropyl)methanone (54, 13 mg, 26%) as a TFA salt. $_1$H NMR (400 MHz, DMSO-d$_6$) δ ppm 0.81 (d, J=6.06 Hz, 4 H) 1.87-2.00 (m, 7 H) 6.92-6.97 (m, 1 H) 7.12 (d, J=9.60 Hz, 1 H) 7.55 (dd, J=8.97, 6.69 Hz, 1 H) 7.87-8.01 (m, 3H) 8.04 (s, 1 H) 11.16 (s, 1 H). ESI-MS: m/z 362.1 (M+H)$^+$.

Compound 55: N-(6-(1-(6-(4-fluorophenyl)-[1,2,4]triazolo[4,3-a]pyridin-3-yl)ethyl)imidazo[1,2-b]pyridazin-2-yl)cyclopropanecarboxamide

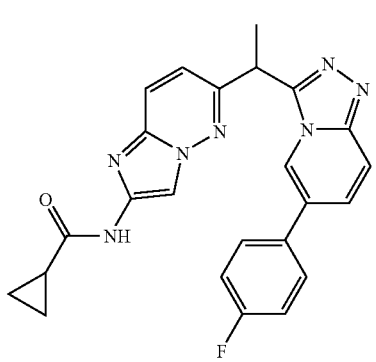

The title compound was synthesized using an analogous procedure to that described in the preparation of Compound 49 using 4-fluorophenylboronic acid. The crude reaction mixture was purified by preparative LCMS, and the product was isolated as the TFA salt. $^1$H NMR (400 MHz, DMSO-d6) δ ppm 0.72-0.88 (m, 4 H) 1.81-1.98 (m, 4 H) 5.30 (d, J=7.07 Hz, 1 H) 7.30 (d, J=9.35 Hz, 1 H) 7.32-7.40 (m, 2 H) 7.76-7.82 (m, 2 H) 7.82-7.88 (m, 1 H) 7.95 (t, J=9.09 Hz, 2 H) 8.09 (s, 1 H) 8.78 (s, 1 H) 11.14 (s, 1 H). ESI-MS:m/z 442.2 (M+H)$^+$.

Compound 56: N-(6-(1-(6-(4-methoxyphenyl)-[1,2,4]triazolo[4,3-a]pyridin-3-yl)ethyl)imidazo[1,2-b]pyridazin-2-yl)cyclopropanecarboxamide

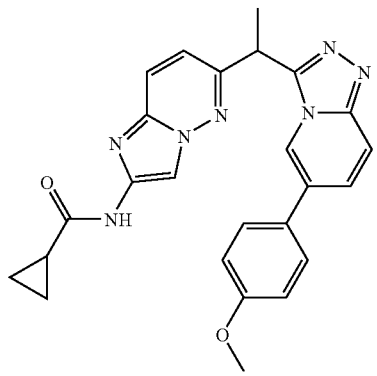

The title compound was synthesized using an analogous procedure to that described in the preparation of Compound 49 using 4-methoxyphenylboronic acid. The crude reaction mixture was purified by preparative LCMS, and the product was isolated as the TFA salt. $^1$H NMR (400 MHz, DMSO-d6) δ ppm 0.73-0.87 (m, 5 H) 1.84-2.00 (m, 5 H) 5.30 (d, J=7.33 Hz, 1 H) 7.02-7.14 (m, 3 H) 7.29 (d, J=9.35 Hz, 1 H) 7.61-7.72 (m, 3 H) 7.83-8.00 (m, 4 H) 8.10 (s, 1 H) 8.71 (s, 1 H) 11.15 (s, 1 H). ESI-MS:m/z 454.2 (M+H)$^+$.

Compound 57: N-(6-(1-(6-(3-cyanophenyl)-[1,2,4]triazolo[4,3-a]pyridin-3-yl)ethyl)imidazo[1,2-b]pyridazin-2-yl)cyclopropanecarboxamide

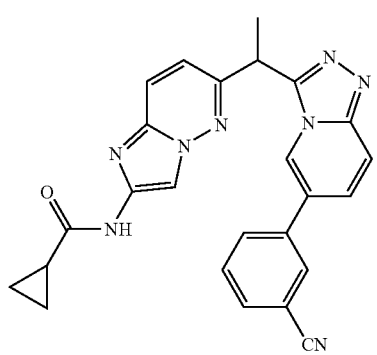

The title compound was synthesized using an analogous procedure to that described in the preparation of Compound 49 using 3-cyanophenylboronic acid. The crude reaction mixture was purified by preparative LCMS, and the product was isolated as the TFA salt. $^1$H NMR (400 MHz, DMSO-d6) δ ppm 0.71-0.86 (m, 4H) 1.82-1.97 (m, 4 H) 5.24-5.37 (m, 1 H) 7.31 (d, J=9.60 Hz, 1 H) 7.69-7.75 (m, 1 H) 7.87-7.99 (m, 4 H)

8.05-8.13 (m, 2 H) 8.31 (t, J=1.52 Hz, 1 H) 8.94 (s, 1 H) 11.12 (s, 1 H). ESI-MS:m/z 449.2 (M+H)+.

Compound 58: 4-(3-(1-(2-(cyclopropanecarboxamido)imidazo[1,2-b]pyridazin-6-yl)ethyl)-[1,2,4]triazolo[4,3-a]pyridin-6-yl)-2-fluoro-N-methylbenzamide

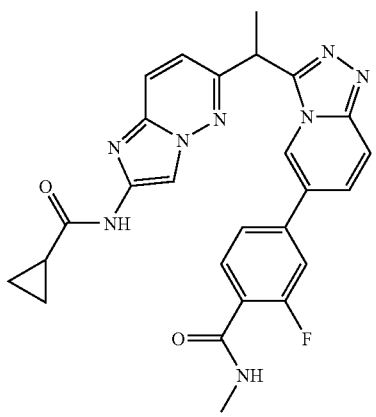

The title compound was synthesized using an analogous procedure to that described in the preparation of Compound 49 using 3-fluoro-4-(methylcarbamoyl)phenylboronic acid. The crude reaction mixture was purified by preparative LCMS, and the product was isolated as the TFA salt. $^1$H NMR (400 MHz, DMSO-d6) δ ppm 0.72-0.86 (m, 4 H) 1.84-1.98 (m, 4 H) 2.80 (d, J=4.55 Hz, 3 H) 5.31 (d, J=7.07 Hz, 1 H) 7.30 (d, J=9.35 Hz, 1 H) 7.66-7.71 (m, 1 H) 7.71-7.81 (m, 2 H) 7.83-7.88 (m, 1 H) 7.89-7.98 (m, 2 H) 8.09 (s, 1 H) 8.30 (dd, J=4.55, 2.53 Hz, 1H) 8.89 (s, 1 H) 11.13 (s, 1 H). ESI-MS:m/z 499.2 (M+H)+.

Compound 59: N-(6-(1-(6-(3-(methylsulfonyl)phenyl)-[1,2,4]triazolo[4,3-a]pyridin-3-yl)ethyl)imidazo[1,2-b]pyridazin-2-yl)cyclopropanecarboxamide

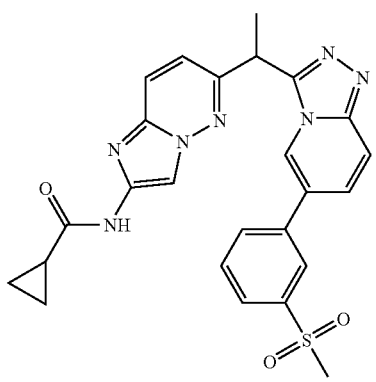

The title compound was synthesized using an analogous procedure to that described in the preparation of Compound 49 using 3-(methylsulfonyl)phenylboronic acid. The crude reaction mixture was purified by preparative LCMS, and the product was isolated as the TFA salt. $^1$H NMR (400 MHz, DMSO-d6) δ ppm 0.74-0.85 (m, 5 H) 1.83-1.98 (m, 5 H) 5.34 (d, J=7.07 Hz, 1 H) 7.32 (d, J=9.35 Hz, 1 H) 7.73-7.85 (m, 1 H) 7.89-8.03 (m, 5 H) 8.05-8.14 (m, 2 H) 8.27 (t, J=1.64 Hz, 1 H) 8.93 (s, 1 H) 11.13 (s, 1 H). ESI-MS:m/z 502.2 (M+H)+.

Compound 60: N-(6-(1-(6-(4-(methylsulfonyl)phenyl)-[1,2,4]triazolo[4,3-a]pyridin-3-yl)ethyl)imidazo[1,2-b]pyridazin-2-yl)cyclopropanecarboxamide

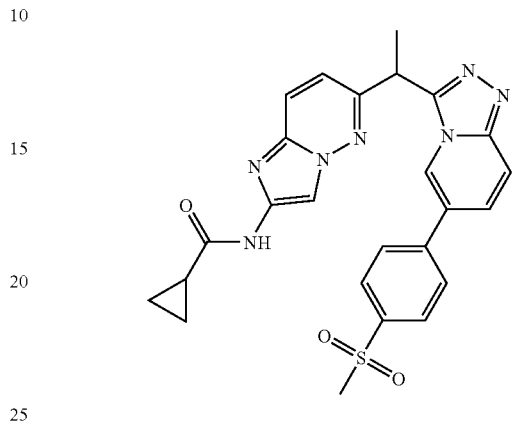

The title compound was synthesized using an analogous procedure to that described in the preparation of Compound 49 using 4-(methylsulfonyl)phenylboronic acid. The crude reaction mixture was purified by preparative LCMS, and the product was isolated as the TFA salt. $^1$H NMR (400 MHz, DMSO-d6) δ ppm 0.73-0.87 (m, 5 H) 1.83-1.98 (m, 5 H) 5.31 (d, J=7.07 Hz, 1 H) 7.30 (d, J=9.35 Hz, 1 H) 7.85-7.90 (m, 1 H) 7.93-7.99 (m, 2 H) 7.99-8.07 (m, 5 H) 8.09 (s, 1 H) 8.90 (s, 1 H) 11.13 (s, 1 H). ESI-MS:m/z 502.2 (M+H)+.

Compound 61: N-(6-(1-(6-(3-methoxyphenyl)-[1,2,4]triazolo[4,3-a]pyridin-3-yl)ethyl)imidazo[1,2-b]pyridazin-2-yl)cyclopropanecarboxamide

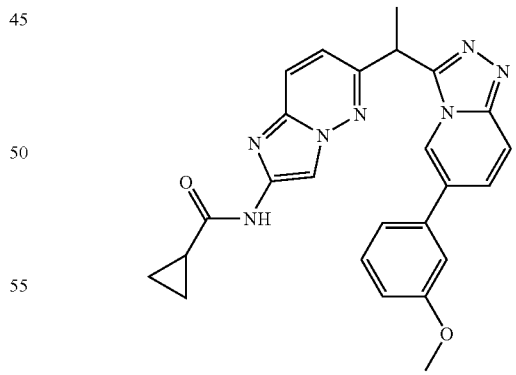

The title compound was synthesized using an analogous procedure to that described in the preparation of Compound 49 using 3-methoxyphenylboronic acid. The crude reaction mixture was purified by preparative LCMS, and the product was isolated as the TFA salt. $^1$H NMR (400 MHz, DMSO-d6) δ ppm 0.74-0.85 (m, 4 H) 1.90 (d, J=7.33 Hz, 4 H) 3.61 (s, 3 H) 5.32 (d, J=7.07 Hz, 1 H) 7.02 (ddd, J=8.21, 2.40, 0.76 Hz, 1 H) 7.21-7.34 (m, 3 H) 7.37-7.49 (m, 1 H) 7.87-8.00 (m, 3 H) 8.09 (s, 1 H) 8.77 (s, 1 H) 11.14 (s, 1 H). ESI-MS:m/z 454.2 (M+H)⁺.

Compound 62: N-(6-(1-(6-(4-methylthiophen-2-yl)-[1,2,4]triazolo[4,3-a]pyridin-3-yl)ethyl)imidazo[1,2-b]pyridazin-2-yl)cyclopropanecarboxamide

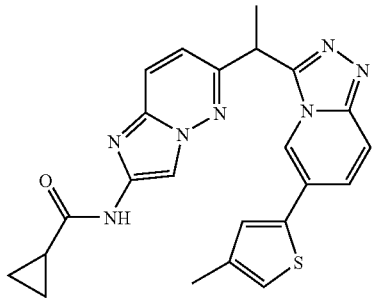

The title compound was synthesized using an analogous procedure to that described in the preparation of Compound 49 using 4-methylthiophen-2-ylboronic acid. The crude reaction mixture was purified by preparative LCMS, and the product was isolated as the TFA salt. ¹H NMR (400 MHz, DMSO-d6) δ ppm 0.75-0.87 (m, 4 H) 1.82-1.98 (m, 4 H) 2.24 (d, J=0.76 Hz, 3 H) 5.24 (d, J=7.33 Hz, 1 H) 7.17-7.30 (m, 2 H) 7.45 (d, J=1.26 Hz, 1 H) 7.71 (dd, J=9.60, 1.52 Hz, 1 H) 7.86 (dd, J=9.47, 0.88 Hz, 1 H) 7.95 (d, J=9.60 Hz, 1 H) 8.13 (s, 1H) 8.64 (s, 1 H) 11.15 (s, 1 H). ESI-MS:m/z 444.2 (M+H)⁺.

Compound 63: N-(6-(1-(6-(4-cyanophenyl)-[1,2,4]triazolo[4,3-a]pyridin-3-yl)ethyl)imidazo[1,2-b]pyridazin-2-yl)cyclopropanecarboxamide

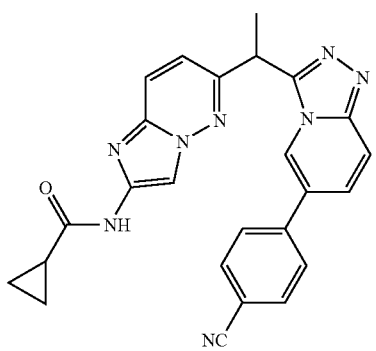

The title compound was synthesized using an analogous procedure to that described in the preparation of Compound 49 using 4-cyanophenylboronic acid. The crude reaction mixture was purified by preparative LCMS, and the product was isolated as the TFA salt. ¹H NMR (400 MHz, DMSO-d6) δ ppm 0.73-0.87 (m, 4 H) 1.83-2.00 (m, 4 H) 5.29 (d, J=7.07

Hz, 1 H) 7.29 (d, J=9.35 Hz, 1 H) 7.80-7.89 (m, 1 H) 7.90-8.04 (m, 6H) 8.08 (s, 1 H) 8.90 (s, 1 H) 11.13 (s, 1 H). ESI-MS:m/z 449.2 (M+H)⁺.

Compound 64: N-(6-(1-(6-(1H-pyrazol-4-yl)-[1,2,4]triazolo[4,3-a]pyridin-3-yl)ethyl)imidazo[1,2-b]pyridazin-2-yl)cyclopropanecarboxamide

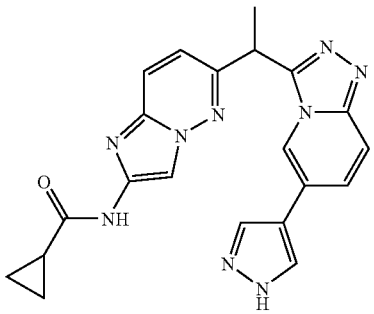

The title compound was synthesized using an analogous procedure to that described in the preparation of Compound 49 using 1H-pyrazol-4-ylboronic acid. The crude reaction mixture was purified by preparative LCMS, and the product was isolated as the TFA salt. ¹H NMR (400 MHz, DMSO-d6) δ ppm 0.73-0.86 (m, 4 H) 1.82-1.99 (m, 4 H) 5.21 (d, J=7.33 Hz, 1H) 7.31 (d, J=9.60 Hz, 1 H) 7.88 (d, J=6.06 Hz, 2 H) 7.97 (d, J=9.35 Hz, 1 H) 8.11 (s, 1 H) 8.19 (s, 2 H) 8.75 (s, 1 H) 11.13 (s, 1 H). ESI-MS:m/z 414.2 (M+H)⁺.

Compound 65: N-(6-(1-(6-(3-fluorophenyl)-[1,2,4]triazolo[4,3-a]pyridin-3-yl)ethyl)imidazo[1,2-b]pyridazin-2-yl)cyclopropanecarboxamide

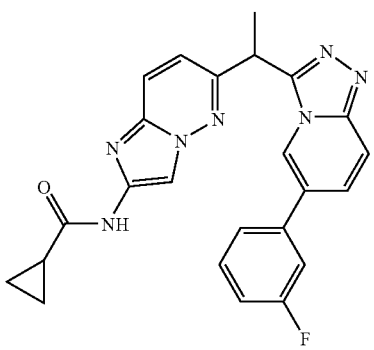

The title compound was synthesized using an analogous procedure to that described in the preparation of Compound 49 using 4-fluorophenylboronic acid. The crude reaction mixture was purified by preparative LCMS, and the product was isolated as the TFA salt. ¹H NMR (400 MHz, DMSO-d6) δ ppm 0.72-0.87 (m, 4 H) 1.83-1.97 (m, 4 H) 5.29 (d, J=7.33 Hz, 1 H) 7.51-7.61 (m, 2 H) 7.64 (dt, J=10.29, 2.05 Hz, 1 H)

7.81 (dd, J=9.73, 1.64 Hz, 1 H) 7.87-7.92 (m, 1H) 7.94 (d, J=9.35 Hz, 1 H) 8.09 (s, 1 H) 8.80 (s, 1 H) 11.08 (s, 1 H). ESI-MS:m/z 442.2 (M+H)⁺.

Compound 66: 3-(3-(1-(2-(cyclopropanecarboxamido)imidazo[1,2-b]pyridazin-6-yl)ethyl)-[1,2,4]triazolo[4,3-a]pyridin-6-yl)benzamide

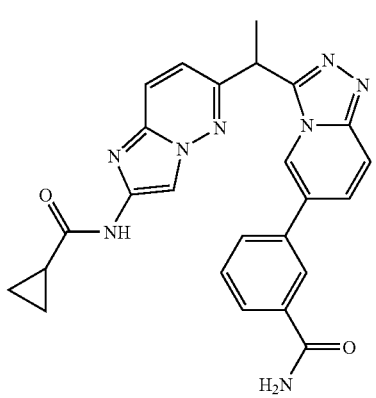

The title compound was synthesized using an analogous procedure to that described in the preparation of Compound 49 using 3-carbamoylphenylboronic acid. The crude reaction mixture was purified by preparative LCMS, and the product was isolated as the TFA salt. ¹H NMR (400 MHz, DMSO-d6) ppm 0.71-0.89 (m, 4 H) 1.83-2.00 (m, 4 H) 7.31 (d, J=9.35 Hz, 1 H) 7.46 (br. s., 1 H) 7.60 (t, J=7.71 Hz, 1 H) 7.82-8.03 (m, 5 H) 8.04-8.14 (m, 2 H) 8.22 (t, J=1.52 Hz, 1 H) 8.86 (s, 1 H) 11.09 (s, 1 H). ESI-MS:m/z 467.2 (M+H)⁺.

Compound 67: 4-(3-(1-(2-(cyclopropanecarboxamido)imidazo[1,2-b]pyridazin-6-yl)ethyl)-[1,2,4]triazolo[4,3-a]pyridin-6-yl)benzamide

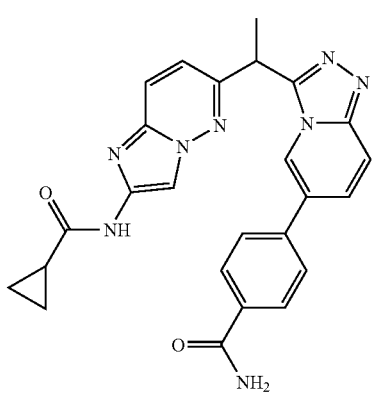

The title compound was synthesized using an analogous procedure to that described in the preparation of Compound 49 using 4-carbamoylphenylboronic acid. The crude reaction mixture was purified by preparative LCMS, and the product was isolated as the TFA salt. ¹H NMR (400 MHz, DMSO-d6) δ ppm 0.73-0.89 (m, 4 H) 1.83-1.99 (m, 4 H) 5.29 (d, J=7.33 Hz, 1 H) 7.28 (d, J=9.35 Hz, 1 H) 7.77-7.86 (m, 3 H) 7.87- 7.92 (m, 1 H) 7.94 (d, J=9.35 Hz, 1 H) 7.97-8.06 (m, 3 H) 8.10 (s, 1 H) 8.79 (s, 1 H) 11.08 (s, 1 H). ESI-MS:m/z 467.2 (M+H)⁺.

Compound 68: 4-(3-(1-(2-(cyclopropanecarboxamido)imidazo[1,2-b]pyridazin-6-yl)ethyl)-[1,2,4]triazolo[4,3-a]pyridin-6-yl)-N-methylbenzamide

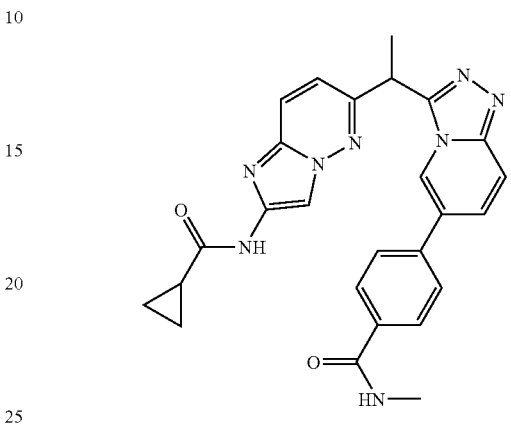

The title compound was synthesized using an analogous procedure to that described in the preparation of Compound 49 using 4-(methylcarbamoyl)phenylboronic acid. The crude reaction mixture was purified by preparative LCMS, and the product was isolated as the TFA salt. ¹H NMR (400 MHz, DMSO-d6) δ ppm 0.72-0.88 (m, 4 H) 1.83-1.99 (m, 4 H) 2.81 (d, J=4.55 Hz, 3 H) 5.30 (d, J=7.07 Hz, 1 H) 7.28 (d, J=9.35 Hz, 1 H) 7.78-7.87 (m, 3 H) 7.87-8.00 (m, 4 H) 8.10 (s, 1 H) 8.49 (d, J=4.55 Hz, 1 H) 8.81 (s, 1 H) 11.09 (s, 1H). ESI-MS: m/z 481.2 (M+H)⁺.

Compound 69: N-(6-(1-(6-(4-ethoxyphenyl)-[1,2,4]triazolo[4,3-a]pyridin-3-yl)ethyl)imidazo[1,2-b]pyridazin-2-yl)cyclopropanecarboxamide

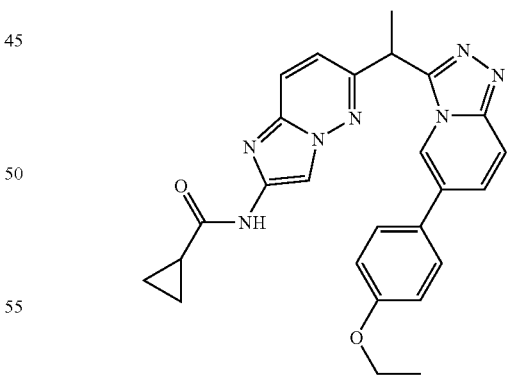

The title compound was synthesized using an analogous procedure to that described in the preparation of Compound 49 using 4-ethoxyphenylboronic acid. The crude reaction mixture was purified by preparative LCMS, and the product was isolated as the TFA salt. ¹H NMR (400 MHz, DMSO-d6) δ ppm 0.72-0.87 (m, 4 H) 1.34 (t, J=6.95 Hz, 3 H) 1.82-1.98 (m, 4 H) 5.27 (d, J=7.07 Hz, 1 H) 6.99-7.10 (m, 2 H) 7.26 (d, J=9.35 Hz, 1 H) 7.57-7.69 (m, 2 H) 7.74-7.83 (m, 1 H)

7.84-7.91 (m, 1 H) 7.94 (d, J=9.60 Hz, 1 H) 8.10 (s, 1 H) 8.64 (s, 1H) 11.09 (s, 1 H). ESI-MS:m/z 468.2 (M+H)+.

Compound 70: N-(6-(1-(6-(4-methoxy-3-methylphenyl)-[1,2,4]triazolo[4,3-a]pyridin-3-yl)ethyl)imidazo[1,2-b]pyridazin-2-yl)cyclopropanecarboxamide

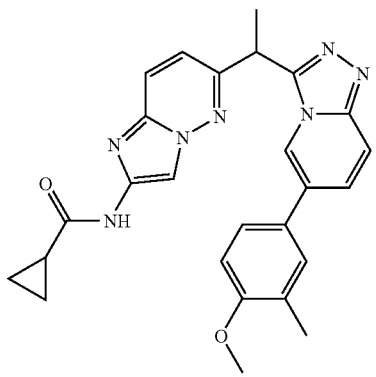

The title compound was synthesized using an analogous procedure to that described in the preparation of Compound 49 using 4-methoxy-3-methylphenylboronic acid. The crude reaction mixture was purified by preparative LCMS, and the product was isolated as the TFA salt. $^1$H NMR (400 MHz, DMSO-d6) δ ppm 0.74-0.86 (m, 5 H) 1.85-1.99 (m, 5 H) 2.21 (s, 4H) 5.29 (d, J=7.33 Hz, 2 H) 7.06 (d, J=8.59 Hz, 1 H) 7.28 (d, J=9.35 Hz, 1 H) 7.42-7.57 (m, 2H) 7.78-7.99 (m, 4 H) 8.12 (s, 1 H) 8.65 (s, 1 H) 11.10 (s, 1 H). ESI-MS:m/z 468.2 (M+H)+.

Compound 71: N-(6-(1-(6-(3-cyano-4-fluorophenyl)-[1,2,4]triazolo[4,3-a]pyridin-3-yl)ethyl)imidazo[1,2-b]pyridazin-2-yl)cyclopropanecarboxamide

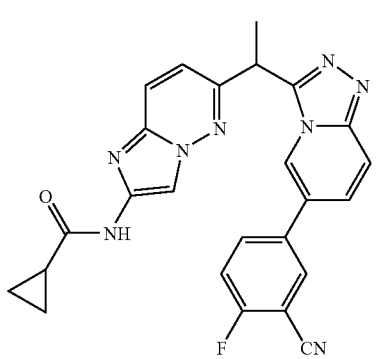

The title compound was synthesized using an analogous procedure to that described in the preparation of Compound 49 using 3-cyano-4-fluorophenylboronic acid. The crude reaction mixture was purified by preparative LCMS, and the product was isolated as the TFA salt. $^1$H NMR (400 MHz, DMSO-d6) δ ppm 0.73-0.86 (m, 4 H) 1.84-1.99 (m, 5 H) 5.26 (d, J=7.33 Hz, 1 H) 7.29 (d, J=9.60 Hz, 1 H) 7.68 (t, J=8.97 Hz, 1 H) 7.75-7.84 (m, 1 H) 7.87-7.98 (m, 2 H) 8.08 (s, 1 H) 8.12-8.22 (m, 1 H) 8.38 (dd, J=6.19, 2.40 Hz, 1 H) 8.86 (s, 1 H) 11.08 (s, 1 H). ESI-MS:m/z 467.2 (M+H)+.

Compound 72: N-(6-(1-(6-(4-cyano-3-fluorophenyl)-[1,2,4]triazolo[4,3-a]pyridin-3-yl)ethyl)imidazo[1,2-b]pyridazin-2-yl)cyclopropanecarboxamide

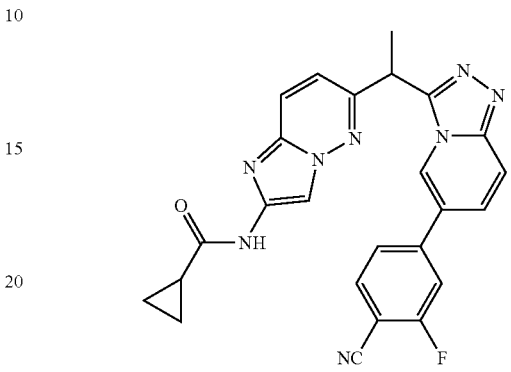

The title compound was synthesized using an analogous procedure to that described in the preparation of Compound 49 using 4-cyano-3-fluorophenylboronic acid. The crude reaction mixture was purified by preparative LCMS, and the product was isolated as the TFA salt. $^1$H NMR (400 MHz, DMSO-d6) δ ppm 0.73-0.86 (m, 4 H) 1.82-2.00 (m, 4 H) 5.29 (d, J=7.33 Hz, 1 H) 7.29 (d, J=9.60 Hz, 1 H) 7.82-7.88 (m, 2 H) 7.89-7.97 (m, 2 H) 8.02 (dd, J=10.99, 1.64 Hz, 1 H) 8.05-8.10 (m, 2 H) 8.95 (s, 1 H) 11.08 (s, 1 H). ESI-MS:m/z 467.2 (M+H)+.

Compound 73: N-(6-(1-(6-(3-(dimethylamino)phenyl)-[1,2,4]triazolo[4,3-a]pyridin-3-yl)ethyl)imidazo[1,2-b]pyridazin-2-yl)cyclopropanecarboxamide

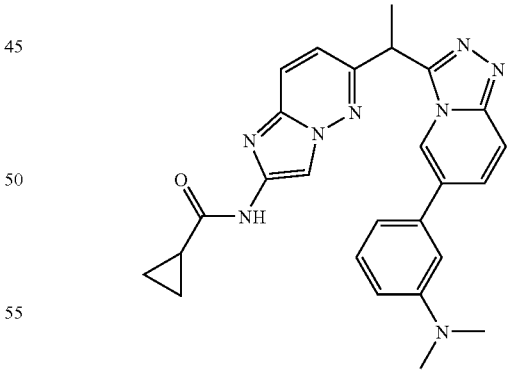

The title compound was synthesized using an analogous procedure to that described in the preparation of Compound 49 using 3-(dimethylamino)phenylboronic acid. The crude reaction mixture was purified by preparative LCMS, and the product was isolated as the TFA salt. $^1$H NMR (400 MHz, DMSO-d6) δ ppm 0.74-0.86 (m, 4 H) 1.91 (d, J=7.07 Hz, 4 H) 2.94 (s, 6 H) 5.29 (d, J=7.33 Hz, 1 H) 6.82 (dd, J=8.21, 2.15 Hz, 1 H) 6.90 (s, 1 H) 6.97 (d, J=7.83 Hz, 1 H) 7.25-7.34 (m, 2 H) 7.83-7.89 (m, 1 H) 7.89-7.98 (m, 2 H) 8.09 (s, 1 H) 8.62 (s, 1 H) 11.09 (s, 1 H). ESI-MS:m/z 467.2 (M+H)⁺.

Compound 74: N-(6-(difluoro(6-(4-fluorophenyl)-[1,2,4]triazolo[4,3-a]pyridin-3-yl)methyl)imidazo[1,2-b]pyridazin-2-yl)cyclopropanecarboxamide

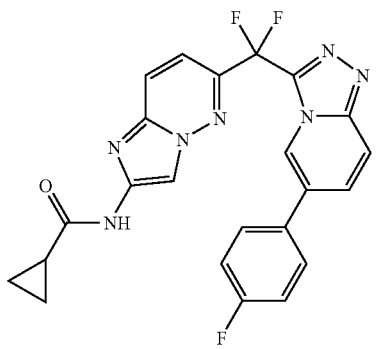

The title compound was synthesized using an analogous procedure to that described in the preparation of Compound 45 using 4-fluorophenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.96 (quin, J=6.19 Hz, 1 H) 7.37 (t, J=8.84 Hz, 2 H) 7.71 (d, J=9.35 Hz, 1 H) 7.79-7.85 (m, 2 H) 7.96 (dd, J=9.73, 1.39 Hz, 1 H) 8.12 (d, J=9.60 Hz, 1 H) 8.24 (s, 1 H) 8.28 (d, J=9.35 Hz, 1 H) 8.74 (s, 1 H) 11.35 (s, 1 H). ESI-MS:m/z 464.2 (M+H)⁺.

Compound 75: N-(6-(difluoro(6-(4-methoxyphenyl)-[1,2,4]triazolo[4,3-a]pyridin-3-yl)methyl)imidazo[1,2-b]pyridazin-2-yl)cyclopropanecarboxamide

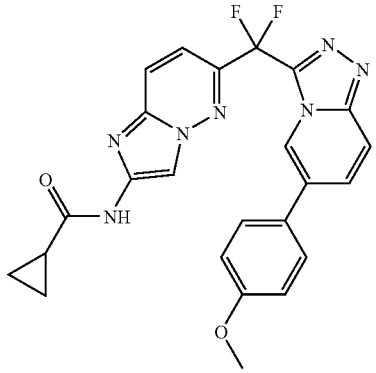

The title compound was synthesized using an analogous procedure to that described in the preparation of Compound 45 (Method B) using 4-methoxyphenylboronic acid. The crude reaction mixture was purified by preparative LCMS, and the product was isolated as the TFA salt. ¹H NMR (400 MHz, DMSO-d₆) δ ppm 0.83 (d, J=6.32 Hz, 4 H) 1.92-2.00 (m, 1H) 3.82 (s, 3 H) 7.09 (d, J=8.84 Hz, 2 H) 7.70 (d, 2 H) 7.72 (s, 1 H) 7.95 (dd, J=9.60, 1.52 Hz, 1 H) 8.08 (d, J=9.60 Hz, 1 H) 8.25 (s, 1 H) 8.27 (d, J=9.60 Hz, 1 H) 8.66 (s, 1 H) 11.35 (s, 1 H). ESI-MS:m/z 476.2 (M+H)⁺.

Compound 76: N-(6-(difluoro(6-(3-methoxyphenyl)-[1,2,4]triazolo[4,3-a]pyridin-3-yl)methyl)imidazo[1,2-b]pyridazin-2-yl)cyclopropanecarboxamide

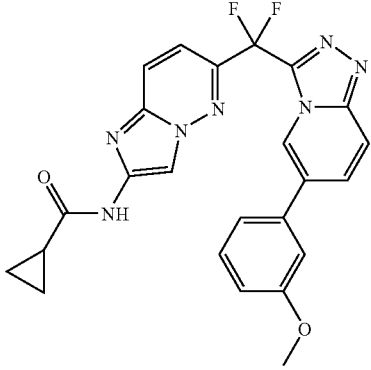

The title compound was synthesized using an analogous procedure to that described in the preparation of Compound 45 using 3-methoxyphenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.91-2.01 (m, 1 H) 3.83 (s, 3 H) 7.05 (dd, J=8.21, 1.89 Hz, 1 H) 7.26 (d, J=2.02 Hz, 1 H) 7.30 (d, J=7.58 Hz, 1 H) 7.44 (t, 1 H) 7.71 (d, J=9.35 Hz, 1 H) 7.98 (dd, J=9.60, 1.52 Hz, 1 H) 8.11 (d, J=8.84 Hz, 1 H) 8.24 (s, 1 H) 8.28 (d, J=9.35 Hz, 1 H) 8.73 (s, 1 H) 11.35 (s, 1 H). ESI-MS:m/z 476.2 (M+H)⁺.

Compound 77: N-(6-(difluoro(6-(3-fluorophenyl)-[1,2,4]triazolo[4,3-a]pyridin-3-yl)methyl)imidazo[1,2-b]pyridazin-2-yl)cyclopropanecarboxamide

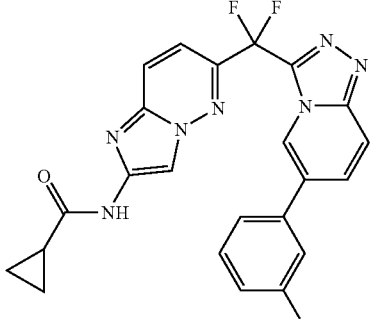

The title compound was synthesized using an analogous procedure to that described in the preparation of Compound 45 using 3-fluorophenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.96 (quin, J=6.19 Hz, 1 H) 7.32 (dt, 1 H) 7.54-7.59 (m, 1 H) 7.62 (t, J=7.58 Hz, 1 H) 7.68 (dt, 1 H) 7.71 (d, 1 H) 8.00 (dd, J=9.60, 1.52 Hz, 1H) 8.13 (d, J=9.60 Hz, 1 H) 8.23 (s, 1 H) 8.28 (d, J=9.60 Hz, 1 H) 8.81 (s, 1 H) 11.34 (s, 1 H). ESI-MS:m/z 464.2 (M+H)⁺.

Compound 78: N-(6-(difluoro(6-(pyridin-3-yl)-[1,2,4]triazolo[4,3-a]pyridin-3-yl)methyl)imidazo[1,2-b]pyridazin-2-yl)cyclopropanecarboxamide

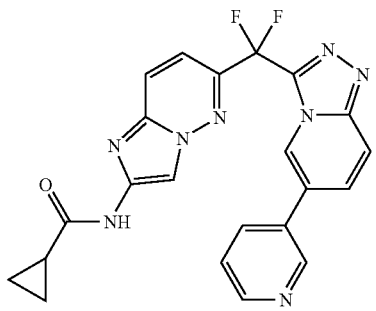

The title compound was synthesized using an analogous procedure to that described in the preparation of Compound 45 using pyridin-3-ylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.96 (quin, J=6.13 Hz, 1 H) 7.61 (dd, J=7.96, 4.93 Hz, 1 H) 7.73 (d, J=9.35 Hz, 1 H) 8.02 (dd, J=9.60, 1.52 Hz, 1 H) 8.17 (d, J=9.09 Hz, 1 H) 8.22 (s, 1 H) 8.25 (s, 1 H) 8.26-8.32 (m, 1 H) 8.69 (d, J=4.29 Hz, 1 H) 8.90 (s, 1H) 9.00 (br. s., 1 H) 11.34 (s, 1 H). ESI-MS:m/z 447.2 (M+H)⁺.

Compound 79: N-(6-(difluoro(6-(pyridin-4-yl)-[1,2,4]triazolo[4,3-a]pyridin-3-yl)methyl)imidazo[1,2-b]pyridazin-2-yl)cyclopropanecarboxamide

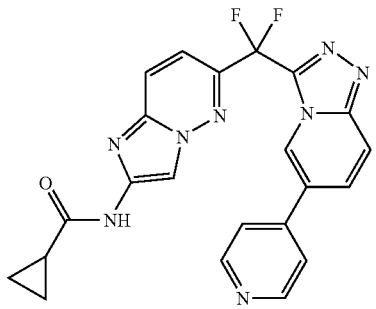

The title compound was synthesized using an analogous procedure to that described in the preparation of Compound 45 using pyridin-4-ylboronic acid. The crude reaction mixture was purified by preparative LCMS, and the product was isolated as the TFA salt. ¹H NMR (400 MHz, DMSO-d₆) δ ppm 0.83 (d, J=5.31 Hz, 4 H) 1.96 (quin, J=6.13 Hz, 1 H) 7.69-7.77 (m, 1 H) 7.93 (d, J=5.05 Hz, 2 H) 8.07 (dd, J=9.60, 1.52 Hz, 1 H) 8.19 (d, J=9.85 Hz, 1 H) 8.23 (s, 1 H) 8.29 (d, J=9.35 Hz, 1 H) 8.76 (br. s., 2 H) 8.98 (s, 1 H) 11.34 (s, 1 H). ESI-MS:m/z 447.2 (M+H)⁺.

Compound 80: N-(6-(difluoro(6-(4-isopropylphenyl)-[1,2,4]triazolo[4,3-a]pyridin-3-yl)methyl)imidazo[1,2-b]pyridazin-2-yl)cyclopropanecarboxamide

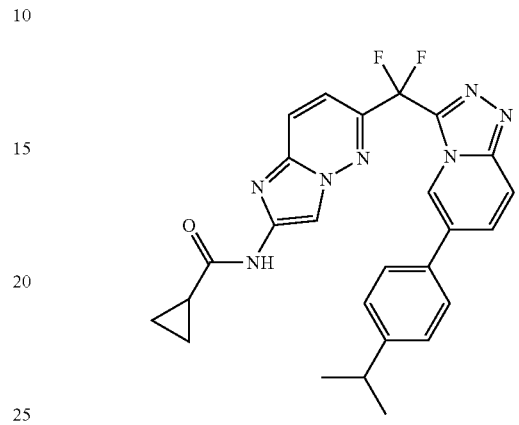

The title compound was synthesized using an analogous procedure to that described in the preparation of Compound 45 using 4-isopropylphenylboronic acid. The crude reaction mixture was purified by preparative LCMS, and the product was isolated as the TFA salt. ¹H NMR (400 MHz, DMSO-d₆) δ ppm 0.84 (d, J=6.06 Hz, 4 H) 1.24 (d, J=6.82 Hz, 6 H) 1.95 (q, 1 H) 2.96 (spt, J=6.86 Hz, 1 H) 7.40 (d, J=8.34 Hz, 2 H) 7.67 (d, J=8.34 Hz, 2 H) 7.71 (d, J=9.35 Hz, 1 H) 7.96 (dd, J=9.60, 1.26 Hz, 1 H) 8.11 (d, J=9.60 Hz, 1 H) 8.24 (s, 1 H) 8.28 (d, J=9.35 Hz, 1 H) 8.70 (s, 1 H) 11.36 (s, 1 H). ESI-MS:m/z 488.2 (M+H)⁺.

Compound 81: N-(6-((6-(3,5-difluorophenyl)-[1,2,4]triazolo[4,3-a]pyridin-3-yl)difluoromethyl)imidazo[1,2-b]pyridazin-2-yl)cyclopropanecarboxamide

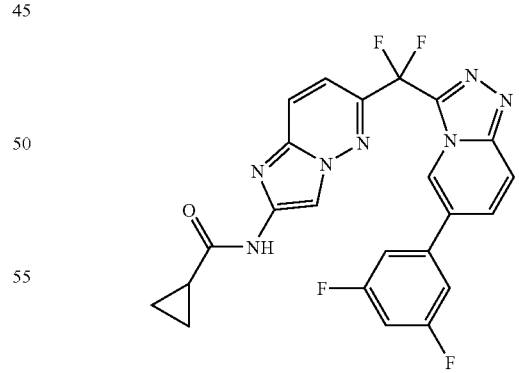

The title compound was synthesized using an analogous procedure to that described in the preparation of Compound 45 using 3,5-difluorophenylboronic acid. The crude reaction mixture was purified by preparative LCMS, and the product was isolated as the TFA salt. ¹H NMR (400 MHz, DMSO-d₆) δ ppm 0.83 (d, J=5.81 Hz, 4 H) 1.95 (quin, 1 H) 7.32-7.42 (m, 1 H) 7.56-7.66 (m, 2 H) 7.73 (d, J=9.60 Hz, 1 H) 8.01 (dd, J=9.73, 1.39 Hz, 1 H) 8.14 (d, J=9.60 Hz, 1 H) 8.21 (s, 1 H) 8.28 (d, J=9.35 Hz, 1 H) 8.88 (s, 1 H) 11.34 (s, 1 H). ESI-MS:m/z 482.2 (M+H)⁺.

Compound 82: N-(6-((6-(3-cyanophenyl)-[1,2,4]triazolo[4,3-a]pyridin-3-yl)difluoromethyl)imidazo[1,2-b]pyridazin-2-yl)cyclopropanecarboxamide

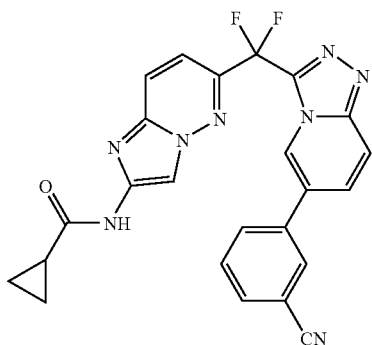

The title compound was synthesized using an analogous procedure to that described in the preparation of Compound 45 using 3-cyanophenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.96 (quin, J=6.13 Hz, 1 H) 7.68 -7.77 (m, 2 H) 7.94 (d, J=7.83 Hz, 1 H) 8.03 (dd, J=9.73, 1.14 Hz, 1 H) 8.12 (d, J=8.34 Hz, 1 H) 8.16 (d, J=9.60 Hz, 1 H) 8.23 (s, 1 H) 8.29 (d, J=9.35 Hz, 1 H) 8.33 (s, 1 H) 8.93 (s, 1 H) 11.35 (s, 1 H). ESI-MS:m/z 471.2 (M+H)⁺.

Compound 83: N-(6-((6-(4-cyanophenyl)-[1,2,4]triazolo[4,3-a]pyridin-3-yl)difluoromethyl)imidazo[1,2-b]pyridazin-2-yl)cyclopropanecarboxamide

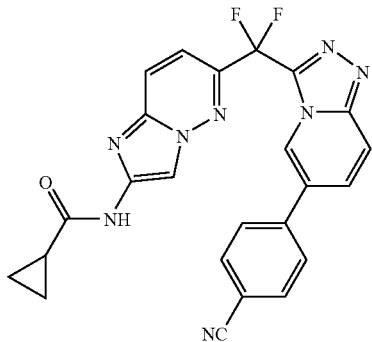

The title compound was synthesized using an analogous procedure to that described in the preparation of Compound 45 using 4-cyanophenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.96 (quin, J=6.19 Hz, 1 H) 7.72 (d, J=9.60 Hz, 1 H) 8.00 (s, 4 H) 8.03 (d, J=9.60 Hz, 1 H) 8.16

(d, J=9.60 Hz, 1 H) 8.20-8.24 (m, 1 H) 8.28 (d, J=9.60 Hz, 1 H) 8.89 (s, 1 H) 11.35 (s, 1 H). ESI-MS:m/z 471.2 (M+H)⁺.

Compound 84: N-(6-(difluoro(6-(4-methylthiophen-2-yl)-[1,2,4]triazolo[4,3-a]pyridin-3-yl)methyl)imidazo[1,2-b]pyridazin-2-yl)cyclopropanecarboxamide

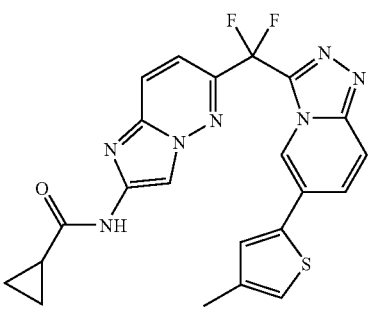

The title compound was synthesized using an analogous procedure to that described in the preparation of Compound 45 using 4-methylthiophen-2-ylboronic acid. The crude reaction mixture was purified by preparative LCMS, and the product was isolated as the TFA salt. ¹H NMR (400 MHz, DMSO-d₆) δ ppm 0.84 (d, J=6.32 Hz, 4 H) 1.95 (q, 1 H) 2.26 (s, 3 H) 7.29 (s, 1 H) 7.59 (s, 1 H) 7.70 (d, J=9.35 Hz, 1 H) 7.91 (dd, J=9.73, 1.64 Hz, 1 H) 8.07 (d, J=9.60 Hz, 1 H) 8.26 (s, 1 H) 8.25 -8.30 (m, 1 H) 8.69 (s, 1 H) 11.36 (s, 1 H). ESI-MS: m/z 466.2 (M+H)⁺.

Compound 85: N-(6-(difluoro(6-(4-(methylsulfonyl)phenyl)-[1,2,4]triazolo[4,3-a]pyridin-3-yl)methyl)imidazo[1,2-b]pyridazin-2-yl)cyclopropanecarboxamide

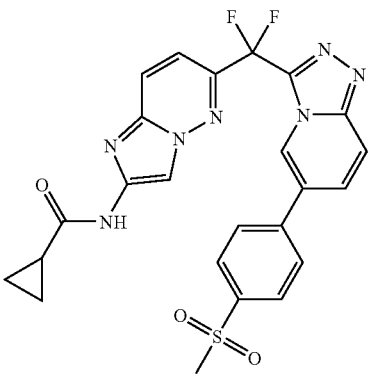

The title compound was synthesized using an analogous procedure to that described in the preparation of Compound 45 using 4-(methylsulfonyl)phenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.96 (q, 1 H) 3.28 (s, 3 H) 7.72 (d, J=9.35 Hz, 1 H) 8.02 (dd, 1 H) 8.05 (s, 4 H)

8.17 (d, J=9.60 Hz, 1 H) 8.23 (s, 1 H) 8.28 (d, J=9.60 Hz, 1 H) 8.88 (s, 1 H) 11.35 (s, 1 H). ESI-MS:m/z 524.2 (M+H)+.

Compound 86: N-(6-(difluoro(6-(6-methoxypyridin-3-yl)-[1,2,4]triazolo[4,3-a]pyridin-3-yl)methyl)imidazo[1,2-b]pyridazin-2-yl)cyclopropanecarboxamide

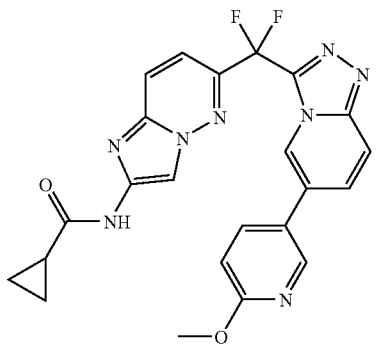

The title compound was synthesized using an analogous procedure to that described in the preparation of Compound 45 using 6-methoxypyridin-3-ylboronic acid. The crude reaction mixture was purified by preparative LCMS, and the product was isolated as the TFA salt. $^1$H NMR (400 MHz, DMSO-d$_6$) δ ppm 0.83 (d, J=6.06 Hz, 4 H) 1.96 (quin, J=6.19 Hz, 1 H) 3.91 (s, 3 H) 6.97 (d, J=8.59 Hz, 1 H) 7.72 (d, J=9.35 Hz, 1 H) 7.97 (dd, J=9.60, 1.52 Hz, 1 H) 8.09 -8.15 (m, 2 H) 8.22 (s, 1 H) 8.28 (d, J=9.35 Hz, 1 H) 8.56 (d, J=2.53 Hz, 1 H) 8.78 (s, 1 H) 11.35 (s, 1 H). ESI-MS:m/z 477.2 (M+H)+.

Compound 87: N-(6-(difluoro(6-(pyrimidin-5-yl)-[1,2,4]triazolo[4,3-a]pyridin-3-yl)methyl)imidazo[1,2-b]pyridazin-2-yl)cyclopropanecarboxamide

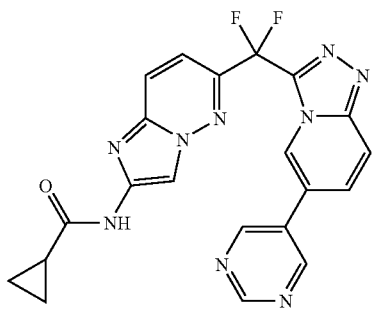

The title compound was synthesized using an analogous procedure to that described in the preparation of Compound 45 using pyrimidin-5-ylboronic acid. The crude reaction mixture was purified by preparative LCMS, and the product was isolated as the TFA salt. $^1$H NMR (400 MHz, DMSO-d$_6$) δ ppm 0.83 (d, J=5.56 Hz, 4 H) 1.90 -2.00 (m, 1 H) 7.74 (d, J=9.60 Hz, 1 H) 8.06 (dd, J=9.60, 1.26 Hz, 1 H) 8.17 -8.25 (m, 2 H) 8.29 (d, J=9.35 Hz, 1 H) 9.03 (s, 1 H) 9.21 (s, 2 H) 9.24 -9.29 (m, 1 H) 11.34 (s, 1 H). ESI-MS:m/z 448.2 (M+H)+.

Compound 88: N-(6-(difluoro(6-(3-(methylsulfonyl)phenyl)-[1,2,4]triazolo[4,3-a]pyridin-3-yl)methyl)imidazo[1,2-b]pyridazin-2-yl)cyclopropanecarboxamide

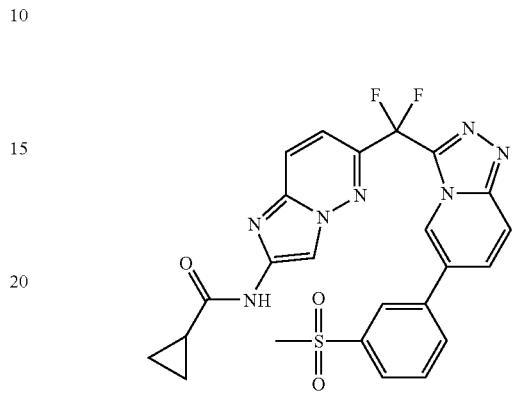

The title compound was synthesized using an analogous procedure to that described in the preparation of Compound 45 using 3-(methylsulfonyl)phenylboronic acid. The crude reaction mixture was purified by preparative LCMS, and the product was isolated as the TFA salt. $^1$H NMR (400 MHz, DMSO-d$_6$) δ ppm 0.83 (d, J=6.06 Hz, 4 H) 1.91 -2.01 (m, 1 H) 3.32 (s, 3 H) 7.72 (d, J=9.35 Hz, 1 H) 7.81 (t, J=7.83 Hz, 1 H) 8.02 (d, J=7.83 Hz, 1 H) 8.06 (dd, J=9.60, 1.52 Hz, 1 H) 8.13 (d, J=7.83 Hz, 1 H) 8.18 (d, J=9.60 Hz, 1 H) 8.23 -8.31 (m, 3 H) 8.92 (s, 1 H) 11.35 (s, 1 H). ESI-MS:m/z 524.2 (M+H)+.

Compound 89: 4-(3-((2-(cyclopropanecarboxamido)imidazo[1,2-b]pyridazin-6-yl)difluoromethyl)-[1,2,4]triazolo[4,3-a]pyridin-6-yl)benzamide

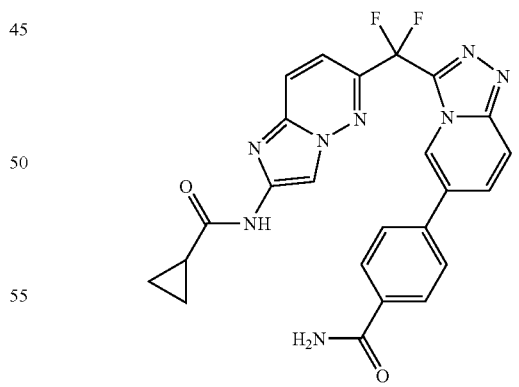

The title compound was synthesized using an analogous procedure to that described in the preparation of Compound 45 using 4-carbamoylphenylboronic acid. The crude reaction mixture was purified by preparative LCMS, and the product was isolated as the TFA salt. $^1$H NMR (400 MHz, DMSO-d$_6$) δ ppm 0.83 (d, J=6.32 Hz, 4 H) 1.90 -2.01 (m, 1 H) 7.48 (br. s., 1 H) 7.72 (d, J=9.35 Hz, 1 H) 7.87 (d, J=8.34 Hz, 2 H)

7.98-8.06 (m, 3 H) 8.10 (br. s., 1 H) 8.11-8.17 (m, 1 H) 8.24 (s, 1 H) 8.28 (d, J=9.35 Hz, 1 H) 8.82 (s, 1 H) 11.35 (s, 1 H). ESI-MS:m/z 489.2 (M+H)+.

Compound 90: 3-(3-((2-(cyclopropanecarboxamido)imidazo[1,2-b]pyridazin-6-yl)difluoromethyl)-[1,2,4]triazolo[4,3-a]pyridin-6-yl)benzamide

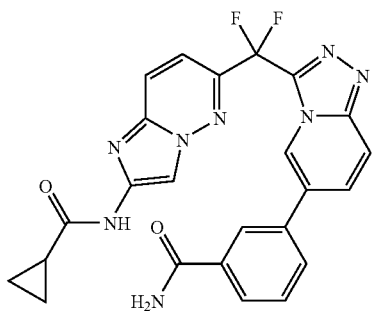

The title compound was synthesized using an analogous procedure to that described in the preparation of Compound 45 using 3-carbamoylphenylboronic acid. The crude reaction mixture was purified by preparative LCMS, and the product was isolated as the TFA salt. $^1$H NMR (400 MHz, DMSO-d$_6$) δ ppm 0.84 (d, J=6.06 Hz, 4 H) 1.96 (quin, J=6.13 Hz, 1 H) 7.53 (s, 1 H) 7.62 (t, J=7.70 Hz, 1 H) 7.72 (d, J=9.60 Hz, 1 H) 7.90-7.98 (m, 2 H) 8.04 (dd, J=9.73, 1.39 Hz, 1 H) 8.16 (d, J=9.60 Hz, 1 H) 8.19 (br. s., 1 H) 8.22 (s, 1 H) 8.25 (s, 1 H) 8.28 (d, J=9.35 Hz, 1 H) 8.85 (s, 1 H) 11.35 (s, 1 H). ESI-MS:m/z 489.2 (M+H)+.

Compound 91: N-(6-(difluoro(6-(4-(2-methoxyethoxy)phenyl)-[1,2,4]triazolo[4,3-a]pyridin-3-yl)methyl)imidazo[1,2-b]pyridazin-2-yl)cyclopropanecarboxamide

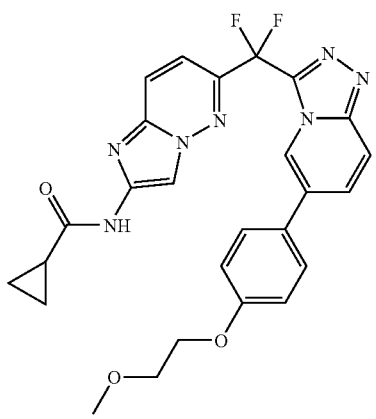

The title compound was synthesized using an analogous procedure to that described in the preparation of Compound 45 using 4-(2-methoxyethoxy)phenylboronic acid. The crude reaction mixture was purified by preparative LCMS, and the product was isolated as the TFA salt. $^1$H NMR (400 MHz, DMSO-d$_6$) δ ppm 0.84 (d, J=6.32 Hz, 4 H) 1.96 (quin, J=6.13 Hz, 1 H) 3.32 (s, 3 H) 3.66-3.71 (m, 2 H) 4.13-4.19 (m, 2 H) 7.09 (d, J=8.59 Hz, 2 H) 7.70 (dd, J=9.09, 2.78 Hz, 3 H) 7.95 (dd, J=9.60, 1.52 Hz, 1 H) 8.08 (d, J=9.60 Hz, 1 H) 8.25 (s, 1 H) 8.28 (d, J=9.35 Hz, 1 H) 8.67 (s, 1 H) 11.36 (s, 1 H). ESI-MS:m/z 520.2 (M+H)+.

Compound 92: N-(6-(((6-(1H-pyrazol-4-yl)-[1,2,4]triazolo[4,3-a]pyridin-3-yl)difluoromethyl)imidazo[1,2-b]pyridazin-2-yl)cyclopropanecarboxamide

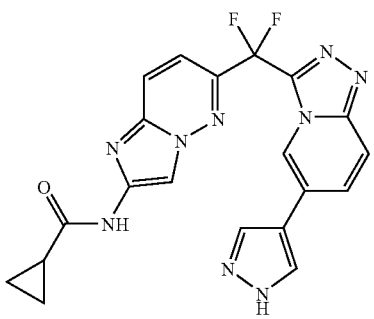

The title compound was synthesized using an analogous procedure to that described in the preparation of Compound 45 using $^1$H-pyrazol-4-ylboronic acid. The crude reaction mixture was purified by preparative LCMS, and the product was isolated as the TFA salt. $^1$H NMR (400 MHz, DMSO-d$_6$) δ ppm 0.84 (d, J=6.06 Hz, 4 H) 1.96 (quin, J=6.19 Hz, 1 H) 7.71 (d, J=9.35 Hz, 1 H) 7.97 (dd, 1 H) 8.03-8.08 (m, 1 H) 8.17-8.43 (m, 2 H) 8.25 (s, 1 H) 8.28 (d, J=9.35 Hz, 1 H) 8.75 (s, 1 H) 11.35 (s, 1 H). ). ESI-MS:m/z 436.2 (M+H)+.

Compound 93: N-(6-(difluoro(6-(3-isopropoxyphenyl)-[1,2,4]triazolo[4,3-a]pyridin-3-yl)methyl)imidazo[1,2-b]pyridazin-2-yl)cyclopropanecarboxamide

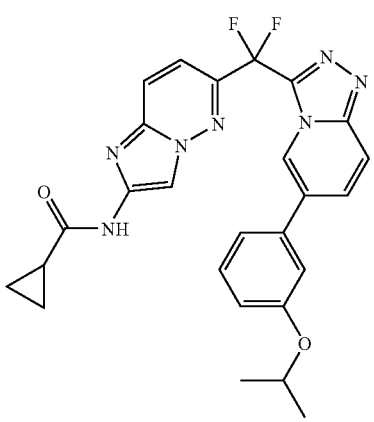

The title compound was synthesized using an analogous procedure to that described in the preparation of Compound 45 using 3-isopropoxyphenylboronic acid. The crude reaction mixture was purified by preparative LCMS, and the product was isolated as the TFA salt. $^1$H NMR (400 MHz, DMSO-d$_6$) δ ppm 0.83 (d, J=6.06 Hz, 4 H) 1.28 (d, J=6.06 Hz, 6 H) 1.96 (quin, J=6.13 Hz, 1 H) 4.65-4.76 (m, 1 H) 7.02 (dd, J=8.21, 1.89 Hz, 1 H) 7.21 (s, 1 H) 7.26 (d, J=7.83 Hz, 1 H) 7.38-7.46 (m, 1 H) 7.71 (d, J=9.35 Hz, 1 H) 7.96 (dd, J=9.60, 1.26 Hz, 1 H) 8.10 (d, J=9.60 Hz, 1 H) 8.24 (s, 1 H) 8.28 (d, J=9.35 Hz, 1 H) 8.71 (s, 1 H) 11.36 (s, 1 H). ESI-MS:m/z 504.2 (M+H)⁺.

Compound 94: N-(6-(difluoro(6-(4-methylpyridin-3-yl)-[1,2,4]triazolo[4,3-a]pyridin-3-yl)methyl)imidazo[1,2-b]pyridazin-2-yl)cyclopropanecarboxamide

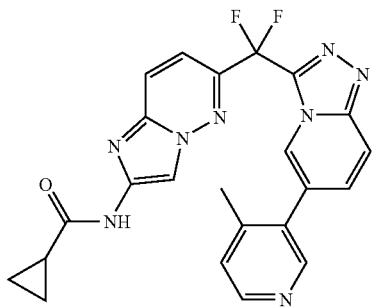

The title compound was synthesized using an analogous procedure to that described in the preparation of Compound 45 using 4-methylpyridin-3-ylboronic acid. The crude reaction mixture was purified by preparative LCMS, and the product was isolated as the TFA salt. ¹H NMR (400 MHz, DMSO-d₆) δ ppm 0.79-0.89 (m, 4 H) 1.19-1.29 (m, 3 H) 1.89-2.00 (m, 1 H) 6.87 (s, 1 H) 7.43 (br. s., 1 H) 7.68-7.76 (m, 2 H) 8.11 (d, J=8.84 Hz, 1 H) 8.22 (s, 1 H) 8.28 (d, J=9.35 Hz, 1 H) 8.51 (br. s., 1 H) 8.68 (s, 1 H) 11.35 (s, 1 H). ESI-MS:m/z 461.2 (M+H)⁺.

Compound 95: 4-(3-((2-(cyclopropanecarboxamido)imidazo[1,2-b]pyridazin-6-yl)difluoromethyl)-[1,2,4]triazolo[4,3-a]pyridin-6-yl)-N-methylbenzamide

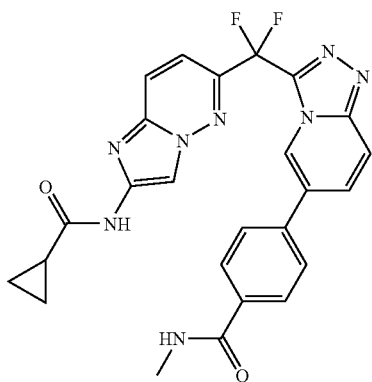

The title compound was synthesized using an analogous procedure to that described in the preparation of Compound 45 using 4-(methylcarbamoyl)phenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.96 (quin, J=6.13 Hz, 1 H) 2.76-2.86 (m, 3 H) 7.72 (d, J=9.60 Hz, 1 H) 7.88 (d, J=8.34 Hz, 2 H) 7.93-8.00 (m, 2 H) 8.03 (dd, J=9.73, 1.39 Hz, 1 H) 8.14 (d, J=9.35 Hz, 1 H) 8.24 (s, 1 H) 8.28 (d, J=9.35 Hz, 1 H) 8.57 (d, J=4.55 Hz, 1 H) 8.83 (s, 1 H) 11.35 (s, 1 H). ). ESI-MS:m/z 503.2 (M+H)⁺.

Compound 96: N-(6-(((6-(3-(dimethylamino)phenyl)-[1,2,4]triazolo[4,3-a]pyridin-3-yl)difluoromethyl)imidazo[1,2-b]pyridazin-2-yl)cyclopropanecarboxamide

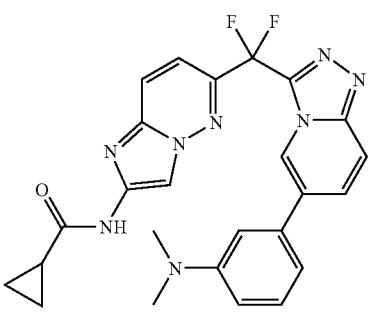

The title compound was synthesized using an analogous procedure to that described in the preparation of Compound 45 using 3-(dimethylamino)phenylboronic acid. The crude reaction mixture was purified by preparative LCMS, and the product was isolated as the TFA salt. ¹H NMR (400 MHz, DMSO-d₆) δ ppm 0.84 (d, J=6.06 Hz, 4 H) 1.96 (quin, J=6.13 Hz, 1 H) 2.96 (s, 6 H) 6.85 (d, J=8.34 Hz, 1 H) 6.94 (br. s., 1 H) 6.98 (d, J=7.33 Hz, 1 H) 7.33 (t, J=7.83 Hz, 1 H) 7.68-7.74 (m, 1 H) 7.93-7.99 (m, 1 H) 8.09 (d, J=9.60 Hz, 1 H) 8.25 (s, 1 H) 8.28 (d, J=9.60 Hz, 1 H) 8.65 (s, 1 H) 11.32-11.40 (m, 1 H). ESI-MS:m/z 489.2 (M+H)⁺.

Compound 97: N-(6-(difluoro(6-(3-fluoro-5-methylphenyl)-[1,2,4]triazolo[4,3-a]pyridin-3-yl)methyl)imidazo[1,2-b]pyridazin-2-yl)cyclopropanecarboxamide

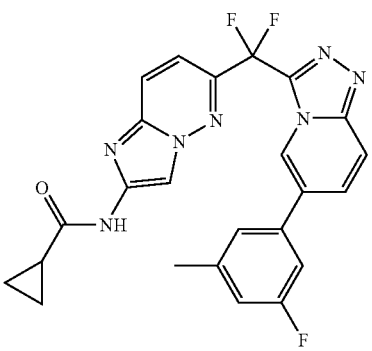

The title compound was synthesized using an analogous procedure to that described in the preparation of Compound 45 using 3-fluoro-5-methylphenylboronic acid. The crude reaction mixture was purified by preparative LCMS, and the product was isolated as the TFA salt. ¹H NMR (400 MHz, DMSO-d₆) δ ppm 0.83 (d, J=6.06 Hz, 4 H) 1.95 (q, 1 H) 2.41 (s, 3 H) 7.15 (d, J=9.60 Hz, 1 H) 7.42-7.50 (m, 2 H) 7.72 (d, J=9.35 Hz, 1 H) 7.98 (dd, J=9.73, 1.39 Hz, 1 H) 8.12 (d, J=9.60 Hz, 1 H) 8.24 (s, 1 H) 8.28 (d, J=9.60 Hz, 1 H) 8.80 (s, 1 H) 11.36 (s, 1 H). ESI-MS:m/z 478.2 (M+H)⁺.

Compound 98: 4-(3-((2-(cyclopropanecarboxamido)imidazo[1,2-b]pyridazin-6-yl)difluoromethyl)-[1,2,4]triazolo[4,3-a]pyridin-6-yl)-2-fluoro-N-methylbenzamide

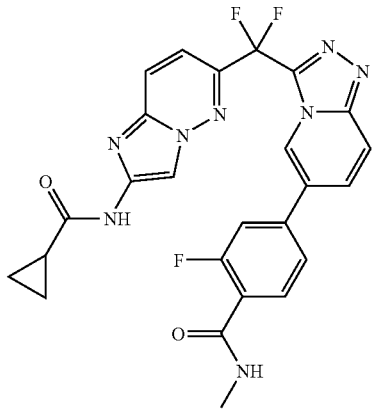

The title compound was synthesized using an analogous procedure to that described in the preparation of Compound 45 using 3-fluoro-4-(methylcarbamoyl)phenylboronic acid. The crude reaction mixture was purified by preparative LCMS, and the product was isolated as the TFA salt. ¹H NMR (400 MHz, DMSO-d₆) δ ppm 0.83 (d, J=5.81 Hz, 4 H) 1.90-2.00 (m, 1 H) 2.80 (d, J=4.55 Hz, 3 H) 7.68-7.78 (m, 2 H) 7.81 (d, J=111.87 Hz, 1 H) 8.00-8.07 (m, 1 H) 8.11-8.18 (m, 1 H) 8.22 (s, 1 H) 8.28 (d, J=9.35 Hz, 1 H) 8.33 (d, J=4.55 Hz, 1 H) 8.88 (s, 1 H) 11.35 (s, 1 H). ). ESI-MS:m/z 521.2 (M+H)⁺.

Compound 99: 6-(difluoro(6-(1-methyl-1H-pyrazol-4-yl)-[1,2,4]triazolo[4,3-a]pyridin-3-yl)methyl)imidazo[1,2-b]pyridazin-2-amine

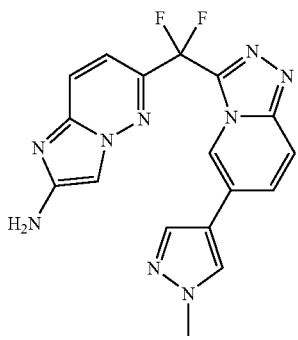

A solution of 45 (100 mg) in 3N HCl:50% MeOH:water was heated at 50° C. for 3 hrs. The reaction was concentrated and purified by preparative LCMS to provide the title compound, 6-(difluoro(6-(1-methyl-1H-pyrazol-4-yl)-[1,2,4]triazolo[4,3-a]pyridin-3-yl)methyl)imidazo[1,2-b]pyridazin-2-amine (30 mg) as the TFA salt. ¹H NMR (400 MHz, DMSO-d₆) δ ppm 3.89 (s, 3 H) 7.46 (br. s., 1 H) 7.51-7.58 (m, 1 H) 7.90 (dd, J=9.47, 1.39 Hz, 1 H) 7.93-7.99 (m, 1 H) 8.04 (d, J=9.60 Hz, 1 H) 8.08 (s, 1 H) 8.39-8.43 (m, 2 H) 8.67 (s, 1 H). ESI-MS:m/z 382.2 (M+H)⁺.

Compound 100: N-(6-(6-(5-methyl-1H-1,2,4-triazol-3-yl)-[1,2,4]triazolo[4,3-a]pyridin-3-ylthio)imidazo[1,2-b]pyridazin-2-yl)cyclopropanecarboxamide

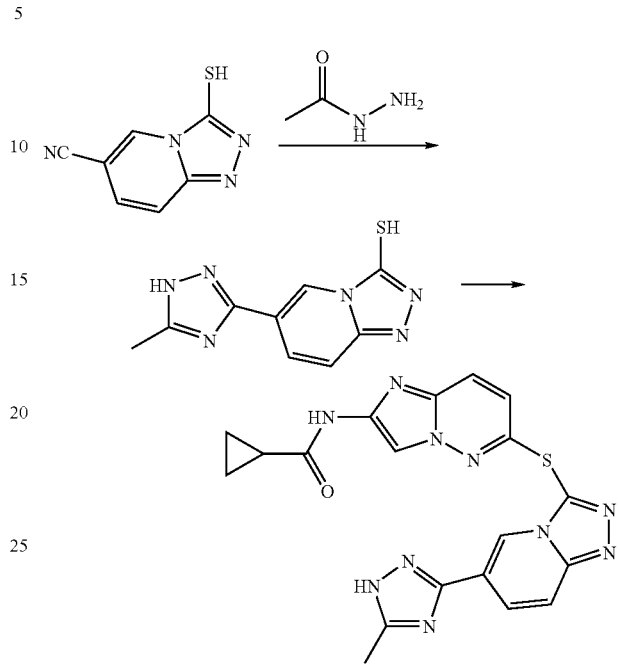

6-(5-methyl-]H-1,2,4-triazol-3-yl)-[1,2,4]triazolo[4,3-a]pyridine-3-thiol: A mixture of 3-mercapto-[1,2,4]triazolo[4,3-a]pyridine-6-carbonitrile (38A, 450 mg, 2.56 mmol), acetohydrazide (400 mg, 5.4 mmol), and sodium 2-methyl-propan-2-olate (200 mg, 2.08 mmol) in propan-2-ol (2.5 ml) was heated at 180° C. under microwave condition for 2 hrs. The product was purified by preparative LCMS to provide the title compound, 6-(5-methyl-1H-1,2,4-triazol-3-yl)-[1,2,4]triazolo[4,3-a]pyridine-3-thiol.

N-(6-(6-(5-methyl-1H-1,2,4-triazol-3-yl)-[ 1,2,4]triazolo[4,3-a]pyridin-3-ylthio)imidazo[1,2-b]pyridazin-2-yl)cyclopropanecarboxamide: The title compound was synthesized using an analogous procedure to that described in the preparation of Compound 4 using 6-(5-methyl-1H-1,2,4-triazol-3-yl)-[1,2,4]triazolo[4,3-a]pyridine-3-thiol. The crude reaction mixture was purified by preparative LCMS, and the product was isolated as the TFA salt. ¹H NMR (DMSO-d₆, 400 MHz): δ=11.26 (s, 1 H), 9.25 (s, 1 H), 8.19-8.29 (m, 2 H), 8.00 (d, J=9.6 Hz, 1 H), 7.85-7.93 (m, 1 H), 7.40 (d, J=9.3 Hz, 1 H), 2.43 (s, 3 H), 1.96 (br, s., 1 H), 0.75-0.93 ppm (m, 5 H). ESI-MS:m/z 433.1 (M+H)⁺.

Compound 101: N-(6-(6-(6-methoxypyridin-2-yl)-[1,2,4]triazolo[4,3-a]pyridin-3-ylthio)imidazo[1,2-b]pyridazin-2-yl)cyclopropanecarboxamide

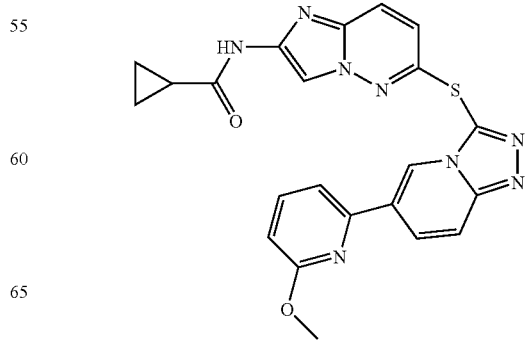

The title compound was synthesized using an analogous procedure to that described in the preparation of Compound 5 using 6-methoxypyridin-2-ylboronic acid. The crude reaction mixture was purified by preparative LCMS, and the product was isolated as the TFA salt. $^1$H NMR (METHANOL-d$_4$, 400 MHz): δ=9.09 (s, 1 H), 8.35 (d, J=9.9 Hz, 1 H), 7.95-8.04 (m, 2 H), 7.84 (d, J=9.3 Hz, 1 H), 7.71-7.78 (m, 1 H), 7.55 (d, J=7.3 Hz, 1 H), 7.23 (d, J=9.1 Hz, 1 H), 6.79 (d, J=8.3 Hz, 1 H), 3.85 (s, 3 H), 1.84 (m, 1 H), 0.82-0.96 ppm (m,4 ESI-MS:m/z 459.2 (M+H)$^+$.

Compound 102: N-(6-(6-(6-methoxypyridin-3-yl)-[1,2,4]triazolo[4,3-a]pyridin-3-ylthio)imidazo[1,2-b]pyridazin-2-yl)cyclopropanecarboxamide

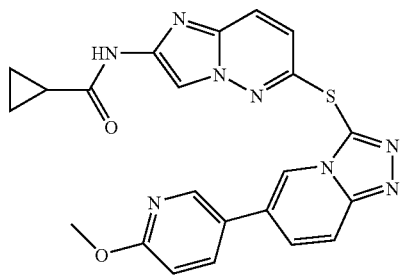

The title compound was synthesized using an analogous procedure to that described in the preparation of Compound 5 using 6-methoxypyridin-3-ylboronic acid. The crude reaction mixture was purified by preparative LCMS, and the product was isolated as the TFA salt. $^1$H NMR (METHANOL-d$_4$, 400 MHz): δ=8.71 (br. s., 1 H), 8.40 (br. s., 1 H), 7.86-8.16 (m, 4 H), 7.80 (br. s., 1 H), 7.20 (br. s., 1 H), 6.87 (d, J=8.8 Hz, 1 H), 3.92 (s, 3 H), 1.85 (br, s., 1 H), 0.73-1.02 ppm (m, 4 H). ESI-MS:m/z 459.2 (M+H)$^+$.

Compound 103: N-(6-(6-(6-morpholinopyridin-3-yl)-[1,2,4]triazolo[4,3-a]pyridin-3-ylthio)imidazo[1,2-b]pyridazin-2-yl)cyclopropanecarboxamide

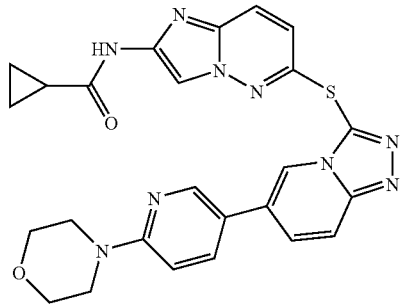

The title compound was synthesized using an analogous procedure to that described in the preparation of Compound 5 using 4-(5-(4,4,5,5-tetramethyl-1,3,2-dioxaborolan-2-yl)pyridin-2-yl)morpholine. The crude reaction mixture was purified by preparative LCMS, and the product was isolated as the TFA salt.

Compound 104: N-(6-(6-(3-cyanophenyl)-[1,2,4]triazolo[4,3-a]pyridin-3-ylthio)imidazo[1,2-b]pyridazin-2-yl)cyclopropanecarboxamide

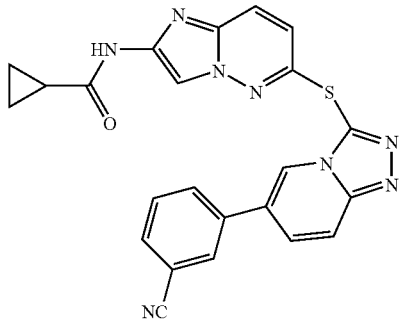

The title compound was synthesized using an analogous procedure to that described in the preparation of Compound 5 using 3-cyanophenylboronic acid. The crude reaction mixture was purified by preparative LCMS, and the product was isolated as the TFA salt. $^1$H NMR (METHANOL-d$_4$, 400 MHz): δ=8.72 (s, 1 H), 8.34 (d, J=2.3 Hz, 1 H), 8.12 (dd, J=9.2, 2.4 Hz, 1 H), 8.04 (d, J=9.6 Hz, 1 H), 7.92 (d, J=8.8 Hz, 1 H), 7.82 (s, 2 H), 7.16-7.27 (m, 2 H), 3.80-3.89 (m, 4 H), 3.61-3.69 (m, 4 H), 1.85 (br. s., 1 H), 0.95 (m, 2 H), 0.80-0.92 ppm (m, 2 H). ESI-MS:m/z 514.2 (M+H)$^+$.

Compound 105: N-(6-(6-(1-methyl-6-oxo-1,6-dihydropyridin-3-yl)-[1,2,4]triazolo[4,3-a]pyridin-3-ylthio)imidazo[1,2-b]pyridazin-2-yl)cyclopropanecarboxamide

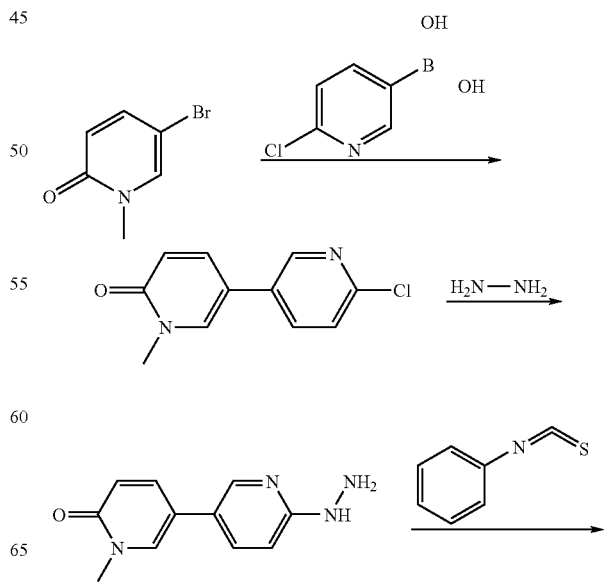

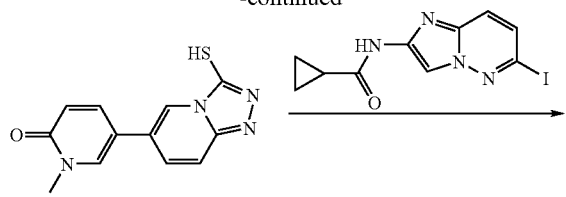

5-(6-Chloropyridin-3-yl)-1-methylpyridin-2(1H)-one: A mixture of 5-bromo-1-methylpyridin-2(1H)-one (2.2 g, 11.7 mmol), 6-chloropyridin-3-ylboronic acid (1.57 g, 9.98 mmol), Na$_2$CO$_3$ (2.2 g, 20.76 mmol), and tetrakis(triphenylphosphine)palladium (0) (500 mg, 0.05 mmol) in dioxane:water (15:1, 20 ml) was degassed and heated at 110° C. in a microwave for 1 hr. The reaction was diluted with EtOAc and washed with water. The organic layer was dried over Na$_2$SO$_4$, filtered, and concentrated to dryness. The resulting residue was purified by silica gel chromatography (AcOEt-Hexanes) to provide title compound, 5-(6-Chloropyridin-3-yl)-1-methylpyridin-2(1H)-one (1.6 g, 73% yield).

5-(6-hydrazinylpyridin-3-yl)-1-methylpyridin-2(1H)-one: A mixture of 5-(6-chloropyridin-3-yl)-1-methylpyridin-2(1H)-one (1.2 g, 5.44 mmol) and hydrazine (870 mg, 2.2 mmol) in 2-propanol (5ml) was heated in a microwave at 140° C. for 5 hrs. The reaction mixture was co-evaporated with MeOH (3×) and then suspended in water (50 ml). Solid product was collected by filtration and dried under high vacuum for 24 hrs to provide the title compound, 5-(6-hydrazinylpyridin-3-yl)-1-methylpyridin-2(1H)-one (600 mg, 51% yield).

5-(3-mercapto-[1,2,4]triazolo[4,3-a]pyridin-6-yl)-1-methylpyridin-2(]H)-one: A mixture of 5-(6-hydrazinylpyridin-3-yl)-1-methylpyridin-2(1H)-one (600 mg, 2.78 mmol) and isothiocyanatobenzene (450 mg, 3.33 mmol) in NMP-1,3-dichlorobenzene (1:1, 10 mL) was heated in a microwave at 160° C. for 1 hr and then purified by preparative LCMS to provide the title compound, 5-(3-mercapto-[1,2,4]triazolo[4,3-a]pyridin-6-yl)-1-methylpyridin-2(1H)-one (310 mg, 43% yield).

N-(6-(6-(1-methyl-6-oxo-1,6-dihydropyridin-3-yl)-[1,2,4]triazolo[4,3-a]pyridin-3-ylthio)imidazo[1,2-b]pyridazin-2-yl)cyclopropanecarboxamide: The title compound was prepare from N-(6-iodoimidazo[1,2-b]pyridazin-2-yl)cyclopropanecarboxamide and 5-(3-mercapto-[1,2,4]triazolo[4,3-a]pyridin-6-yl)-1-methylpyridin-2(1H)-one following the procedure for the synthesis of compound 4. The crude reaction mixture was purified by preparative LCMS, and the product was isolated as the TFA salt. The product was then dissolved in MeOH, treated 4M HCl in dioxane, and concentrated to dryness to provide the HCl salt of the title compound. $^1$H NMR (METHANOL-d$_4$, 400 MHz): δ=8.83 (s, 1 H), 8.18 (d, J=9.9 Hz, 2 H), 8.11 (d, J=9.6 Hz, 1 H), 7.98 (d, J=9.3 Hz, 1 H), 7.77-7.92 (m, 2 H), 7.55 (d, J=9.1 Hz, 1 H), 6.58 (d, J=9.3 Hz, 1 H), 3.52-3.59 (m, 3 H), 1.73 (br. s., 1 H), 0.80-0.90 ppm (m, 4 H). ESI-MS:m/z 459.2 (M+H)$^+$.

Compound 106: N-(6-(6-(1-ethyl-6-oxo-1,6-dihydropyridin-3-yl)-[1,2,4]triazolo[4,3-a]pyridin-3-ylthio)imidazo[1,2-b]pyridazin-2-yl)cyclopropanecarboxamide

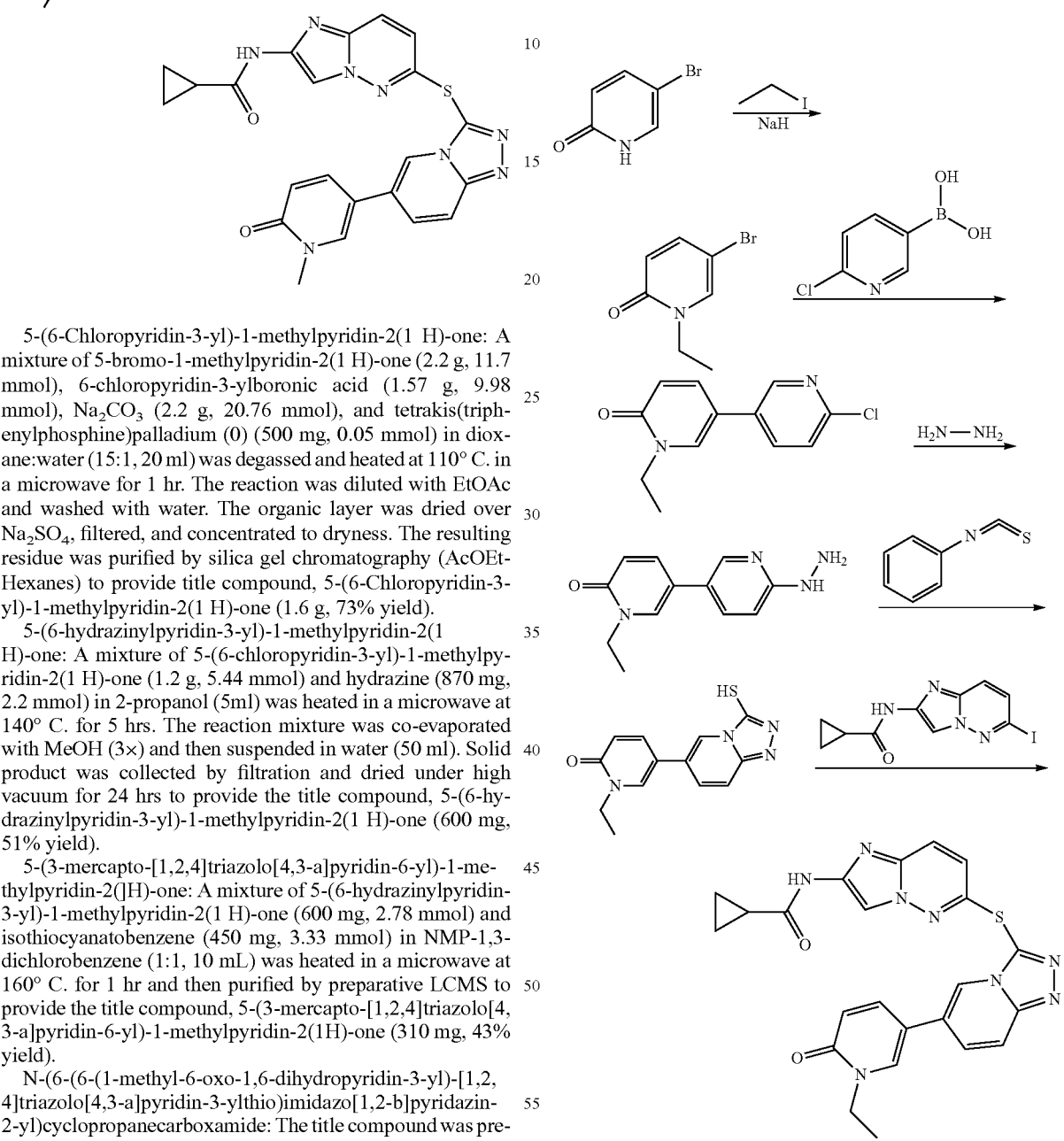

5-bromo-1-ethylpyridin-2(1H)-one: A solution of 5-bromopyridin-2-ol (1.74 g, 10.00 mmol) in DMF (20 ml) was treated with NaH at room temperature and then stirred for 30 min. Iodoethane (0.823 ml, 12.00 mmol) was added to the mixture and the reaction was stirred overnight at room temperature. The reaction was diluted with DCM, washed with water, dried over Na$_2$SO$_4$, and concentrated to dryness via rotary evaporation to provide the title compound as a crude product which was used without further purification.

5-(6-chloropyridin-3-yl)-1-ethylpyridin-2(1 H)-one: A mixture of 5-bromo-1-ethylpyridin-2(1 H)-one (1.9 g, 9.45 mmol), 6-chloropyridin-3-ylboronic acid (1.8 g, 11.46 mmol), $Cs_2CO_3$ (9.9 g, 30.37 mmol) and tetrakis(triphenylphosphine)palladium (0) (543 mg, 0.55 mmol) were suspended in dioxane:water (15:1, 20 ml). After degassing, the mixture was heated in a microwave at 140° C. for 30 min. The reaction was then diluted with EtOAc and washed with water. The organic layer was dried over $Na_2SO_4$, filtered, and concentrated to dryness via rotary evaporation. The resulting residue was purified by LCMS to provide the title compound, 5-(6-chloropyridin-3-yl)-1-ethylpyridin-2(1 H)-one (1.2 g, 51% yield).

5-(6-hydrazinylpyridin-3-yl)-1-ethylpyridin-2(1 H)-one: A mixture of 5-(6-chloropyridin-3-yl)-1-ethylpyridin-2(1 H)-one (1.2 g, 5.44 mmol) and hydrazine (820 mg, 25.62 mmol) in 2-propanol (5 ml) was heated in a microwave at 140° C. for 4 hrs. The mixture was co-evaporated with MeOH (3x) and then suspended in water (50 ml). The resulting solid was collected by filtration and dried under high vacuum for one day to give crude title compound, 5-(6-hydrazinylpyridin-3-yl)-1-ethylpyridin-2(1 H)-one (1.2 g, 95.9% yield).

5-(3-mercapto-[1,2,4]triazolo[4,3-a]pyridin-6-yl)-1-ethylpyridin-2(1 H)-one: A mixture of 5-(6-hydrazinylpyridin-3-yl)-1-ethylpyridin-2(1 H)-one (1.2 g, 5.22 mmol) and isothiocyanatobenzene (775 mg, 5.74 mmol) in NMP(3 ml) and DCM (10 ml) was stirred at room temperature for 30 min. The DCM was removed via rotary evaporation and the reaction was diluted with 1,3-dichlorobenzene (7 mL). The mixture was then heated in a microwave at 160° C. for 1 hr. Ether (10 ml) was added to the reaction and the resulting solid was collected by filtration and washed with ether to provide the title compound, 5-(3-mercapto-[1,2,4]triazolo[4,3-a]pyridin-6-yl)-1-ethylpyridin-2(1 H)-one (600 mg, 42.3% yield).

N-(6-(6-(1-ethyl-6-oxo-1,6-dihydropyridin-3-yl)-[1,2,4]triazolo[4,3-a]pyridin-3-ylthio)imidazo[1,2-b]pyridazin-2-yl)cyclopropanecarboxamide: The title compound was prepare from N-(6-iodoimidazo[1,2-b]pyridazin-2-yl)cyclopropanecarboxamide and 5-(3-mercapto-[1,2,4]triazolo[4,3-a]pyridin-6-yl)-1-ethylpyridin-2(1 H)-one followed the procedure of the synthesis of compound 4. The crude reaction mixture was purified by preparative LCMS, and the product was isolated as the TFA salt. The product was then dissolved in MeOH, treated 4M HCl in dioxane, and concentrated to dryness to provide the HCl salt of the title compound. $^1$H NMR (DMSO-$d_6$, 400 MHz): δ=11.15 (s, 1 H), 8.66-8.72 (m, 1 H), 8.24 (d, J=2.5Hz, 1 H), 8.08 (dd, J=9.6, 1.0 Hz, 1 H), 7.93 (s, 2 H), 7.90-7.92 (m, 1 H), 7.87 (dd, J=9.5, 2.9 Hz, 1 H), 7.06 (d, J=9.3 Hz, 2 H), 6.47 (d, J=9.3 Hz, 1 H), 3.96 (q, J=7.1 Hz, 2 H), 1.92 (t, J=6.1 Hz, 1 H), 1.24 (t, J=7.2 Hz, 3 H), 0.75-0.82 ppm (m, 4 H). ESI-MS:m/z 473.2 $(M+H)^+$.

Compound 107: N-(6-(6-(3-cyano-4-(2-hydroxyethoxy)phenyl)-[1,2,4]triazolo[4,3-a]pyridin-3-ylthio)imidazo[1,2-b]pyridazin-2-yl)cyclopropanecarboxamide

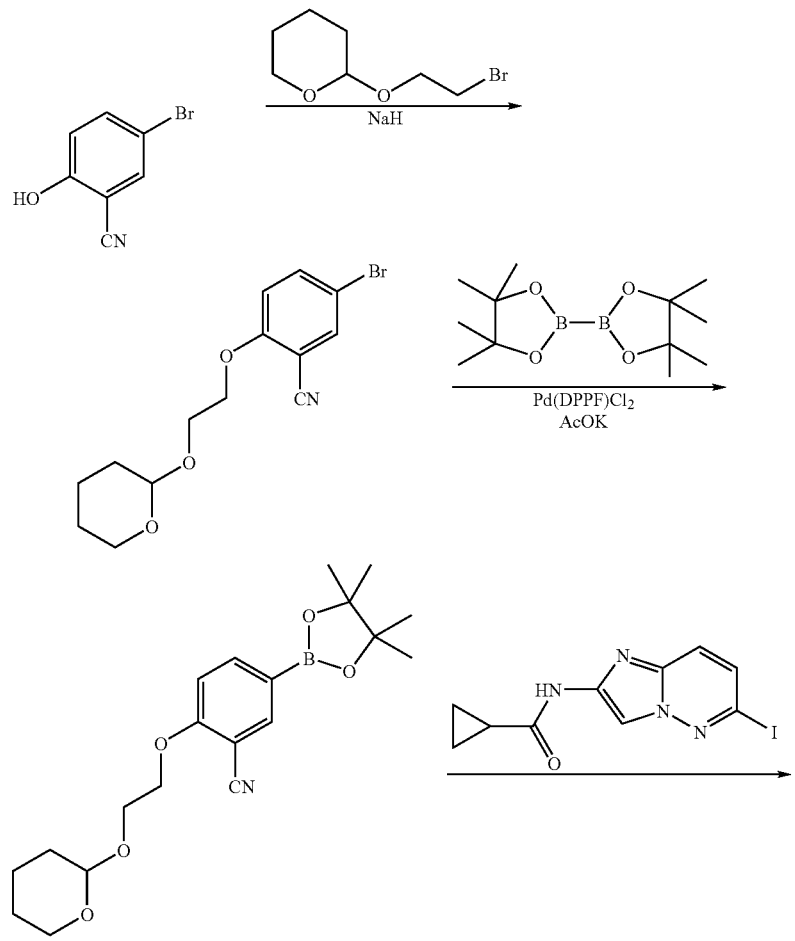

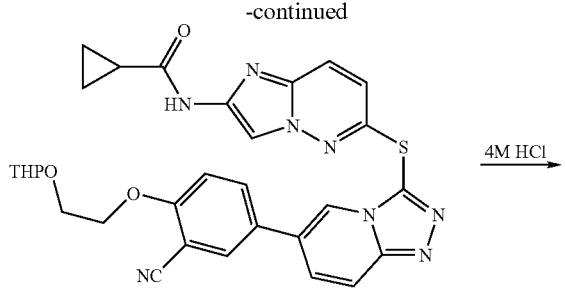

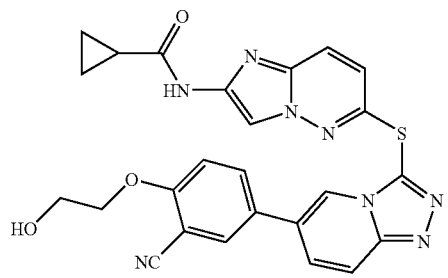

5-bromo-2-(2-(tetrahydro-2H-pyran-2-yloxy)ethoxy)benzonitrile: A solution of 5-bromo-2-hydroxybenzonitrile (1 g, 5.05 mmol) in DMF was treated with 95% NaH (242 mg, 9.6 mmol) for 20 min at room temperature. 2-(2-Bromoethoxy) tetrahydro-2H-pyran (0.839 ml, 5.56 mmol) was then added to the reaction and the mixture was stirred at room temperature for 5 hrs. The reaction was then diluted with DCM and washed with water. The organic phase was dried over $Na_2SO_4$, filtered, and concentrated to dryness to provide the crude title compound, 5-bromo-2-(2-(tetrahydro-2H-pyran-2-yloxy)ethoxy)benzonitrile (1.6 g, 9.75% yield) which was used without further purification.

2-(2-(tetrahydro-2H-pyran-2-yloxy)ethoxy)-5-(4,4,5,5-tetramethyl-1,3,2-dioxaborolan-2-yl)benzonitrile: A mixture of 5-bromo-2-(2-(tetrahydro-2H-pyran-2-yloxy)ethoxy)benzonitrile (1.6 g, 4.92 mmol), 4,4,4',4',5,5,5',5'-octamethyl-2,2'-bi(1,3,2-dioxaborolane) (1.9 g, 7.48 mmol), AcOK (1.47 g, 15 mmol) and $Pd(DPPF)Cl_2$ (366 mg, 0.5 mmol) in dioxane (50 ml) was heated at 110° C. for 60 min. The reaction was evaporated to dryness via rotary evaporation and the resulting residue was purified by silica gel chromatography (DCM-Hexane) to provide the title compound, 2-(2-(tetrahydro-2H-pyran-2-yloxy)ethoxy)-5-(4,4,5,5-tetramethyl-1,3,2-dioxaborolan-2-yl)benzonitrile (1.7 g, 92.6% yield).

N-(6-(6-(3-cyano-4-(3-(tetrahydro-2H-pyran-2-yloxy) propyl)phenyl)-[1,2,4]triazolo[4,3-a]pyridin-3-ylthio)imidazo[1,2-b]pyridazin-2-yl)cyclopropanecarboxamide: The title compound was prepared from compound 4 and 2-(2-(tetrahydro-2H-pyran-2-yloxy)ethoxy)-5-(4,4,5,5-tetramethyl-1,3,2-dioxaborolan-2-yl)benzonitrile following the procedure for the synthesis of compound 5. The reaction mixture was used without further purification.

N-(6-(6-(3-cyano-4-(2-hydroxyethoxy)phenyl)-[1,2,4] triazolo[4,3-a]pyridin-3-ylthio)imidazo[1,2-b]pyridazin-2-yl)cyclopropanecarboxamide: As a crude reaction mixture, N-(6-(6-(3-cyano-4-(3-(tetrahydro-2H-pyran-2-yloxy)propyl)phenyl)-[1,2,4]triazolo[4,3-a]pyridin-3-ylthio)imidazo [1,2-b]pyridazin-2-yl)cyclopropanecarboxamide was treated with [HCl]:dioxane (1:5) at 70° C. for 30 min. The reaction was concentrated and purified by LCMS to provide the title compound as a TFA salt. The product was then dissolved in MeOH, treated 4M HCl in dioxane, and concentrated to dryness to provide the HCl salt of the title compound. $^1$H NMR (METHANOL-$d_4$, 400MHz): δ=9.00 (br. s., 1 H), 8.36 (br. s., 1 H), 8.24 (br. s., 1 H), 8.08 (br, s., 2 H), 8.01 (br. s., 1 H), 7.94 (br. s., 1 H), 7.66-7.74 (m, 1 H), 7.36 (br. s., 1H), 4.27 (br, s., 2 H), 3.95 (br. s., 2 H), 1.83 (br. s., 1 H), 0.84-1.04 ppm (m, 4 H). ESI-MS:m/z 513.4 (M+H)$^+$.

Compound 108: N-(6-(6-(5-cyano-6-hydroxypyridin-3-yl)-[1,2,4]triazolo[4,3-a]pyridin-3-ylthio)imidazo[1,2-b]pyridazin-2-yl)cyclopropanecarboxamide

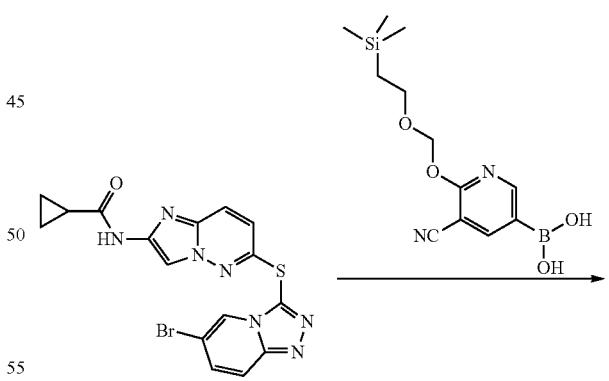

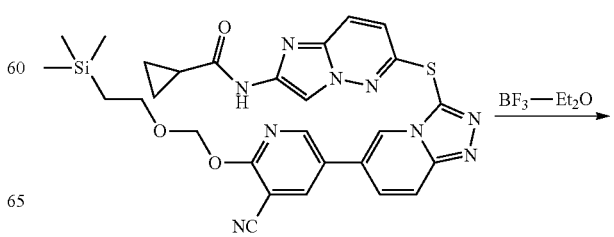

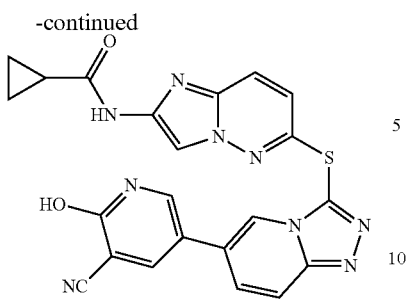

N-(6-(6-(5-cyano-6-((2-(trimethylsilyl)ethoxy)methoxy)pyridin-3-yl)-[1,2,4]triazolo[4,3-a]pyridin-3-ylthio)imidazo[1,2-b]pyridazin-2-yl)cyclopropanecarboxamide: The title compound was synthesized using an analogous procedure to that described in the preparation of Compound 5 using 5-cyano-6-((2-(trimethylsilyl)ethoxy)methoxy)pyridin-3-ylboronic acid. The crude reaction was used for the next step without further purification.

N-(6-(6-(5-cyano-6-hydroxypyridin-3-yl)-[1,2,4]triazolo[4,3-a]pyridin-3-ylthio)imidazo[1,2-b]pyridazin-2-yl)cyclopropanecarboxamide: As a crude reaction mixture, N-(6-(6-(5-cyano-6-((2-(trimethylsilyl)ethoxy)methoxy)pyridin-3-yl)-[1,2,4]triazolo[4,3-a]-pyridin-3-ylthio)imidazo[1,2-b]pyridazin-2-yl)cyclopropanecarboxamide was refluxed in TFA:DCM (1:1, 5 mL) for 30 min. The reaction was then concentrated and purified by preparative LCMS to provide the title compound, N-(6-(6-(5-cyano-6-hydroxypyridin-3-yl)-[1,2,4]triazolo[4,3-a]pyridin-3-ylthio)imidazo[1,2-b]pyridazin-2-yl)cyclopropanecarboxamide as a TFA salt. The product was then dissolved in MeOH, treated 4M HCl in dioxane, and concentrated to dryness to provide the HCl salt of the title compound. $^1$H NMR (METHANOL-$d_4$, 400 MHz): δ=8.80 (br. s., 1 H), 8.51 (d, J=2.5 Hz, 1 H), 8.13 (d, J=2.8 Hz, 1 H), 8.04 (d, J=9.6 Hz, 1 H), 7.79-7.96 (m, 3 H), 7.27 (d, J=7.8 Hz, 1 H), 1.83 (br. s., 1 H), 0.91 ppm (d, J=16.7 Hz, 4 H). ESI-MS:m/z 513.4 (M+H)$^+$.

Compound 109: N-(6-(6-(2-(3-hydroxypropylamino)pyrimidin-5-yl)-[1,2,4]triazolo[4,3-a]pyridin-3-ylthio)imidazo[1,2-b]pyridazin-2-yl)cyclopropanecarboxamide

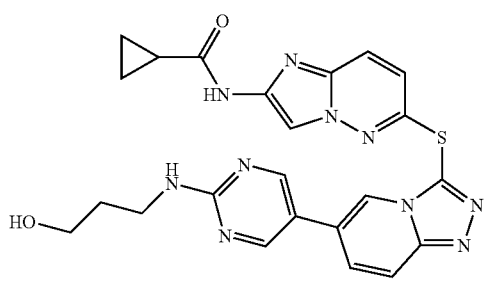

The title compound was synthesized using an analogous procedure to that described in the preparation of Compound 5 using 2-(3-hydroxypropylamino)pyrimidin-5-ylboronic acid. The crude reaction mixture was purified by preparative LCMS, and the product was isolated as the TFA salt. $^1$H NMR (ACETONITRILE-$d_3$, 400 MHz): δ=8.50 (s, 2 H), 8.44 (s, 1 H), 7.89-8.00 (m, 2 H), 7.67-7.78 (m, 2 H), 7.62 (s, 3 H), 7.01 (d, J=9.3 Hz, 1 H), 3.55 (t, J=6.1 Hz, 2H), 3.45 (t, J=6.6 Hz, 2 H), 1.70-1.79 (m, 3 H), 0.85 ppm (d, J=16.2 Hz, 4 H). ESI-MS:m/z 503.3 (M+H)$^+$.

Compound 110: N-(6-(6-(2-morpholinothiazol-4-yl)-[1,2,4]triazolo[4,3-a]pyridin-3-ylthio)imidazo[1,2-b]pyridazin-2-yl)cyclopropanecarboxamide

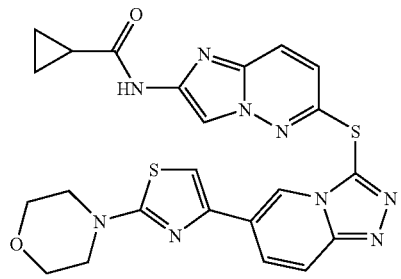

The title compound was synthesized using an analogous procedure to that described in the preparation of Compound 5 using 2-morpholinothiazol-4-ylboronic acid. The crude reaction mixture was purified by preparative LCMS, and the product was isolated as the TFA salt. $^1$H NMR (ACETONITRILE-$d_3$, 400 MHz): δ=8.74 (s, 1 H), 8.03 (br. s., 1 H), 7.91-7.97 (m, 1H), 7.83-7.90 (m, 1 H), 7.71 (br. s., 1 H), 7.15 (s, 1 H), 7.03 (br. s., 1 H), 3.75 (s, 4 H), 3.39-3.45 (m, 4 H), 1.78 (dt, J=5.0, 2.4 Hz, 1 H), 0.81-0.92 ppm (m, 4 H). ESI-MS:m/z 520.2 (M+H)$^+$.

Compound 111: N-(6-(6-(3-(3-hydroxypropyl)phenyl)-[1,2,4]triazolo[4,3-a]pyridin-3-ylthio)imidazo[1,2-b]pyridazin-2-yl)cyclopropanecarboxamide

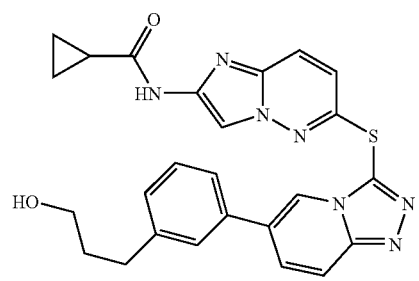

The title compound was synthesized using an analogous procedure to that described in the preparation of Compound 5 using 3-(3-hydroxypropyl)phenylboronic acid. The crude reaction mixture was purified by preparative LCMS, and the product was isolated as the TFA salt. $^1$H NMR (METHANOL-$d_4$, 400 MHz): δ=8.54 (s, 1 H), 7.84-7.94 (m, 3 H), 7.72 (d, J=9.3 Hz, 1 H), 7.33-7.39 (m, 2 H), 7.25-7.32 (m, 1 H), 7.18 (d, J=7.6 Hz, 1 H), 7.10 (d, J=9.3 Hz, 1 H), 3.46 (t, J=6.3

Hz, 2 H), 2.58-2.67 (dd, J=8.0 and 7.6, 2 H), 1.67-1.79 (m, 3 H), 0.72-0.87 ppm (m, 4 H). ESI-MS:m/z 486.3 (M+H)+.

Compound 112: N-(6-(6-((2-methoxyethoxy)methyl)-[1,2,4]triazolo[4,3-a]pyridin-3-ylthio)imidazo[1,2-b]pyridazin-2-yl)cyclopropanecarboxamide

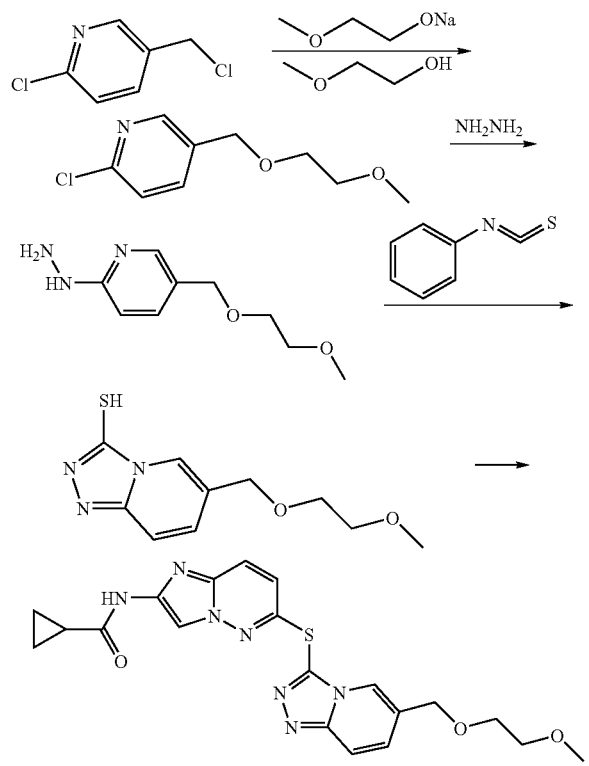

2-hydrazinyl-5-((2-methoxyethoxy)methyl)pyridine: To a solution of 2-chloro-5-(chloromethyl)pyridine (1620 mg, 10 mmol) in 2-methoxyethanol (10 mL) was added sodium 2-methoxyethanolate (5.9 g, 12.00 mmol). The mixture was stirred at room temperature for 10 min and then at 50° C. for 2 hrs. Hydrazine (1.6 g, 50.0 mmol) was then added to the mixture and the reaction was heated at 120° C. for 1 hr. The mixture was purified by preparative LCMS to provide the title compound, 2-hydrazinyl-5-((2-methoxyethoxy)methyl)pyridine (540 mg, 27.4% yield).

6-((2-methoxyethoxy)methyl)-[1,2,4]triazolo[4,3-a]pyridine-3-thiol: The title compound was prepared from 2-hydrazinyl-5-((2-methoxyethoxy)methyl)pyridine and isothiocyanatobenzene following the procedure described in the synthesis of compound 4A.

N-(6-(6-((2-methoxyethoxy)methyl)-[1,2,4]triazolo[4,3-a]pyridin-3-ylthio)imidazo[1,2-b]pyridazin-2-yl)cyclopropanecarboxamide: The title compound was prepared from N-(6-iodoimidazo[1,2-b]pyridazin-2-yl)cyclopropanecarboxamide and 6-((2-methoxyethoxy)methyl)-[1,2,4]triazolo[4,3-a]pyridine-3-thiol following the procedure described for the synthesis of Compound 4. 1H NMR (METHANOL-d4, 400 MHz): δ=8.75-8.78 (m, 1H), 8.15 (dd, J=9.3, 1.0 Hz, 1 H), 8.04-8.11 (m, 1 H), 8.02 (d, J=9.3 Hz, 1 H), 7.94 (s, 1 H), 7.56 (d, J=9.3 Hz, 1 H), 4.71 (d, J=1.0 Hz, 2 H), 3.61-3.67 (m, 2 H), 3.47-3.53 (m, 2 H), 3.29 (s, 3 H), 1.80-1.87 (m, 1 H), 0.88-1.01 ppm (m, 4 H). ESI-MS:m/z 440.2 (M+H)+.

Compound 113: N-(6-(6-fluoro-5-methyl-[1,2,4]triazolo[4,3-a]pyridin-3-ylthio)imidazo[1,2-b]pyridazin-2-yl)cyclopropanecarboxamide

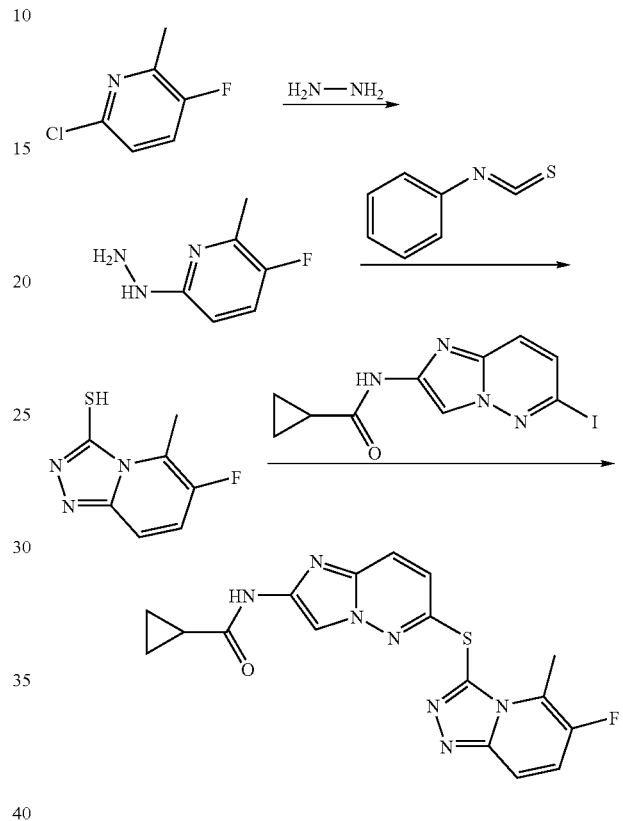

3-fluoro-6-hydrazinyl-2-methylpyridine: To a mixture of 6-chloro-3-fluoro-2-methylpyridine (4.7 g, 32.3 mmol) in isopropanol (100 mL) was added hydrazine hydrate (5 g, 100 mmol). After the mixture was refluxed for 5 hrs, additional hydrazine hydrate (5 g, 100 mmol) was added, and the reaction was refluxed for 3 days. The mixture was then concentrated to dryness and stored under high vacuum overnight. This material was used without further purification.

6-fluoro-5-methyl-[1,2,4]triazolo[4,3-a]pyridine-3-thiol: The title compound was prepared from 3-fluoro-6-hydrazinyl-2-methylpyridine and isothiocyanatobenzene following the procedure described for the synthesis of compound 4A.

N-(6-(6-fluoro-5-methyl-[1,2,4]triazolo[4,3-a]pyridin-3-ylthio)imidazo[1,2-b]pyridazin-2-yl)cyclopropanecarboxamide: The title compound was prepared from N-(6-iodoimidazo[1,2-b]pyridazin-2-yl)cyclopropanecarboxamide and 6-fluoro-5-methyl-[1,2,4]triazolo[4,3-a]pyridine-3-thiol following the procedure described for the synthesis of compound 4. The crude reaction mixture was purified by preparative LCMS, and the product was isolated as the TFA salt. The product was then dissolved in MeOH, treated 4M HCl in dioxane, and concentrated to dryness to provide the HCl salt of the title compound. 1H NMR (METHANOL-d4, 400 MHz): δ=8.00 (s, 1 H), 7.83-7.89 (m, 3 H), 7.63 (dd, J=9.9, 8.3 Hz, 1H), 7.22 (d, J=9.6 Hz, 1 H), 2.96 (d, J=3.5 Hz, 4 H), 1.81-1.91 (m, 1 H), 0.96 (dt, J=4.5, 3.0 Hz, 2 H), 0.86-0.92 (m, 2 H). ESI-MS:m/z 384.3 (M+H)⁺.

Compound 114: 6-([1,2,4]triazolo[4,3-a]pyridin-3-ylthio)imidazo[1,2-b]pyridazin-2-amine

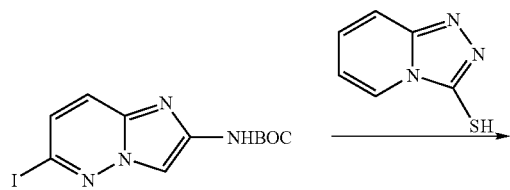

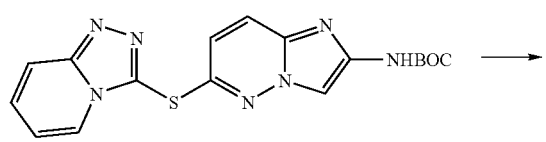

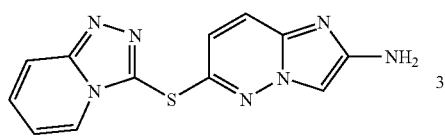

tert-Butyl 6-([1,2,4]triazolo[4,3-a]pyridin-3-ylthio)imidazo[1,2-b]pyridazin-2-ylcarbamate: The title compound was prepared from tert-butyl 6-iodoimidazo[1,2-b]pyridazin-2-ylcarbamate and [1,2,4]triazolo[4,3-a]pyridine-3-thiol following the procedure for the synthesis of compound 4.

6-([1,2,4]triazolo[4,3-a]pyridin-3-ylthio)imidazo[1,2-b]pyridazin-2-amine: A solution of tert-butyl 6-([1,2,4]triazolo[4,3-a]pyridin-3-ylthio)imidazo[1,2-b]pyridazin-2-ylcarbamate (300 mg, 0.78 mmol) in dioxane (5 ml) was treated with 4M HCl in dioxane (5 ml) at 80° C. for 1 hr. The mixture was concentrated and purified by LCMS to give the title compound, 6-([1,2,4]triazolo[4,3-a]pyridin-3-ylthio)imidazo[1,2-b]pyridazin-2-amine (201 mg, 68% yield) as the TFA salt. ¹H NMR (400 MHz, DMSO-d₆) δ ppm 7.00 (d, J=9.35 Hz, 1 H) 7.16 (t, J=6.44 Hz, 1 H) 7.22 (s, 1 H) 7.54-7.65 (m, 1 H) 7.73 (d, J=9.35 Hz, 1 H) 8.00 (d, J=9.09 Hz, 1 H) 8.47 (d, J=6.82 Hz, 1 H). ESI-MS:m/z 284.2 (M+H)⁺.

General Procedure for Free Base and HCl Salt Formation

The free base forms of the above exemplary compounds can be prepared by purifying the crude material by MPLC using Hex:EtOAc (9:1→4:6) or DCM:MeOH (99:1→9:1) as eluent. Specifically, the free base forms of compounds 3, 13, 45 and 49 were prepared.

The HCl salts of the above exemplary compounds can be prepared by dissolving the TFA salt in water, treating the solution with concentrated HCl, and lyophilizing to dryness. Specifically, the HCl salts of compounds 3, 13, 45, 49 and 112 were prepared.

In addition to the foregoing, the above reaction schemes and variations thereof can be used to prepare compounds having the formula:

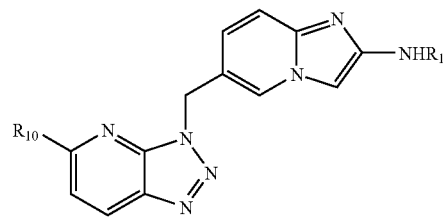

wherein

R₁ is selected from the group consisting of hydrogen,

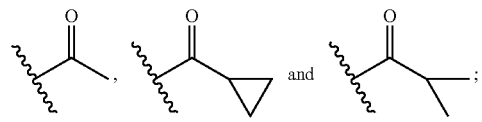

and

R₁₀ is selected from the group consisting of

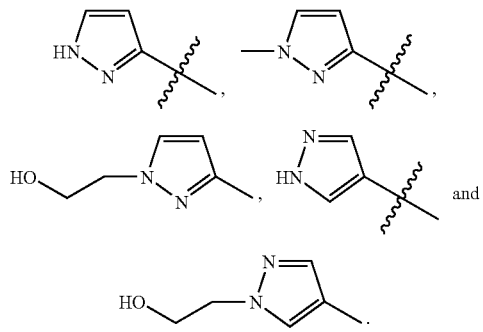

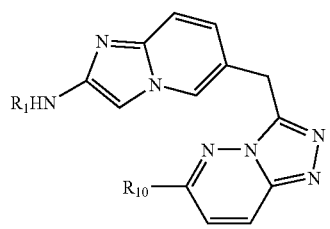

Further, the above reaction schemes and variations thereof can be used to prepare compounds having the formula:

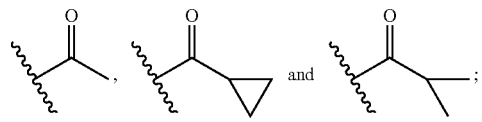

wherein

R₁ is selected from the group consisting of hydrogen, and

R₁₀ is selected from the group consisting of

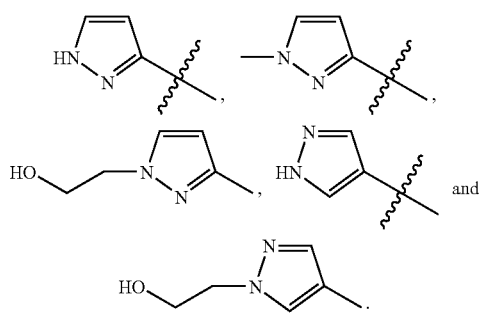

Further, the above reaction schemes and variations thereof can be used to prepare compounds having the formula:

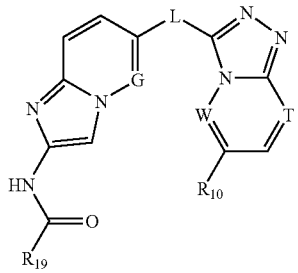

wherein
L is selected from the group consisting of S, CH₂, CH(CH₃), C(CH₃)₂ AND CF₂;
G, T and W are each independently selected from the group consisting of CH and N;
R₁ is selected from the group consisting of Cl, Br, I, CH₃, CF₃, CN,

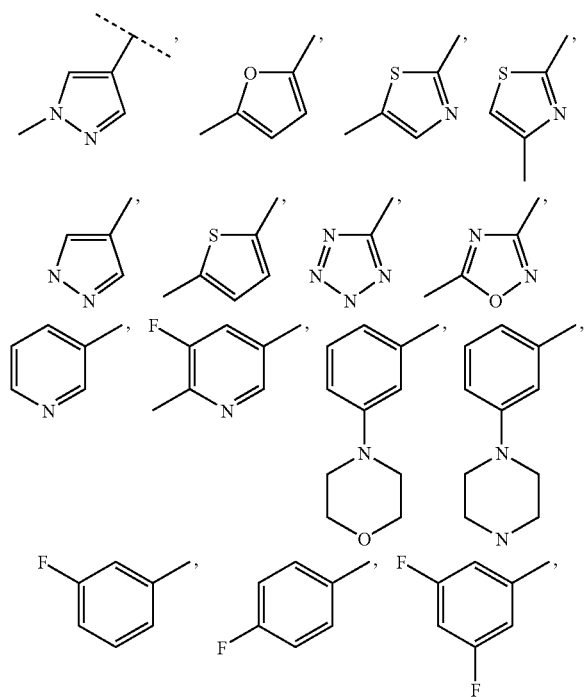

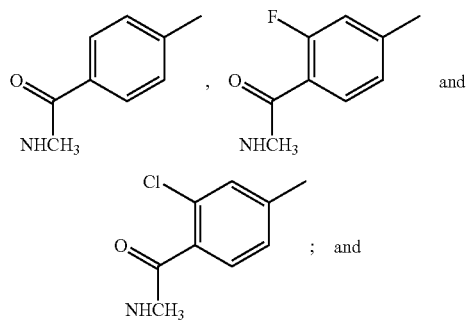

R₁₉ is selected from the group consisting of

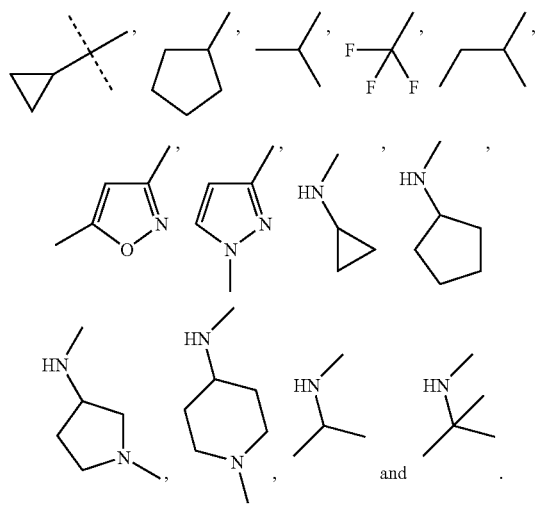

In addition to the foregoing, the above reaction schemes and variations thereof can be used to prepare the following:

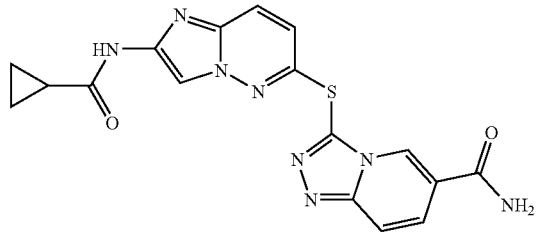

3-(2-(cyclopropanecarboxamido)imidazo[1,2-b]pyridazin-6-ylthio)-[1,2,4]triazolo[4,3-a]pyridine-6-carboxamide

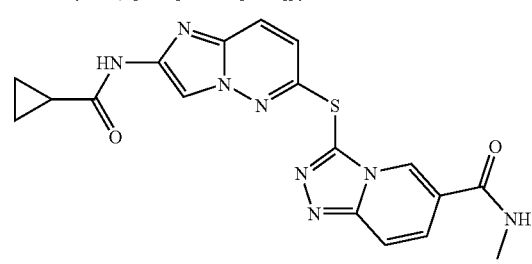

3-(2-(cyclopropanecarboxamido)imidazo[1,2-b]pyridazin-6-ylthio)-N-methyl-[1,2,4]triazolo[4,3-a]pyridine-6-carboxamide

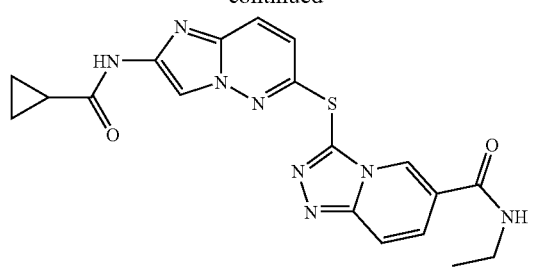

3-(2-(cyclopropanecarboxamido)imidazo[1,2-b]pyridazin-6-ylthio)-N-ethyl-[1,2,4]triazolo[4,3-a]pyridine-6-carboxamide

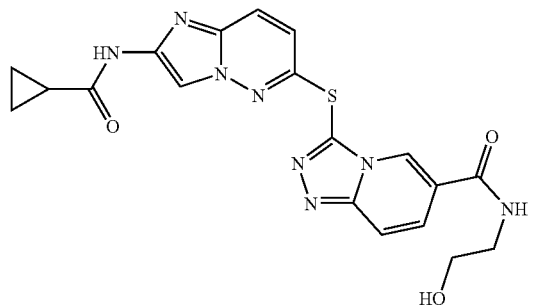

3-(2-(cyclopropanecarboxamido)imidazo[1,2-b]pyridazin-6-ylthio)-N-(2-hydroxyethyl)-[1,2,4]triazolo[4,3-a]pyridine-6-carboxamide

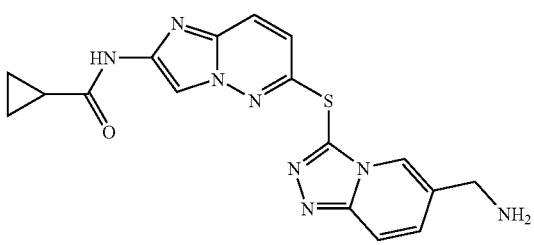

N-(6-(6-(aminomethyl)-[1,2,4]triazolo[4,3-a]pyridin-3-ylthio)imidazo[1,2-b]pyridazin-2-yl)cyclopropanecarboxamide

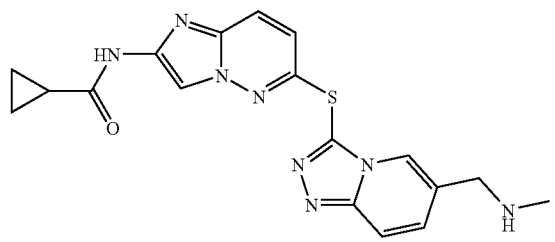

N-(6-(6-((methylamino)methyl)-[1,2,4]triazolo[4,3-a]pyridin-3-ylthio)imidazo[1,2-b]pyridazin-2-yl)cyclopropanecarboxamide

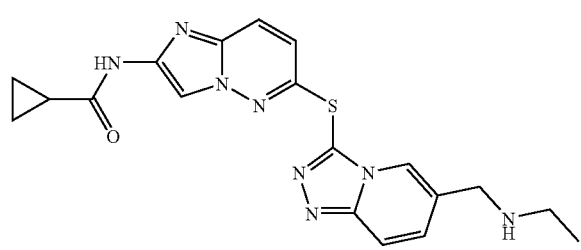

N-(6-(6-((ethylamino)methyl)-[1,2,4]triazolo[4,3-a]pyridin-3-ylthio)imidazo[1,2-b]pyridazin-2-yl)cyclopropanecarboxamide

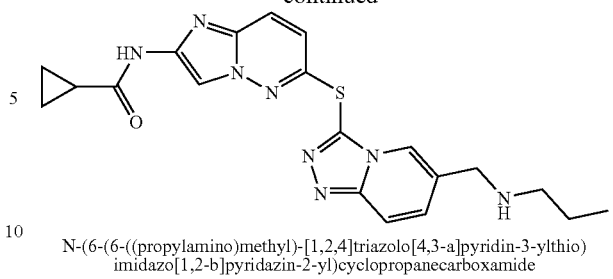

N-(6-(6-((propylamino)methyl)-[1,2,4]triazolo[4,3-a]pyridin-3-ylthio)imidazo[1,2-b]pyridazin-2-yl)cyclopropanecarboxamide

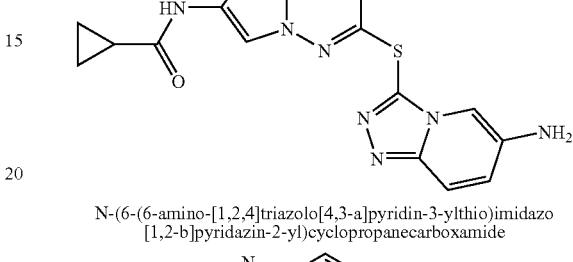

N-(6-(6-amino-[1,2,4]triazolo[4,3-a]pyridin-3-ylthio)imidazo[1,2-b]pyridazin-2-yl)cyclopropanecarboxamide

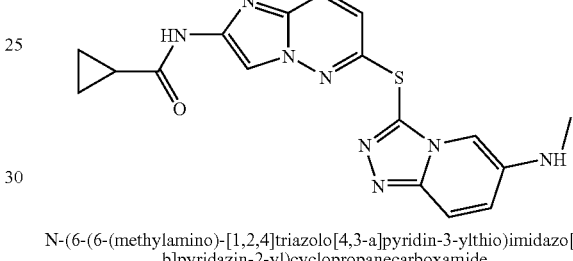

N-(6-(6-(methylamino)-[1,2,4]triazolo[4,3-a]pyridin-3-ylthio)imidazo[1,2-b]pyridazin-2-yl)cyclopropanecarboxamide

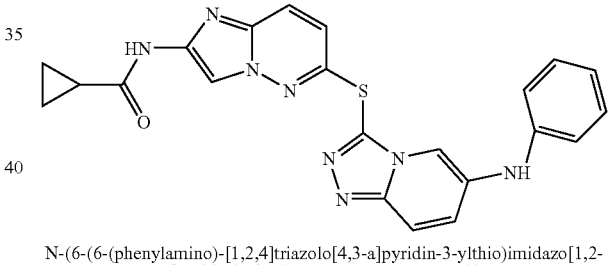

N-(6-(6-(phenylamino)-[1,2,4]triazolo[4,3-a]pyridin-3-ylthio)imidazo[1,2-b]pyridazin-2-yl)cyclopropanecarboxamide

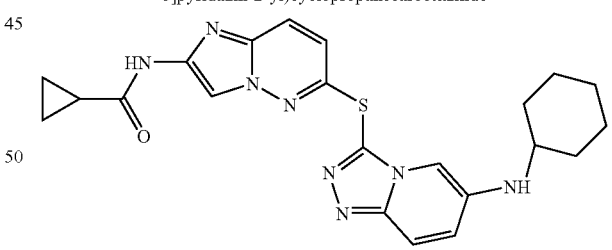

N-(6-(6-(cyclohexylamino)-[1,2,4]triazolo[4,3-a]pyridin-3-ylthio)imidazo[1,2-b]pyridazin-2-yl)cyclopropanecarboxamide

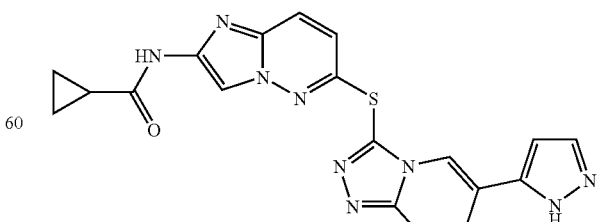

N-(6-(6-(1H-pyrazol-5-yl)-[1,2,4]triazolo[4,3-a]pyridin-3-ylthio)imidazo[1,2-b]pyridazin-2-yl)cyclopropanecarboxamide

209

-continued

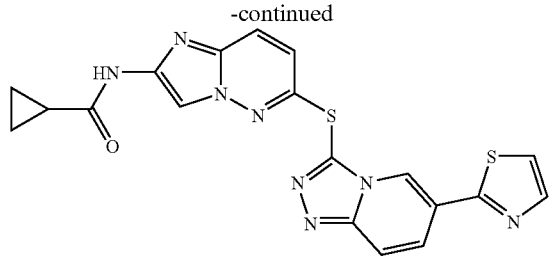

N-(6-(6-(thiazol-2-yl)-[1,2,4]triazolo[4,3-a]pyridin-3-ylthio)imidazo[1,2-b]pyridazin-2-yl)cyclopropanecarboxamide

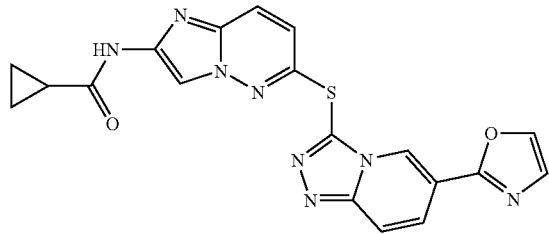

N-(6-(6-(oxazol-2-yl)-[1,2,4]triazolo[4,3-a]pyridin-3-ylthio)imidazo[1,2-b]pyridazin-2-yl)cyclopropanecarboxamide

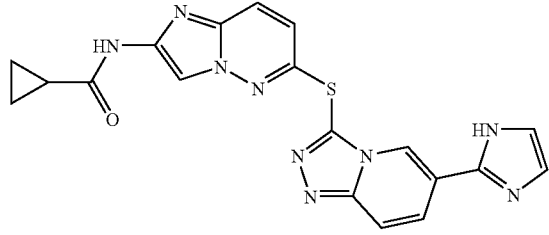

N-(6-(6-(1H-imidazol-2-yl)-[1,2,4]triazolo[4,3-a]pyridin-3-ylthio)imidazo[1,2-b]pyridazin-2-yl)cyclopropanecarboxamide

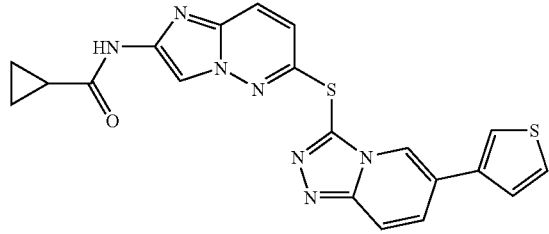

N-(6-(6-(thiophen-3-yl)-[1,2,4]triazolo[4,3-a]pyridin-3-ylthio)imidazo[1,2-b]pyridazin-2-yl)cyclopropanecarboxamide

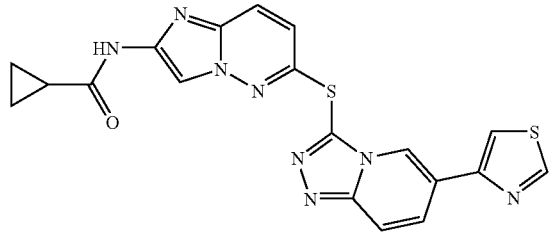

N-(6-(6-(thiazol-4-yl)-[1,2,4]triazolo[4,3-a]pyridin-3-ylthio)imidazo[1,2-b]pyridazin-2-yl)cyclopropanecarboxamide

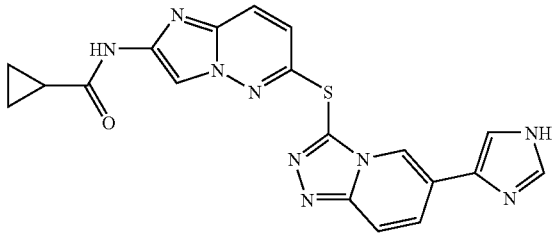

N-(6-(6-(1H-imidazol-4-yl)-[1,2,4]triazolo[4,3-a]pyridin-3-ylthio)imidazo[1,2-b]pyridazin-2-yl)cyclopropanecarboxamide

210

-continued

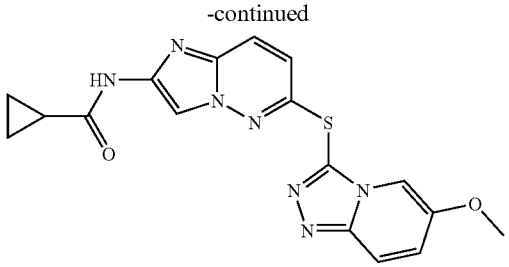

N-(6-(6-methoxy-[1,2,4]triazolo[4,3-a]pyridin-3-ylthio)imidazo[1,2-b]pyridazin-2-yl)cyclopropanecarboxamide

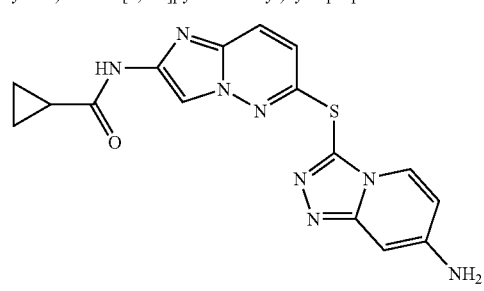

N-(6-(7-amino-[1,2,4]triazolo[4,3-a]pyridin-3-ylthio)imidazo[1,2-b]pyridazin-2-yl)cyclopropanecarboxamide

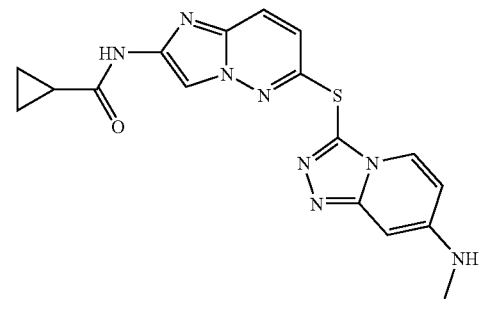

N-(6-(7-(methylamino)-[1,2,4]triazolo[4,3-a]pyridin-3-ylthio)imidazo[1,2-b]pyridazin-2-yl)cyclopropanecarboxamide

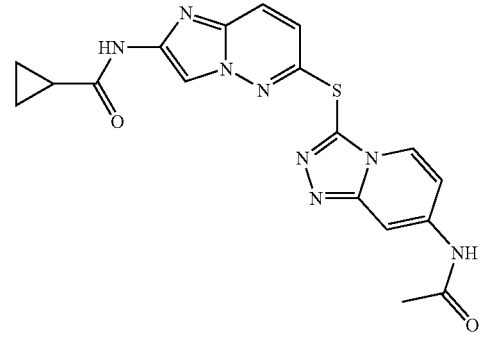

N-(6-(7-acetamido-[1,2,4]triazolo[4,3-a]pyridin-3-ylthio)imidazo[1,2-b]pyridazin-2-yl)cyclopropanecarboxamide

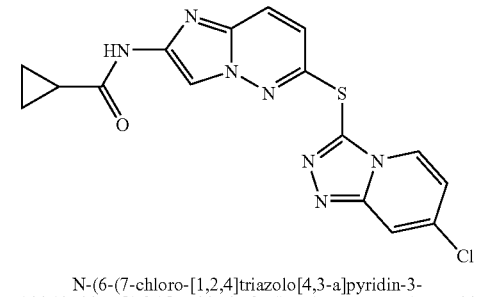

N-(6-(7-chloro-[1,2,4]triazolo[4,3-a]pyridin-3-ylthio)imidazo[1,2-b]pyridazin-2-yl)cyclopropanecarboxamide

211

-continued

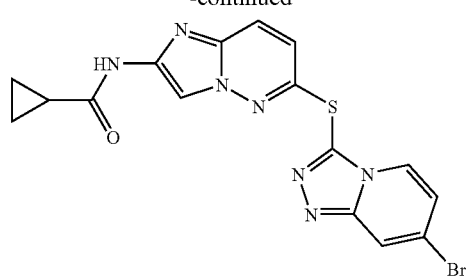

N-(6-(7-bromo-[1,2,4]triazolo[4,3-a]pyridin-3-ylthio)imidazo[1,2-b]pyridazin-2-yl)cyclopropanecarboxamide

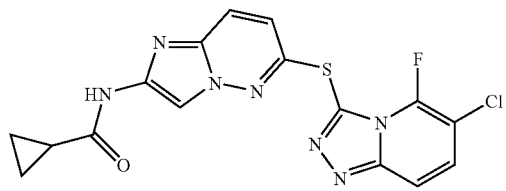

N-(6-(6-chloro-5-fluoro-[1,2,4]triazolo[4,3-a]pyridin-3-ylthio)imidazo[1,2-b]pyridazin-2-yl)cyclopropanecarboxamide

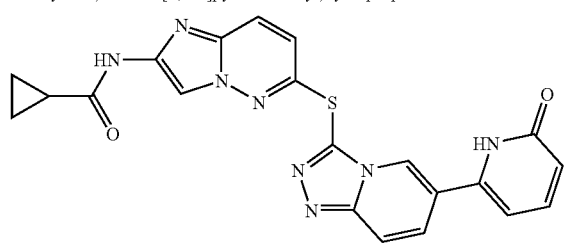

3-(2N-(6-(6-(6-oxo-1,6-dihydropyridin-2-yl)-[1,2,4]triazolo[4,3-a]pyridin-3-ylthio)imidazo[1,2-b]pyridazin-2-yl)cyclopropanecarboxamide

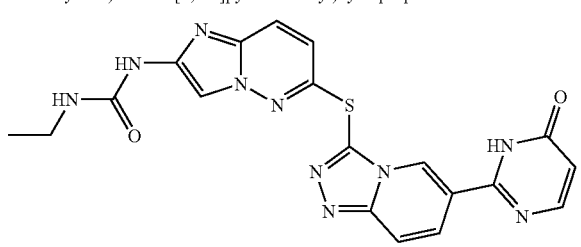

3-(2l-ethyl-3-(6-(6-(6-oxo-1,6-dihydropyrimidin-2-yl)-[1,2,4]triazolo[4,3-a]pyridin-3-ylthio)imidazo[1,2-b]pyridazin-2-yl)urea

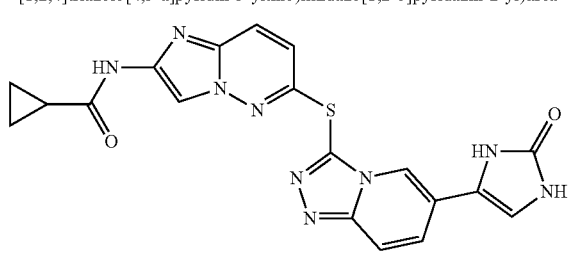

3-(2N-(6-(6-(2-oxo-2,3-dihydro-1H-imidazol-4-yl)-[1,2,4]triazolo[4,3-a]pyridin-3-ylthio)imidazo[1,2-b]pyridazin-2-yl)cyclopropanecarboxamide

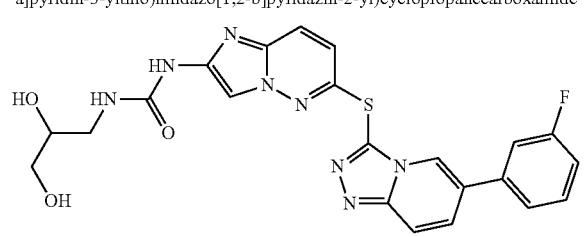

1-(2,3-dihydroxypropyl)-3-(6-(6-(3-fluorophenyl)-[1,2,4]triazolo[4,3-a]pyridin-3-ylthio)imidazo[1,2-b]pyridazin-2-yl)-urea

212

-continued

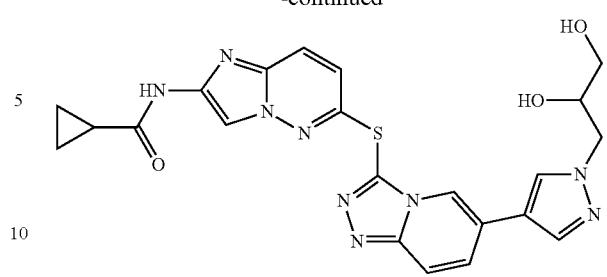

N-(6-(6-(1-(2,3-dihydroxypropyl)-1H-pyrazol-4-yl)-[1,2,4]triazolo[4,3-a]pyridin-3-ylthio)imidazo[1,2-b]pyridazin-2-yl)cyclopropanecarboxamide

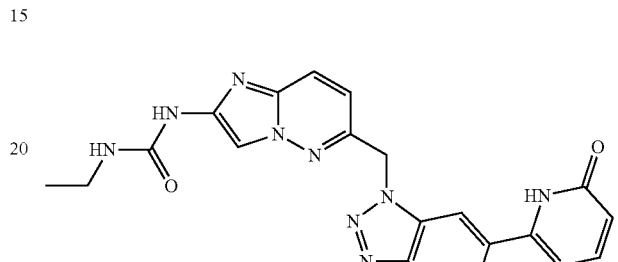

1-ethyl-3-(6-((6-(6-oxo-1,6-dihydropyridin-2-yl)-1H-benzo[d][1,2,3]triazol-1-yl)methyl)imidazo[1,2-b]pyridazin-2-yl)urea

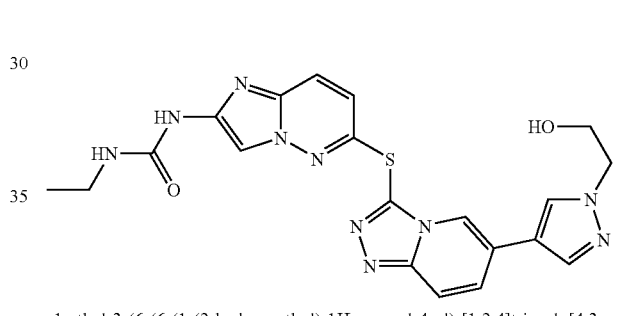

1-ethyl-3-(6-(6-(1-(2-hydroxyethyl)-1H-pyrazol-4-yl)-[1,2,4]triazolo[4,3-a]pyridin-3-ylthio)imidazo[1,2-b]pyridazin-2-yl)urea

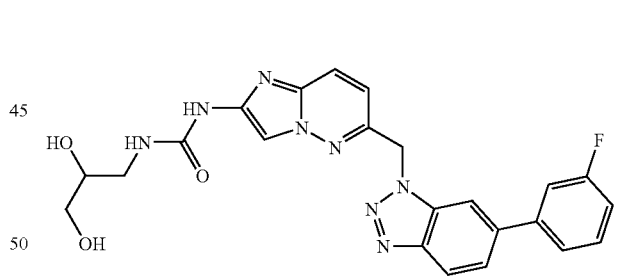

1-(2,3-dihydroxypropyl)-3-(6-((6-(3-fluorophenyl)-1H-benzo[d][1,2,3]triazol-1-yl)methyl)imidazo[1,2-b]pyridazin-2-yl)urea

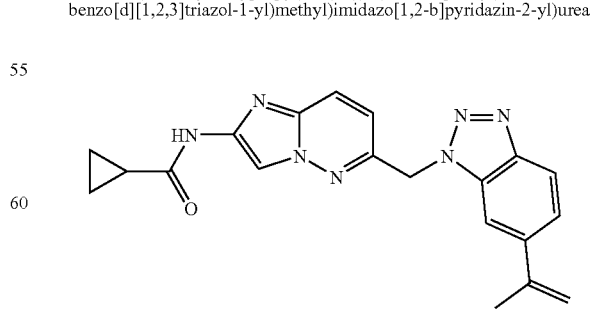

N-(6-((6-(prop-1-en-2-yl)-1H-benzo[d][1,2,3]triazol-1-yl)methyl)imidazo[1,2-b]pyridazin-2-yl)cyclopropanecarboxamide

213

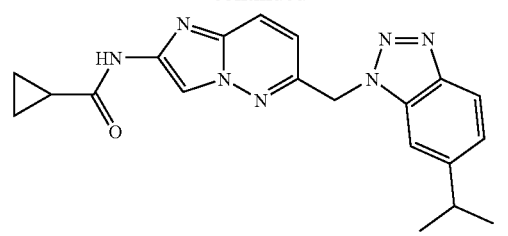

N-(6-((6-isopropyl-1H-benzo[d][1,2,3]triazol-1-yl)methyl)imidazo[1,2-b]pyridazin-2-yl)cyclopropanecarboxamide

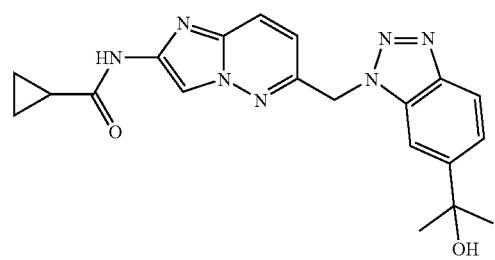

N-(6-((6-(2-hydroxypropan-2-yl)-1H-benzo[d][1,2,3]triazol-1-yl)methyl)imidazo[1,2-b]pyridazin-2-yl)cyclopropanecarboxamide

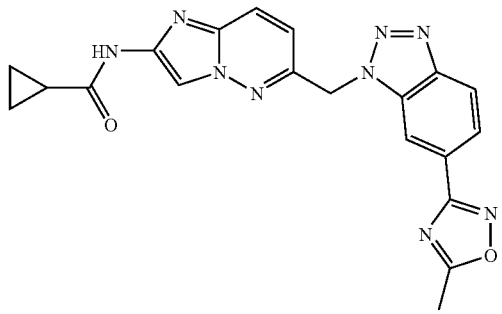

N-(6-((6-(5-methyl-1,2,4-oxadiazol-3-yl)-1H-benzo[d][1,2,3]triazol-1-yl)methyl)imidazo[1,2-b]pyridazin-2-yl)cyclopropanecarboxamide

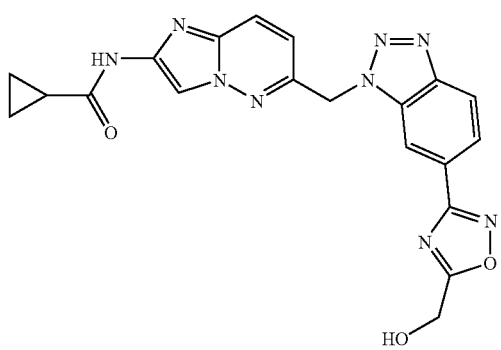

N-(6-((6-(5-(hydroxymethyl)-1,2,4-oxadiazol-3-yl)-1H-benzo[d][1,2,3]triazol-1-yl)methyl)imidazo[1,2-b]pyridazin-2-yl)cyclopropanecarboxamide

214

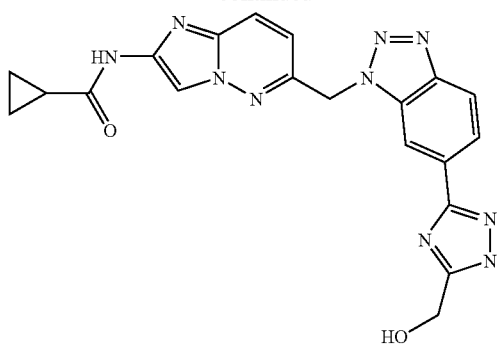

N-(6-((6-(5-(hydroxymethyl)-1H-1,2,4-triazol-3-yl)-1H-benzo[d][1,2,3]triazol-1-yl)methyl)imidazo[1,2-b]pyridazin-2-yl)cyclopropanecarboxamide

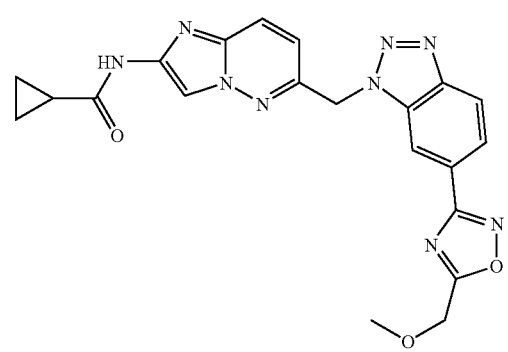

N-(6-((6-(5-(methoxymethyl)-1,2,4-oxadiazol-3-yl)-1H-benzo[d][1,2,3]triazol-1-yl)methyl)imidazo[1,2-b]pyridazin-2-yl)cyclopropanecarboxamide

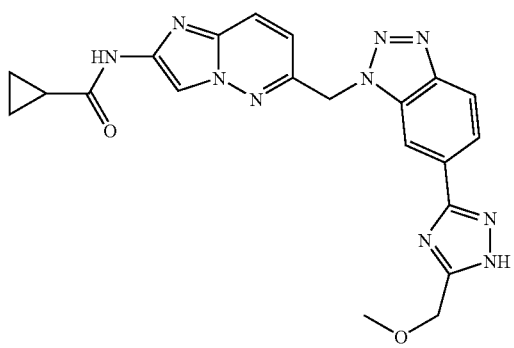

N-(6-((6-(5-(methoxymethyl)-1H-1,2,4-triazol-3-yl)-1H-benzo[d][1,2,3]triazol-1-yl)methyl)imidazo[1,2-b]pyridazin-2-yl)cyclopropanecarboxamide

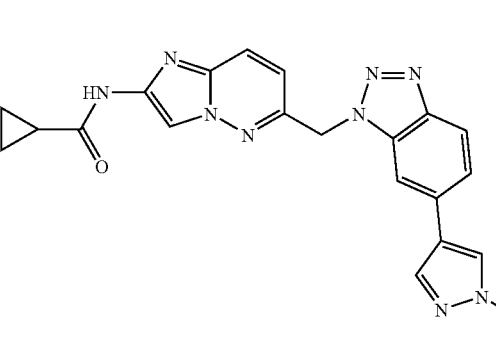

N-(6-((6-(1-(2-methoxyethyl)-1H-pyrazol-4-yl)-1H-benzo[d][1,2,3]triazol-1-yl)methyl)imidazo[1,2-b]pyridazin-2-yl)cyclopropanecarboxamide

215

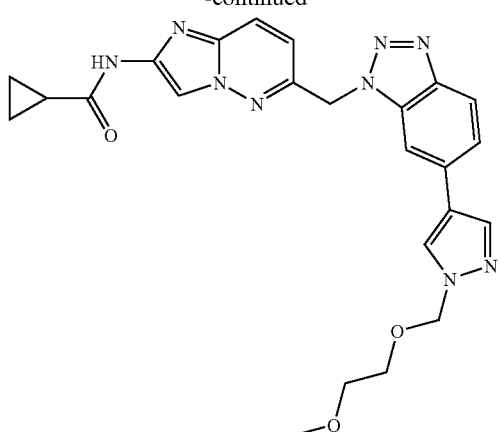

N-(6-((6-(((2-methoxyethoxy)methyl)-1H-pyrazol-4-yl)-1H-
benzo[d][1,2,3]triazol-1-yl)methyl)imidazo[1,2-b]pyridazin-2-
yl)cyclopropanecarboxamide

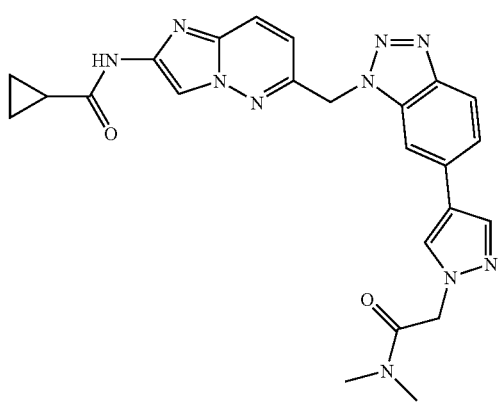

N-(6-((6-(1-(2-(dimethylamino)-2-oxoethyl)-1H-pyrazol-4-yl)-1H-
benzo[d][1,2,3]triazol-1-yl)methyl)imidazo[1,2-b]pyridazin-2-
yl)cyclopropanecarboxamide

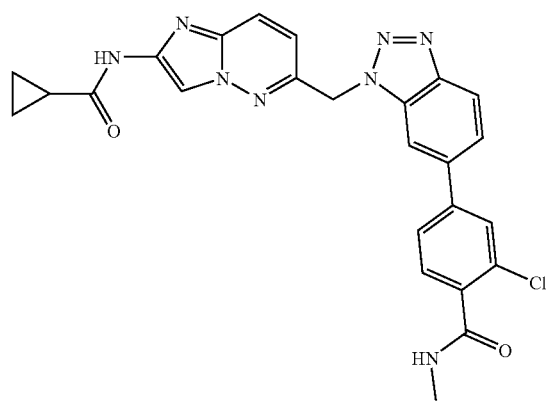

2-chloro-4-(1-((2-(cyclopropanecarboxamido)imidazo[1,2-b]pyridazin-6-
yl)methyl)-1H-benzo[d][1,2,3]triazol-6-yl)-N-methylbenzamide

216

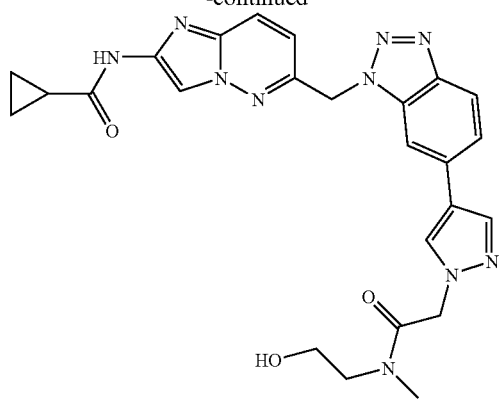

N-(6-((6-(1-(2-((2-hydroxyethyl(methyl)amino-2-oxoethyl)-1H-pyrazol-
4-yl)-1H-benzo[d][1,2,3]triazol-1-yl)methyl)imidazo[1,2-b]pyridazin-2-
yl)cyclopropanecarboxamide

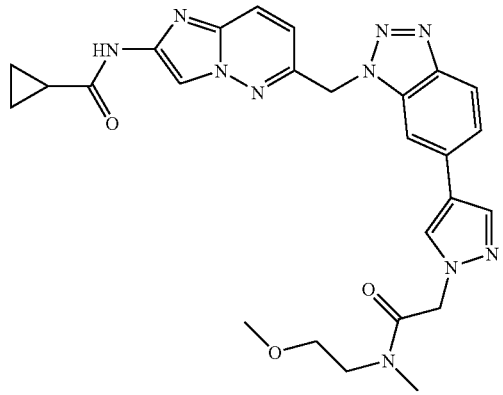

N-(6-((6-(1-((2-methoxyethyl)(methyl)amino-2-oxoethyl)-1H-pyrazol-
4-yl)-1H-benzo[d][1,2,3]triazol-1-yl)methyl)imidazo[1,2-b]pyridazin-2-
yl)cyclopropanecarboxamide

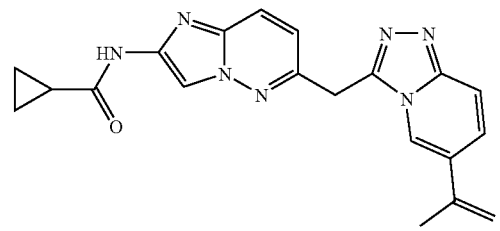

N-(6-((6-(prop-1-en-2-yl)-[1,2,4]triazolo[4,3-a]pyridin-3-
yl)methy)imidazo[1,2-b]pyridazin-2-yl)cyclopropanecarboxamide

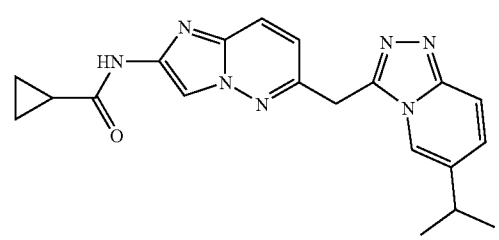

N-(6-((6-isopropyl-[1,2,4]triazolo[4,3-a]pyridin-3-yl)methy)imidazo[1,2-
b]pyridazin-2-yl)cyclopropanecarboxamide

217

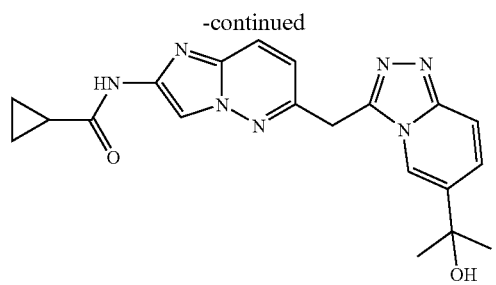

N-(6-((6-(2-hydroxypropan-2-yl)-[1,2,4]triazolo[4,3-a]pyridin-3-yl)methy)imidazo[1,2-b]pyridazin-2-yl)cyclopropanecarboxamide

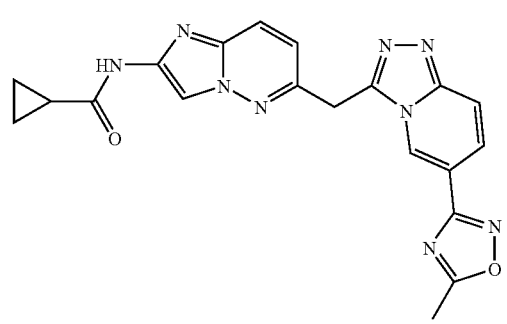

N-(6-((6-(5-methyl-1,2,4-oxadiazol-3-yl)-[1,2,4]triazolo[4,3-a]pyridin-3-yl)methyl)imidazo[1,2-b]pyridazin-2-yl)cyclopropanecarboxamide

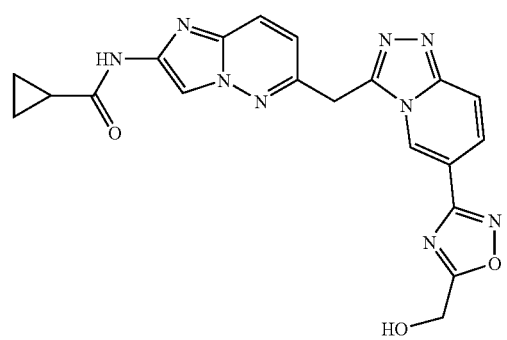

N-(6-((6-(5-(hydroxymethyl)-1,2,4-oxadiazol-3-yl)-[1,2,4]triazolo[4,3-a]pyridin-3-yl)methyl)imidazo[1,2-b]pyridazin-2-yl)cyclopropanecarboxamide N-(6-((6-(5-(hydroxymethyl)-1H-1,2,4-triazol-3-yl)-[1,2,4]triazolo[4,3-a]pyridin-3-yl)methyl)imidazo[1,2-b]pyridazin-2-yl)cyclopropanecarboxamide

218

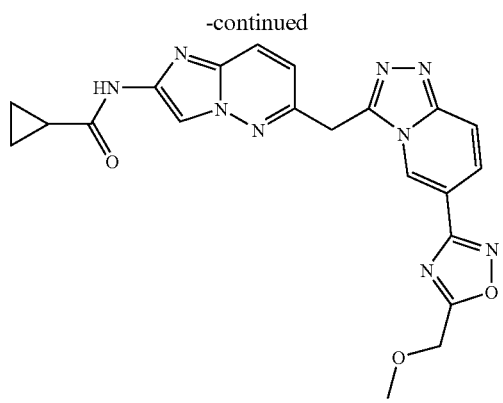

N-(6-((6-(5-(methoxymethyl)-1,2,4-oxadiazol-3-yl)-[1,2,4]triazolo[4,3-a]pyridin-3-yl)methyl)imidazo[1,2-b]pyridazin-2-yl)cyclopropanecarboxamide

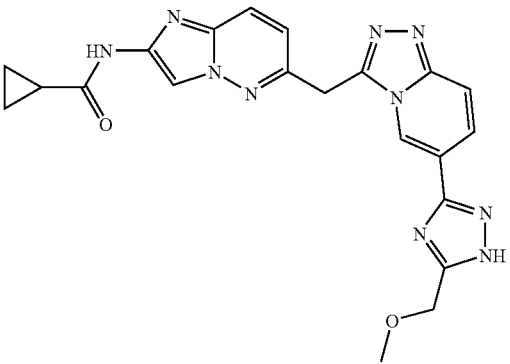

N-(6-((6-(5-(methoxymethyl)-1H-1,2,4-triazol-3-yl)-[1,2,4]triazolo[4,3-a]pyridin-3-yl)methyl)imidazo[1,2-b]pyridazin-2-yl)cyclopropanecarboxamide

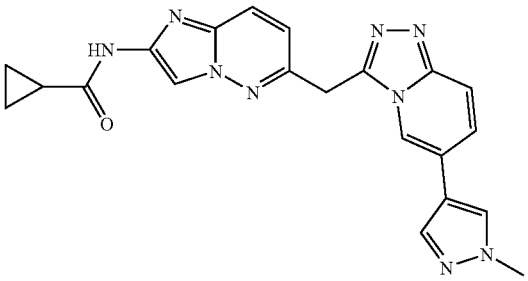

N-(6-((6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide

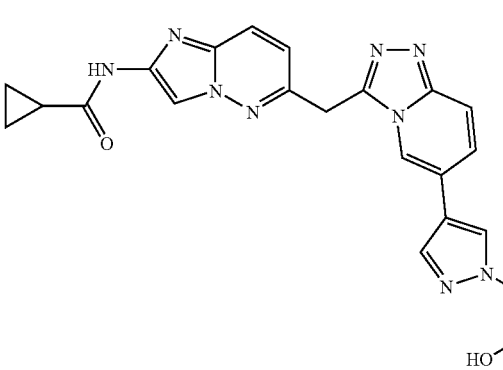

N-(6-((6-(1-(2-hydroxyethyl)-1H-pyrazol-4-yl)-[1,2,4]triazolo[4,3-a]pyridin-3-yl)methyl)imidazo[1,2-b]pyridazin-2-yl)cyclopropanecarboxamide

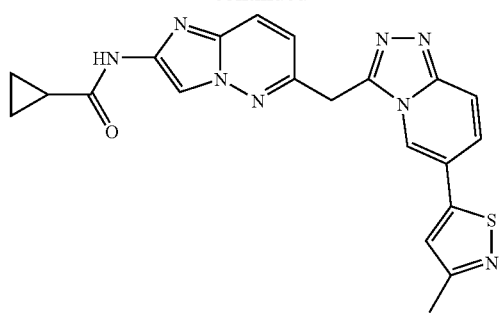

N-(6-((6-(3-methylisothiazol-5-yl)-[1,2,4]triazolo[4,3-a]pyridin-3-yl)methyl)imidazo[1,2-b]pyridazin-2-yl)cyclopropanecarboxamide

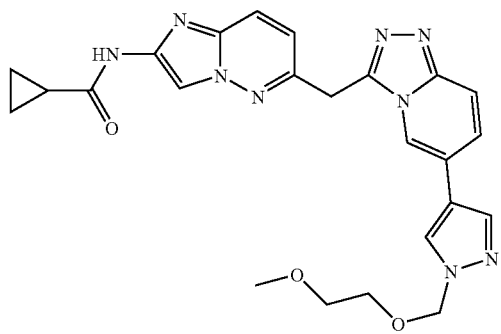

N-(6-((6-(1-((2-methoxyethoxy)methyl)-1H-pyrazol-4-yl)-[1,2,4]triazolo[4,3-a]pyridin-3-yl)methyl)imidazo[1,2-b]pyridazin-2-yl)cyclopropanecarboxamide

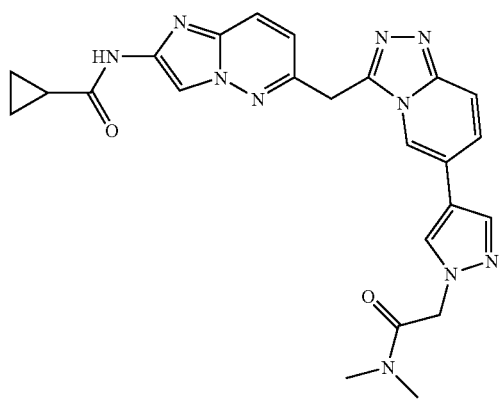

N-(6-((6-(1-(2-(dimethylamino)-2-oxoethyl)-1H-pyrazol-4-yl)-[1,2,4]triazolo[4,3-a]pyridin-3-yl)methyl)imidazo[1,2-b]pyridazin-2-yl)cyclopropanecarboxamide

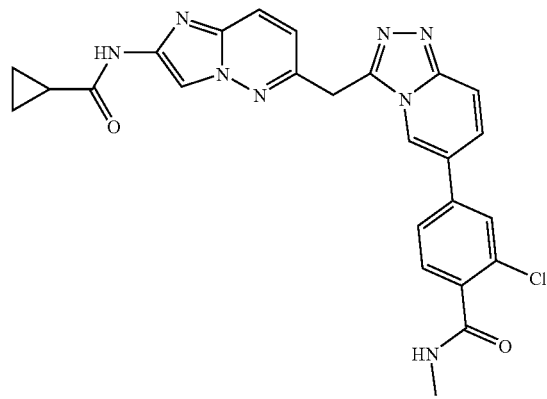

2-chloro-4-(3-((2-(cyclopropanecarboxamido)imidazo[1,2-b]pyridazin-6-yl)methyl)-[1,2,4]triazolo[4,3-a]pyridin-6-yl)-N-methylbenzamide

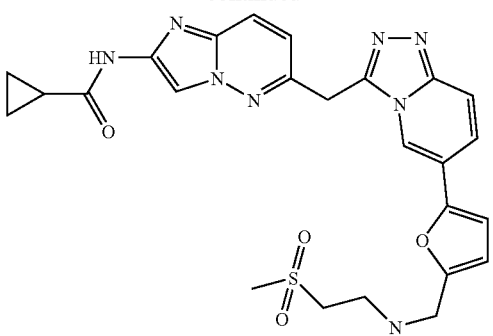

N-(6-((6-(5-((2-(methylsulfonyl)ethylamino)methyl)furan-2-yl)-[1,2,4]triazolo[4,3-a]pyridin-3-yl)methyl)imidazo[1,2-b]pyridazin-2-yl)cyclopropanecarboxamide

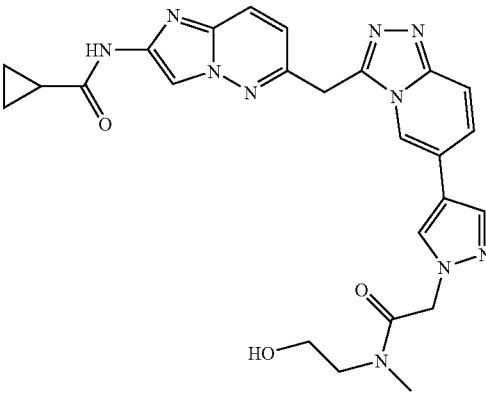

N-(6-((6-(1-(2-((2-hydroxyethyl)(methyl)amino)-2-oxoethyl)-1H-pyrazol-4-yl)-[1,2,4]triazolo[4,3-a]pyridin-3-yl)methyl)imidazo[1,2-b]pyridazin-2-yl)cyclopropanecarboxamide

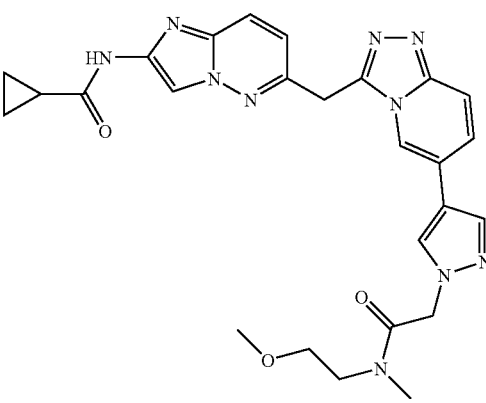

N-(6-((6-(1-(2-((2-methoxyethyl)(methyl)amino)-2-oxoethyl)-1H-pyrazol-4-yl)-[1,2,4]triazolo[4,3-a]pyridin-3-yl)methyl)imidazo[1,2-b]pyridazin-2-yl)cyclopropanecarboxamide

221

-continued

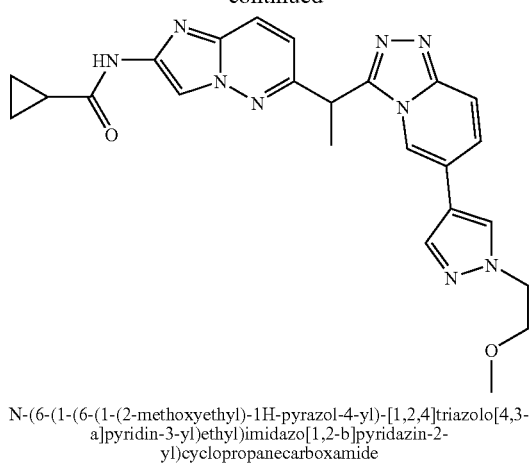

N-(6-(1-(6-(1-(2-methoxyethyl)-1H-pyrazol-4-yl)-[1,2,4]triazolo[4,3-a]pyridin-3-yl)ethyl)imidazo[1,2-b]pyridazin-2-yl)cyclopropanecarboxamide

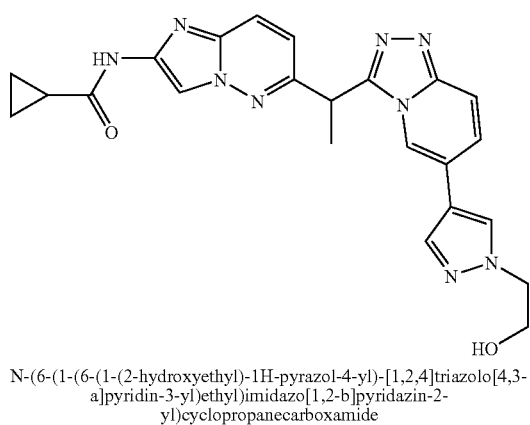

N-(6-(1-(6-(1-(2-hydroxyethyl)-1H-pyrazol-4-yl)-[1,2,4]triazolo[4,3-a]pyridin-3-yl)ethyl)imidazo[1,2-b]pyridazin-2-yl)cyclopropanecarboxamide

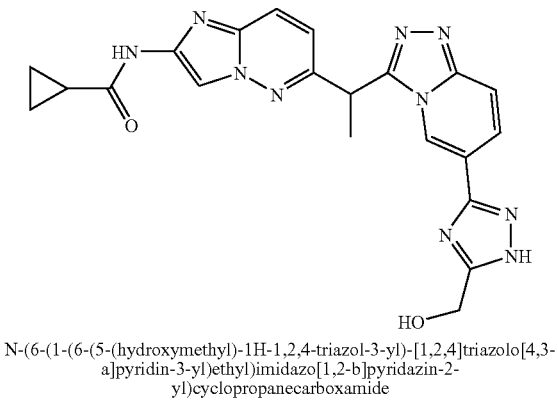

N-(6-(1-(6-(5-(hydroxymethyl)-1H-1,2,4-triazol-3-yl)-[1,2,4]triazolo[4,3-a]pyridin-3-yl)ethyl)imidazo[1,2-b]pyridazin-2-yl)cyclopropanecarboxamide

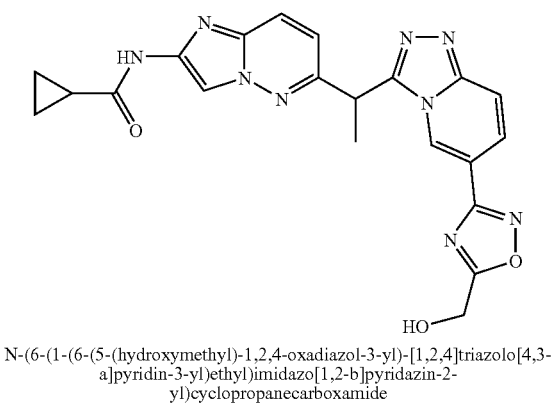

N-(6-(1-(6-(5-(hydroxymethyl)-1,2,4-oxadiazol-3-yl)-[1,2,4]triazolo[4,3-a]pyridin-3-yl)ethyl)imidazo[1,2-b]pyridazin-2-yl)cyclopropanecarboxamide

222

-continued

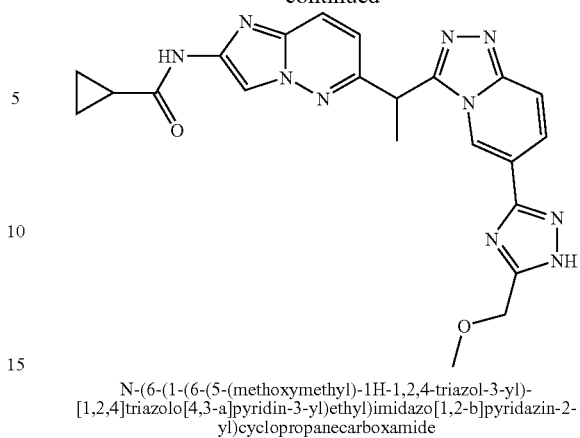

N-(6-(1-(6-(5-(methoxymethyl)-1H-1,2,4-triazol-3-yl)-[1,2,4]triazolo[4,3-a]pyridin-3-yl)ethyl)imidazo[1,2-b]pyridazin-2-yl)cyclopropanecarboxamide

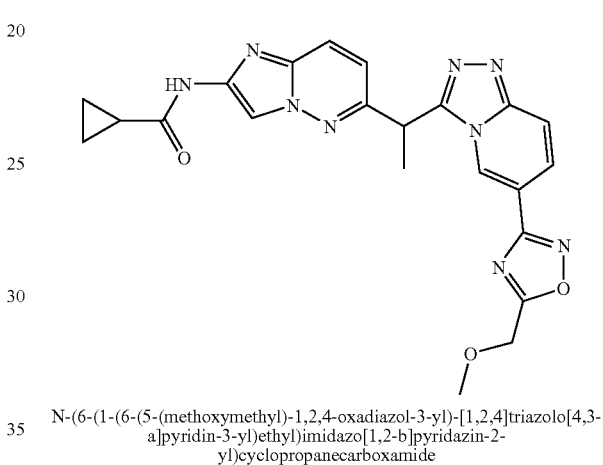

N-(6-(1-(6-(5-(methoxymethyl)-1,2,4-oxadiazol-3-yl)-[1,2,4]triazolo[4,3-a]pyridin-3-yl)ethyl)imidazo[1,2-b]pyridazin-2-yl)cyclopropanecarboxamide

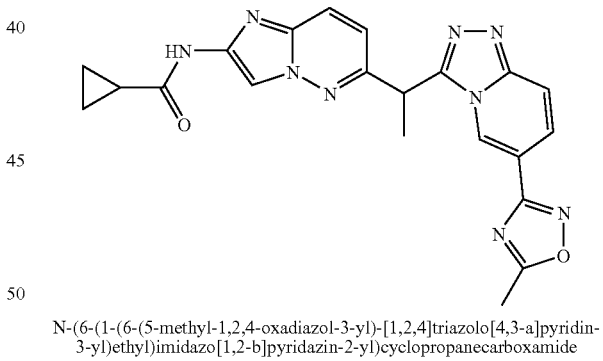

N-(6-(1-(6-(5-methyl-1,2,4-oxadiazol-3-yl)-[1,2,4]triazolo[4,3-a]pyridin-3-yl)ethyl)imidazo[1,2-b]pyridazin-2-yl)cyclopropanecarboxamide

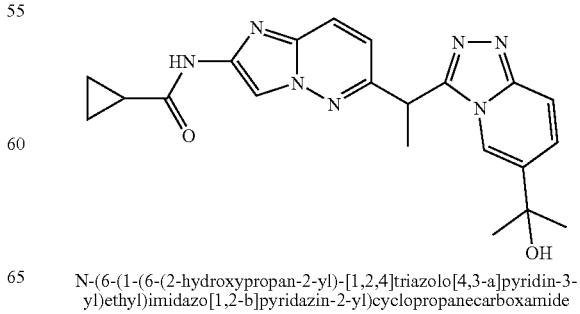

N-(6-(1-(6-(2-hydroxypropan-2-yl)-[1,2,4]triazolo[4,3-a]pyridin-3-yl)ethyl)imidazo[1,2-b]pyridazin-2-yl)cyclopropanecarboxamide

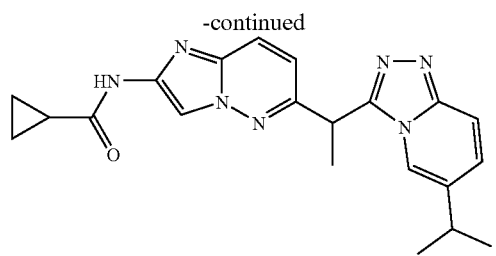

N-(6-(1-(6-isopropyl-[1,2,4]triazolo[4,3-a]pyridin-3-yl)ethyl)imidazo[1,2-b]pyridazin-2-yl)cyclopropanecarboxamide

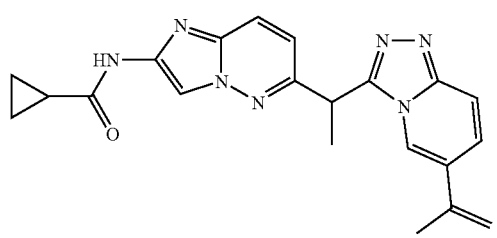

N-(6-(1-(6-(prop-1-en-2-yl)-[1,2,4]triazolo[4,3-a]pyridin-3-yl)ethyl)imidazo[1,2-b]pyridazin-2-yl)cyclopropanecarboxamide

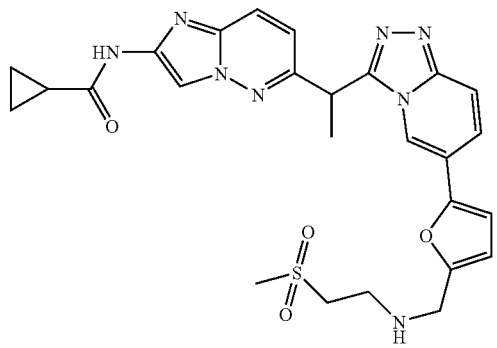

N-(6-(1-(6-(5-((2-(methylsulfonyl)ethylamino)methyl)furan-2-yl)-[1,2,4]triazolo[4,3-a]pyridin-3-yl)ethyl)imidazo[1,2-b]pyridazin-2-yl)cyclopropanecarboxamide

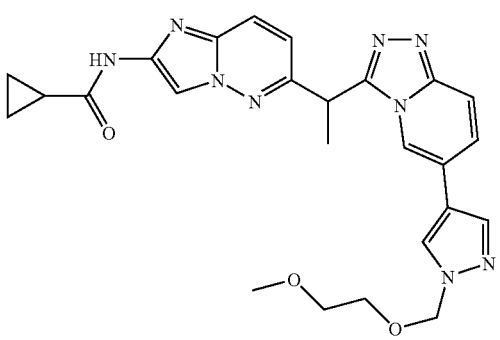

N-(6-(1-(6-(1-((2-(methoxyethoxy)methyl)-1H-pyrazol-4-yl)-[1,2,4]triazolo[4,3-a]pyridin-3-yl)ethyl)imidazo[1,2-b]pyridazin-2-yl)cyclopropanecarboxamide

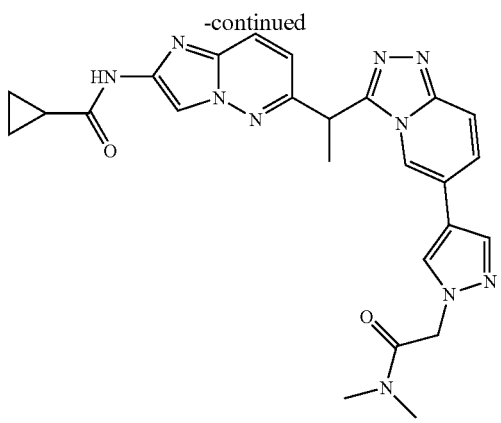

N-(6-(1-(6-(1-(2-(dimethylamino)-2-oxoethyl)-1H-pyrazol-4-yl)-[1,2,4]triazolo[4,3-a]pyridin-3-yl)ethyl)imidazo[1,2-b]pyridazin-2-yl)cyclopropanecarboxamide

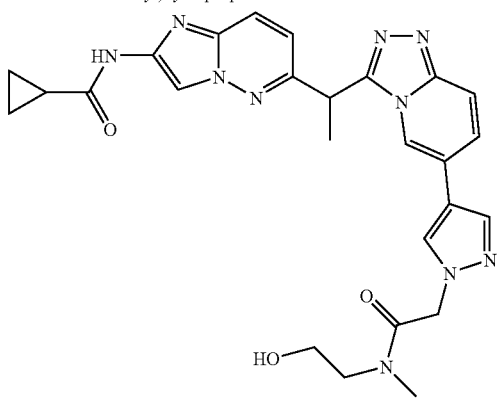

N-(6-(1-(6-(1-(2-((2-hydroxyethyl)(methyl)amino)-2-oxoethyl)-1H-pyrazol-4-yl)-[1,2,4]triazolo[4,3-a]pyridin-3-yl)ethyl)imidazo[1,2-b]pyridazin-2-yl)cyclopropanecarboxamide

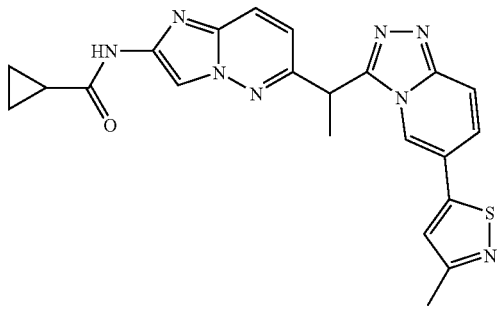

N-(6-(1-(6-(3-methylisothiazol-5-yl)-[1,2,4]triazolo[4,3-a]pyridin-3-yl)ethyl)imidazo[1,2-b]pyridazin-2-yl)cyclopropanecarboxamide

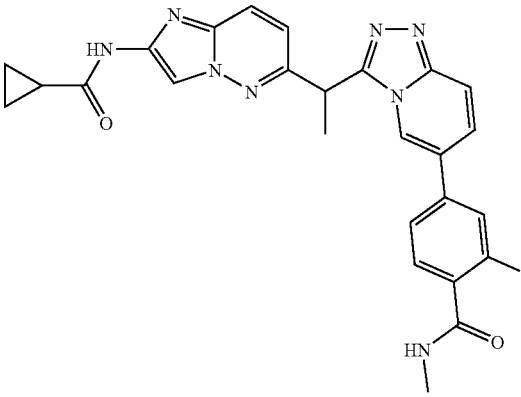

2-chloro-4-(3-(1-(2-(cyclopropanecarboxamido)imidazo[1,2-b]pyridazin-6-yl)ethyl)-[1,2,4]triazolo[4,3-a]pyridin-6-yl)-N-methylbenzamide

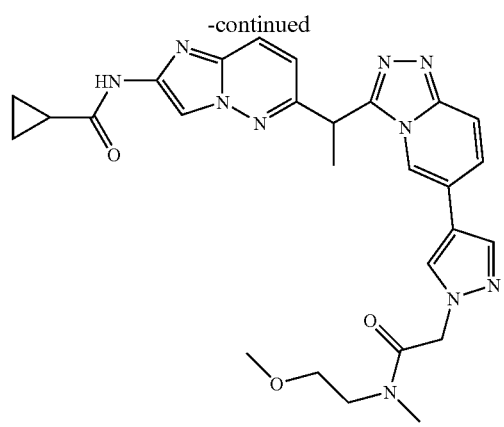

N-(6-(1-(6-(1-(2-((2-methoxyethyl)(methyl)amino)-2-oxoethyl)-1H-pyrazol-4-yl)-[1,2,4]triazolo[4,3-a]pyridin-3-yl)ethyl)imidazo[1,2-b]pyridazin-2-yl)cyclopropanecarboxamide

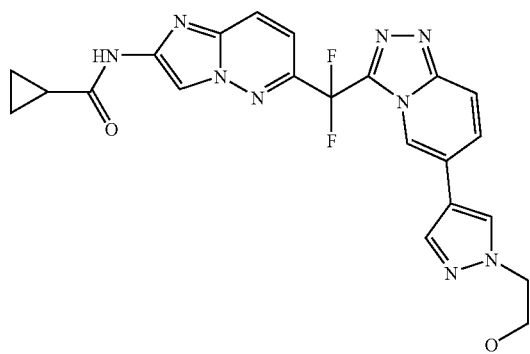

N-(6-(difluoro(6-(1-(2-methoxyethyl)-1H-pyrazol-4-yl)-[1,2,4]triazolo[4,3-a]pyridin-3-yl)methyl)imidazo[1,2-b]pyridazin-2-yl)cyclopropanecarboxamide

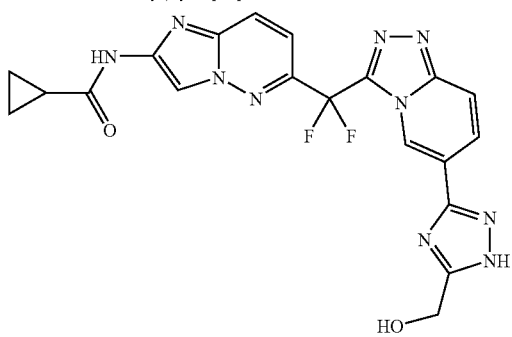

N-(6-(difluoro(6-(5-(hydroxymethyl)-1H-1,2,4-triazol-3-yl)-[1,2,4]triazolo[4,3-a]pyridin-3-yl)methyl)imidazo[1,2-b]pyridazin-2-yl)cyclopropanecarboxamide

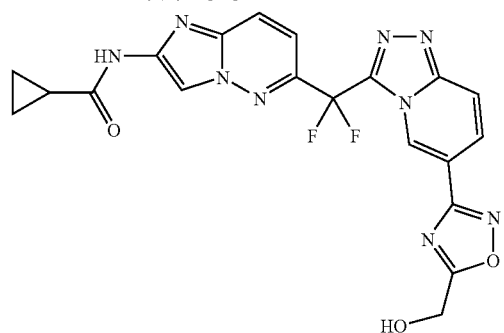

N-(6-(difluoro(6-(5-(hydroxymethyl)-1,2,4-oxadiazol-3-yl)-[1,2,4]triazolo[4,3-a]pyridin-3-yl)methyl)imidazo[1,2-b]pyridazin-2-yl)cyclopropanecarboxamide

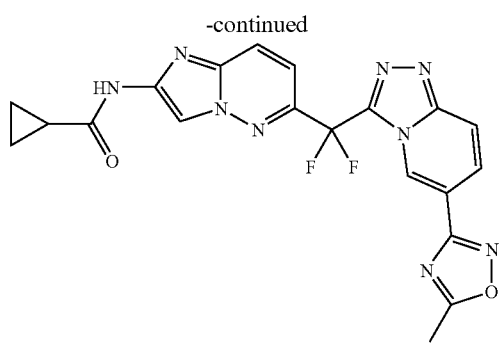

N-(6-(difluoro(6-(5-methyl-1,2,4-oxadiazol-3-yl)-[1,2,4]triazolo[4,3-a]pyridin-3-yl)methyl)imidazo[1,2-b]pyridazin-2-yl)cyclopropanecarboxamide

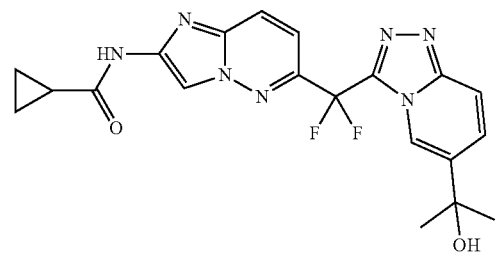

N-(6-(difluoro(6-(2-hydroxypropan-2-yl)-[1,2,4]triazolo[4,3-a]pyridin-3-yl)methyl)imidazo[1,2-b]pyridazin-2-yl)cyclopropanecarboxamide

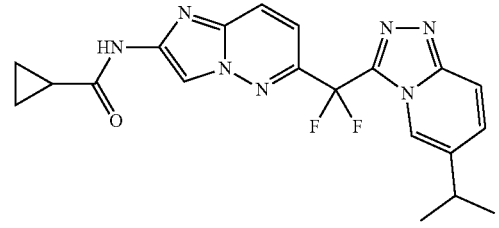

N-(6-(difluoro(6-isopropyl-[1,2,4]triazolo[4,3-a]pyridin-3-yl)methyl)imidazo[1,2-b]pyridazin-2-yl)cyclopropanecarboxamide

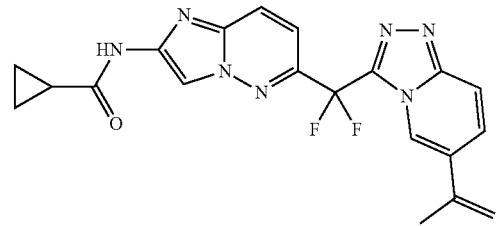

N-(6-(difluoro(6-(prop-1-en-2-yl)-[1,2,4]triazolo[4,3-a]pyridin-3-yl)methyl)imidazo[1,2-b]pyridazin-2-yl)cyclopropanecarboxamide

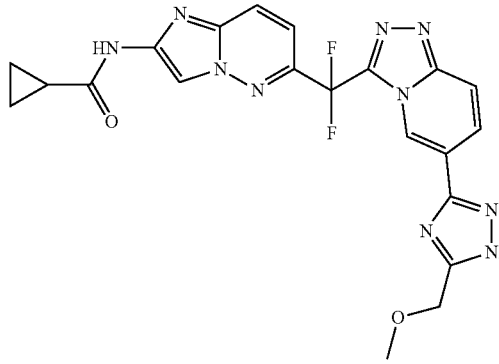

N-(6-(difluoro(6-(5-(methoxymethyl)-1H-1,2,4-triazol-3-yl)-[1,2,4]triazolo[4,3-a]pyridin-3-yl)methyl)imidazo[1,2-b]pyridazin-2-yl)cyclopropanecarboxamide

227

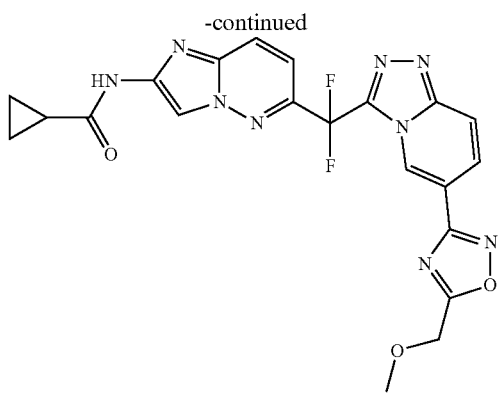

N-(6-(difluoro(6-(5-(methoxymethyl)-1,2,4-oxadiazol-3-yl)-
[1,2,4]triazolo[4,3-a]pyridin-3-yl)methyl)imidazo[1,2-b]pyridazin-2-
yl)cyclopropanecarboxamide

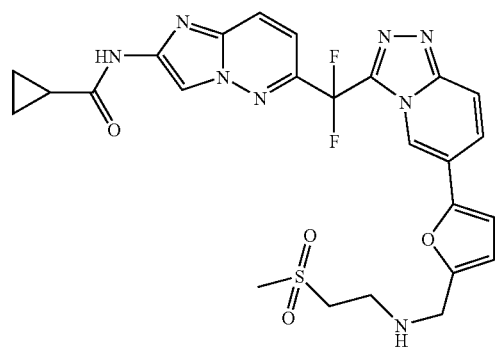

N-(6-(difluoro(6-(5-((2-(methylsulfonyl)ethylamino)methyl)furan-2-yl)-
[1,2,4]triazolo[4,3-a]pyridin-3-yl)methyl)imidazo[1,2-b]pyridazin-2-
yl)cyclopropanecarboxamide

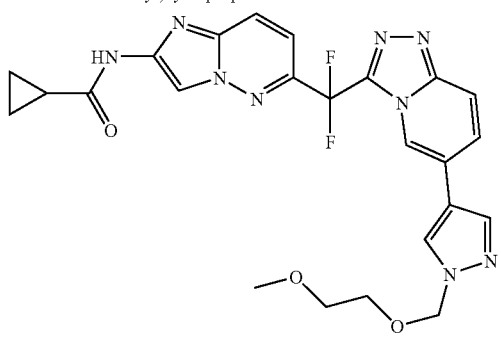

N-(6-(difluoro(6-(1-((2-methoxyethoxy)methyl)1H-pyrazol-4-yl)-
[1,2,4]triazolo[4,3-a]pyridin-3-yl)methyl)imidazo[1,2-b]pyridazin-2-
yl)cyclopropanecarboxamide

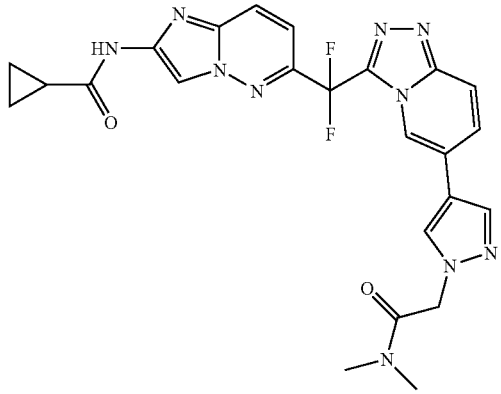

N-(6-((6-(1-(2-(dimethylamino)-2-oxoethyl)-1H-pyrazol-4-yl)-
[1,2,4]triazolo[4,3-a]pyridin-3-yl)difluoromethyl)imidazo[1,2-b]pyridazin-
2-yl)cyclopropanecarboxamide

228

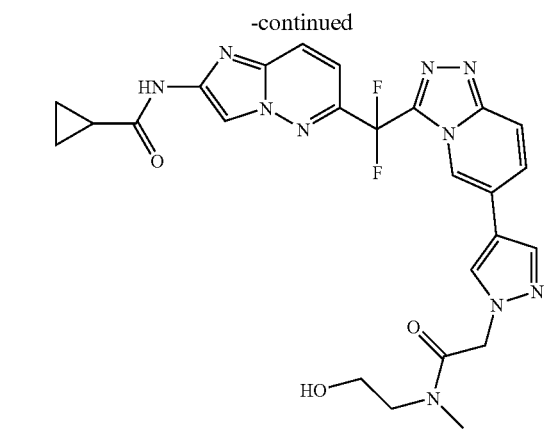

N-(6-(difluoro(6-(1-(2-((2-hydroxyethyl)(methyl)amino)-2-oxoethyl)-1H-
pyrazol-4-yl)-[1,2,4]triazolo[4,3-a]pyridin-3-yl)methyl)imidazo[1,2-
b]pyridazin-2-yl)cyclopropanecarboxamide

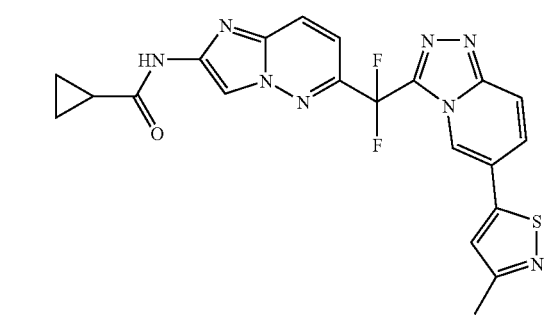

N-(6-(difluoro(6-(3-methylisothiazol-5-yl)-[1,2,4]triazolo[4,3-a]pyridin-3-
yl)methyl)imidazo[1,2-b]pyridazin-2-yl)cyclopropanecarboxamide

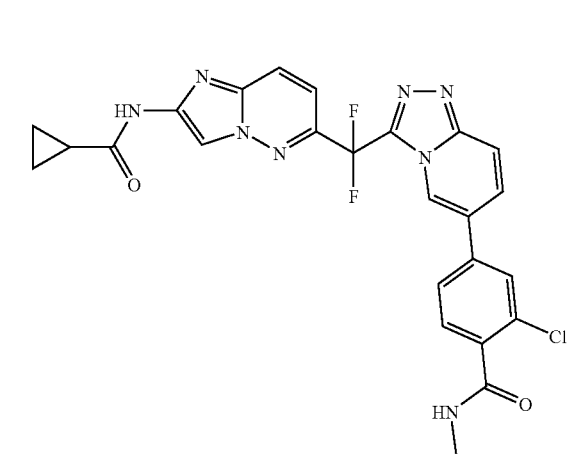

2-chloro-4-(3-((2-(cyclopropanecarboxamido)imidazo[1,2-b]pyridazin-6-
yl)difluoromethyl)-[1,2,4]triazolo[4,3-a]pyridin-6-yl)-N-methylbenzamide

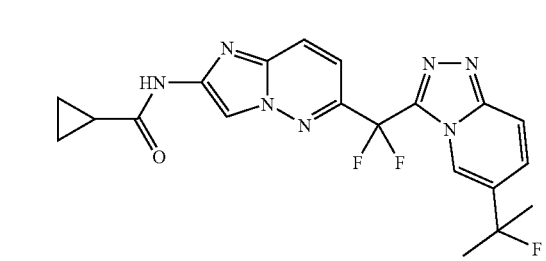

N-(6-(difluoro(6-(2-fluoropropan-2-yl)-[1,2,4]triazolo[4,3-a]pyridin-3-
yl)methyl)imidazo[1,2-b]pyridazin-2-yl)cyclopropanecarboxamide

229

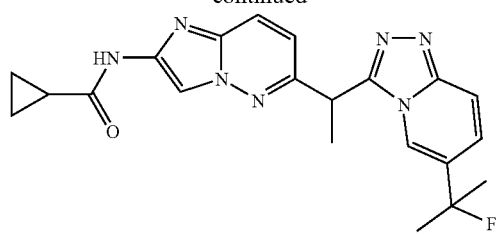

N-(6-(1-(6-(2-fluoropropan-2-yl)-[1,2,4]triazolo[4,3-a]pyridin-3-yl)ethyl)imidazo[1,2-b]pyridazin-2-yl)cyclopropanecarboxamide

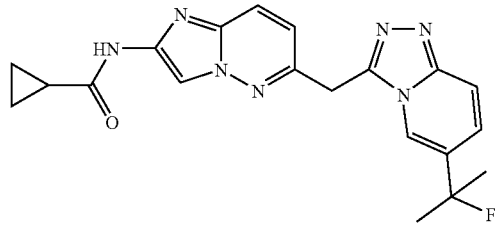

N-(6-((6-(2-fluoropropan-2-yl)-[1,2,4]triazolo[4,3-a]pyridin-3-yl)methyl)imidazo[1,2-b]pyridazin-2-yl)cyclopropanecarboxamide

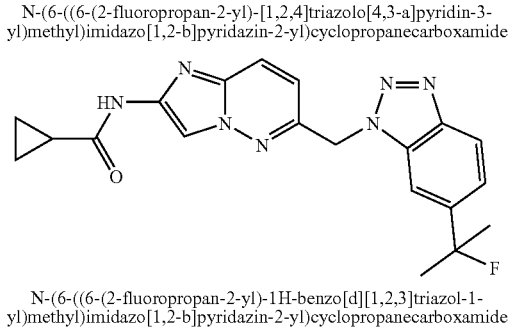

N-(6-((6-(2-fluoropropan-2-yl)-1H-benzo[d][1,2,3]triazol-1-yl)methyl)imidazo[1,2-b]pyridazin-2-yl)cyclopropanecarboxamide

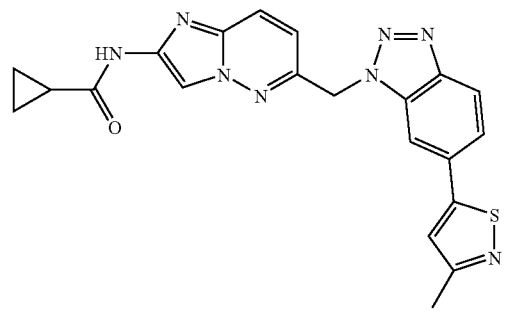

N-(6-((6-(3-methylisothiazol-5-yl)-1H-benzo[d][1,2,3]triazol-1-yl)methyl)imidazo[1,2-b]pyridazin-2-yl)cyclopropanecarboxamide

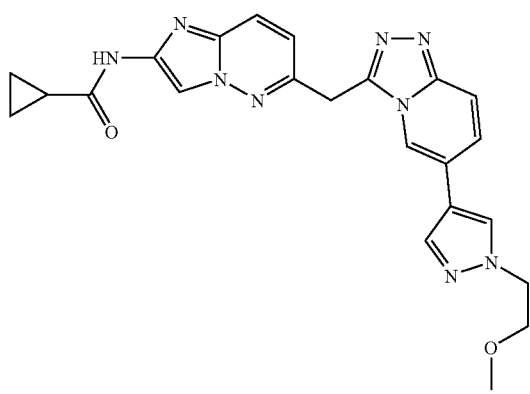

N-(6-((6-(1-(2-methoxyethyl-1H-pyrazol-4-yl)-[1,2,4]triazolo[4,3-a]pyridin-3-yl)methyl)imidazo[1,2-b]pyridazin-2-yl)cyclopropanecarboxamide

230

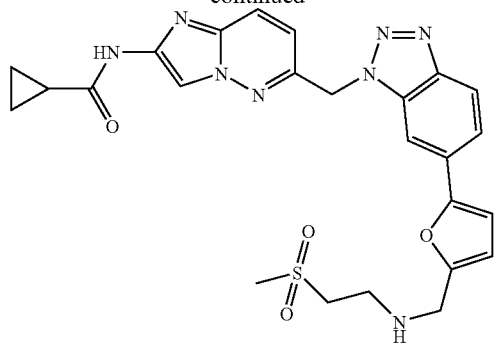

N-(6-((6-(5-((2-(methylsulfonyl)ethylamino)methyl)furan-2-yl)-1H-benzo[d][1,2,3]triazol-1-yl)methyl)imidazo[1,2-b]pyridazin-2-yl)cyclopropanecarboxamide

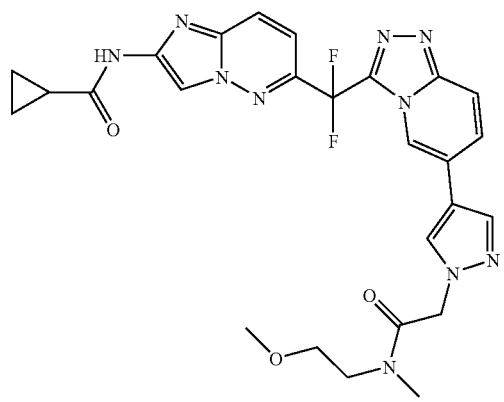

N-(6-(difluoro(6-(1-(2-((2-(methoxyethyl)(methyl)amino)-2-oxoethyl)-1H-pyrazol-4-yl)-[1,2,4]triazolo[4,3-a]pyridin-3-yl)methyl)imidazo[1,2-b]pyridazin-2-yl)cyclopropanecarboxamide

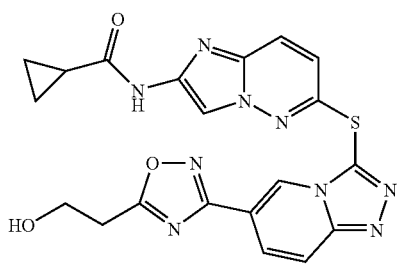

N-(6-(6-(5-(2-hydroxyethyl)-1,2,4-oxadiazol-3-yl)-[1,2,4]triazolo[4,3-a]pyridin-3-ylthio)imidazo[1,2-b]pyridazin-2-yl)cyclopropanecarboxamide

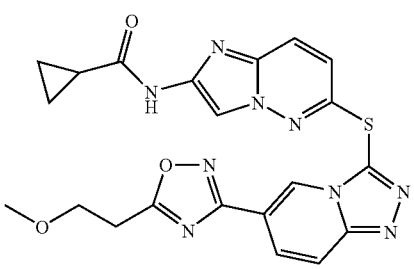

N-(6-(6-(5-(2-methoxyethyl)-1,2,4-oxadiazol-3-yl)-[1,2,4]triazolo[4,3-a]pyridin-3-ylthio)imidazo[1,2-b]pyridazin-2-yl)cyclopropanecarboxamide -continued

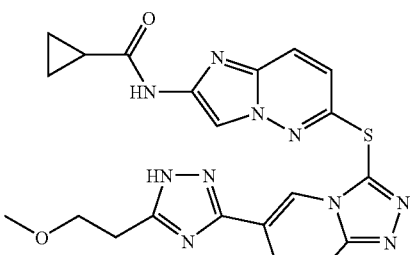

N-(6-(6-(5-(2-methoxyethyl)-1H-1,2,4-triazol-3-yl)-[1,2,4]triazolo[4,3-a]pyridin-3-ylthio)imidazo[1,2-b]pyridazin-2-yl)cyclopropanecarboxamide

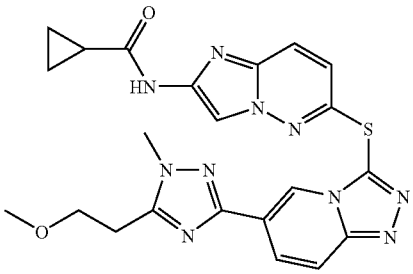

N-(6-(6-(5-(2-methoxyethyl)-1-methyl-1H-1,2,4-triazol-3-yl)-[1,2,4]triazolo[4,3-a]pyridin-3-ylthio)imidazo[1,2-b]pyridazin-2-yl)cyclopropanecarboxamide

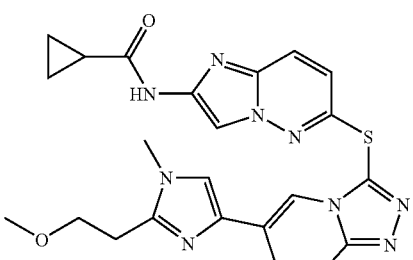

N-(6-(6-(2-(2-methoxyethyl)-1-methyl-1H-imidazol-4-yl)-[1,2,4]triazolo[4,3-a]pyridin-3-ylthio)imidazo[1,2-b]pyridazin-2-yl)cyclopropanecarboxamide

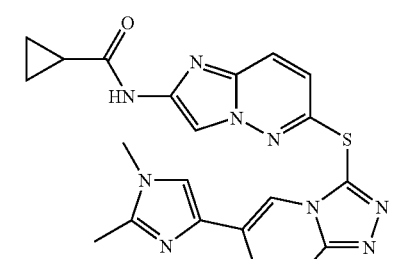

N-(6-(6-(1,2-dimethyl-1H-imidazol-4-yl)-[1,2,4]triazolo[4,3-a]pyridin-3-ylthio)imidazo[1,2-b]pyridazin-2-yl)cyclopropanecarboxamide

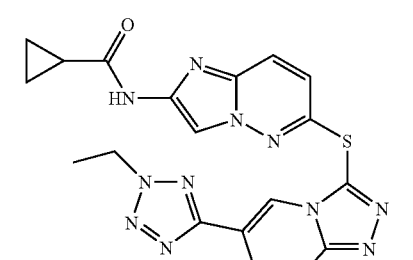

N-(6-(6-(2-ethyl-2H-tetrazol-5-yl)-[1,2,4]triazolo[4,3-a]pyridin-3-ylthio)imidazo[1,2-b]pyridazin-2-yl)cyclopropanecarboxamide -continued

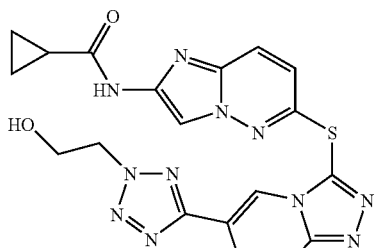

N-(6-(6-(2-(2-hydroxyethyl)-2H-tetrazol-5-yl)-[1,2,4]triazolo[4,3-a]pyridin-3-ylthio)imidazo[1,2-b]pyridazin-2-yl)cyclopropanecarboxamide

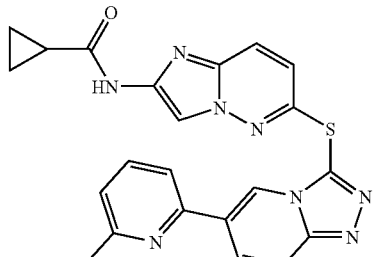

N-(6-(6-(6-hydroxypyridin-2-yl)-[1,2,4]triazolo[4,3-a]pyridin-3-ylthio)imidazo[1,2-b]pyridazin-2-yl)cyclopropanecarboxamide

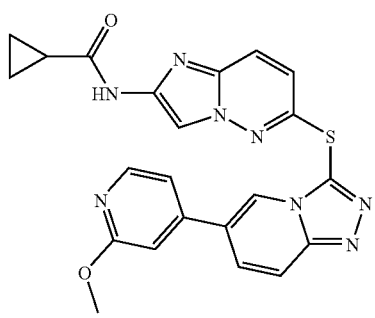

N-(6-(6-(2-methoxypyridin-4-yl)-[1,2,4]triazolo[4,3-a]pyridin-3-ylthio)imidazo[1,2-b]pyridazin-2-yl)cyclopropanecarboxamide

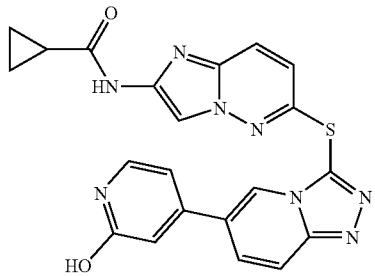

N-(6-(6-(2-hydroxypyridin-4-yl)-[1,2,4]triazolo[4,3-a]pyridin-3-ylthio)imidazo[1,2-b]pyridazin-2-yl)cyclopropanecarboxamide

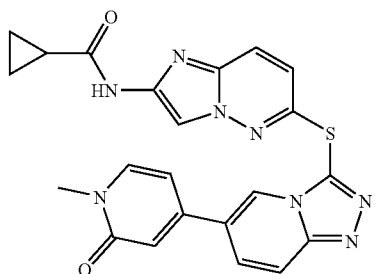

N-(6-(6-(1-methyl-2-oxo-1,2-dihydropyridin-4-yl)-[1,2,4]triazolo[4,3-a]pyridin-3-ylthio)imidazo[1,2-b]pyridazin-2-yl)cyclopropanecarboxamide

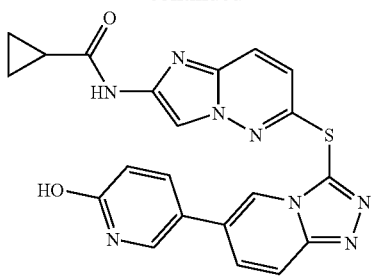

N-(6-(6-(6-hydroxypyridin-3-yl)-[1,2,4]triazolo[4,3-a]pyridin-3-ylthio)imidazo[1,2-b]pyridazin-2-yl)cyclopropanecarboxamide

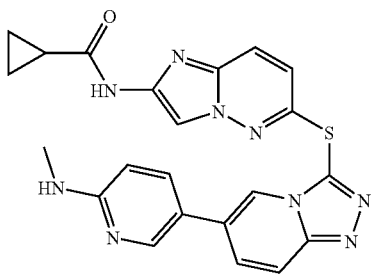

N-(6-(6-(6-methylamino)pyridin-3-yl)-[1,2,4]triazolo[4,3-a]pyridin-3-ylthio)imidazo[1,2-b]pyridazin-2-yl)cyclopropanecarboxamide

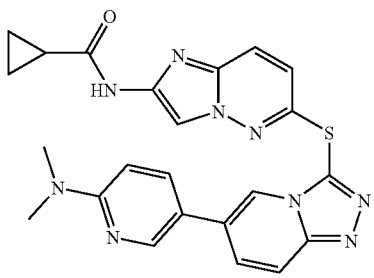

N-(6-(6-(6-(dimethylamino)pyridin-3-yl)-[1,2,4]triazolo[4,3-a]pyridin-3-ylthio)imidazo[1,2-b]pyridazin-2-yl)cyclopropanecarboxamide

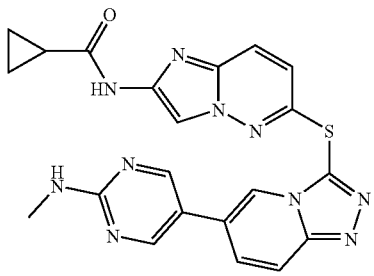

N-(6-(6-(2-(methylamino)pyrimidin-5-yl)-[1,2,4]triazolo[4,3-a]pyridin-3-ylthio)imidazo[1,2-b]pyridazin-2-yl)cyclopropanecarboxamide

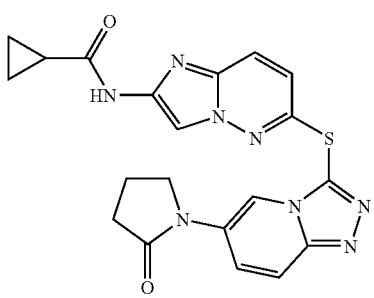

N-(6-(6-(2-oxopyrrolidin-1-yl)-[1,2,4]triazolo[4,3-a]pyridin-3-ylthio)imidazo[1,2-b]pyridazin-2-yl)cyclopropanecarboxamide

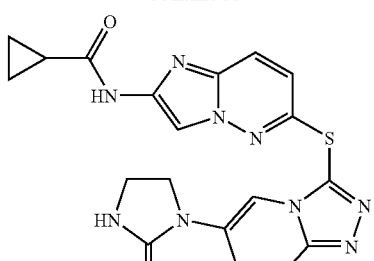

N-(6-(6-(2-oximidazolidin-1-yl)-[1,2,4]triazolo[4,3-a]pyridin-3-ylthio)imidazo[1,2-b]pyridazin-2-yl)cyclopropanecarboxamide

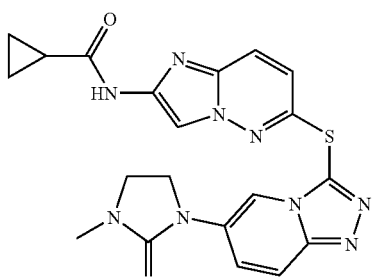

N-(6-(6-(3-methyl-2-oximidazolidin-1-yl)-[1,2,4]triazolo[4,3-a]pyridin-3-ylthio)imidazo[1,2-b]pyridazin-2-yl)cyclopropanecarboxamide

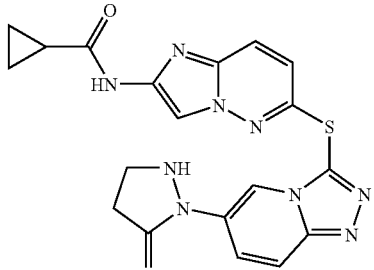

N-(6-(6-(5-oxopyrazolidin-1-yl)-[1,2,4]triazolo[4,3-a]pyridin-3-ylthio)imidazo[1,2-b]pyridazin-2-yl)cyclopropanecarboxamide

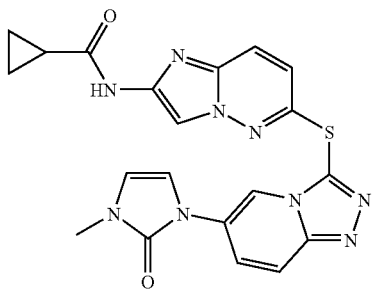

N-(6-(6-(3-methyl-2-oxo-2,3-dihydro-1H-imidazol-1-yl)-[1,2,4]triazolo[4,3-a]pyridin-3-ylthio)imidazo[1,2-b]pyridazin-2-yl)cyclopropanecarboxamide

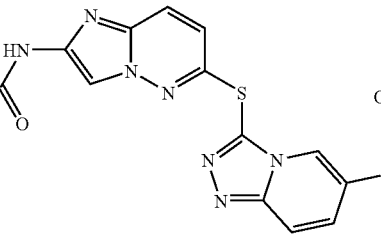

N-(6-(6-(2,5-dioxopyrrolidin-1-yl)-[1,2,4]triazolo[4,3-a]pyridin-3-ylthio)imidazo[1,2-b]pyridazin-2-yl)cyclopropanecarboxamide

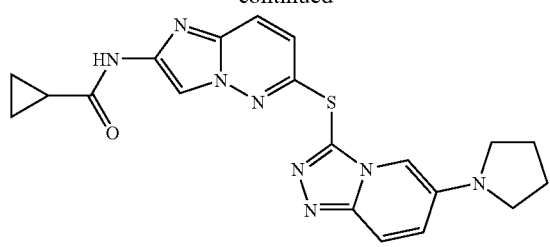

N-(6-(6-(pyrrolidin-1-yl)-[1,2,4]triazolo[4,3-a]pyridin-3-ylthio)imidazo[1,2-b]pyridazin-2-yl)cyclopropanecarboxamide

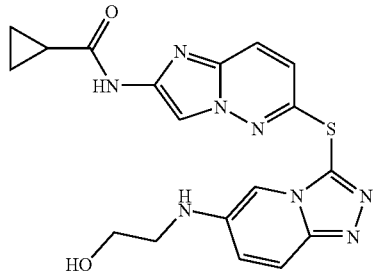

N-(6-(6-(2-hydroxyethylamino)-[1,2,4]triazolo[4,3-a]pyridin-3-ylthio)imidazo[1,2-b]pyridazin-2-yl)cyclopropanecarboxamide

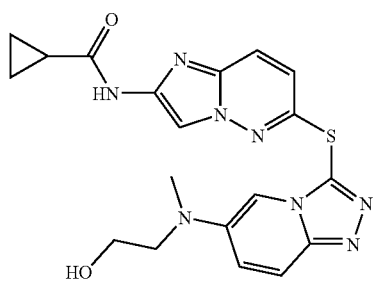

N-(6-(6-((2-hydroxyethyl)(methyl)amino)-[1,2,4]triazolo[4,3-a]pyridin-3-ylthio)imidazo[1,2-b]pyridazin-2-yl)cyclopropanecarboxamide

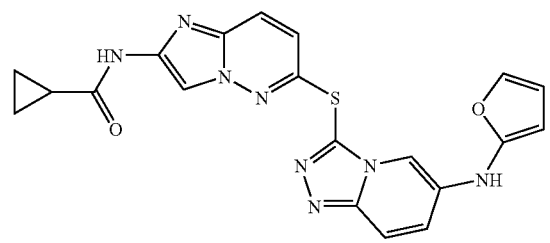

N-(6-(6-(furan-2-ylamino)-[1,2,4]triazolo[4,3-a]pyridin-3-ylthio)imidazo[1,2-b]pyridazin-2-yl)cyclopropanecarboxamide

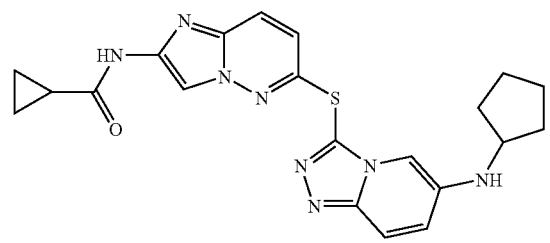

N-(6-(6-(cyclopentylamino)-[1,2,4]triazolo[4,3-a]pyridin-3-ylthio)imidazo[1,2-b]pyridazin-2-yl)cyclopropanecarboxamide

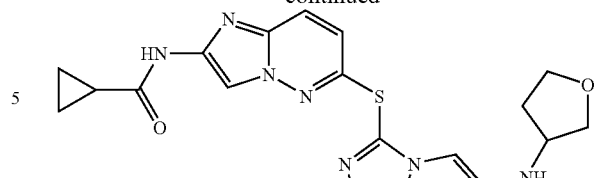

N-(6-(6-(tetrahydrofuran-3-ylamino)-[1,2,4]triazolo[4,3-a]pyridin-3-ylthio)imidazo[1,2-b]pyridazin-2-yl)cyclopropanecarboxamide

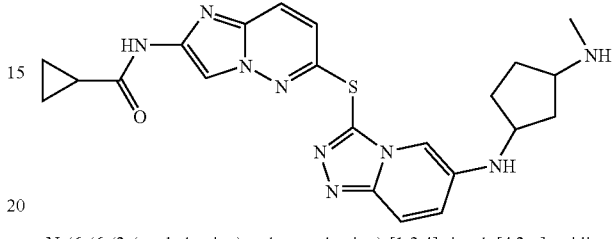

N-(6-(6-(3-(methylamino)cyclopentylamino)-[1,2,4]triazolo[4,3-a]pyridin-3-ylthio)imidazo[1,2-b]pyridazin-2-yl)cyclopropanecarboxamide

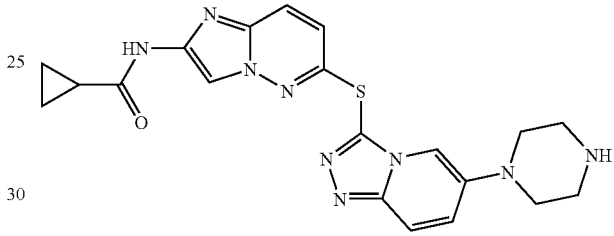

N-(6-(6-(piperazin-1-yl)-[1,2,4]triazolo[4,3-a]pyridin-3-ylthio)imidazo[1,2-b]pyridazin-2-yl)cyclopropanecarboxamide

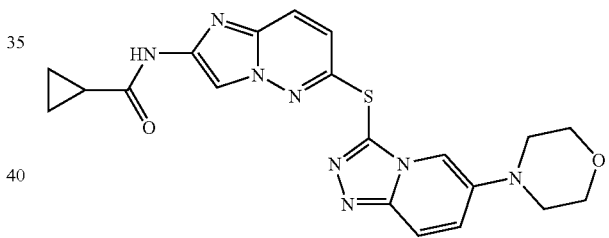

N-(6-(6-morpholino-[1,2,4]triazolo[4,3-a]pyridin-3-ylthio)imidazo[1,2-b]pyridazin-2-yl)cyclopropanecarboxamide

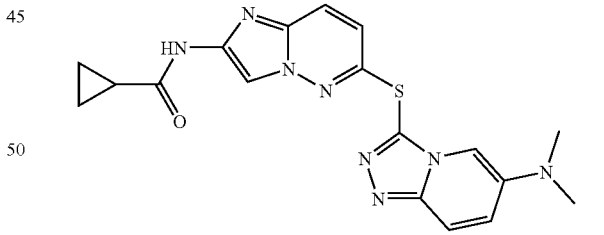

N-(6-(6-(dimethylamino)-[1,2,4]triazolo[4,3-a]pyridin-3-ylthio)imidazo[1,2-b]pyridazin-2-yl)cyclopropanecarboxamide

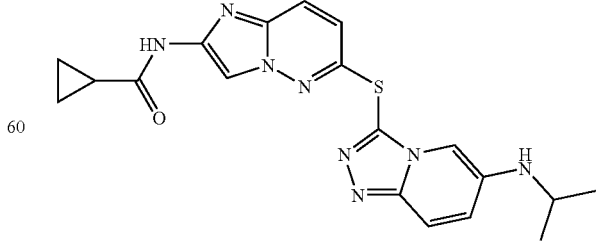

N-(6-(6-(isopropylamino)-[1,2,4]triazolo[4,3-a]pyridin-3-ylthio)imidazo[1,2-b]pyridazin-2-yl)cyclopropanecarboxamide -continued

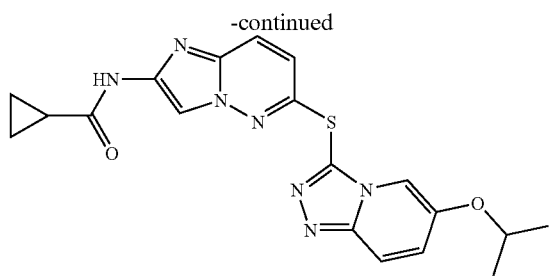

N-(6-(6-isopropoxy-[1,2,4]triazolo[4,3-a]pyridin-3-ylthio)imidazo[1,2-b]pyridazin-2-yl)cyclopropanecarboxamide

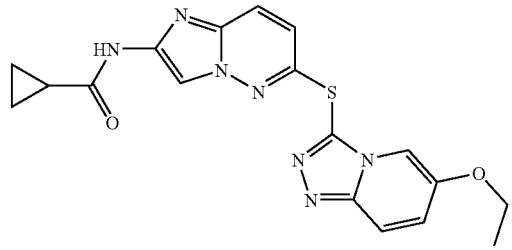

N-(6-(6-ethoxy-[1,2,4]triazolo[4,3-a]pyridin-3-ylthio)imidazo[1,2-b]pyridazin-2-yl)cyclopropanecarboxamide

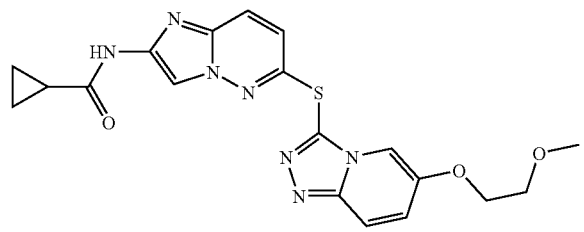

N-(6-(6-(2-methoxyethoxy)-[1,2,4]triazolo[4,3-a]pyridin-3-ylthio)imidazo[1,2-b]pyridazin-2-yl)cyclopropanecarboxamide

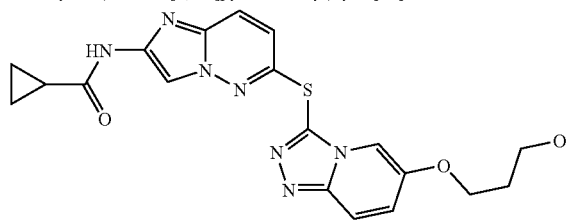

N-(6-(6-(3-hydroxypropoxy)-[1,2,4]triazolo[4,3-a]pyridin-3-ylthio)imidazo[1,2-b]pyridazin-2-yl)cyclopropanecarboxamide

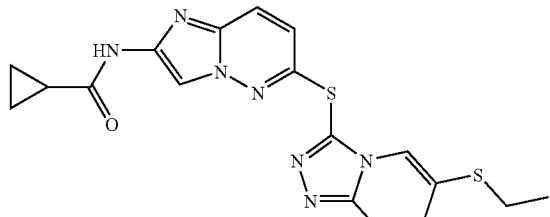

N-(6-(6-(ethylthio)-[1,2,4]triazolo[4,3-a]pyridin-3-ylthio)imidazo[1,2-b]pyridazin-2-yl)cyclopropanecarboxamide

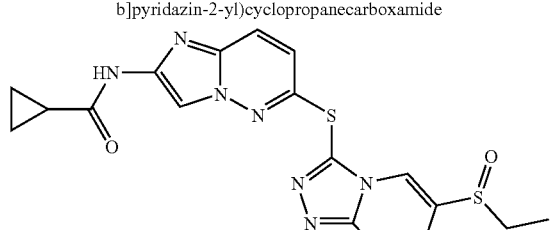

N-(6-(6-(ethylsulfinyl)-[1,2,4]triazolo[4,3-a]pyridin-3-ylthio)imidazo[1,2-b]pyridazin-2-yl)cyclopropanecarboxamide -continued

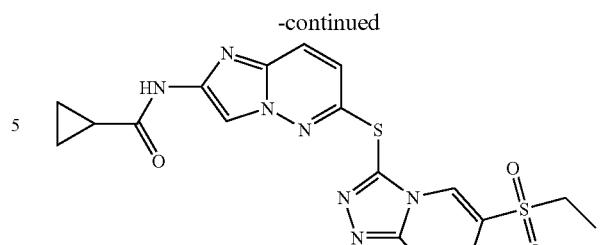

N-(6-(6-(ethylsulfonyl)-[1,2,4]triazolo[4,3-a]pyridin-3-ylthio)imidazo[1,2-b]pyridazin-2-yl)cyclopropanecarboxamide

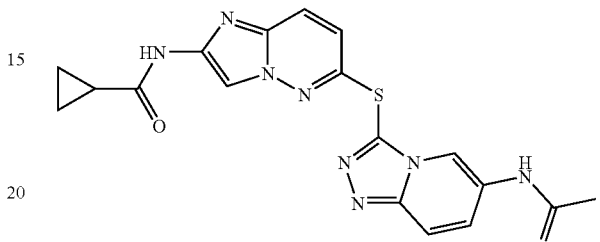

N-(6-(6-acetamido-[1,2,4]triazolo[4,3-a]pyridin-3-ylthio)imidazo[1,2-b]pyridazin-2-yl)cyclopropanecarboxamide

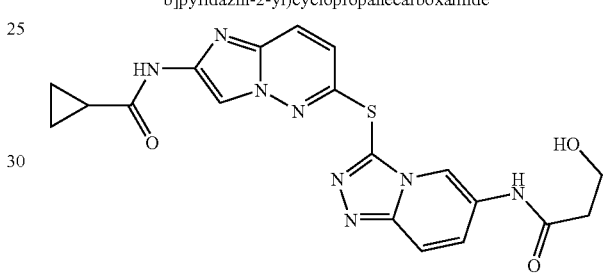

N-(6-(6-(3-hydroxypropanamido)-[1,2,4]triazolo[4,3-a]pyridin-3-ylthio)imidazo[1,2-b]pyridazin-2-yl)cyclopropanecarboxamide

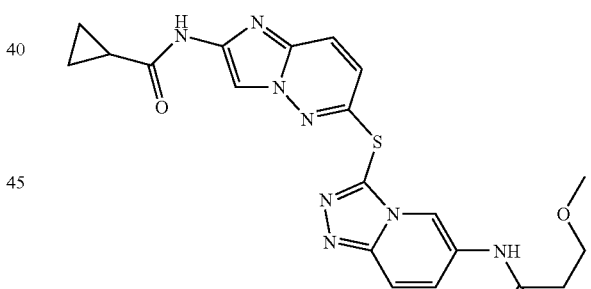

N-(6-(6-(3-methoxypropanamido)-[1,2,4]triazolo[4,3-a]pyridin-3-ylthio)imidazo[1,2-b]pyridazin-2-yl)cyclopropanecarboxamide

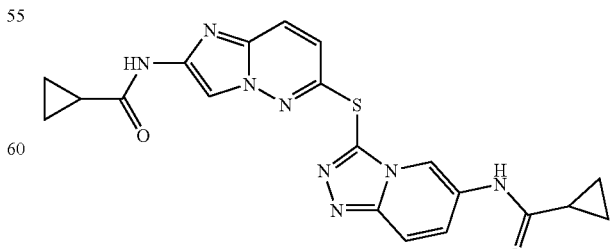

N-(6-(6-(cyclopropanecarboxamido)-[1,2,4]triazolo[4,3-a]pyridin-3-ylthio)imidazo[1,2-b]pyridazin-2-yl)cyclopropanecarboxamide -continued

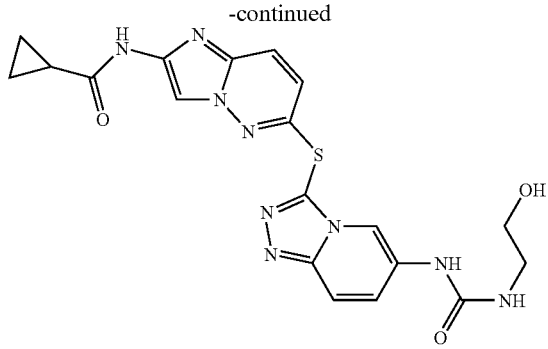

N-(6-(6-(3-(2-hydroxyethyl)ureido)-[1,2,4]triazolo[4,3-a]pyridin-3-ylthio)imidazo[1,2-b]pyridazin-2-yl)cyclopropanecarboxamide

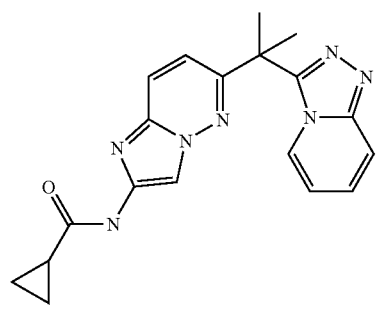

N-(6-(2-([1,2,4]triazolo[4,3-a]pyridin-3-yl)propan-2-yl)imidazo[1,2-b]pyridazin-2-yl)cyclopropanecarboxamide

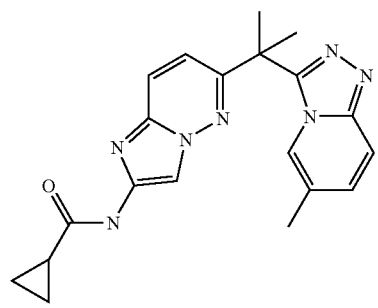

N-(6-(2-(6-methyl-[1,2,4]triazolo[4,3-a]pyridin-3-yl)propan-2-yl)imidazo[1,2-b]pyridazin-2-yl)cyclopropanecarboxamide

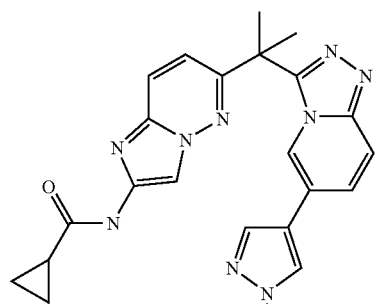

N-(6-(2-(6-(1-methyl-1H-pyrazol-4-yl)-[1,2,4]triazolo[4,3-a]pyridin-3-yl)propan-2-yl)imidazo[1,2-b]pyridazin-2-yl)cyclopropanecarboxamide -continued

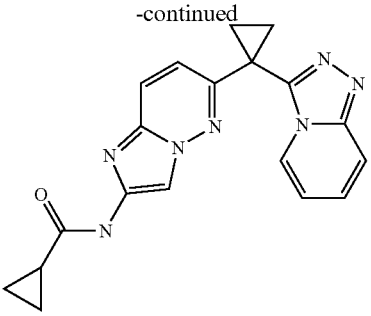

N-(6-(1-([1,2,4]triazolo[4,3-a]pyridin-3-yl)cyclopropyl)imidazo[1,2-b]pyridazin-2-yl)cyclopropanecarboxamide

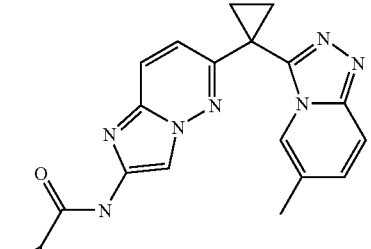

N-(6-(1-(6-methyl-[1,2,4]triazolo[4,3-a]pyridin-3-yl)cyclopropyl)imidazo[1,2-b]pyridazin-2-yl)cyclopropanecarboxamide

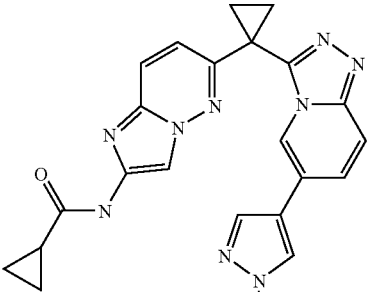

N-(6-(1-(6-(1-methyl-1H-pyrazol-4-yl)-[1,2,4]triazolo[4,3-a]pyridin-3-yl)cyclopropyl)imidazo[1,2-b]pyridazin-2-yl)cyclopropanecarboxamide Biological Testing The activity of compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

A. Determination of Inhibition of cMET

The inhibitory property of a compound relative to cMET catalysis was determined by use of capillary electrophoresis with fluorescence quantification of a phosphorylated peptide product for cMET. The cMET enzyme (amino acids 1023-1360) nominally at 24 μM was held at −80° C. until use, in a buffer containing 25 mM Tris-HCl pH 8.5, 150 mM NaCl, 3 mM DTT and 10% glycerol. Enzyme was prepared from Sf9 cells using nickel affinity chromatography of N-terminal histidine tagged cMET kinase domain. Following purification, the tag was removed and enzyme concentrated. The final enzyme was partially phosphorylated and partially catalytically active. To activate the enzyme fully, frozen cMET was thawed quickly and activated with the addition of assay buffer (50 mM HEPES pH 7.5, 10 mM NaCl, 10 mM $MgCl_2$, 0.01% Brij® 35), 1.25 mM ATP, 5 mM $MgCl_2$ and 5 mM DTT at a cMET concentration of 2.4 μM followed by a 30 minute incubation at room temperature. Solutions of test compounds in varying concentrations were prepared in DMSO and diluted to a final DMSO concentration of 2% into assay cocktail containing assay buffer, 0.5 mM EDTA, and 2 μM of the peptide substrate FL-2 (5-FAM-EAIYAAPFAKKK-CONH2 where 5-FAM=5-carboxyfluorescein). Next, cMET enzyme (1.2 nM final) was added and the system incubated at room temperature for 20 minutes. Catalysis was initiated by the addition of ATP (50 μM final). Assays were incubated at room temperature for 2 hours then quenched by the addition of EDTA. Phosphorylated peptide product was quantified by monitoring fluorescence during capillary electrophoresis with Caliper LifeSciences LabChip 3000 under the following settings: base pressure=−0.1 psi, screen pressure=−1.2 psi, downstream voltage=−500 V, upstream voltage=−2300 V, chip type=TC372. The elution buffer was identical to the assay buffer except for the absence of DTT, FL-2 and ATP and the addition of 0.1% coating reagent (Caliper). Under these conditions, phosphorylated product eluted at 37 seconds and the unphosphorylated substrate eluted at 45 seconds. Peak height was quantified and used to determine enzyme velocities.

$IC_{50}$ values were calculated by non-linear least squares curve fitting of the standard $IC_{50}$ equation to background-corrected cMET velocity versus compound concentration. As a reference point for this assay, staurosporin displayed an $IC_{50}$ of ~150 nM. $IC_{50}$ values for select compounds of the invention against cMET are given in Table 1.

B. Determination of Inhibition of Cell Viability

Cells were maintained at 37° C. in a humidified atmosphere containing 5%-8% $CO_2$ following the instructions of the supplier (American Type Culture Collection (Rockville, Md.)). Inhibition of cell viability was determined for a panel of tumor cell lines (MKN45, EBC1 and A549), using the soluble tetrazolium salt, MTS (Promega, Madison, Wis.). Cells were seeded at 2,000-7,500 cells/well in 96-well tissue culture plates and were allowed to attach for approximately 24 hours prior to addition of compounds or DMSO vehicle. After 96 hours of incubation with test compounds, MTS conversion by metabolically active cells was determined by measuring the OD490 nm with a Spectamax microplate reader (Molecular Devices, San Diego, Calif.). Cells were treated in duplicate with test compounds. Compounds were serially diluted (1:2.5) from column 1 to 11 and column 12 contained DMSO vehicle. Compounds were diluted into cell growth medium then compound solution was added to cells. Equal amounts of DMSO were added to cells (final concentration is 0.5%). After background correction and normalization against DMSO-treated cells, $EC_{50}$ values were calculated using non-linear curve-fitting of the cell viability as a function of compound concentration. The MKN45 and EBC1 cell lines contain high levels of phospho-Met and are dependent on cMET for proliferation, whereas the A549 line is used as negative control.

$EC_{50}$ values may be calculated by non-linear curve fitting of the compound concentrations and fluorescence intensities to the standard $EC_{50}$ equation. $EC_{50}$ values for select compounds of the invention against MKN45, EBC1 and A549 are given in Table 1.

TABLE 1

| Compound | cMet $IC_{50}$, nm | MKN45 $EC_{50}$, nm | EBC1 $EC_{50}$, nm | A549 $EC_{50}$, nm |
|---|---|---|---|---|
| 1 | >100 | — | — | — |
| 2 | >100 | — | — | — |
| 3 (HCl Salt) | >100 | 250-630 | 100-199 | 8000-25000 |
| 3 (TFA Salt) | >100 | 250-630 | 100-199 | 8000-25000 |
| 3 (free base) | >100 | 100-199 | 60-100 | 8000-25000 |
| 4 | 30-59 | 100-249 | <35 | >50000 |
| 5 | <30 | <100 | <35 | >50000 |
| 6 | >100 | >630 | >200 | >50000 |
| 9 | 60-100 | 250-630 | 100-199 | 8000-25000 |
| 12 | >100 | >630 | >200 | >50000 |
| 13 (HCl Salt) | 30-59 | 100-249 | <35 | 8000-25000 |
| 13 (TFA Salt) | 30-59 | 60-100 | <30 | 5000-8000 |
| 13 (free base) | 30-59 | <30 | <30 | >50000 |
| 14 | 30-59 | 250-630 | 100-199 | 600-1600 |
| 15 | 60-100 | 250-630 | 100-199 | 8000-25000 |
| 16 | >100 | >630 | >200 | >50000 |
| 17 | 60-100 | <100 | <35 | >19500 |
| 18 | 30-59 | 100-249 | 100-199 | >19500 |
| 19 | 60-100 | 250-630 | 100-199 | >19500 |
| 20 | 60-100 | 250-630 | >200 | >50000 |
| 21 | >100 | >630 | >200 | >50000 |
| 22 | 60-100 | >630 | >200 | >50000 |
| 23 | 30-59 | 250-630 | 100-199 | >50000 |
| 24 | 60-100 | 100-249 | 35-99 | >50000 |
| 25 | <30 | <100 | <35 | 8000-25000 |
| 26 | <30 | <100 | <35 | >19500 |
| 27 | <30 | <100 | 35-99 | >50000 |
| 28 | <30 | <100 | <35 | >50000 |
| 29 | 60-100 | <100 | 35-99 | >50000 |
| 30 | 30-59 | >630 | >200 | >19500 |
| 31 | 30-59 | <100 | <35 | >50000 |
| 32 | <30 | 100-249 | 35-99 | >50000 |
| 33 | >100 | >630 | >200 | >50000 |
| 34 | 60-100 | >630 | >200 | >50000 |
| 35 | >100 | >630 | 100-199 | >19500 |
| 36 | <30 | 250-630 | 35-99 | >50000 |
| 37 | 30-59 | 250-630 | 100-199 | >50000 |
| 38 | >100 | >630 | >200 | >50000 |
| 39 | 60-100 | 100-249 | 35-99 | 600-1600 |
| 40 | >100 | >630 | >200 | >50000 |
| 41 | 60-100 | 100-249 | 35-99 | 8000-25000 |
| 42 | 60-100 | 100-249 | 35-99 | >50000 |
| 43 | >100 | — | — | — |
| 44 | <30 | <100 | <35 | 600-1600 |
| 45 (HCl Salt) | <30 | <30 | <30 | >50000 |
| 45 (TFA Salt) | 30-59 | — | — | — |
| 46 | 30-59 | 60-100 | 60-100 | >50000 |
| 47 | <30 | <30 | <30 | >50000 |
| 49 (HCl Salt) | <30 | 30-59 | <30 | 8000-25000 |
| 49 (TFA Salt) | 30-59 | 60-100 | 60-100 | >50000 |
| 49 (free base) | <30 | 60-100 | <30 | >50000 |
| 50 | <30 | 30-59 | <30 | >50000 |
| 51 | >100 | >100 | >100 | >50000 |
| 52 | >100 | >100 | >100 | >50000 |
| 53 | 250-630 | 250-630 | 250-630 | >50000 |
| 55 | <30 | <30 | <30 | >50000 |
| 56 | <30 | <30 | <30 | >50000 |
| 57 | <30 | <30 | <30 | >50000 |
| 58 | <30 | <30 | <30 | >50000 |
| 59 | <30 | 100-249 | 60-100 | >50000 |
| 60 | <30 | 60-100 | 60-100 | >50000 |
| 61 | <30 | <30 | <30 | >50000 |
| 62 | <30 | <30 | <30 | 5000-8000 |
| 63 | <30 | <30 | <30 | >50000 |
| 64 | <30 | 100-249 | 100-249 | >50000 |
| 65 | <30 | <30 | <30 | >50000 |
| 66 | <30 | 100-249 | 100-249 | >50000 |
| 67 | <30 | 100-249 | 60-100 | >50000 |
| 68 | <30 | 30-59 | 30-59 | >50000 |
| 69 | <30 | <30 | <30 | >50000 |
| 70 | <30 | <30 | <30 | >50000 |
| 71 | <30 | <30 | <30 | >50000 |
| 72 | <30 | <30 | <30 | >50000 |
| 73 | <30 | <30 | <30 | 8000-25000 |
| 74 | <30 | <30 | <30 | 8000-25000 |
| 75 | <30 | <30 | <30 | 8000-25000 |
| 76 | <30 | <30 | <30 | >50000 |

TABLE 1-continued

| Compound | cMet IC$_{50}$, nm | MKN45 EC$_{50}$, nm | EBC1 EC$_{50}$, nm | A549 EC$_{50}$, nm |
|---|---|---|---|---|
| 77 | <30 | <30 | <30 | >50000 |
| 78 | 30-59 | <30 | <30 | >50000 |
| 79 | 60-100 | <30 | <30 | >50000 |
| 80 | 30-59 | <30 | 30-59 | >50000 |
| 81 | <30 | <30 | <30 | >50000 |
| 82 | <30 | <30 | <30 | >50000 |
| 83 | <30 | <30 | <30 | >50000 |
| 84 | <30 | <30 | <30 | >50000 |
| 85 | <30 | <30 | <30 | >50000 |
| 86 | 30-59 | <30 | <30 | >50000 |
| 87 | 100-249 | 30-59 | 30-59 | >50000 |
| 88 | <30 | <30 | <30 | >50000 |
| 89 | <30 | — | — | — |
| 90 | <30 | <30 | <30 | >50000 |
| 91 | <30 | <30 | <30 | >50000 |
| 92 | <30 | <30 | <30 | >50000 |
| 93 | 60-100 | 30-59 | 30-59 | 8000-25000 |
| 94 | 250-630 | — | — | — |
| 95 | <30 | — | — | — |
| 96 | <30 | <30 | <30 | 8000-25000 |
| 97 | <30 | <30 | <30 | >50000 |
| 98 | <30 | <30 | <30 | >50000 |
| 99 | 250-630 | 100-249 | 100-249 | >50000 |
| 101 | <30 | 100-249 | 30-59 | >50000 |
| 102 | 30-59 | 60-100 | 30-59 | >50000 |
| 103 | <30 | 30-59 | <30 | >50000 |
| 104 | <30 | <30 | <30 | >50000 |
| 105 | <30 | 250-630 | 100-249 | >50000 |
| 106 | <30 | 60-100 | 30-59 | >50000 |
| 107 | <30 | 100-249 | 60-10 | >50000 |
| 108 | 30-59 | 8000-25000 | 8000-25000 | >50000 |
| 109 | 250-630 | 8000-25000 | 8000-25000 | 8000-25000 |
| 110 | 30-59 | 100-249 | 30-59 | >50000 |
| 111 | <30 | 100-249 | 30-59 | 8000-25000 |
| 112 | 100-249 | — | — | — |
| 113 | 250-630 | — | — | — |
| 114 | >630 | >630 | >630 | >50000 |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound having the formula:

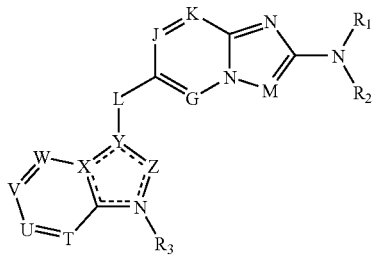

or a pharmaceutically acceptable salt thereof, wherein
G is selected from the group consisting of CR$_4$ and N;
J is selected from the group consisting of CR$_5$ and N;
K is selected from the group consisting of CR$_6$ and N;
M is selected from the group consisting of CR$_7$ and N;
L is absent or a linker providing 1,2,3,4,5 or 6 atom separation between the rings to which L is attached, wherein the atoms of the linker providing the separation are selected from the group consisting of carbon, oxygen, nitrogen, and sulfur;
T is selected from the group consisting of CR$_8$ and N;
U is selected from the group consisting of CR$_9$ and N;
V is selected from the group consisting of CR$_{10}$ and N;
W is selected from the group consisting of CR$_{11}$ and N;
X is selected from the group consisting of CR$_{12}$ and N;
Y is selected from the group consisting of CR$_{13}$ and N;
Z is selected from the group consisting of CR$_{14}$R$_{15}$ and NR$_{16}$;
R$_1$ is selected from the group consisting of hydrogen, (C$_{1-10}$)alkoxy, (C$_{4-12}$)aryloxy, hetero(C$_{1-10}$)aryloxy, aminocarbonyl, (C$_{1-10}$)alkylcarbonyl, (C$_{3-12}$)cycloalkyl (C$_{1-5}$)carbonyl, hetero(C$_{3-12}$)cycloalkyl(C$_{1-10}$)carbonyl, aryl(C$_{1-10}$)carbonyl, hetero(C$_{1-10}$)aryl(C$_{1-5}$)carbonyl, (C$_{9-12}$)bicycloaryl(C$_{1-5}$)carbonyl, hetero(C$_{8-12}$)bicycloaryl(C$_{1-5}$)carbonyl, amino, (C$_{1-10}$)alkylamino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted, or R$_1$ has the formula

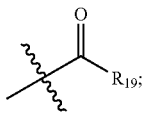

R$_2$ is hydrogen or a substituent convertible in vivo to hydrogen;
R$_3$ is selected from the group consisting of hydrogen, (C$_{1-10}$)alkoxy, (C$_{4-12}$)aryloxy, hetero(C$_{1-10}$)aryloxy, aminocarbonyl, amino, (C$_{1-10}$)alkylamino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted, or R$_3$ is absent when the nitrogen to which it is bound forms part of a double bond;
R$_4$ is selected from the group consisting of hydrogen, halo, nitro, cyano, hydroxy, (C$_{1-10}$)alkoxy, (C$_{4-12}$)aryloxy, hetero(C$_{1-10}$)aryloxy, aminocarbonyl, amino, (C$_{1-10}$)alkylamino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted;
R$_5$ is selected from the group consisting of hydrogen, halo, nitro, cyano, hydroxy, (C$_{1-10}$)alkoxy, (C$_{4-12}$)aryloxy, hetero(C$_{1-10}$)aryloxy, aminocarbonyl, amino, (C$_{1-10}$)

alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_6$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicyoloaryl, each substituted or unsubstituted;

$R_7$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicyoloaryl, each substituted or unsubstituted;

$R_8$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicyoloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_9$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, amido, $(C_{1-10})$alkyl, halo$(C_{1-10})$alkyl, hydroxy$(C_{1-10})$alkyl, amino$(C_{1-10})$alkyl, amido$(C_{1-10})$alkylamino$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_{10}$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, amido, $(C_{1-10})$alkyl, halo$(C_{1-10})$alkyl, hydroxy$(C_{1-10})$alkyl, amino$(C_{1-10})$alkyl, amido$(C_{1-10})$alkylamino$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_{11}$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicyoloaryl, each substituted or unsubstituted;

$R_{12}$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicyoloaryl, each substituted or unsubstituted, or $R_{12}$ is absent when the carbon to which it is bound forms part of a double bond;

$R_{13}$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicyoloaryl, each substituted or unsubstituted, or $R_{13}$ is absent when the carbon to which it is bound forms part of a double bond;

$R_{14}$ and $R_{15}$ are each independently selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted, or $R_{15}$ is absent when the carbon to which it is bound forms part of a double bond;

$R_{16}$ is selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero ($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted, or $R_{16}$ is absent when the nitrogen to which it is bound forms part of a double bond; and $R_{19}$ selected from the group consisting of hydrogen, hydroxy, ($C_{1-10}$)alkoxy, ($C_{4-12}$)aryloxy, hetero($C_{1-10}$)aryloxy, aminocarbonyl, amino, ($C_{1-10}$)alkylamino, ($C_{1-10}$)alkyl, halo($C_{1-10}$)alkyl, hydroxy($C_{1-10}$)alkyl, aza($C_{1-10}$)alkyl, ($C_{1-10}$)oxaalkyl, ($C_{1-10}$)oxoalkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

2. The compound according to claim 1 having the formula:

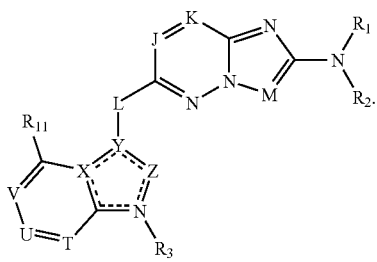

3. The compound according to claim 1 having the formula:

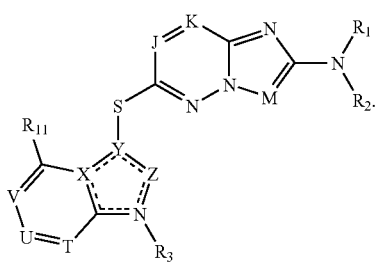

4. The compound according to claim 1 having the formula:

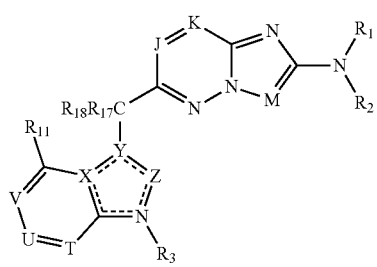

wherein $R_{17}$ and $R_{18}$ are each independently elected from the group consisting of hydrogen, halo, nitro, cyano, hydroxy, ($C_{1-10}$)alkoxy, ($C_{4-12}$)aryloxy, hetero($C_{1-10}$)aryloxy, aminocarbonyl, amino, ($C_{1-10}$)alkylamino, ($C_{1-10}$)alkyl, halo($C_{1-10}$)alkyl, hydroxy($C_{1-10}$)alkyl, aza($C_{1-10}$)alkyl, ($C_{1-10}$)oxaalkyl, ($C_{1-10}$)oxoalkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

5. The compound according to claim 4, wherein $R_{17}$ is selected from the group consisting of hydrogen, halo and a substituted or unsubstituted ($C_{1-3}$)alkyl.

6. The compound according to claim 4, wherein $R_{18}$ is hydrogen.

7. The compound according to claim 1 having the formula:

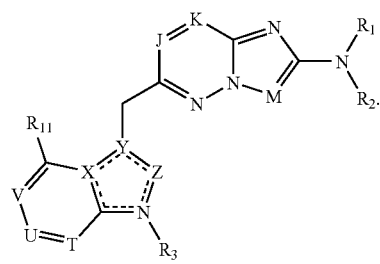

8. The compound according to claim 1 having the formula:

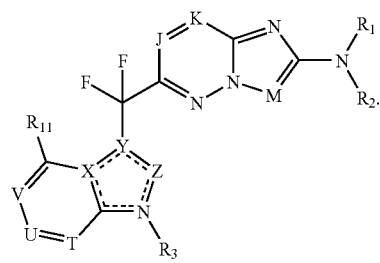

9. The compound according to claim 1 having the formula:

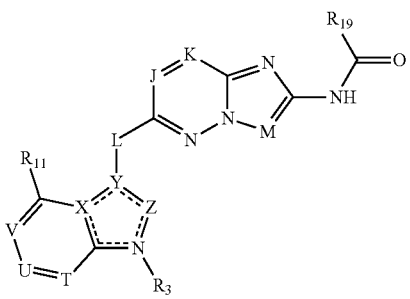

wherein $R_{19}$ selected from the group consisting of hydrogen, hydroxy, ($C_{1-10}$)alkoxy, ($C_{4-12}$)aryloxy, hetero($C_{1-10}$)aryloxy, aminocarbonyl, amino, ($C_{1-10}$)alkylamino, ($C_{1-10}$)alkyl, halo($C_{1-10}$)alkyl, hydroxy($C_{1-10}$)alkyl, aza($C_{1-10}$)alkyl, ($C_{1-10}$)oxaalkyl, ($C_{1-10}$)oxoalkyl, ($C_{3-12}$)cycloalkyl($C_{1-5}$)alkyl, hetero($C_{3-12}$)cycloalkyl (C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

10. The compound according to claim 1 having the formula:

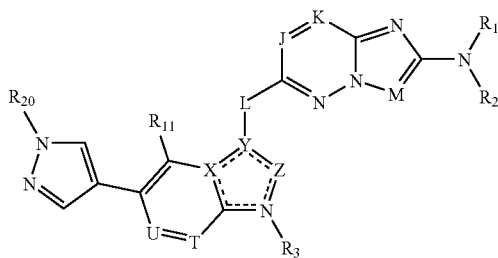

wherein R$_{20}$ selected from the group consisting of hydrogen, halo, nitro, cyano, hydroxy, (C$_{1-10}$)alkoxy, (C$_{4-12}$)aryloxy, hetero(C$_{1-10}$)aryloxy, aminocarbonyl, amino, (C$_{1-10}$)alkylamino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

11. The compound according to claim 10, wherein R$_{20}$ is selected from the group consisting of hydrogen, halo, a substituted or unsubstituted (C$_{1-5}$)alkyl, a substituted or unsubstituted aryl, a substituted or unsubstituted (C$_{3-12}$)cycloalkyl, a substituted or unsubstituted hetero(C$_{4-10}$)aryl, a substituted or unsubstituted hydroxy(C$_{1-6}$)alkyl and a substituted or unsubstituted hetero(C$_{3-6}$)cycloalkyl(C$_{1-4}$)alkyl.

12. The compound according to claim 10, wherein R$_{20}$ is hydrogen.

13. The compound according to claim 10, wherein R$_{20}$ is methyl.

14. The compound according to claim 1 having the formula:

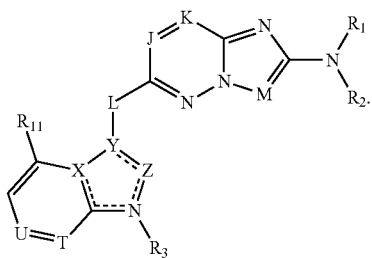

15. The compound according to claim 1 having the formula:

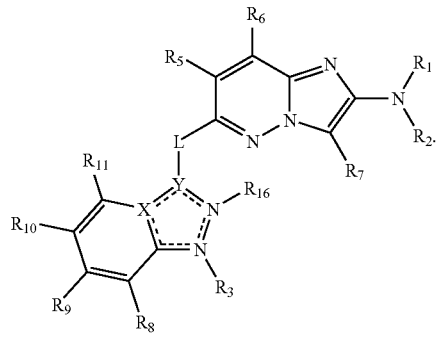

16. The compound according to claim 1 having the formula:

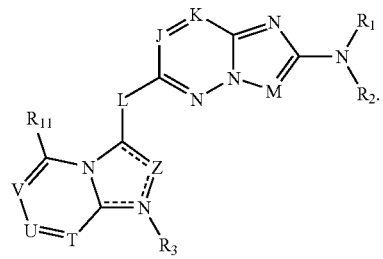

17. The compound according to claim 1 having the formula:

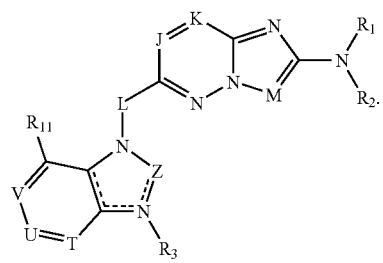

18. The compound according to claim 1 having the formula:

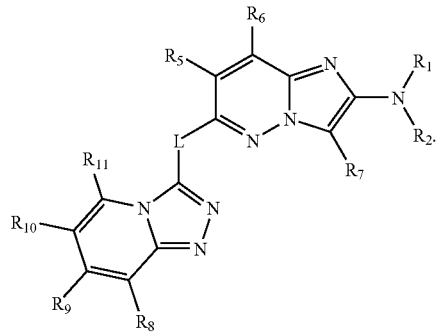

19. The compound according to claim 1 having the formula:

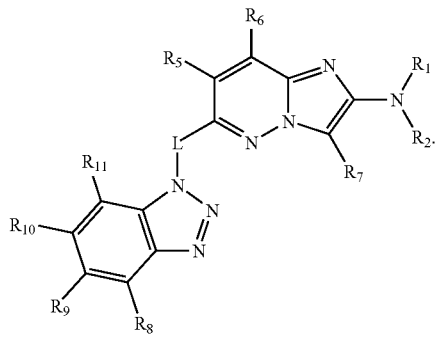

20. The compound according to claim 1, wherein $R_1$ has the formula

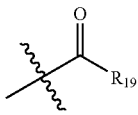

wherein $R_{19}$ selected from the group consisting of hydrogen, hydroxy, $(C_{1-10})$alkoxy, $(C_{4-12})$aryloxy, hetero $(C_{1-10})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl, $(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

21. The compound according to claim 1, wherein $R_2$ is hydrogen.

22. The compound according to claim 1, wherein $R_3$ is absent.

23. The compound according to claim 1, wherein $R_4$ is selected from the group consisting of hydrogen, halo and a substituted or unsubstituted $(C_{1-3})$alkyl.

24. The compound according to claim 1, wherein $R_5$ is selected from the group consisting of hydrogen, halo and a substituted or unsubstituted $(C_{1-3})$alkyl.

25. The compound according to claim 1, wherein $R_6$ is selected from the group consisting of hydrogen, halo and a substituted or unsubstituted $(C_{1-3})$alkyl.

26. The compound according to claim 1, wherein $R_7$ is selected from the group consisting of hydrogen, halo and a substituted or unsubstituted $(C_{1-3})$alkyl.

27. The compound according to claim 1, wherein $R_8$ is selected from the group consisting of hydrogen, halo and a substituted or unsubstituted $(C_{1-3})$alkyl.

28. The compound according to claim 1, wherein $R_9$ is selected from the group consisting of hydrogen, halo and a substituted or unsubstituted $(C_{1-3})$alkyl.

29. The compound according to claim 1, wherein $R_{10}$ has the formula

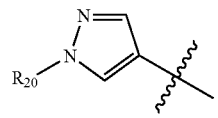

wherein $R_{20}$ selected from the group consisting of hydrogen, halo, nitro, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, $(C_{1-10})$alkyl, halo $(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero $(C_{4-12})$bicycloaryl, each substituted or unsubstituted.

30. The compound according to claim 1, wherein $R_{11}$ is selected from the group consisting of hydrogen, halo and a substituted or unsubstituted $(C_{1-3})$alkyl.

31. The compound according to claim 1, wherein $R_{12}$ is absent.

32. The compound according to claim 1, wherein $R_{13}$ is absent.

33. The compound according to claim 1, wherein $R_{14}$ is selected from the group consisting of hydrogen, halo and a substituted or unsubstituted $(C_{1-3})$alkyl.

34. The compound according to claim 1, wherein $R_{15}$ is absent.

35. The compound according to claim 1, wherein $R_{16}$ is absent.

36. The compound according to claim 1, wherein $R_{19}$ is a substituted or unsubstituted $(C_{1-5})$alkyl.

37. The compound according to claim 1, wherein $R_{19}$ is a substituted or unsubstituted $(C_{3-6})$cycloalkyl.

38. The compound according to claim 1, wherein $R_{19}$ is a substituted or unsubstituted cyclopropyl.

39. The compound according to claim 1, wherein the compound is in the form of a pharmaceutically acceptable salt.

40. A pharmaceutical composition comprising a compound according to claim 1; and
a pharmaceutically acceptable excipient.

41. A kit comprising:
a compound of claim 1; and
instructions which comprise one or more forms of information selected from the group consisting of indicating a disease state for which the compound is to be administered, storage information for the compound, dosing information and instructions regarding how to administer the compound.

42. An article of manufacture comprising:
a compound of claim 1; and
packaging materials.

43. The compound of any one of claim 18 or 19 wherein
$R_2$ is hydrogen;
$R_5$ is hydrogen;
$R_6$ is hydrogen;
$R_7$ is hydrogen;
L is selected from the group consisting of —CH$_2$—, —CH(CH$_3$)—, —C(CH$_3$)$_2$—, —CF$_2$—, and —S—;
$R_8$ is hydrogen;
$R_9$ is hydrogen;
$R_{10}$ is a substituted or unsubstituted hetero$(C_{1-10})$aryl; and
$R_{11}$ is hydrogen.

44. The compound according to claim 43, wherein L is —CF$_2$—.

45. The compound according to claim 44, wherein R$_{10}$ has the formula

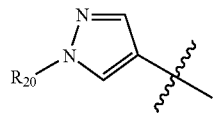

wherein R$_{20b}$) is selected from the group consisting of hydrogen, (C$_{1-5}$)alkyl, (C$_{4-12}$)aryl, (C$_{3-12}$)cycloalkyl, hetero(C$_{4-10}$)aryl, hydroxy(C$_{1-6}$)alkyl, and hetero(C$_{3-6}$) cycloalkyl(C$_{1-4}$)alkyl; each substituted or unsubstituted.

46. The compound according to claim 45, wherein R$_{19}$ is a cyclopropyl unsubstituted or substituted.

47. The compound according to claim 46, wherein R$_{20b}$ is hydrogen.

48. The compound according to claim 46, wherein R$_{20b}$ is methyl.

49. A compound of claim 1 selected from the group consisting of

N-(6-([1,2,4]triazolo[4,3-a]pyridin-3-ylthio)imidazo[1,2-b]pyridazin-2-yl)cyclo -propanecarboxamide;

N-(6-(6-bromo-[1,2,4]triazolo[4,3-a]pyridin-3-ylthio) imidazo[1,2-b]pyridazin-2-yl)cyclopropanecarboxamide;

N-(6-(6-(1-methyl-1H-pyrazol-4-yl)-[1,2,4]triazolo [4,3 -a]pyridin-3 -ylthio)-imidazo [1,2-b ]pyridazin-2-yl)cyclopropanecarboxamide;

N-(6-(6-cyano-[1,2,4]triazolo[4,3-a]pyridin-3-ylthio)imidazo[1,2-b]pyridazin-2-yl)cyclopropanecarboxamide;

Cyclopropanecarboxylic acid [6-(6-bromo-benzotriazol-1-ylmethyl)-imidazo[1,2-b]pyridazin-2-yl]-amide;

N-(6-((6-methyl-1H-benzo[d][1,2,3]triazol-1-yl)methyl) imidazo[1,2-b]pyridazin-2-yl)cyclopropanecarboxamide;

Cyclopropanecarboxylic acid {6-[6-(1-methyl-1H-pyrazol-4-yl)-benzotriazol-1-ylmethyl]-imidazo[1 ,2-b]pyridazin-2-yl}-amide;

N-(6-((6-(3-fluorophenyl)-1H-benzo[d][1,2,3]triazol-1-yl)methyl)imidazo[1,2-b]pyridazin-2-yl)cyclopropanecarboxamide;

N-(6-((6-phenyl-1H-benzo[d][1,2,3]triazol-1-yl)methyl) imidazo[1,2-b]pyridazin-2-yl)cyclopropanecarboxamide;

N-(6-((6-(pyridin-3-yl)-1H-benzo[d][1,2,3]triazol-1-yl) methyl)imidazo[1,2-b]pyridazin-2-yl)cyclopropanecarboxamide;

N-(6-((6-(5-methoxypyridin-3-yl)-1H-benzo[d][1,2,3] triazol-1-yl)methyl)imidazo[1,2-b]pyridazin-2-yl)cyclopropanecarboxamide;

N-(6-((6-(3,5-dimethyl-1H-pyrazol-4-yl)-1H-benzo[d][1,2,3]triazol-1-yl)methyl)imidazo[1,2-b]pyridazin-2-yl) cyclopropanecarboxamide;

N-(6-((6-(5-(methylsulfonyl)pyridin-3-yl)-1H-benzo[d][1,2,3]triazol-1-yl)methyl)imidazo[1,2-b]pyridazin-2-yl)cyclopropanecarboxamide;

(S)-N-(6-((6-(1-(2,3-dihydroxypropyl)-1H-pyrazol-4-yl)-1H-benzo[d][1,2,3]triazol-1-yl)methyl)imidazo[1,2-b] pyridazin-2-yl)cyclopropanecarboxamide;

(R)-N-(6-((6-(1-(2,3-dihydroxypropyl)-1H-pyrazol-4-yl)-1H-benzo[d][1,2,3]triazol-1-yl)methyl)imidazo[1,2-b] pyridazin-2-yl)cyclopropanecarboxamide;

N-(6-((6-(1-(2-hydroxyethyl)-1H-pyrazol-4-yl)-1H-benzo[d][1,2,3]triazol-1-yl)methyl)imidazo[1,2-b]pyridazin-2-yl)cyclopropanecarboxamide;

N-(6-(6-isopropyl-[1,2,4]triazolo[4,3-a]pyridin-3-ylthio) imidazo[1,2-b]pyridazin-2-yl)cyclopropanecarboxamide N-(6-(6-(1-(2-methoxyethyl)-1H-pyrazol-4-yl)-[1,2,4] triazolo[4,3-a]pyridin-3-ylthio)imidazo[1,2-b]pyridazin-2-yl)cyclopropanecarboxamide;

N-(6-(6-(1-(2-hydroxyethyl)-1H-pyrazol-4-yl)[1,2,4]triazolo[4,3-a]pyridin-3-ylthio)imidazo[1,2-b]pyridazin-2-yl)cyclopropanecarboxamide;

N-(6-(6-(4-(piperazin-1-yl)phenyl)-[1,2,4]triazolo[4,3-a] pyridin-3-ylthio)imidazo[1,2-b]pyridazin-2-yl)cyclopropanecarboxamide;

N-(6-(6-(2H-tetrazol-5-yl)-[1,2,4]triazolo[4,3-a]pyridin-3-ylthio)imidazo[1,2-b]pyridazin-2-yl)cyclopropanecarboxamide;

N-(6-(6-(5-(methoxymethyl)-1,2,4-oxadiazol-3-yl)-[1,2,4]triazolo[4,3-a]pyridin-3-ylthio)imidazo[1,2-b]pyridazin-2-yl)cyclopropanecarboxamide;

N-(6-(6-(2-hydroxypropan-2-yl)-[1,2,4]triazolo[4,3-a]pyridin-3-ylthio)imidazo[1,2-b]pyridazin-2-yl)cyclopropanecarboxamide;

N-(6-(6-(trifluoromethyl)-[1,2,4]triazolo[4,3-a]pyridin-3-ylthio)imidazo[1,2-b]pyridazin-2-yl)cyclopropanecarboxamide;

N-(6-(6-methyl-[1,2,4]triazolo[4,3-a]pyridin-3-ylthio) imidazo[1,2-b]pyridazin-2-yl)cyclopropanecarboxamide;

N-(6-(6-(3 -fluorophenyl)-[1,2,4]triazolo[4,3 -a]pyridin-3 -ylthio)imidazo [1,2-b]pyridazin-2-yl)cyclopropanecarboxamide;

N-(6-(difluoro(6-(isoxazol-4-yl)-[1,2,4]triazolo [4,3 -a]pyridin-3-yl)methyl)imidazo [1,2-b]pyridazin-2-yl)cyclopropanecarboxamide;

N-(6-(difluoro(6-(1-(2-hydroxyethyl)-1H-pyrazol-4-yl)-[1,2,4]triazolo[4,3 -a]pyridin-3-yl)methyl)imidazo[1,2-b]pyridazin-2-yl)cyclopropanecarboxamide;

N-(6-(1-(6-bromo-[1,2,4]triazolo[4,3-a]pyridin-3-yl) ethyl)imidazo[1,2-b]pyridazin-2-yl)cyclopropanecarboxamide;

N-(6-(1-(6-(1-methyl-1H-pyrazol-4-yl)-[1,2,4]triazolo[4,3-a]pyridin-3-yl)ethyl)imidazo[1,2-b]pyridazin-2-yl) cyclopropanecarboxamide;

(S)-N-(6-(1-(6-(1-methyl-1H-pyrazol-4-yl)-[1,2,4]triazolo[4,3-a]pyridin-3-yl)ethyl)imidazo[1,2-b]pyridazin-2-yl)cyclopropanecarboxamide;

(R)-N-(6-(1-(6-(1-methyl-1H-pyrazol-4-yl)-[1,2,4]triazolo[4,3-a]pyridin-3-yl)ethyl)imidazo[1,2-b]pyridazin-2-yl)cyclopropanecarboxamide;

N-(6-(1-([1,2,4]triazolo[4,3-a]pyridin-3-yl)ethyl)imidazo [1,2-b]pyridazin-2-yl)cyclopropanecarboxamide;

N-(6-(1-(6-methyl-[1,2,4]triazolo[4,3-a]pyridin-3-yl) ethyl)imidazo[1,2-b]pyridazin-2-yl)cyclopropanecarboxamide;

N-(6-(1-(6-(4-fluorophenyl)-[1,2,4]triazolo[4,3-a]pyridin-3-yl)ethyl)imidazo[1,2-b]pyridazin-2-yl)cyclopropanecarboxamide;

N-(6-(1-(6-(4-methylthiophen-2-yl)-[1,2,4]triazolo[4,3-a]pyridin-3-yl)ethyl)imidazo[1,2-b]pyridazin-2-yl)cyclopropanecarboxamide;

N-(6-(1-(6-(1H-pyrazol-4-yl)-[1,2,4]triazolo[4,3 -a]pyridin-3-yl)ethyl)imidazo[1,2-b]pyridazin-2-yl)cyclopropanecarboxamide;

N-(6-(1-(6-(3-fluorophenyl)-[1,2,4]triazolo[4,3-a]pyridin-3-yl)ethyl)imidazo[1,2-b]pyridazin-2-yl)cyclopropanecarboxamide;

N-(6-(difluoro(6-(4-fluorophenyl)-[1,2,4]triazolo[4,3-a]pyridin-3-yl)methyl)imidazo[1,2-b]pyridazin-2-yl)cyclopropanecarboxamide;

N-(6-(difluoro(6-(pyridin-3-yl)-[1,2,4]triazolo[4,3-a]pyridin-3-yl)methyl)imidazo[1,2-b]pyridazin-2-yl)cyclopropanecarboxamide;

N-(6-(difluoro(6-(pyridin-4-yl)-[1,2,4]triazolo[4,3-a]pyridin-3-yl)methyl)imidazo[1,2-b]pyridazin-2-yl)cyclopropanecarboxamide;

N-(6-(difluoro(6-(4-isopropylphenyl)-[1,2,4]triazolo[4,3-a]pyridin-3-yl)methyl)imidazo[1,2-b]pyridazin-2-yl)cyclopropanecarboxamide;

N-(6-((6-(3,5-difluorophenyl)-[1,2,4]triazolo[4,3-a]pyridin-3-yl)difluoromethyl)imidazo[1,2-b]pyridazin-2-yl)cyclopropanecarboxamide;

N-(6-(difluoro(6-(4-methylthiophen-2-yl)-[1,2,4]triazolo[4,3-a]pyridin-3-yl)methyl)imidazo[1,2-b]pyridazin-2-yl)cyclopropanecarboxamide;

N-(6-(difluoro(6-(6-methoxypyridin-3-yl)-[1,2,4]triazolo[4,3-a]pyridin-3-yl)methyl)imidazo[1,2-b]pyridazin-2-yl)cyclopropanecarboxamide;

N-(6-(difluoro(6-(pyrimidin-5-yl)-[1,2,4]triazolo[4,3-a]pyridin-3-yl)methyl)imidazo[1,2-b]pyridazin-2-yl)cyclopropanecarboxamide;

N-(6-((6-(1H-pyrazol-4-yl)-[1,2,4]triazolo[4,3-a]pyridin-3-yl)difluoromethyl)imidazo[1,2-b]pyridazin-2-yl)cyclopropanecarboxamide;

N-(6-(difluoro(6-(4-methylpyridin-3-yl)-[1,2,4]triazolo[4,3-a]pyridin-3-yl)methyl)imidazo[1,2-b]pyridazin-2-yl)cyclopropanecarboxamide;

N-(6-(difluoro(6-(3-fluoro-5-methylphenyl)-[1,2,4]triazolo[4,3-a]pyridin-3-yl)methyl)imidazo[1,2-b]pyridazin-2-yl)cyclopropanecarboxamide;

N-(6-(6-(5-methyl-1H-1,2,4-triazol-3-yl)-[1,2,4]triazolo[4,3-a]pyridin-3-ylthio)imidazo[1,2-b]pyridazin-2-yl)cyclopropanecarboxamide;

N-(6-(6-(6-methoxypyridin-2-yl)-[1,2,4]triazolo[4,3-a]pyridin-3-ylthio)imidazo[1,2-b]pyridazin-2-yl)cyclopropanecarboxamide;

N-(6-(6-(6-methoxypyridin-3-yl)-[1,2,4]triazolo[4,3-a]pyridin-3-ylthio)imidazo[1,2-b]pyridazin-2-yl)cyclopropanecarboxamide;

N-(6-(6-(6-morpholinopyridin-3-yl)-[1,2,4]triazolo[4,3-a]pyridin-3-ylthio)imidazo[1,2-b]pyridazin-2-yl)cyclopropanecarboxamide;

N-(6-(6-(1-methyl-6-oxo-1,6-dihydropyridin-3-yl)-[1,2,4]triazolo[4,3-a]pyridin-3-ylthio)imidazo[1,2-b]pyridazin-2-yl)cyclopropanecarboxamide;

N-(6-(6-(1-ethyl-6-oxo-1,6-dihydropyridin-3-yl)-[1,2,4]triazolo[4,3-a]pyridin-3-ylthio)imidazo[1,2-b]pyridazin-2-yl)cyclopropanecarboxamide;

N-(6-(6-(2-(3-hydroxypropylamino)pyrimidin-5-yl)-[1,2,4]triazolo[4,3-a]pyridin-3-ylthio)imidazo[1,2-b]pyridazin-2-yl)cyclopropanecarboxamide;

N-(6-(6-(2-morpholinothiazol-4-yl)-[1,2,4]triazolo[4,3-a]pyridin-3-ylthio)imidazo[1,2-b]pyridazin-2-yl)cyclopropanecarboxamide; and N-(6-(6-(3-(3-hydroxypropyl)phenyl)-[1,2,4]triazolo[4,3-a]pyridin-3-ylthio)imidazo[1,2-b]pyridazin-2-yl)cyclopropanecarboxamide;

or a pharmaceutically acceptable salt of the above-mentioned compounds.

50. A compound of claim 1 wherein the compound is N-(6-(6-chloro-[1,2,4]triazolo[4,3-a]pyridin-3-ylthio)imidazo[1,2-b]pyridazin-2-yl)cyclopropanecarboxamide or a pharmaceutically acceptable salt thereof.

51. A compound of claim 1 wherein the compound is N-(6-(difluoro(6-(1-methyl-1H-pyrazol-4-yl)-[1,2,4]triazolo[4,3-a]pyridin-3-yl)methyl)imidazo[1,2-b]pyridazin-2-yl)cyclopropanecarboxamide or a pharmaceutically acceptable salt thereof.

52. A compound of claim 1 wherein the compound is N-(6-(difluoro(6-(3-fluorophenyl)-[1,2,4]triazolo[4,3-a]pyridin-3-yl)methyl)imidazo[1,2-b]pyridazin-2-yl)cyclopropanecarboxamide or a pharmaceutically acceptable salt thereof.

53. A compound of claim 1 wherein the compound is N-(6-(6-(5-cyano-6-hydroxypyridin-3-yl)-[1,2,4]triazolo[4,3-a]pyridin-3-ylthio)imidazo[1,2-b]pyridazin-2-yl)cyclopropanecarboxamide or a pharmaceutically acceptable salt thereof.

\* \* \* \* \*